(12) United States Patent
Luo et al.

(10) Patent No.: US 8,802,925 B2
(45) Date of Patent: Aug. 12, 2014

(54) METHOD FOR MODIFYING ANTHOCYANIN EXPRESSION IN SOLANACEOUS PLANTS

(75) Inventors: Jie Luo, Norwich (GB); Eugenio Butelli, Norwich (GB); Jonathan Jones, Norwich (GB); Laurence Tomlinson, Norwich (GB); Catherine Rosemary Martin, Norwich (GB)

(73) Assignee: Norfolk Plant Sciences Limited, Norfolk (GB)

( * ) Notice: Subject to any disclaimer, the term of this patent is extended or adjusted under 35 U.S.C. 154(b) by 724 days.

(21) Appl. No.: 12/918,248

(22) PCT Filed: Feb. 18, 2009

(86) PCT No.: PCT/GB2009/000431
§ 371 (c)(1),
(2), (4) Date: Dec. 20, 2010

(87) PCT Pub. No.: WO2009/103960
PCT Pub. Date: Aug. 27, 2009

(65) Prior Publication Data
US 2011/0126313 A1 May 26, 2011

Related U.S. Application Data

(60) Provisional application No. 61/029,416, filed on Feb. 18, 2008.

(51) Int. Cl.
*C12N 15/29* (2006.01)
*C12N 15/82* (2006.01)
*A01H 5/00* (2006.01)
*A01H 5/10* (2006.01)

(52) U.S. Cl.
USPC ........ 800/282; 800/298; 800/317; 800/317.2; 800/317.3

(58) Field of Classification Search
CPC ............. C12N 15/825; C12N 15/8234; C12N 15/8261; C07K 14/415; C07K 14/4702; A61H 3/04
See application file for complete search history.

(56) References Cited

U.S. PATENT DOCUMENTS 6,881,430 B2 * 4/2005 Kohler et al. ................. 426/250

FOREIGN PATENT DOCUMENTS

KR 2009111404 A * 10/2009 ........... C07K 14/415
WO WO2006/062698 A2 * 6/2006 ............... A01H 1/00

OTHER PUBLICATIONS

Mehrtens et al (2005) Plant Physiology 138: 1083-1096.*
Stracke et al (2007) The Plant Journal 50:660-677.*
Schwinn et al (2006),The Plant Cell, 18 (April):831-851.*
Gonzalez et al (2008), The Plant Journal 53: 814-827.*
Shang et al (2007) Plant Methods 3:1, 12 pages.*
Matthews et al (2003) The Plant Cell 15(August):1689-1703.*
Oregon State University (2006, 2009) Dept. of Horticulture "Oregon Vegetables: Purple Tomato FAQ".*
Pelegrinni et al (2005) Intl Jnl Biochem Cell Biol 37(11): 2239-2253.*
Nature Reviews-Genetics (2003) Glossary Terms for Clegg et al, vol. 4 (March): 206-215.*
USDA-Agriculture Research Service (2006). Germplasm Resources Information Network (ARS-GRIN), Genus "*Antirrhinum L.*".*
Du, H. et al (2009) Biochemistry (Moscow) 74(1): 1-11.*
Jung et al (2009) Theoretical and Applied Genetics 120 (1): 45-57.*
Luo, Jie et al., "AtMYB12 regulates caffeoyl quinic acid and flavonol synthesis in tomato: expression in fruti results in very high levels of both types of polyphenol," The Plan Journal, vol. 56, pp. 316-326 (2008).
Mehrtens, Frank et al., "The *Arabidopsis* Transcription Factor MYB12 Is a Flavonol-Specific Regulator of Phenylpropanoid Biosynthesis," Plant Physiology, vol. 138, pp. 1083-1096 (Jun. 2005).
Stracke, Ralf et al., "Differential regulation of closely related R2R3-MYB transcription factors controls flavonol accumulation in different parts of the *Arabidopsis thaliana* seedling," The Plant Jouranl, vol. 50, pp. 660-677 (2007).
Kinney, Anthony J., "Metabolic engineering in plants for human health and nutrition," Current Opinion in Biotechnology, vol. 17, pp. 130-138 (2006).
Allan, Andrew C. et al., "MYB Transcription Fac5tors that Colour our Fruit," Trends in Plant Science, vol. 13, No. 3, pp. 99-102 (Feb. 2008).

* cited by examiner

*Primary Examiner* — Russell Kallis
(74) *Attorney, Agent, or Firm* — Alston & Bird LLP

(57) ABSTRACT

The invention provides methods, compositions and transformation systems for modifying the levels of transcription factors in plants such as *Solanaceous* plants, and introducing disease resistance genes into plants, to produce products with elevated levels of antioxidant compounds, including but not limited to flavonols and chlorogenic acid, as well as exhibiting enhanced disease resistance, and optionally altered appearance. Preferred plants are those in which introduced genes are from *Solanaceous* species.

29 Claims, 24 Drawing Sheets

MGRTPCCEKVGIKRGRWTAEEDQILTNYIISNGEGSWRSLPKNAGLLRCGKSCRLRWINYLRS
DLKRGNITSQEEDIIIKLHATLGNRWSLIAEHLSGRTDNEIKNYWNSHLSRKVDSLRIPSDEKLP
KAVVDLAKKGIPKPIKKSSISRPKNKKSNLLEKEALCCTNMPACDSAMELMQEDLAKIEVPNS
WAGPIEAKGSLSSDSDIEWPRLEEIMPDVVIDDEDKNTNFILNCFREEVTSNNVGNSYSCIEEGN
KKISSDDEKIKLLMDWQDNDELVWPTLPWELETDIVPSWPQWDDTDTNLLQNCTNDNNNYEE
ATTMEINNQNHSTIVSWLLS

B

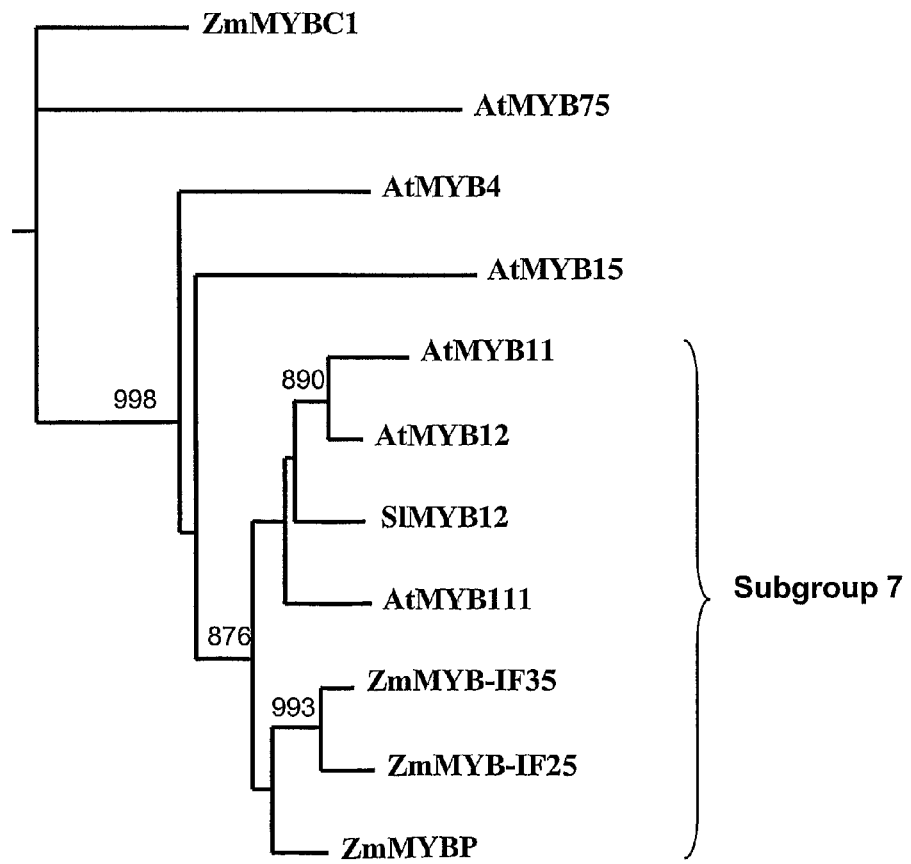

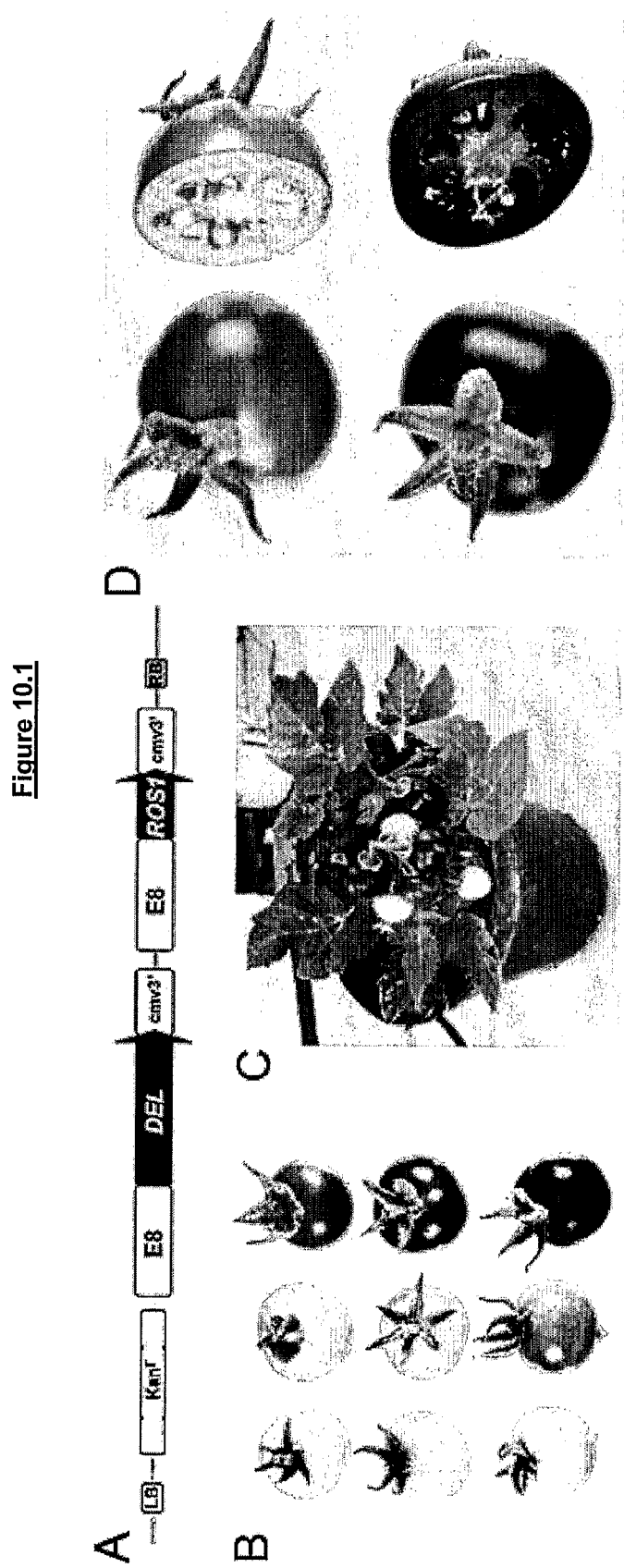
Figure 10.1

Figure 10.2
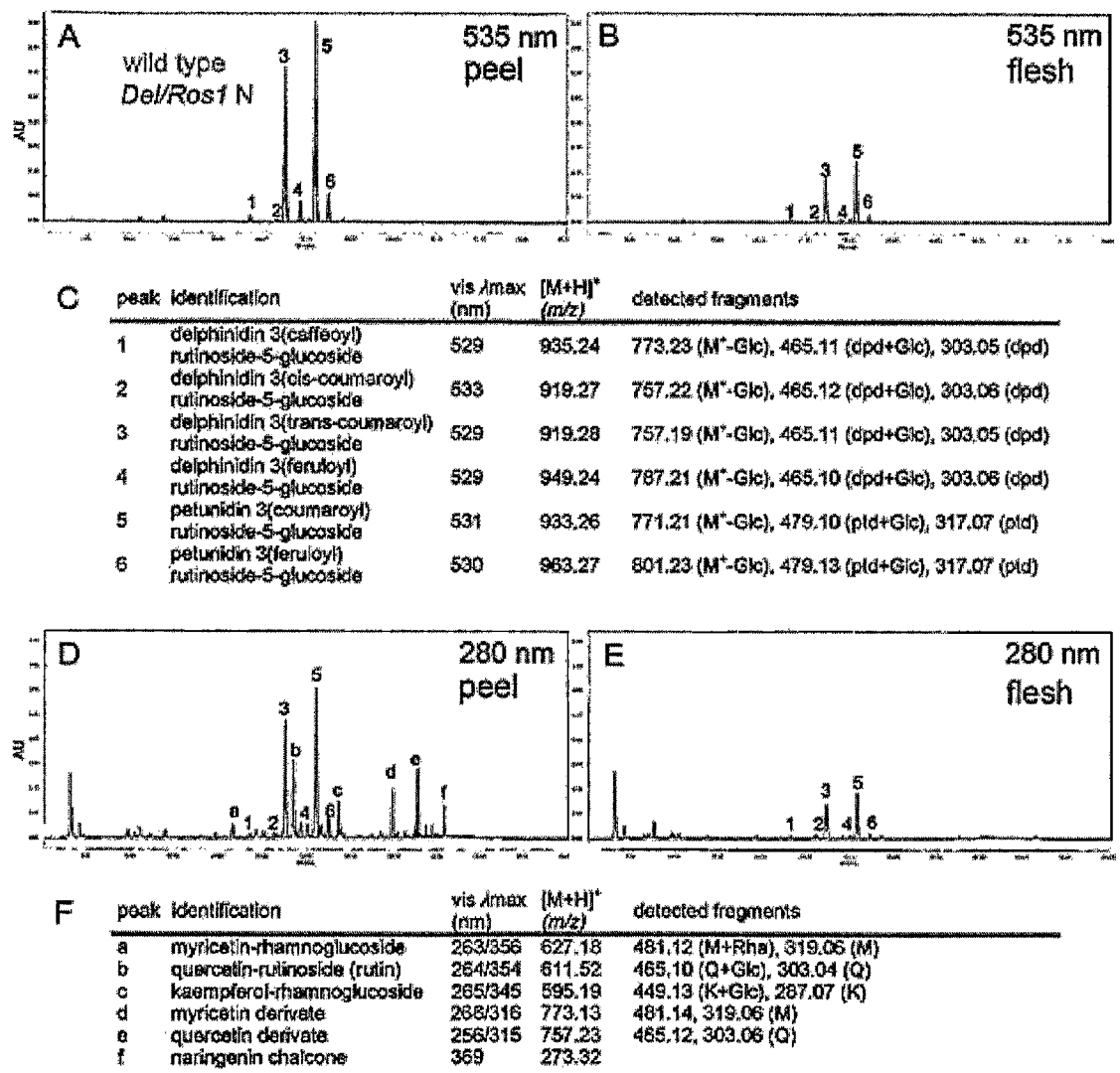

Figure 10.3
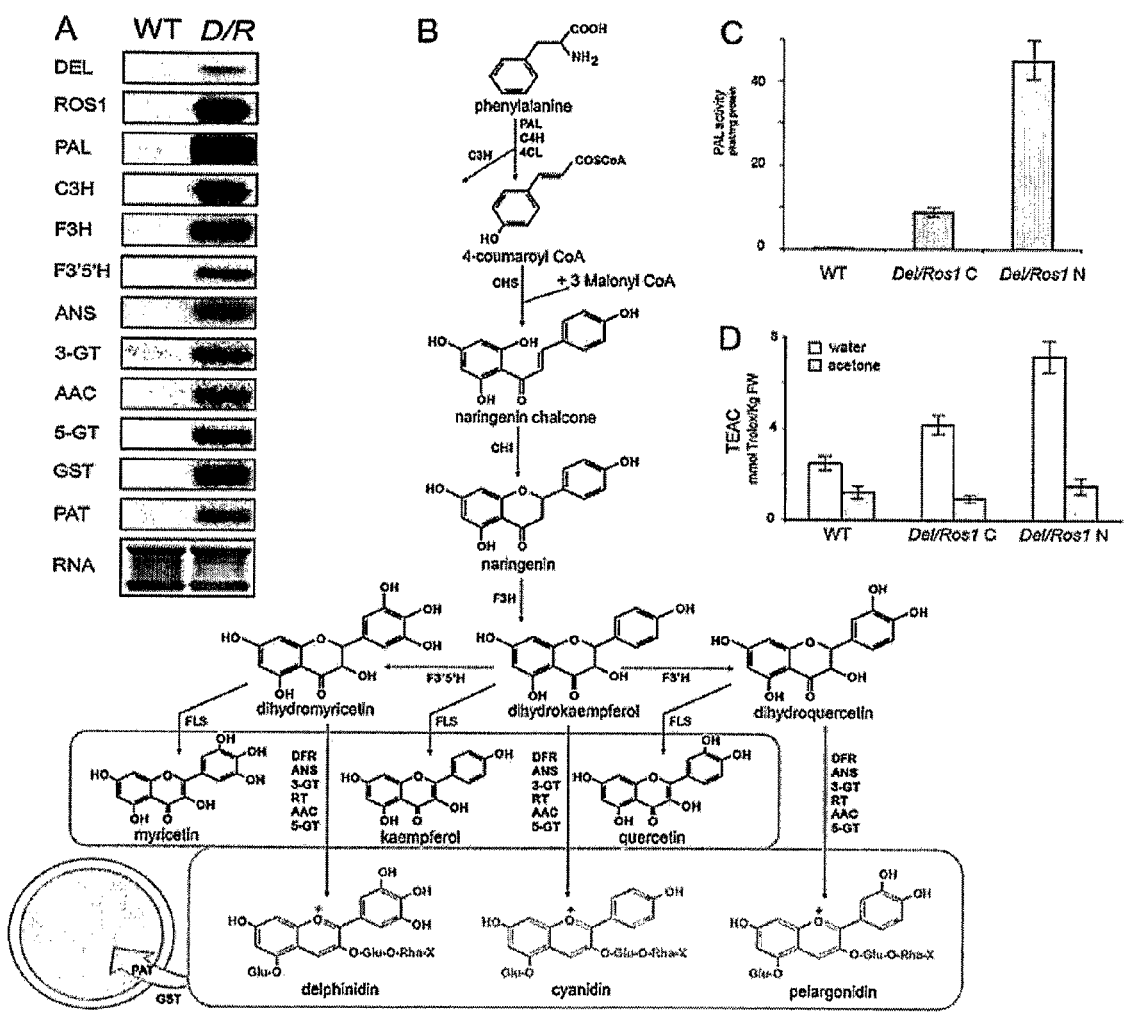

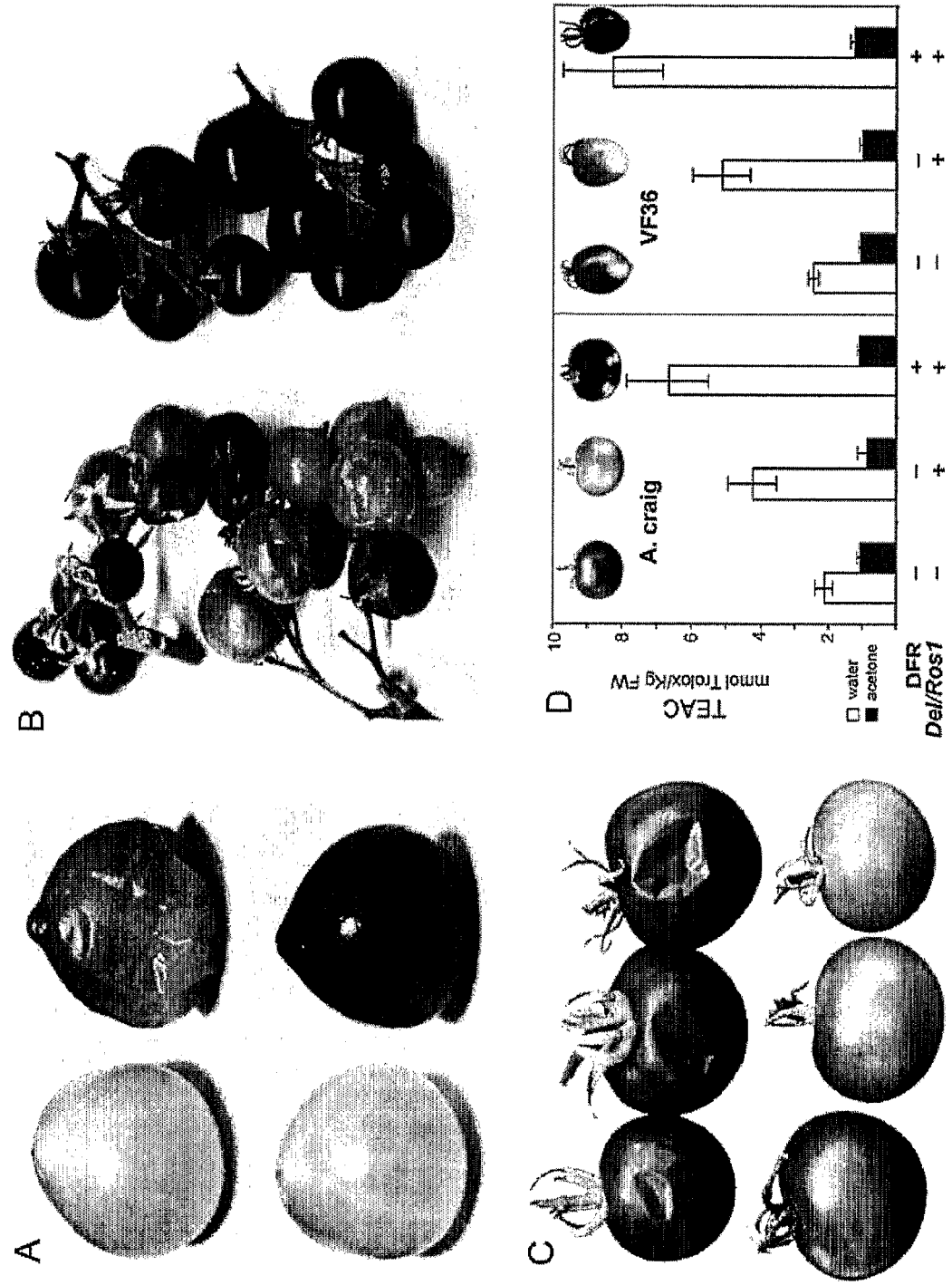
Figure 10.4

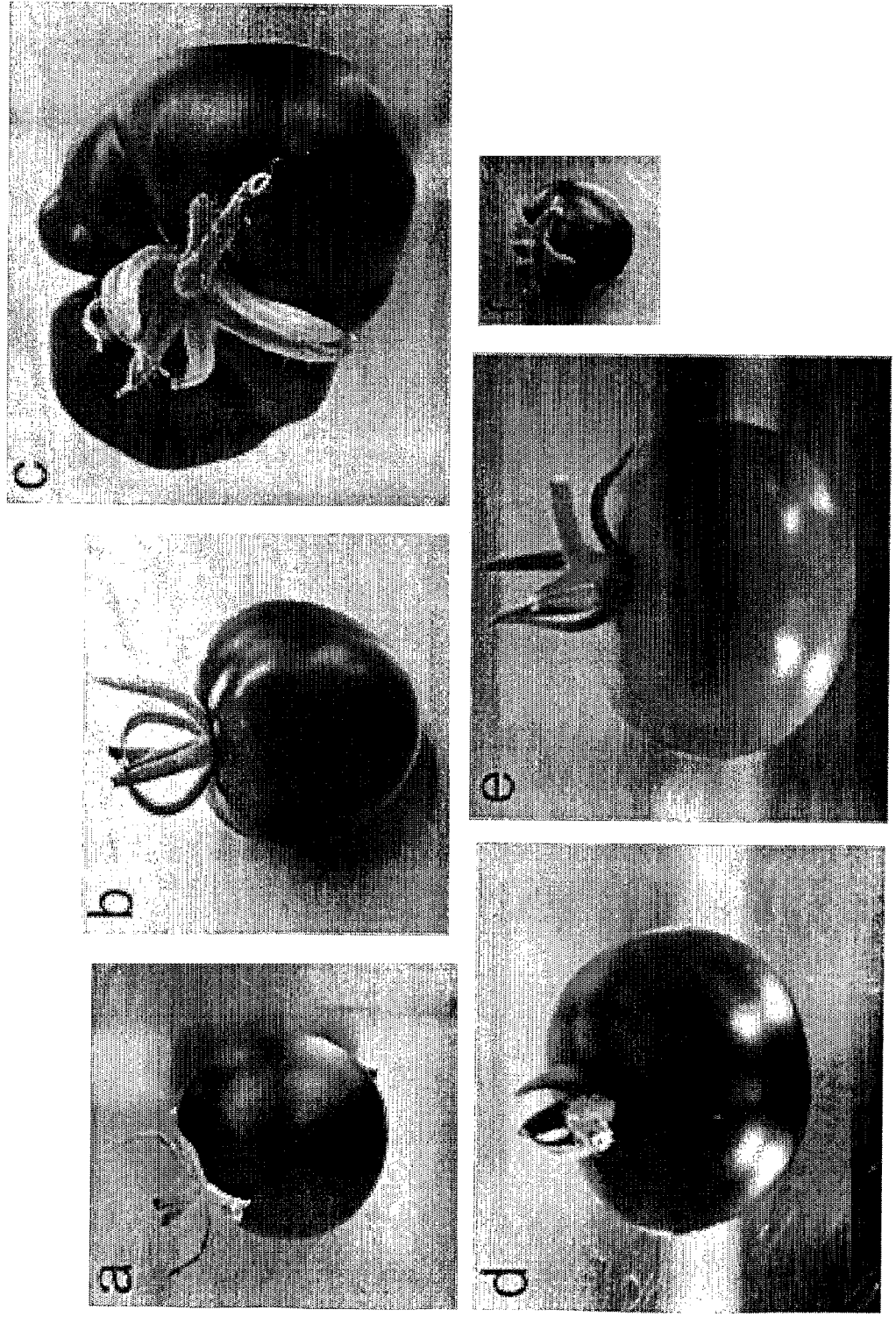
Figure 10.5

Figure 10.6
A
| Sample | Anthocyanin levels; mg per g fresh weight tomato |
|---|---|
| Control 1 | 0.008 ± 0.001 |
| Control 2 | 0.016 ± 0.003 |
| Del/Ros1 line C | 0.464 ± 0.062 |
| Del/Ros1 line N | 2.835 ± 0.456 |
| Del/Ros1 line Y | 0.458 ± 0.042 |
| Del/Ros1 line Z | 0.230 ± 0.029 |
B
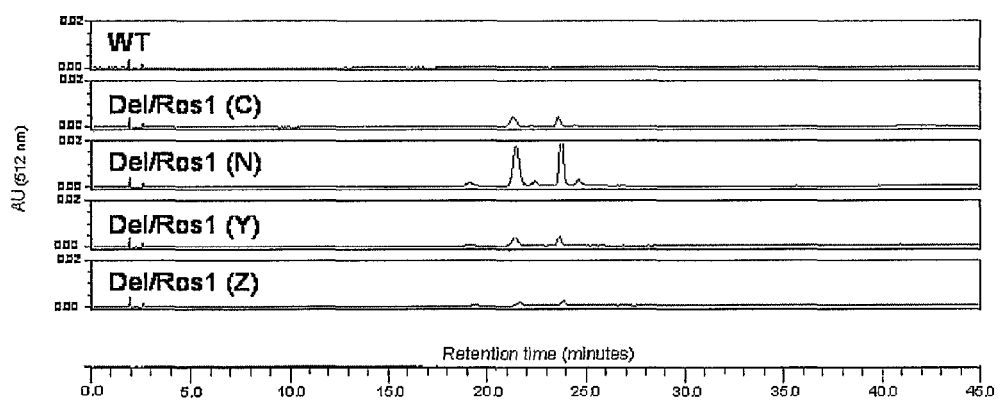
C
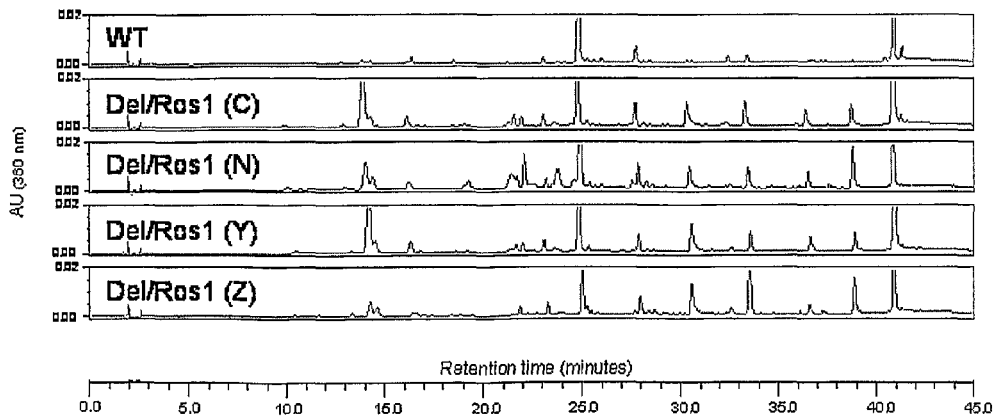

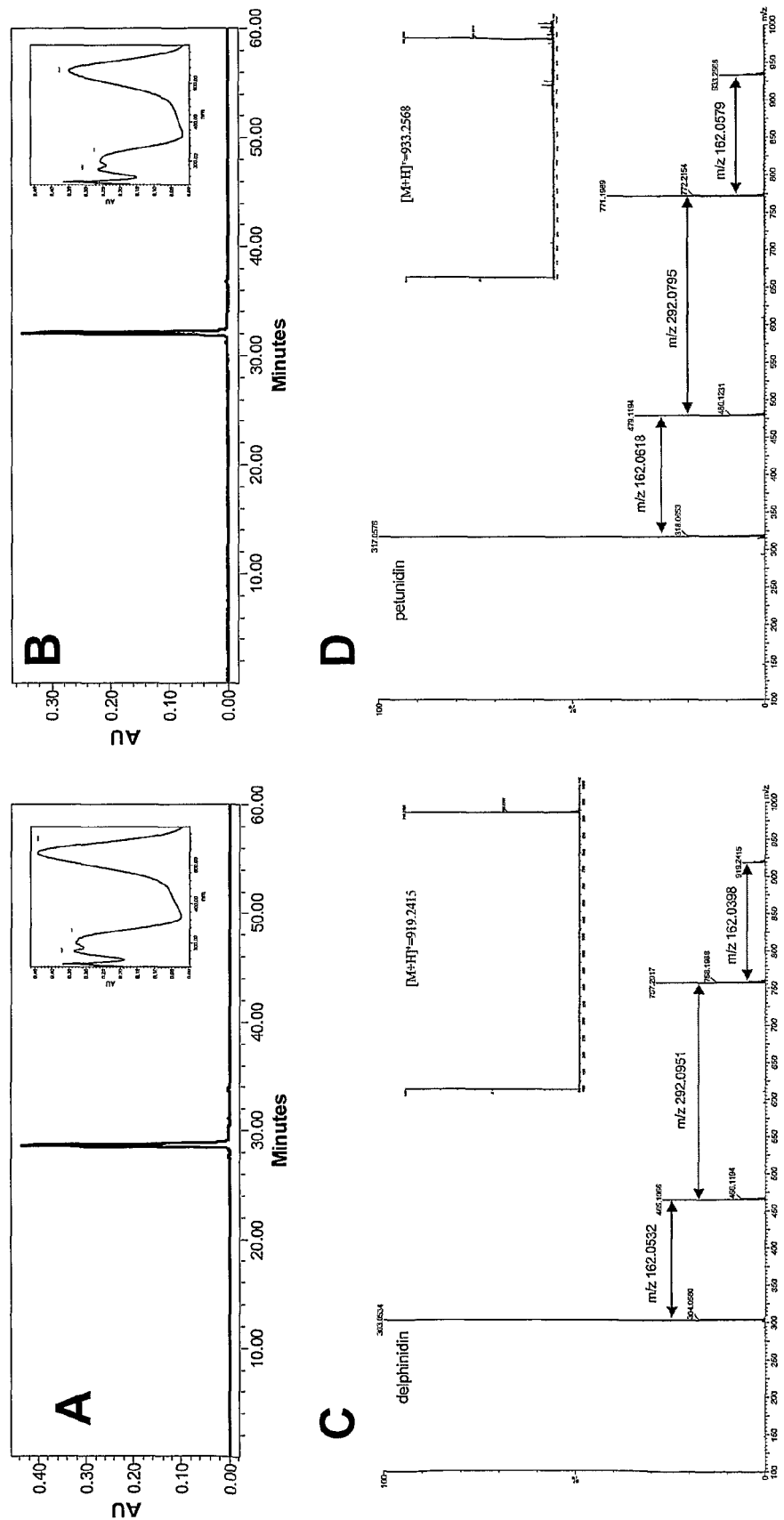
Figure 10.7

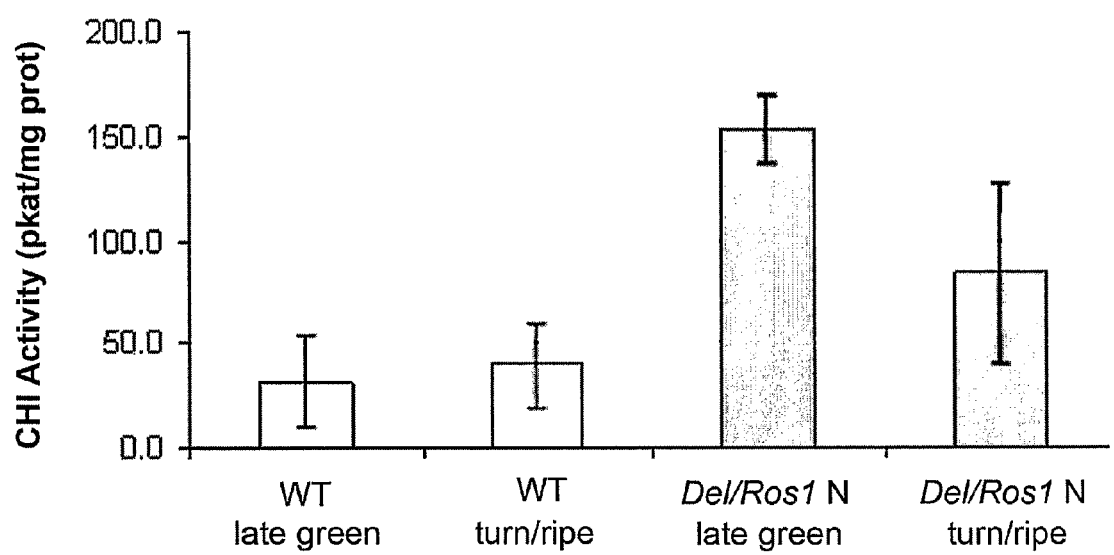
Figure 10.8

Figure 10.9
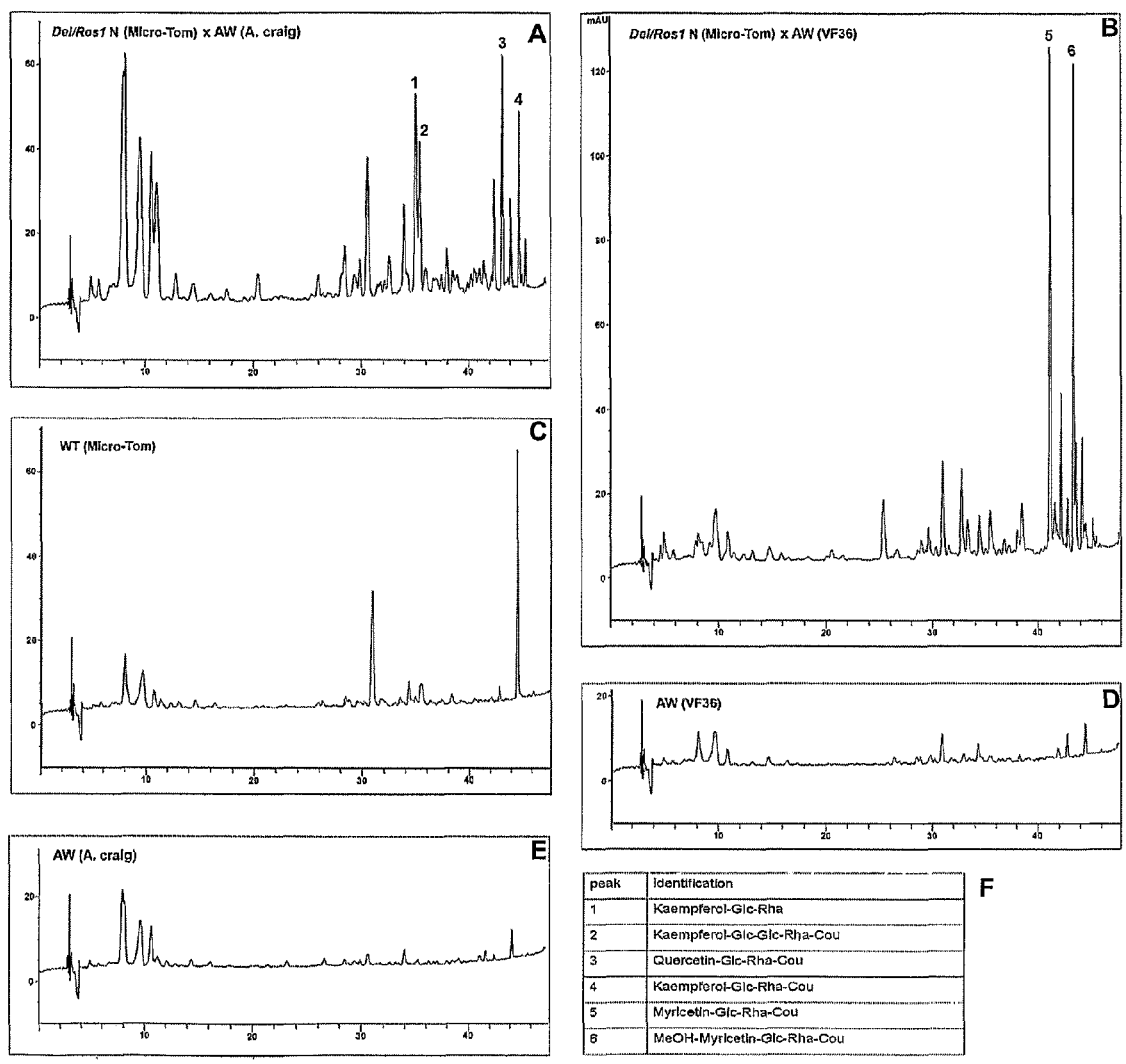

Figure 10.10
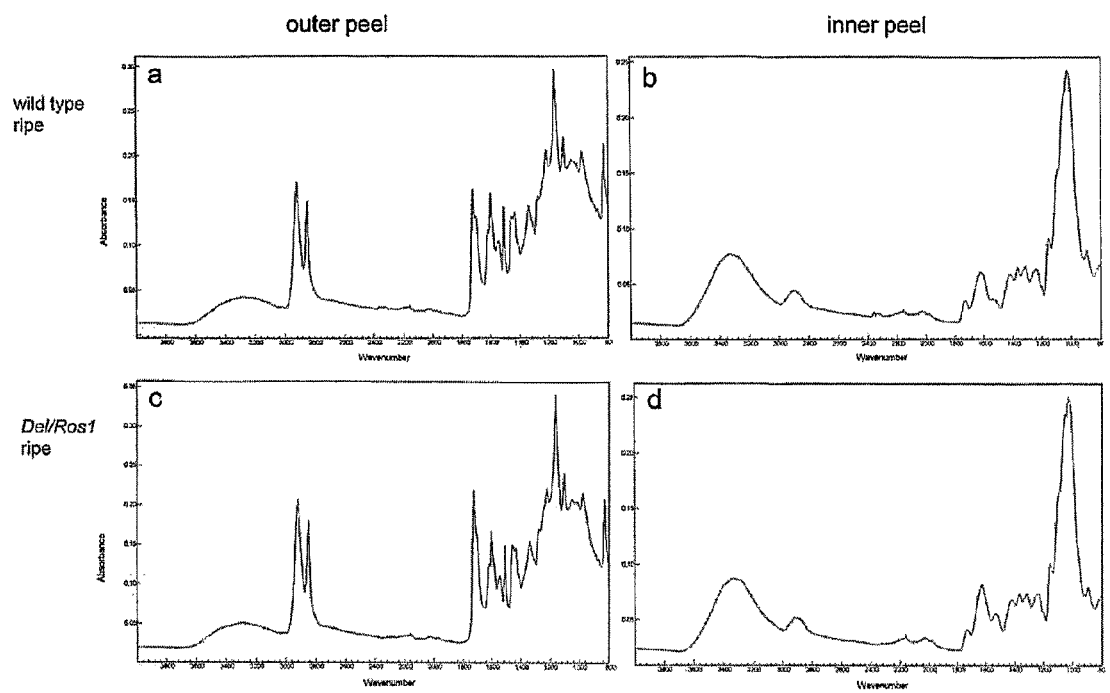
e
| material obtained in September 2004 | | | | |
|---|---|---|---|---|
| | | | | mg/gDW mean |
| flesh | WT | 1 | 2,15 | |
| | | 2 | 2,15 | 2,15 |
| | Del/Ros1N | 1 | 2,58 | |
| | | 2 | 2,89 | 2,73 |
| | Del/Ros1C | 1 | 2,23 | |
| | | 2 | 2,46 | 2,34 |
| peel | WT | 1 | 22,05 | |
| | | 2 | 21,04 | 21,54 |
| | Del/Ros1N | 1 | 22,53 | |
| | | 2 | 13,16 | 17,85 |
| | Del/Ros1C | 1 | 19,31 | |
| | | 2 | 21,95 | 20,63 |
| material obtained in November 2005 | | | | |
| | | | | mg/gFW mean |
| flesh | WT | 1 | 0,37 | |
| | | 2 | 0,32 | 0,35 |
| | Del/Ros1N | 1 | 0,22 | |
| | | 2 | 0,39 | 0,30 |
| peel | WT | 1 | 3,86 | |
| | | 2 | 4,86 | 4,36 |
| | Del/Ros1N | 1 | 3,60 | |
| | | 2 | 4,25 | 3,93 |

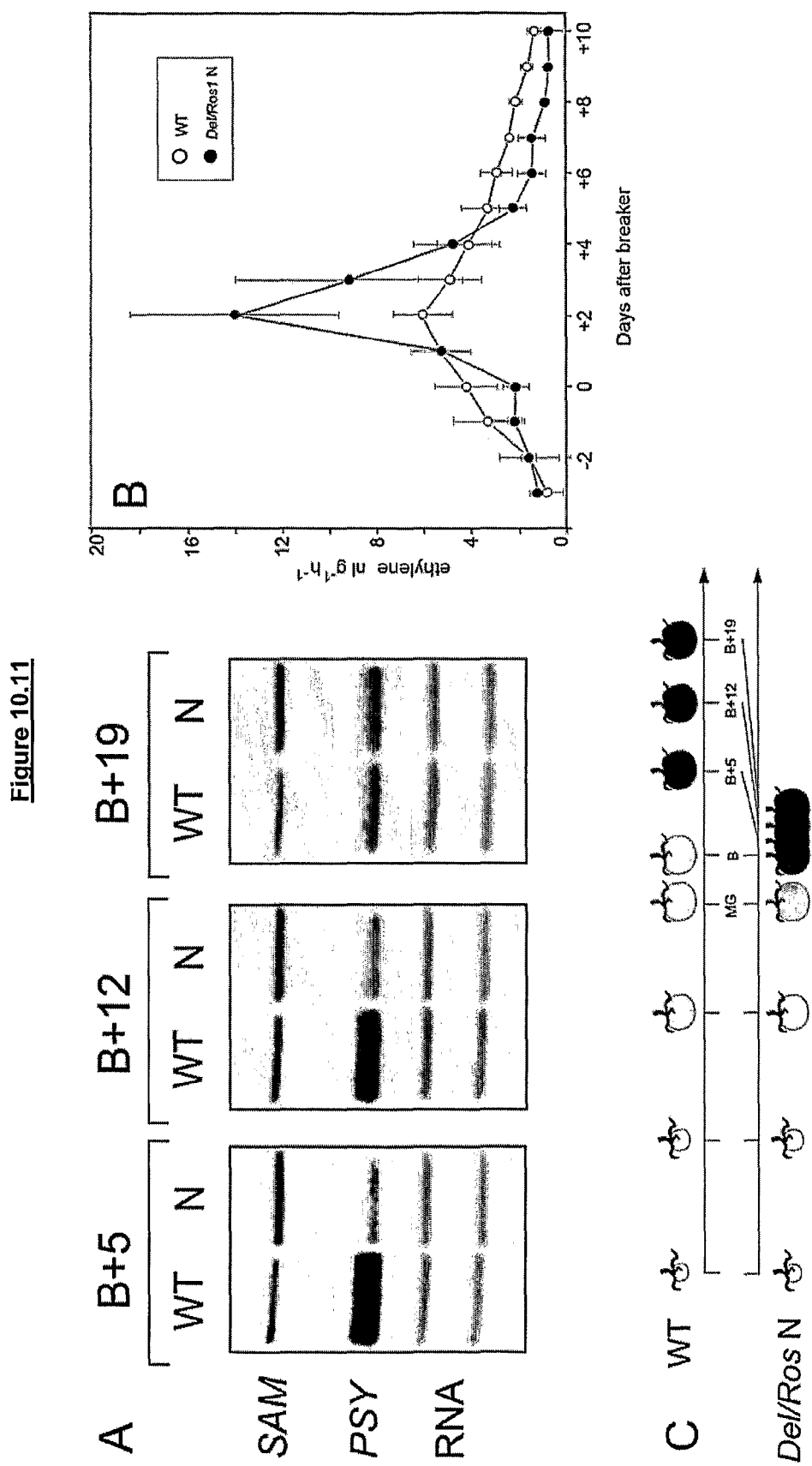
Figure 10.11

Figure 10.12
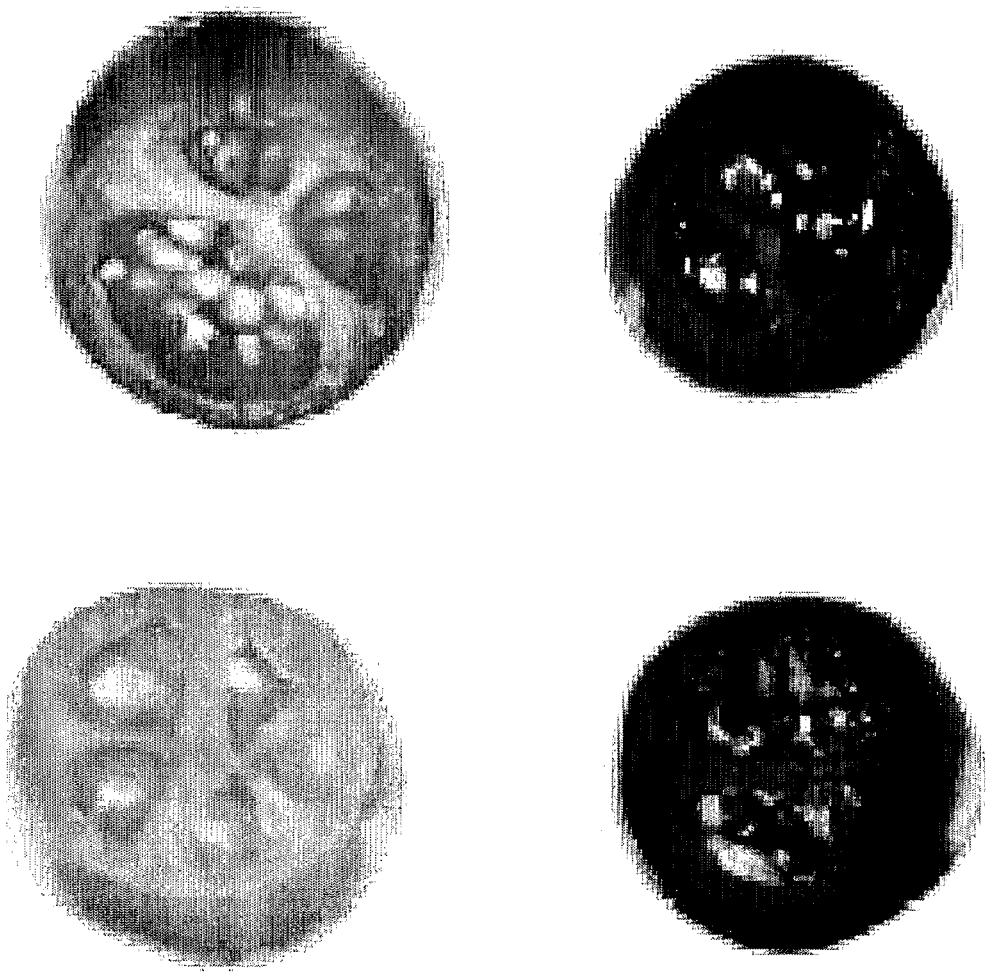

Figure 11.1
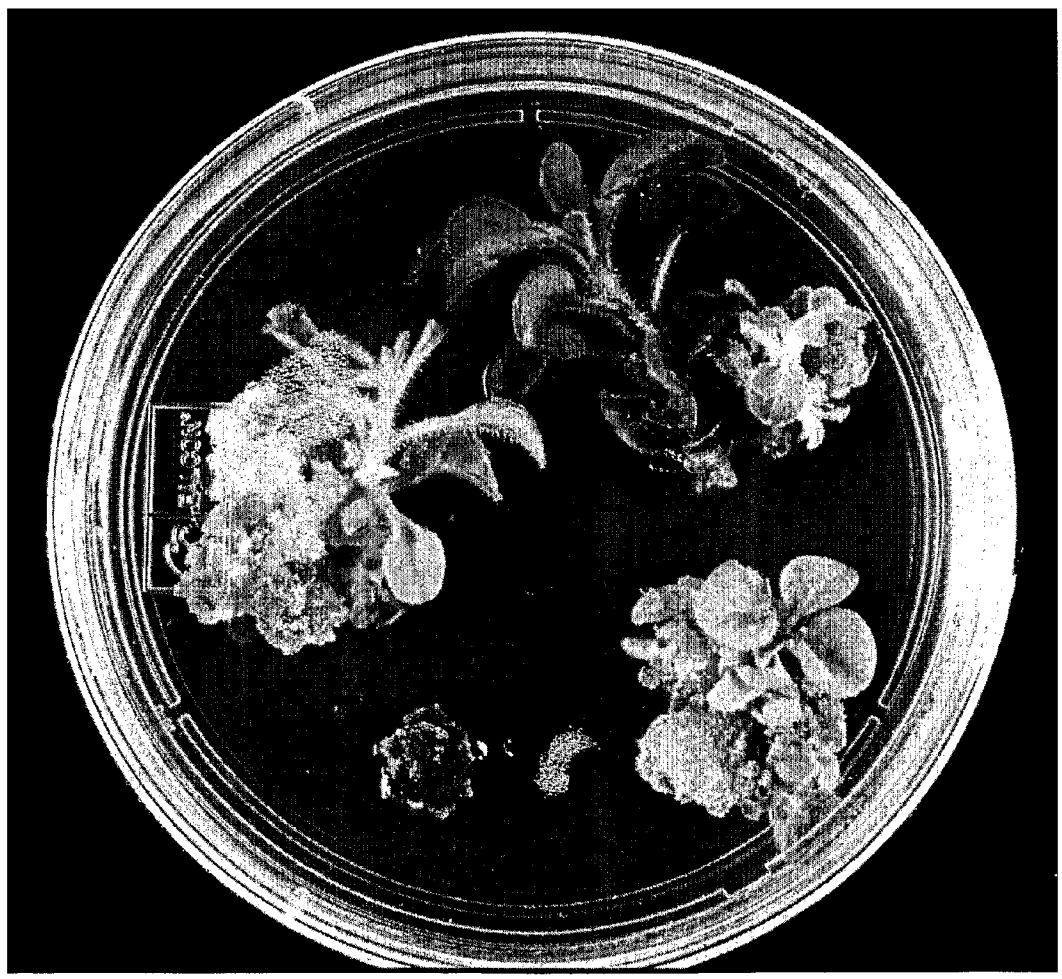

Figure 11.2
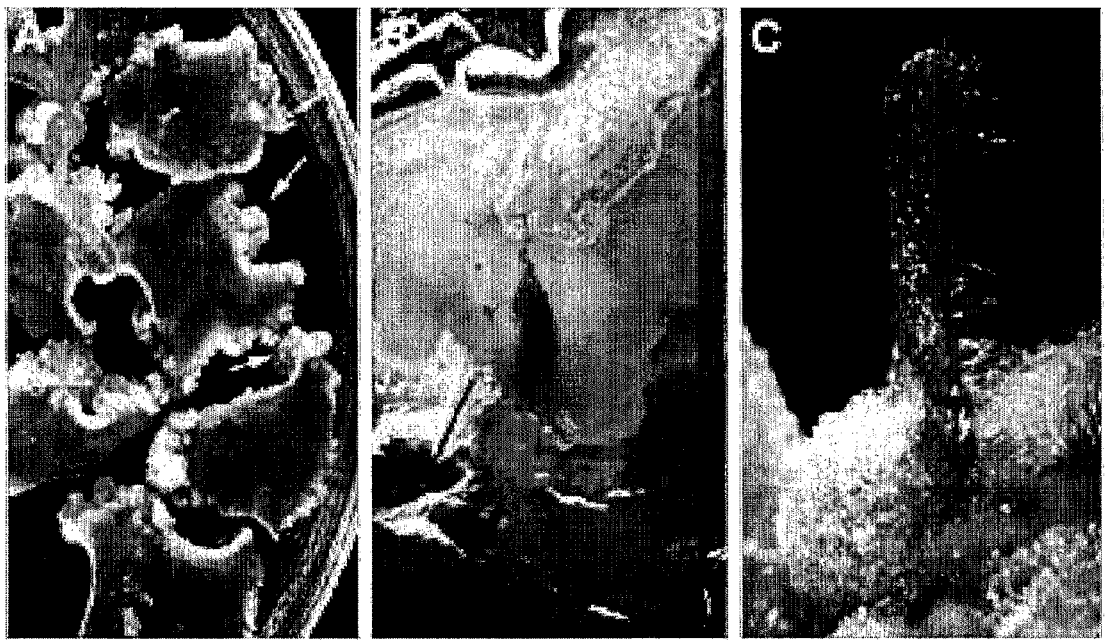

ered embodiments of the invention below.

METHOD FOR MODIFYING ANTHOCYANIN EXPRESSION IN SOLANACEOUS PLANTS

REFERENCE TO RELATED APPLICATIONS

This application is the US national phase entry of International Patent Application No. PCT/GB2009/000431, filed Feb. 18, 2009, which claims priority to U.S. Provisional Patent Application No. 61/029,416, filed Feb. 18, 2008.

TECHNICAL FIELD

The present invention relates generally to methods and compositions for modifying the levels of transcription factors in plants, and introducing disease resistance genes into plants, to produce products with elevated levels of antioxidant compounds, including but not limited to flavonols and chlorogenic acid, as well as exhibiting enhanced disease resistance, and optionally altered appearance.

BACKGROUND ART

There is a growing literature, some of which is discussed below, which provides insights into the structure and function of certain plant genes, including transcription factors in the MYB superfamily. There is also a growing literature providing insights into the structure and function of certain plant disease resistance genes.

This invention provides novel compositions and methods for producing a novel class of plants, including but not limited to crop plants such as potato, exhibiting enhanced levels of antioxidant compounds, including but not limited to flavonols, chlorogenic acid, anthocyanins, and the like, as well as enhanced disease resistance.

In "The *Arabidopsis* Transcription Factor MYB12 is a Flavonol-Specific Regulator of Phenylpropanoid Biosynthesis", *Plant Phisiology. Vol.* 138, pp. 1083-1096, June 2005, Mehrtens et al., provided evidence that the *Arabidopsis thaliana* R2R3-MYB transcription factor MYB12 acts as a flavonol-specific activator of flavonoid biosynthesis.

In "A Small Family of MYB-Regulatory Genes Controls Floral Pigmentation Intensity and Patterning in the Genus *Antirrhinum*", *The Plant Cell Vol.* 18, pp. 831-851 (2006), Schwinn et al., disclosed that Rosea1, Rosea2, and Venosa genes encode MYB-related transcription factors, active in the flowers of *Antirrhinum majus*, differentially control the level of expression of magenta anthocyanin pigmentation in flowers.

In "High-Flavonol Tomatoes Resulting from the Heterologous Expression of the Maize Transcription Factor Genes LC and C1", *The Plant Cell, Vol.* 14, 2509-2526, October 2002, Bovy et al., showed that the flavonoids kaempferol and naringenin, but not anthocyanins nor quercetin, accumulated in the fruit flesh of transgenic tomato expressing the maize LC and C1 transcription factor genes.

In WO2006/062698, researchers at Cornell reported on "Genes That Determine Plant Color and Uses Thereof", including identification and cloning of a potato gene, referred to as pan1 potato anthocyanin 1, the gene product of which was shown to share extensive homology with the gene product of the Petunia R2R3MYB domain gene An2, the tomato ant1, and pepper A. The expression pattern of the pan1 gene correlated tightly with the production of colored potato progeny, reflecting the role of the pan1 gene in control of coloured anthocyanin production.

WO2007027105 relates to polynucleotides encoding transcription factors and to the encoded transcription factors, that are capable of regulating anthocyanin production in plants. These are mainly derived from apple species.

There remains a need in the art for improved plant and crop species, either transgenic or cisgenic in composition, exhibiting not only enhanced disease resistance, but improved content of beneficial compounds, such as flavonols. This invention provides compositions, methods and plants which significantly advance the art with respect to meeting these needs.

SUMMARY OF THE INVENTION

The present inventors have provided genes encoding MYB12 homologs from *Solanum* species and these form the basis for various aspects of the invention.

They have further demonstrated that a gene encoding MYB12 can be expressed in *Solanum* species and lead to increased levels of flavonols.

They have further demonstrated that other MYB transcription factors (e.g. Rosea1) can be expressed in *Solanum* species and lead to elevated levels of coloured anthocyanins, as well as providing useful markers during transformation, without the necessity for 'foreign' genes. Homologs of these MYB transcription factors from *Solanum* species are already available in the art.

The inventors have further demonstrated that functional homologs of these MYB transcription factors from *solanum* species can induce the production of colored anthocyanins when expressed ectopically in other *solanum* species.

Other aspects of the invention thus include materials (e.g. vectors), methods, and systems utilising these findings in modifying multiple traits in *Solanum* species. Preferably these employ other *Solanum*-derived genes (e.g. pathogen resistance genes), promoters, and other functional sequences (e.g. border sequences for genomic integration).

Various aspects of the invention are set out below, and hereinafter.

In a first aspect, this invention provides genetic constructs useful in the production of plants exhibiting some or all of the following features: elevated levels of colourless antioxidant flavonoids and/or chlorogenic acid; elevated levels of disease resistance; colour-specific identification of successful plants or plant cells transformed with the genetic construct by means of tissue-specific expression of coloured anthocyanins.

While adapted for transgenic plant production, in a preferred aspect of this invention, the genetic construct transfers only genetic material from the same species into the plant, i.e. cis-genic material is used. This aspect of the invention is provided in exemplary embodiments of this aspect of the invention, in which a genetic construct comprising the following elements is utilized to produce a high-flavonoid potato with enhanced disease resistance: (a) an inducible promoter, (for example a promoter responsive to indole acetic acid), driving expression of (b) at least one MYB related gene, expression of which results in enhanced production of coloured anthocyanin secondary metabolites; (c) a plant tissue specific promoter (e.g. a potato tuber specific promoter such as pB33), operatively linked to (d) a AtMYB12 gene or a specific homolog, e.g. the potato homolog, of the AtMYB12 gene and (e) at least one disease resistance gene. In a preferred embodiment of this aspect of the invention, elements (a)-(e) are disposed between left and right P-DNA sequences (which resemble or mimic the T-DNA border sequences of *Agrobacterium tumifaciens*) to facilitate integration of these elements into a target plant genome. Specifics of this aspect of the invention are provided in the detailed disclosure of the preferred embodiments of the invention below.

In a second aspect, this invention provides a plant comprising or transformed with the genetic construct according to the first aspect of this invention, or progeny of the same.

In a third aspect, this invention provides a genetic construct comprising variants on elements (a)-(e) according to the first aspect of the invention. Thus, for example, in one embodiment according to this aspect of the invention, the construct is adapted for optimal expression in a solanceous plant other than potato. According to this embodiment of the invention, for example, the promoters and/or encoded genes operatively linked to said promoters are chosen to be tomato-specific. In another embodiment according to this aspect of the invention, the promoters and/or encoded genes operatively linked to said promoters are chosen for optimal operation in a *brassica* plant.

In a fourth aspect, this invention provides a plant comprising or transformed with the genetic construct according to the third aspect of this invention, or progeny of the same.

In a fifth aspect, this invention provides a genetic construct wherein one or more of the elements (a)-(e) is eliminated to achieve a particular desired result. Thus, for example, in one embodiment according to this aspect of the invention, the genetic construct comprises only elements (a) an inducible promoter, (for example indole acetic acid induced), driving expression of (b) at least one MYB related gene, expression of which results in enhanced production of coloured anthocyanin secondary metabolites.

In one exemplary embodiment according to this aspect of the invention, a novel tomato having a flesh with high-anthocyanin content is produced by means of coordinate expression of the Rosea1 (Ros1) and Delila (Del) genes of Antirrhinum, contrary to the result expected from Bovy et al. 2005. In another embodiment, according to this aspect of the invention, only elements (c) a plant tissue specific promoter, (e.g. a potato tuber specific promoter such as pB33), operatively linked to (d) the AtMYB12 gene or a specific homolog, e.g. the potato homolog, of the AtMYB12 gene, are included in the construct. In such an embodiment of this aspect of the invention, we anticipate production of high levels of flavonoids in the specific tissue of the plant in which the promoter is activated.

In a sixth aspect, this invention provides a plant comprising or transformed with the genetic construct according to the fifth aspect of this invention, or progeny of the same.

In a seventh aspect, this invention provides a method whereby a coloured anthocyanin product produced in a plant or a plant cell transformed with a genetic construct according to the fifth aspect which according to this invention provides a maker for a successful transformation event for any gene linked to said genetic construct.

Further aspects, embodiments and advantages of the invention disclosed herein will be apparent to one of skill in the art upon reading of the entire disclosure provided herein and the appended claims.

Any sub-titles herein are included for convenience only, and are not to be construed as limiting the disclosure in any way.

BRIEF DESCRIPTION OF THE DRAWINGS

FIG. 9 Amino acid sequence of SlMYB12 (A) (SEQ ID NO: 21) and phylogenetic comparison of SlMYB12 with other members of the R2R3MYB subgroup 7; transcription factors which regulate flavonol or phlobaphene production in plants (B).

FIG. 10.1 Fruit-specific phenotypes of T1 generation tomatoes expressing both Delila (Del) and Rosea1 (Ros1) under the control of the E8 promoter. (A) Map of T-DNA region of the binary vector used for transformation. (B) Phenotypic analysis of wild type (upper row), Del/Ros1C (middle) and Del/Ros1N (lower) tomato fruit harvested at the green (left column), breaker (middle) and red (right) ripening stages. (C) Del/Ros1N tomato plant showing fruit at different stages of ripening. (D) Whole and cross-section of ripe wild type and Del/Ros1N tomato fruit.

FIG. 10.2 Comparative analysis of phenylpropanoid content and composition. HPLC chromatogram of methanol extracts from Del/Ros1N (purple line) and wild type (red line) tomato fruit. HPLC analysis, recorded at 535 nm (A and B) or 280 nm (D and E) of extracts from peel (A and D) or flesh (B and E) of ripe fruit. Peaks marked with numbers represent anthocyanins and peaks marked with letters represent other flavonoids. Classification and identification of methanol soluble compounds was performed based on PDA absorbance and ESI-Q-TOF mass spectrometry (Tables C and F). The purified compounds were analyzed by HPLC and ESI-MS/MS. Spectral characteristics, molecular ions and fragments obtained are tabulated. Identification was confirmed by hydrolysis and HPLC analysis of the respective acyl and sugar moieties (data not shown).

FIG. 10.3 Expression of Del and Ros1 causes the upregulation of genes required for anthocyanin biosynthesis and results in increased PAL activity and higher total antioxidant capacity.

Figure 1:
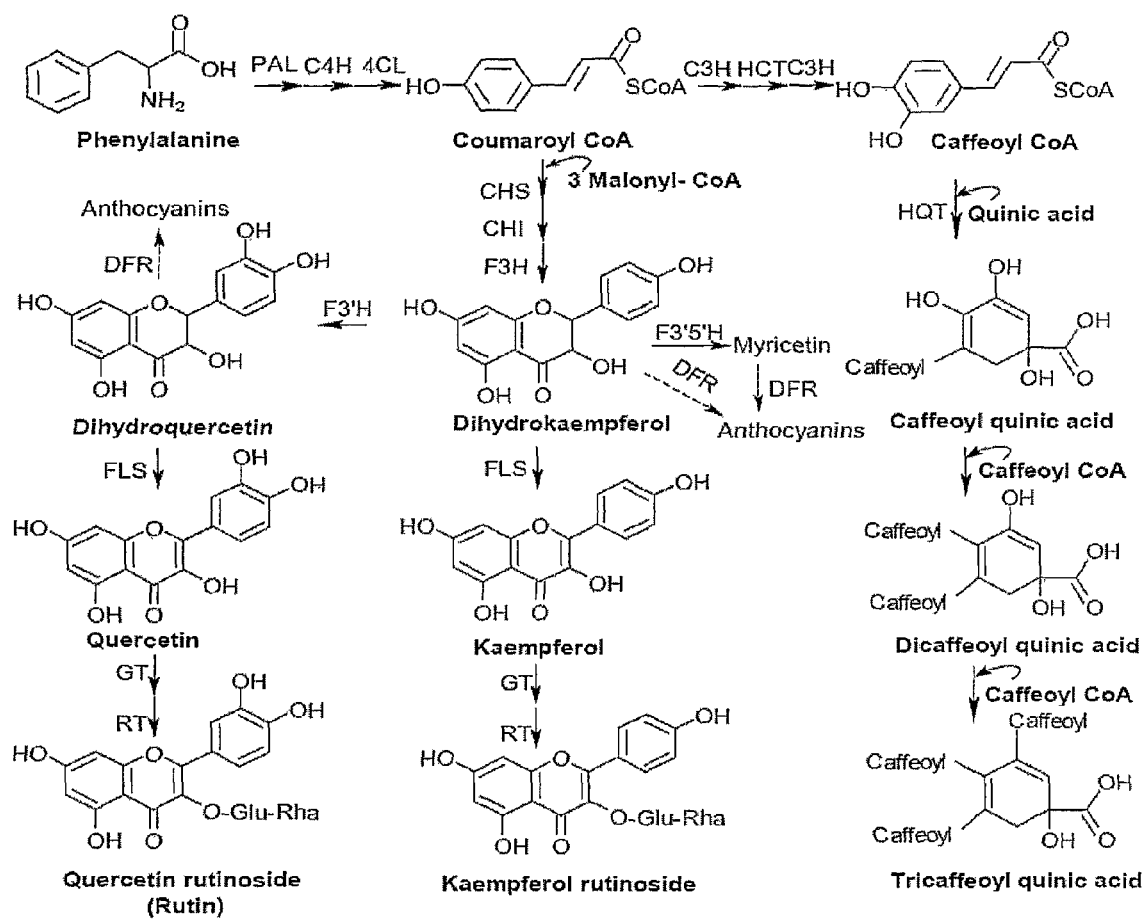
FIG. 1 Scheme of the phenylpropanoid biosynthesis pathway. PAL, phenylalanine ammonia lyase; C4H, cinnamate 4-hydroxylase; 4CL, 4-hydroxycinnamoyl-CoA ligase; CHS, chalcone synthase; CHI, chalcone isomerase; F3H, flavanone-3-hydroxylase; F3'H, flavanone-3'-hydroxylase; F3'5'H, flavanone-3'5'-hydroxylase; FLS, flavonol synthase; DFR, dihydroflavonol reductase; GT, UDPglucose flavonoid-3-glucosyltransferase; RT, UDPrhamnoseflavonoid-3-glucoside-rhamnosyltransferase; C3H, p-coumaroyl ester 3-hydroxylase; HCT, cinnamoyl-CoA shikimate/quinate hydroxycinnamoyl transferase; HQT, hydroxycinnamoyl-CoA quinate hydroxycinnamoyl transferase.

(A) Northern blot showing the differential expression of several anthocyanin biosynthetic genes identified by Suppression Subtractive Hybridization. With the exception of PAL, the transcripts that were upregulated in Del/Ros1N fruit were undetectable in the untransformed control. (B) Schematic representation of the anthocyanin biosynthetic pathway. Enzymes are PAL, phenylalanine ammonia lyase; 4CL, 4-coumarate:coenzyme A ligase; C4H, cinnamic acid 4-hydroxylase; C3H, p-coumaroyl ester 3-hydroxylase; CHS, chalcone synthase; CHI, chalcone isomerase; F3H, flavanone-3-hydroxylase; F3'H, flavanone-3'-hydroxylase; F3'S'H, flavanone-3'5'-hydroxylase; FLS, flavonol synthase; DFR, dihydroflavonol reductase; ANS, anthocyanidin synthase; 3-GT, flavonoid 3-O-glucosyltransferase; RT, flavonoid 3-O-glucoside-rhamnosyltransferase; AAC, anthocyanin acyltransferase; 5-GT, flavonol-5-glucosyltransferase; GST, glutathione S-transferase; PAT, anthocyanin transporter. (C) Analysis of specific PAL activity in ripe tomato fruit from wild type and transgenic lines Del/Ros1C and Del/Ros1N. Histograms represent mean values ±se of n=3 separate measurements. Results were confirmed in two independent experiments. (D) Analysis of hydrophilic and lipophilic antioxidant activity in ripe tomato fruit from wild type and transgenic lines Del/Ros1C and Del/Ros1N. Data represent mean values ±se and are derived from at least seven tomatoes per plant.

FIG. 10.4 Expression of Del and Ros1 extends the shelf life of tomato fruit. (A) Wild type (upper panel) and transgenic lines Del/Ros1N (lower panel) tomato fruit tagged during the first stages of development and harvested and photographed at the end of the green stage (left). The same fruit, stored at room temperature, were re-photographed after three months (right). (B) Severe symptoms of opportunistic infection normally associated with over-ripe wild type tomato fruit (left) are not observed in Del/Ros1N tomato fruit of the same age grown under identical greenhouse conditions (right). (C) Visual phenotypes of F2 tomato fruit obtained crossing Del/Ros1N 'Micro-Tom' plants with aw (dfr-) 'Ailsa Craig' mutant. (bottom panel) compared to tomato fruit obtained crossing wild type 'Micro-Tom' plants with aw (dfr-) 'Ailsa Craig' mutant (top panel). The picture shows the difference in pigmentation and texture in fruit harvested three weeks after the breaker stage. (D) Comparative analysis of hydrophilic and lipophilic antioxidant activity of aw (dfr-) fruit and of fruit obtained by crossing Del/Ros1N 'Micro-Tom' with aw (dfr-) mutants in the background of 'Ailsa' Craig or 'VF36'.

FIG. 10.5 Fruit-specific purple phenotype induced by the expression of Del and Ros1 can be transferred to other genetic backgrounds. Visual phenotypes of F1 tomato fruit obtained crossing Del/Ros1N 'Micro-Tom' plants with 'Money maker' (A), 'VF36' (B) or 'Ailsa Craig' (C and D) tomato varieties. (E) Wild type 'Ailsa Craig' fruit shown as control. (F) Del/Ros1 N tomato fruit from a 'Micro-Tom' plant of the T2 generation.

FIG. 10.6 Measurement of anthocyanin levels and HPLC analysis of flavonoids in tomatoes from independent transgenic lines compared to wild type controls. (A) Anthocyanins were extracted and measured from fruit of the four independent transgenic lines and two wild type control lines as described in the methods section. (B) Anthocyanin profiles in whole fruit extracts of the four transgenic lines and one wild type control determined by absorption at 512 nm. (C) Flavonoid profiles in the whole fruit extracts of four transgenic lines and one wild type control determined by absorption at 360 nm.

FIG. 10.7 Identification of major anthocyanins. UV chromatograms of absorption at 535 nm wavelength are presented for the purified fraction of peak 3 (A) and peak 6 (B). The UV spectra of the purified anthocyanins are depicted in the embedded graph, respectively. MS/MS fragmentation patterns of the purified anthocyanins are shown for the purified fraction of peak 3 (C) and peak 6 (D). Mass spectra of the precursor ions are depicted in the embedded graph, respectively. The purified substances were analysed by ESI-MS/MS (Q-TOF Premier, Waters) as described in the Materials and Methods section. Peaks were identified based on mass fragmentation patterns and PDA absorbance: peak 3, delphindin 3-(p-coumaroyl) rutinoside-5-glucoside; peak 6, petunidin 3-(p-coumaroyl) rutinoside-5-glucoside. Identification was confirmed by hydrolysis and HPLC analysis of the respective acyl and sugar moieties (data not shown).

FIG. 10.8 Expression of Del and Ros1 results in a transient increase in chalcone isomerase (CHI) activity in tomato fruit. Analysis of CHI activity in tomato fruit harvested at the end of the mature green stages (late green) or at later stages of ripening (turn/ripe) from wild type (white histograms) and Del/Ros1N lines (grey histograms). Data represent mean values ±se of n=3 (WT late green), n=6 (WT turn/ripe), n=5 (Del/Ros1N late green) and n=9 (Del/Ros1N turn/ripe) separate measurements. FIG. 10.9 High levels of flavonols are accumulated in F2 tomato fruit obtained by crossing Del/Ros1 N MicroTom with aw (dfr-) mutants. Comparative HPLC analysis of tomato fruit methanol extracts recorded at 325 nm showing the accumulation of several new phenolic compounds when the Del/Ros1N transgene had been introduced in the aw (dfr-) background of Ailsa Craig (A) or VF36 (B) varieties. The same analyses for wild type Micro-Tom (C) and for the parental lines aw VF36 (D) and aw Ailsa Craig (E) are shown as controls. Peaks marked with numbers represent the six most abundant compounds identified as flavonols after HPLC-ESI-MS/MS analysis (F).

FIG. 10.10 FT-IR (Fourier Transform Infrared) spectra of wild type (A and B) and Del/Ros1N(C and D) tomato peel. The analysis of the outer (A and C) and inner side (B and D) of the peel is shown. (E) Analysis of lignin in wild type, Del/Ros1C and Del/Ros1N tomato fruit.

FIG. 10.11 Expression of Del and Ros1 delays tomato fruit ripening. (A) Expression analysis of the ripening-regulated genes encoding S-adenosyl-L-methionine synthase1 (SAM1) and phytoene synthase (PSY) in fruit of wild type (WT) and Del/Ros1N (N) tomato lines harvested 5, 12, an 19 days after the breaker stage. (B) Ethylene production in wild type (o) and Del/Ros1N (•) tomato fruit during ripening. Data represent mean values ±se of at least ten individual fruit of each genotype. (C) Schematic representation of the ripening process in wild type and transgenic lines Del/Ros1N tomato fruit.

FIG. 10.12 Phenotype of AtMYB12/Del/Ros1 tomatoes. The color of the anthocyanins that accumulate in the fruit due to del/ros1 activity is changed by the presence of flavonols accumulating as a result of AtMYB12 activity. The color is more intense and much bluer than in Del/Ros1 fruit (indigo compared to purple). Tomatoes are clockwise from top left: control (WT), Del/Ros1, AtMYB12/Del/Ros1, AtMYB12.

FIG. 11.1 Photograph showing the utility of Ros1 as an early visual marker of transformation.

FIG. 11.2 Effectiveness of promIAA:pan1:Sopan2 3'UTR for use as a screenable marker for transformation in tobacco. Transformed cells are colored red. A. callus on edge of leaf discs, arrows indicate red foci. B. close up of pigmented cells C. regenerating tobacco shoot.

FIG. 12a) Schematic illustration of a vector suitable for engineering flavonol accumulation and other traits into potato tuber by a cis-genic strategy. In this illustration the orthologue of AtMYB12 from tomato (ANT1) is shown, although Pan1 may be preferred.

FIG. 12b) Schematic illustration of a vector suitable for additionally engineering late blight resistance. The constructs show 2 Rpi genes (Rpi-mcq1 and Rpi-oka1) in pIPDNA vectors that confer anthocyanin pigmentation and tuber flavonol elevation

DETAILED DISCLOSURE OF THE PREFERRED EMBODIMENTS OF THE INVENTION

Increase of Flavonols and Other Compounds in Plants

The biosynthetic pathway leading to the synthesis of anthocyanins (the main pigments in flowers), flavones and flavonols (co-pigments) and proanthocyanidins is generally well established (see FIG. 1, plus also e.g. Heller, W. and Forkmann, G. (1988) In: *The Flavonoids* (Harborne, J. B. ed), Chapman and Hall, London, pp 399-425; Stafford, H. A. (1990) Flavonoid Metabolism, CRC Press Inc., Boca Raton, USA).

In support of aspects of this invention wherein the AtMYB12 gene or a plant specific homologue thereof is included, we demonstrate that overexpression of AtMYB12 in both tomato and tobacco results in increased levels of flavonols (quercetin rutinoside [rutin] and kaempferol diglycoside) and the major hydroxycinnamate of Solanaceous plants, chlorogenic acid. The increases in the levels of flavonols are very high (at least 4 mg per gram fresh weight in tomato fruit) which is an increase of at least 200-fold over wild type and 20 fold more than that achieved by Bovy et al. utilizing LC/C1. The increases in chlorogenic acid in tobacco are smaller, but chlorogenic acid is, in any event, present in large amounts in tobacco. In tomato fruit the increases in chlorogenic acid are more significant (20-fold) and we have evidence that AtMYB12 induces the expression of the key enzyme for chlorogenic acid biosynthesis (HQT) in tomato. Both flavonols and chlorogenic acid are important dietary bioactives, and, without wishing to be bound by mechanism, it is thought that this is mainly through their activities as antioxidants or as inducers of endogenous antioxidant defence mechanisms. There is evidence for flavonols and chorogenic acid in protection against cardiovascular disease and cancers. We present evidence for the changes in antioxidant capacity of the tomatoes as a result of AtMYB12 expression. We have transformed two tomato varieties with AtMYB12, MicroTom and Money Maker, a commercial variety. We have also shown the stability of inheritance of the high flavonol trait in subsequent generations of tomato. In one example provided herein, we have used the E8 promoter to drive the expression of AtMYB12 in tomato. With this limited expression pattern, AtMYB12 has no noticeable effects on growth or productivity of tomatoes. We did not quantify such effects in tobacco where the gene was driven by the 35S promoter, reduced growth in AtMYB12 tobacco was not sufficiently noticeable to have been casually observed.

In summary, as exemplified above, and without limitation, the invention provides in various aspects:

Use of AtMYB12 or a variant thereof to increase the levels of flavonols or flavonol derivatives and/or chlorogenic acid (CGA) in a plant;

Methods, materials and processes for achieving the same, optionally in conjunction with the modification of other traits described herein;

Isogenic or transgenic plants obtained by said processes, particularly those also isogenic or transgenic for other traits described below;

Some of these aspects and embodiments are described in more detail below.

The plant will be one other than *Arabidopsis* —preferably it will be of the family Solanaceae, more preferably genus *Solanum*. Optionally the plant may be *S. tuberosum* or *S. lycopersicum*, and AtMYB12 homologs from these plants are described in more detail below.

For example the invention provides a method for increasing the levels of flavonols or flavonol derivatives and/or chlorogenic acid (CGA) in such plants, through flavonoid biosynthesis, such as to enhance the nutritional or nutraceutical properties thereof, by causing or allowing expression of a heterologous MYB12 nucleic acid sequence as discussed above within the cells of the plants. The step may be preceded by the earlier step of introduction of the nucleic acid into a cell of the plant or an ancestor thereof i.e. transforming at least one plant cell with a recombinant DNA construct comprising a nucleic acid sequence encoding the MYB12 transcription factor and regenerating a transgenic plant from the transformed cell, wherein the expression of the MYB12 gene encoding the MYB12 transcription factor is increased relative to a nontransformed plant and whereby the increased expression of the MYB12 transcription factor for increases the levels of flavonols or flavonol derivatives and/or chlorogenic acid (CGA) in the plant.

As demonstrated herein, the method may be used to increase flavonols preferentially to anthocyanins. Levels of rutin and kaempferol rutinoside may be particularly increased—indeed results described herein demonstrate unexpectedly, and unprecedentedly, high levels of flavonol accumulation in tomatoes (up to about 10% of the dry weight in whole tomato fruit). In preferred embodiments of the invention at least 10, 20, 30, 40, 50, 60, 70-fold increases of total flavonols, and greater than 5, 10 or and 20-fold higher levels of CQAs such as CGA may be achieved.

Such plants producing elevated levels of flavonols reduce the growth of adipocytes and reduce the tendency for obesity on a high fat diet, and methods of treatment of the human body (to reduce the tendency for obesity using the MYB12-based methods and products described herein) forms one aspect of the present invention.

Those skilled in the art will appreciate that nucleic acid can be transformed into plant cells, which can be regenerated, using any suitable technology. In a typical transformation strategy useful with potato *Agrobacterium tumefaciens* culture(s) with the appropriate antibiotic selection regime are set up and grown for 24 hours with shaking at 28° C. Stem internode sections (without nodes) are harvested from 4-6 week old potato cv. Desiree plants grown in aseptic culture on MS medium (2% sucrose). The internodes are sliced into 1 cm sections and placed into 20 ml of LSR broth. 100 ul of overnight *Agrobacterium tumefaciens* culture is added to stem sections and incubated for 20 minutes at 40 rpm in the dark at 24° C. The stem sections are removed from the *Agrobacterium tumefaciens* suspension, blotted dry and incubated under low light conditions at 18C for 3 days on LSR1 solid media (around 15-20 explants are plated per dish). Co-cultivated stem sections are then transferred to LSR1 medium with selection antibiotics at around 10 explants per dish. Stem explants are subcultured onto fresh LSR1 media every 7-10 days for around 3-6 weeks or until the appearance of the first small calli. Once the calli have sufficiently developed the stem sections are transferred onto LSR2 media with selection antibiotics. Stem sections are subcultured every 7-10 days until shoots start to develop. Shoots appear within 2 months from the start of transformation. Shoots are removed with a sharp scalpel and planted into MS2R solid media with selection antibiotics. Transgenic plants harbouring appropriate antibiotic or herbicide resistance genes start to root normally within 2 weeks and are weaned out of tissue culture into sterile peat blocks before being transplanted to the glasshouse.

Transformation of tomato is demonstrated in more detail in the Examples hereinafter.

Other strategies, particularly those applicable to the genus *Solanum*, are well known to those skilled in the art (see e.g. Mansure and Magioli, Acta Botanica Brasilica, 2005 (Vol. 19) (No. 1) 139-148). The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

To engineer flavonol accumulation in potato tuber by a cis-genic strategy, the appropriate genes and promoters from potato itself are isolated. For example a construct using the tuber specific B33 patatin gene promoter to drive expression of the potato cDNA encoding the homolog\ortholog of AtMYB12 is utilized to confer on potato plants high-level flavonol production in tubers. Preferred "cis-genic" vectors are described in detail hereinbelow.

AtMYB12 Homologs from Tomato and Potato

As described in the Examples below, in furtherance of the present invention, the present inventors have isolated a *Solanum* homolog of AtMYB12 from tomato termed herein SlMYB12 ((*Solanum lycopersicum* MYB12; see SEQUENCE ANNEX I—unpublished GenBank accession EU419748; SEQ ID NO: 12 and 11). The inventors provided this full length cDNA sequence by extension of a cDNA EST.

Despite significant technical difficulties, the inventors have further isolated the sequence encoding the *Solanum* homolog of AtMYB12 from potato termed herein StMYB12 (*Solanum tuberosum* MYB12; see SEQUENCE ANNEX II describing the amino acid and nucleotide sequences respectively; SEQ ID NO: 14 and 13,respectively).

SEQUENCE ANNEX VIII shows a comparison of the encoded polypeptides with that encoded by the AtMYB12 sequence.

Using LALIGN available on the world wide web at ch.embnet.org/software/LALIGN_form.html) with default settings the sequences showed the following levels of identity with AtMyb12: 39.7% (SlMyb12) and 40.2% (StMyb12).

Isolated or recombinant nucleic acids including either of these AtMYB12 gene homologs from tomato and potato form aspects of the present invention.

For example the invention provides an isolated nucleic acid molecule which nucleic acid comprises a *Solanum*-derived MYB12 nucleotide sequence encoding a transcriptional regulator of a biosynthetic gene encoding a polypeptide with flavonoid-biosynthetic or transport activity.

A nucleic acid of the present invention may include one of the nucleotide sequences described above in SEQUENCE ANNEX I or II (SEQ ID NO: 11 and 13, respectively).

Nucleic acid molecules according to the present invention may be provided, isolated and/or purified from their natural environment, in substantially pure or homogeneous form, or free, or substantially free, of other nucleic acids of the species of origin. Where used herein, the term "isolated" encompasses all of these possibilities.

The nucleic acid molecules may be wholly or partially synthetic. In particular they may be recombinant in that nucleic acid sequences which are not found together in nature (do not run contiguously) have been ligated or otherwise combined artificially.

Preferred nucleic acids consist essentially of the gene in question, optionally in an expression vector as described in more detail below.

Nucleic acid according to the present invention may include cDNA, RNA, genomic DNA and modified nucleic acids or nucleic acid analogs. Where a DNA sequence is specified, e.g. with reference to a figure, unless context requires otherwise the RNA equivalent, with U substituted for T where it occurs, is encompassed. Where a nucleic acid of the invention is referred to herein, the complement of that nucleic acid will also be embraced by the invention. The 'complement' of a given nucleic acid (sequence) is the same length as that nucleic acid (sequence), but is 100% complementary thereto.

Where genomic nucleic acid sequences of the invention are disclosed, nucleic acids comprising any one or more (e.g. 2) introns or exons from any of those sequences are also embraced.

A nucleic acid of the present invention may encode one of the amino acid sequences described above in SEQUENCE ANNEX I or II (SEQ ID NO: 12 and 14, respectively) e.g. be degeneratively equivalent to the corresponding nucleotide sequences.

In a further aspect of the present invention there are disclosed nucleic acids which are variants of the sequences of this aspect.

A variant nucleic acid molecule shares homology with, or is identical to, all or part of the coding sequence discussed above. Variants encode MYB12 transcriptional regulators capable of up-regulating expression of genes involved in flavonoid biosynthesis in a plant into which they are introduced, and in particular genes involved in flavonol synthesis e.g. PAL, CHS, and GT genes.

"Transcriptional regulator" is a term well understood by those skilled in the art to mean a polypeptide or protein that binds to regulatory regions of a gene and controls (increases or reduces) gene expression, here, in respect of flavonoid biosynthetic flux.

Variants of the present invention can be artificial nucleic acids (i.e. containing sequences which have not originated naturally) which can be prepared by the skilled person in the light of the present disclosure. Alternatively they may be novel, naturally occurring, nucleic acids from *Solanum* species, which may be isolatable using the sequences of the present invention.

Thus a variant may be a distinctive part or fragment (however produced) corresponding to a portion of the sequence provided. The fragments may encode particular functional parts of the polypeptide.

Also included are nucleic acids which have been extended at the 3' or 5' terminus.

Sequence variants which occur naturally may include alleles or other *Solanum* homologues.

Artificial variants (derivatives) may be prepared by those skilled in the art, for instance by site-directed or random mutagenesis, or by direct synthesis. Preferably the variant nucleic acid is generated either directly or indirectly (e.g. via one or amplification or replication steps) from an original nucleic acid having all or part of the sequences of the first aspect.

The term "variant" nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Homology (i.e. similarity or identity) may be as defined above using the LALIGN. Homology may be at the nucleotide sequence and/or encoded amino acid sequence level. Preferably, the nucleic acid and/or amino acid sequence shares at least about 50%, or 60%, or 70%, or 80% homology, most preferably at least about 90%, 95%, 96%, 97%, 98% or 99% homology with a sequence of SEQUENCE ANNEX I or II (SEQ ID NO: 11-14).

It further provides an isolated protein having an amino acid sequence which is at least 50, 60, 70, 80, 90 or 100% identical to the amino acid sequence provided herein in SEQUENCE ANNEX I or II (SEQ ID NO: 12 and 14, respectively), or encoded by a nucleic acid described therein.

In a further aspect of this part of the invention there is disclosed a method of producing a derivative nucleic acid comprising the step of modifying the coding sequence of a nucleic acid of the present invention described above.

Changes to a sequence, to produce a derivative, may be by one or more of addition, insertion, deletion or substitution of one or more nucleotides in the nucleic acid, leading to the addition, insertion, deletion or substitution of one or more amino acids in the encoded polypeptide. Changes may be desirable for a number of reasons, including introducing or removing the following features: restriction endonuclease sequences; codon usage; other sites which are required for post translation modification; cleavage sites in the encoded polypeptide; motifs in the encoded polypeptide (e.g. binding sites). Leader or other targeting sequences may be added or removed from the expressed protein to determine its location following expression. All of these may assist in efficiently cloning and expressing an active polypeptide in recombinant form (as described below).

Other desirable mutations may be generated by random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are variants having non-conservative substitutions. As is well known to those skilled in the art, substitutions to regions of a peptide which are not critical in determining its conformation may not greatly affect its activity because they do not greatly alter the peptide's three dimensional structure.

In a further aspect of the present invention there is provided a method of identifying and/or cloning a nucleic acid variant from a plant which method employs a distinctive MYB12 sequence of SEQUENCE ANNEX I or II (SEC/ ID NO: 11 and 13, respectively).

An oligonucleotide for use in probing or amplification reactions comprise or consist of about 30 or fewer nucleotides in length (e.g. 18, 21 or 24). Generally specific primers are upwards of 14 nucleotides in length. For optimum specificity and cost effectiveness, primers of 16-24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

Preferably the probe/primer is distinctive in the sense that it is present in the *Solanum* MYB12 sequences disclosed herein, but not in AtMYB12.

Suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na$_2$HPO$_4$, pH 7.2, 6.5% SDS, 10% dextran sulfate and a final wash at 60° C. in 0.1×SSC, 0.1% SDS.

It is well known in the art to increase stringency of hybridisation gradually until only a few positive clones remain. Suitable conditions would be achieved when a large number of hybridising fragments were obtained while the background hybridisation was low.

Thus one embodiment of this aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein.

The methods described above may also be used to determine the presence of one of the nucleotide sequences of the present invention within the genetic context of an individual plant. This may be useful in plant breeding programmes e.g. to directly select plants containing alleles which are responsible for desirable traits in that plant species, either in parent plants or in progeny (e.g hybrids, F1, F2 etc.), or for assessing expression of genes. For example, the present inventors used the sequences described herein to monitor expression of SIMYB12 in tomato fruit using quantative RT-PCR.

Thus it will be appreciated that, unless context demands otherwise, where the present invention refers to AtMYB12 (for example in discussion of an Example, or aspect or embodiment) this is to be understood as relating likewise to AtMYB12 homologues or orthologs e.g. obtainable from potato or other *Solanum* species, such as the sequences above, or variants thereof.

In one aspect of the present invention, the MYB12-encoding nucleic acid described above is in the form of a recombinant and preferably replicable vector. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic hosts either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operatively linked to a nucleotide sequence provided by the present invention, such as one shown in SEQUENCE ANNEX I or II (SEQ ID NO: 11 and 13, respectively) or a variant thereof.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press (or later editions of this work).

Many known techniques and protocols for manipulation of nucleic acid, for example in preparation of nucleic acid constructs, mutagenesis (see above discussion in respect of variants), sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

In one embodiment of this aspect of the present invention, there is provided a gene construct, preferably a replicable vector, comprising an inducible promoter operatively linked to a nucleotide sequence provided by the present invention. The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Of particular interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148).

Suitable promoters which operate in plants include the Cauliflower Mosaic Virus 35S (CaMV 35S). Other examples are disclosed at pg. 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

It may be desirable to use a strong constitutive promoter. If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a host cell, particularly a plant cell.

In a further aspect of the invention, there is disclosed a host cell containing a heterologous construct according to the present invention, especially a plant or a microbial cell. The term "heterologous" is used broadly in this aspect to indicate that the gene/sequence of nucleotides in question (e.g. the MYB12 encoding gene in this aspect) have been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence.

Nucleic acid heterologous to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homolog is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

The host cell (e.g. plant cell) is preferably transformed by the construct, which is to say that the construct becomes established within the cell, altering one or more of the cell's characteristics and hence phenotype e.g. with respect flavonol synthesis.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Plants which include a plant cell according to the inventions described above are also provided.

In addition to the regenerated plant, the present invention embraces all of the following: a clone of such a plant, selfed or hybrid progeny and descendants (e.g. F1 and F2 descendants) and any part of any of these. The invention also provides parts of such plants e.g. any part which may be used in reproduction or propagation, sexual or asexual, including cuttings, seed and so on, or which may be a commodity per se e.g. tuber.

The present invention also encompasses the expression product of the nucleic acid sequences disclosed above, plus also methods of making the expression product by expression from encoding nucleic acid therefore under suitable conditions, which may be in suitable host cells. Such proteins of the invention may be used to raise antibodies employing techniques which are standard in the art. Specific binding members such as antibodies and polypeptides including antigen binding domains of antibodies that bind and are preferably specific for polypeptides of the invention, and represent further aspects of the present invention, as do their use and methods which employ them.

Decreased Chlorogenic Acid Production by Gene Silencing or Suppresion

In specific enhancements to aspects of this invention, we also disclose further increases in flavonol levels by inhibiting chlorogenic acid production in conjunction with AtMYB12 overexpression.

This is achieved, for example, by gene knockout or silencing of chlorogenic acid production, for example by use of RNAi specific for the HQT gene which catalyses production of caffeoyl quinic acid (see FIG. 1). The sequence of the HQT gene is described by Niggeweg, R., Michael, A. J., & Martin, C. (2004) *Nat Biotechnol* 22, 746-754 (see also WO 2004/001028).

In summary, as exemplified above, and without limitation, the invention provides in various aspects:

A method of inhibiting chlorogenic acid production in a plant in which AtMYB12 or a variant thereof is used to increase the levels of flavonols e.g. in a plant of the family Solanaceae, more preferably genus *Solanum*. Optionally the plant may be S. *tuberosum* or S. lycopersicum. This may be achieved by use of a nucleic acid sequence capable of silencing or downregulating a gene which encodes an enzyme present in the chlorogenic acid production pathway e.g. the HQT gene.

Methods, materials and processes for achieving the same, optionally in conjunction with the modification of yet other traits described herein.

Isogenic or transgenic plants obtained by said processes, particularly those also isogenic or transgenic for other traits described herein.

The nucleic acid sequence capable of silencing or down-regulating a gene which encodes an enzyme present in the chlorogenic acid production pathway e.g. the HQT gene, may be as follows.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al., (1988) *Nature* 334, 724-726; Zhang et al., (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553.

Anti-sense or sense regulation may itself be regulated by employing an inducible promoter in an appropriate construct.

Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi) (See also Fire (1999) *Trends Genet.* 15:

358-363, Sharp (2001) *Genes Dev.* 15: 485-490, Hammond et al. (2001) *Nature Rev. Genes* 2: 1110-1119 and Tuschl (2001) *Chem. Biochem.* 2: 239-245).

RNA interference is a two step process. First, dsRNA is cleaved within the cell to yield short interfering RNAs (siR-NAs) of about 21-23 nt length with 5' terminal phosphate and 3' short overhangs (−2 nt) The siRNAs target the corresponding mRNA sequence specifically for destruction (Zamore P. D. Nature Structural Biology, 8, 9, 746-750, (2001)

Thus one embodiment of the invention utilises double stranded RNA comprising a sequence from part of the HQT gene, which may for example be a "long" double stranded RNA (which will be processed to siRNA, e.g., as described above). These RNA products may be synthesised in vitro, e.g., by conventional chemical synthesis methods.

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologeous genes in a wide range of mammalian cell lines (Elbashir S M. et al. Nature, 411, 494-498, (2001)).

In one embodiment, the vector may comprise a nucleic acid sequence according to the invention in both the sense and antisense orientation, such that when expressed as RNA the sense and antisense sections will associate to form a double stranded RNA. This may for example be a long double stranded RNA (e.g., more than 23 nts) which may be processed in the cell to produce siRNAs (see for example Myers (2003) *Nature Biotechnology* 21:324-328).

Alternatively, the double stranded RNA may directly encode the sequences which form the siRNA duplex, as described above. In another embodiment, the sense and antisense sequences are provided on different vectors.

Another methodology known in the art for down-regulation of target sequences is the use of "microRNA" (miRNA) e.g. as described by Schwab et al 2006, Plant Cell 18, 1121-1133. This technology employs artificial miRNAs, which may be encoded by stem loop precursors incorporating suitable oligonucleotide sequences, which sequences can be generated using well defined rules in the light of the disclosure herein. Thus, for example, in one aspect there is provided a nucleic acid encoding a stem loop structure including a sequence portion of the target HQT gene of around 20-25 nucleotides, optionally including one or more mismatches such as to generate miRNAs (see e.g. http://wmd.weigelworld.org/bin/mirnatools.pl). Such constructs may be used to generate transgenic plants using conventional techniques.

These vectors and RNA products may be useful for example to inhibit de novo production of the HQT polypeptide. They may be used analogously to the expression vectors in the various embodiments of the invention discussed herein.

Notwithstanding the above, it should nevertheless be noted that where increased chlorogenic acid levels are produced according to this invention, we have observed this to limit infection by pathogens and increase innate immunity. It is likely that increasing anthocyanin and flavonol levels also contribute to this effect, thereby providing extended shelf life as a result of reduced opportunistic infection.

Increase of Anthocyanins in Plants

In support of embodiments according to various aspects of this invention in which elevated levels of coloured anthocyanins are required, we present evidence of successful production of purple tomatoes containing high levels of anthocyanins as a result of fruit-specific expression of two transcription factors (Rosea1 and Delila) from *Antirrhinum majus*, under the control of the E8 promoter. These tomatoes have extended shelf life. Shelf life is also extended if anthocyanin synthesis is blocked (using a mutant of tomato called aw) and flavonols accumulate instead. This effect was also observed in the AtMYB12 high flavonol tomatoes.

In summary, as exemplified above, and without limitation, the invention provides in various aspects:

Use of a gene encoding a MYB transcription factor (e.g. Rosea1, or a variant thereof such as Ant1 or pan1) to increase the levels of anthocyanins in a plant e.g. of the family Solanaceae, more preferably genus *Solanum*. Optionally the plant may be *S. tuberosum* or S. lycopersicum.

Methods, materials and processes for achieving the same, including for extending shelf-life, optionally in conjunction with the modification of yet other traits described herein.

Isogenic or transgenic plants obtained by said processes, particularly those also isogenic or transgenic for other traits described herein.

The sequence of Ant1 (nucleotide and encoded protein) is shown in Sequence annex VI (SEQ ID NO: 17 and 18, respectively).

The sequence of pan1 (nucleotide and encoded protein) is shown in Sequence annex VII (SEQ ID NO: 19 and 20, respectively).

For example the invention provides a method for increasing the levels of one or more anthocyanins in plants, through flavonoid biosynthesis, such as to enhance the appearance, nutritional or nutraceutical properties, or shelf-life thereof, by causing or allowing expression of a heterologous MYB-encoding nucleic acid sequence as discussed above within the cells of the plants. The step may be preceded by the earlier step of introduction of the nucleic acid into a cell of the plant or an ancestor thereof.

As demonstrated herein, the method may be used to increase highly coloured anothocyanins such as 3,5-diglucosides acylated with cinnamic acids—indeed results described herein demonstrate a 3-fold increase in antioxidant activity in the water-soluble fraction.

The methods may also be used to increase the expression levels of any of the cloned genes shown in Table 2.S1. of Example 2 (especially those marked ++ or +++).

Vectors, constructs, plants and so on may be prepared and utilised in these methods by those skilled in the art in analogous manner to the methods and materials described above in respect of MYB12.

Plants carrying a combination of Delila, Rosea1 and AtMYB12 genes expressed in tomato fruit that accumulate indigo pigment of high intensity as a result of accumulation of both anthocyanins and flavonols in skin and flesh of the fruit Novel Transformation Markers in *Solanum* and Other Plants For aspects of this invention wherein coloured products indicative of transformation are desired, we provide herein evidence that in transformation experiments with tobacco, expression of just the MYB transcription factor (Rosea1) on its own (under the control of a suitable promoter) gives rise to coloured callus tissue and can be used for selection of transformed tissue (see example herein providing a tobacco callus expressing Rosea1). Accordingly, accumulation of anthocyanins in transformed callus may be used as a selectable marker in the cis-genic transformation of potato and other plants or plant cells.

As described in more detail below in relation to "cis-genic" transformation systems, desirably, the appropriate MYB gene from the particular plant of interest is used. Thus, for potato transformation, the pan1 gene according to this aspect of the invention, used, preferably under the control of an auxin-inducible promoter (e.g. an IAA promoter) to ensure that it is operational during callusing and regeneration of potato tissue.

In summary, as exemplified above, and without limitation, the invention provides in various aspects:

Use of a *Solanum*-derived MYB transcription factor (e.g. Rosea1 homolog, or a variant thereof such as pan1) which increases the levels of anthocyanins in a plant as a visual screen e.g. for identification of transformed cells in *Solanum* species, by virtue of the pigment that they produce. Preferably the transformation is performed in media which ensures transcription of the promoter controlling the anthoxcyanin marker e.g. in high levels of auxin.

Vectors and other transformation constructs employing the same.

Methods of use comprising the step of introducing such a construct into host cells, particularly a plant cell, and selecting host cells containing or transformed with the construct according to their colour or appearance.

Preferred vectors and constructs utilising this system are described in more detail below.

Preferred *Solanum* Plants in which the Invention has Utility

Potato (*Solanum tuberosum* L.) is the fourth most important crop, and the most important non-cereal food crop, in the world.

Basic foodstuffs such as potatoes, with elevated levels of anti-oxidant flavonoids (as described above) could benefit prosperous Westerners and subsistence farmers alike. Potatoes are a globally important crop, with 300 million tonnes being harvested from over 17 million hectares. As well as being widely eaten in industrialised countries, they form an increasingly important staple crop in much of the developing world.

For example, 320 million tonnes of potatoes were harvested across the world in 2004. The biggest growers (2004 figures) are: China (23%), EU (14%), USA (6%, 20.4 million tonnes), India (8%). The great majority of the crop is used for human food, either sold fresh for home preparation, or else processed into chips, crisps etc. The value of the US market alone was estimated at $2.6 billion (Best Food Nation; 2006). Two thirds of the crop is processed, and Russet Burbank is the dominant variety, particularly for French fries.

In preferred aspects of the invention, the plants having multiple improved traits, obtained by the processes described herein, are potato plants.

However it will be appreciated that other crops—in particular other *Solanum* species such as tomatoes, aubergines and also peppers—could also be transformed to confer both disease resistance and high levels of natural antioxidants. Using the methods and techniques disclosed herein with specific reference to potato are utilized in a straightforward way to create other high antioxidant crops, such as broccoli, calabrese, maize, barley, soy.

Enhanced Disease Resistance in Plants of the Invention

Genes conferring resistance to plant disease of economic importance are combined in certain select embodiments according to this invention.

In preferred aspects of the invention—when applied within potato—the invention incorporates the use of at least one heterologous gene encoding resistance to at least one late potato blight (*Phytophthora infestans*).

Late blight is a virulent disease which occurs in all growing areas and can lead to major crop losses. To counteract this, even partially resistant varieties are usually sprayed with fungicides many times a season, which is costly in terms of agrochemicals, tractor fuel, $CO_2$ emissions and soil compaction. The disease is responsible for global losses of £3 billion and can have devastating effects in places where they are a subsistence crop; the 19th Century Irish potato famine is the best known example in Europe.

Late blight was estimated in 2000 to cost US growers $77 million in fungicides, plus an additional $210 million in lost revenues: an average of $507 per acre, not including additional control practices or associated spraying costs (Potato Research; Volume 44, Number 2/June, 2001; Guenthner, Michael and Nolte). In the UK alone, which grows only 10% of the European total crop of 60 million tonnes, fungicide application costs £200 per hectare, a total of £20 million.

The area planted to potatoes in the US and much of Europe has varied little in recent years, but the crop is becoming increasingly important in many developing countries. In India, it is grown as a cash crop and has replaced a number of traditional crops such as buckwheat and millet. 1.4 million hectares were sown in 2003, and there is heavy use of fungicide to control blight. In Indonesia, where potatoes have become an increasingly popular crop for small-scale farmers, late blight can cause yield losses in the range of 12 to 31%, even destroying whole crops in some instances. Fungicides account for 13.5% of the total cost of production.

The International Potato Center in Lima, Peru, estimates late blight losses at $3-5 billion annually worldwide. In China, the world's largest potato producer (with more than 4 million hectares grown), it was estimated that 56% of the total planting area was infected by blight in 1996, giving a total loss of 2.5 million tonnes, worth $170 million at local prices.

Specific resistance to late blight in gene can be introduced by way of major dominant resistance (R) genes. 11R genes (R1-R11) derived from *S. demissum* have been previously identified.

Prior filed, unpublished, UK priority patent application number 0714241.7 (and corresponding PCT publication WO2009013468) disclose several different late blight R genes derived from the potato wild species *S. okadae* plus also from *S. mochiquense* and *S. neorossii*. The disclosure of said patent applications, and in particular the sequences of Rpi-mcq1 and Rpi-oka1, and the manner in which they were provided and may be generally utilised is specifically incorporated herein by reference.

The following sequences are provided herein in SEQUENCE ANNEX III.

| Seq ID | Rpi Sequence |
|--------|--------------|
| 1a | oka1 nt (SEQ ID NO: 1) |
| 1b | oka2 nt (SEQ ID NO: 7) |
| 2a | mcq1 (candidate 1) nt (SEQ ID NO: 2) |
| 2b | mcq1 (candidate 2) nt (SEQ ID NO: 8) |
| 3 | nrs1 nt (SEQ ID NO: 3) |

It will be appreciated that these sequences, or active variants (within the meaning discussed in GB0714241.7 or WO2009013468 and above) of them, or other RPI genes, can be combined with the other genes discussed herein to provide potatoes expressing novel combinations of traits, and that such is a useful addition to the art.

Preferred Combinations of Traits in Plants of the Present Invention

It has been realised for some time that effective metabolic engineering to improve the content of important bioactives is dependent on securing sufficiently large increases to ensure that the engineered changes are nutritionally, and therefore economically, significant. Engineering large changes in target bioactives requires the use of proteins that regulate the activity of all of the enzyme steps in a metabolic pathway. Genes encoding such transcription factors have been identified from various plant species; of particular relevance to the present invention are two MYB-related genes, one of which is responsible for up-regulating flavonol biosynthesis in *Arabidopsis* (AtMYB12) and the other that up-regulates anthocyanin biosynthesis in *Antirrhinum majus* (Rosea1).

Using fruit-specific expression of AtMYB12 in tomato, we demonstrate increased flavonol levels up to about 4 mg per g fresh weight, and, using Rosea1 we demonstrate the ability to switch on anthocyanin production in tomato fruit, achieving accumulation to levels of 3 mg per g fresh weight. Both increases are highly significant: the fruit of the Rosea1 lines are deep purple in colour and the antioxidant level is comparable to that in red wine, moderate consumption of which has a demonstrable protective effect against cardio-vascular disease. Thus these genes have been shown to effectively redirect secondary metabolism, and increase antioxidant activity in particular target tissues of a crop plant. Fruit-specific expression ensured that these engineering steps had no deleterious effects on yield.

The high anthocyanin tomatoes already developed represent a registered food source for extraction of high levels of purple anthocyanins. Crude extraction can be achieved very easily by squeezing the tomatoes. The crude extracts of the purple tomatoes have a good color (stronger and more blue than that of purple sweet potato) but they are less stable than the sweet potato anthocyanins.

In terms of improving the color of the anthocyanins and giving stronger blues, a high flavonol, high anthocyanin tomato has been developed (AtMYB12/Del/Ros1) which is more intensely colored with a pigment that is far bluer than with anthocyanins on their own (indigo as compared to purple). This is due to the copigmentation effect of the flavonols in combination with the anthocyanins. These tomatoes represent an excellent source of this new color which would be easy to extract for preparation of food colorants. Alternatively the anthocyanins and flavonols could be prepared separately from the lines producing high levels of each, and then mixed, post extraction, to develop the color required.

It will be understood that the this paradigmatic demonstration in *solanum* species likewise provides for the analogous use in potato tubers (to give health-promoting potatoes) and also for selection of transformed lines using anthocyanin production. Herein disclosed and enabled appropriate constructs for cis-genic engineering of high level of flavonols. This is accomplished in a range of potato varieties, suitable for different markets, each having both blight resistance and elevated flavonol levels.

Via introduction of appropriate genes and promoters, beneficial flavonols are induced to accumulate in the crop, e.g. potato tuber, thereby enhancing the nutritional quality.

The proven constructs according to this invention may be used to transform appropriate germplasm to give varieties of high commercial value. For most crops, it is sufficient to select one successful transformant and transfer traits to a range of other varieties using conventional back-crossing. In the case of potato, this is not a viable option. Instead, the germplasm transformed must have all the necessary agronomic and culinary traits other than blight resistance: it must be an existing high volume cultivar. Accordingly, for this particular crop, one or more varieties for each market are selected. A range of cultivars appropriate for particular markets (geographical, plus also fresh vs. processing markets) is transformed. These may optionally be selected from: Maris Piper, Wilja or other major northern European variety; A further European variety for the processing market; An appropriate variety for Eastern Europe; Russet Burbank, for US processing market; A further appropriate variety (Russet or Red) for US fresh market; An appropriate variety for India; An appropriate variety for China; and so on.

Additionally, for example, blight resistance genes (e.g. late blight) are combined with anthocyanin and flavonol inducing genes in a construct to achieve a single-stage, multi-gene transformation. Thus, in one specific embodiment according to this invention, Rpi-mcq1, Rpi-oka1, or both genes are combined into, for example, pIPDNA vectors that confer anthocyanin pigmentation, tuber flavonol elevation. Use of more than one Rpi-gene enhances the likelihood that resistance will not be rapidly broken down by new races of *P. infestans* that can overcome resistance. A potato variety of choice, (e.g. Desiree), is selected based in part on experience with transformation of several varieties, and cis-genic transformants are selected for subsequent screening and evaluation for tuber flavonol content and blight resistance In summary, as exemplified herein, and without limitation, the invention provides in various aspects:

A transgenic-, or more preferably cis-genic, potato comprising within its genome the following heterologous nucleic acid encoding for the following traits:
 (i) a gene encoding AtMYB12 or a variant thereof to increase the levels of flavonols and/or chlorogenic acid in the plant. Preferably this is the orthologue of AtMYB12 from tomato or potato. Optionally this is under the control of the tuber specific B33 patatin gene promoter;
 (ii) a gene encoding at least one MYB transcription factor (e.g. Rosea1, or a variant thereof such as pan1 or Ant1) to increase the levels of anthocyanins in the plant. Optionally this is under the control of an auxin specific promoter (e.g. the IAA4 promoter shown in Sequence Annex IV; SEQ ID NO: 15);
 (iii) a gene encoding resistance to at least one late potato blight. Optionally this is under the control of its native promoter;
 (iv) optionally, nucleic acid capable of inhibiting chlorogenic acid production in the plant e.g. by encoding a sequence capable of silencing or downregulating a gene which encodes an enzyme present in the chlorogenic acid production pathway e.g. the HQT gene.

Methods, materials (e.g. vectors) and processes for achieving the same, optionally in conjunction with the modification of yet other traits described herein.

Cis-genic or transgenic plants obtained by said processes, particularly those also cis-genic or transgenic for other traits described herein.

Cis-Genic Transformation Systems of the Invention

It is an unfortunate fact that in many territories, public acceptance of plants obtained utilising recombinant DNA (r-DNA) technology has been cautious to date, irrespective of their nutritional or other benefits.

In one embodiment according to this invention, we provide new high-flavonol, blight-resistant potato germplasm using new "cis-genic" technology involving the transfer of only *Solanum* DNA into potato. Cis-genic gene transfer technology involves the transfer of only same-genus or same species DNA and is based on serendipitous homology between plant sequences and the T-DNA borders in *Agrobacterium*-mediated transformation.

While it is understood "cis-genic" transformation may require the same regulatory oversight as inter-species transformation, and under current legislation will also have the same labelling requirements, the present inventors believe that it nevertheless confers significant potential advantages.

One criticism regularly leveled at the products of r-DNA technology is that they contain DNA combinations which could not be brought about by conventional breeding. Indeed, for many species, it would be irrational to produce by genetic modification something which could be done by breeding without encountering such high regulatory hurdles.

In the case of potatoes, incorporating individual new traits via conventional breeding is all but impossible, so rDNA technology represents the only effective route to providing blight resistance without accompanying undesirable changes to other traits. The cis-genic approach removes one potential barrier to commercialisation. In time, it may also be recognised legislatively as different from trans-genesis.

We disclose a system for crop, including potato, transformation using only genetic material from that crop, e.g. potato itself and related *Solanum* species. Selection is visual, using colour generated by expressing anthocyanins in the plant tissue. This is also, optionally, used to give a distinctive colour to the crop, e.g. potato skin or veins of leaves, making it both distinctive as a variety and easily identifiable by consumers.

Rommens et al (Plant Physiology, May 2004, Vol. 135, pp. 421-431; herein incorporated by reference) report using two T-DNA constructs on compatible plasmids, one of which carries NPT and also a codA counterselectable marker (conferring 5-fluorouracil sensitivity), the other of which carries the gene of interest. This latter construct carries "P-DNA", comprising functional T-DNA borders based on serendipitous homology to T-DNA found in potato genomic DNA. This also carries a counterselectable marker (ipt-isopentenyl-transferase) which enables screening out transformants in which T-DNA transfer extends beyond the left border (LB). Corresponding vectors are also disclosed in U.S. Pat. No. 7,250,554.

In one embodiment according to this invention, an NPT and codA construct is used as a "life support" vector alongside an ipt-, P-DNA construct, pIPDNA, into which is cloned a MYB gene construct that enables cis-genic plant material to be detected by pigmentation.

This construct is used in transformation of several varieties, focusing initially on Desiree because of its amenability for *Agrobacterium* transformation.

Disclosed above is the use of anthocyanin, and in particular genes affecting (enhancing) the biosynthesis of anthocyanins, as transformation markers.

To develop a cis-genic marker for potato transformation, a functional potato ortholog of the Rosea 1 gene is obtained using oligonucleotides designed from the pan1 sequence and function is verified in transient and/or stable assays in tobacco. Pan1 is expressed from an auxin-inducible promoter from tomato (e.g. IAA4 as shown in Sequence Annex IV (SEQ ID NO: 15), or the auxin inducible AUX/IAA protein IAA2 Genbank NP000208), to allow production of high levels of anthocyanin in cells which are transformed and express the cis-genic construct in response to the high levels of auxin present in regeneration media during transformation, as demonstrated herein as a simple visual screen in tobacco, where transformed single cells or clumps of cells were identified by the red pigment they produce (FIG. 11.2). Placing the anthocyanin-inducing regulatory gene under an auxin-inducible promoter ensures that the gene does not stay switched on in the majority of mature and differentiated tissues or in apical meristems so that the gene can be used specifically for selection of transformed groups of cells prior to regeneration. Any pigmentation conferred in regenerated plants by the gene, such as pigment of the epidermal cells overlying the vascular tissues, supports distinctness (results now shown).

In summary, as exemplified herein, and without limitation, the invention provides in various aspects:

A transformation vector, or system of vectors for simultaneous transformation, comprising
(i) a gene encoding at least one MYB transcription factor (e.g. Rosea1, or a variant thereof such as ANT1 or pan1) to increase the levels of anthocyanins in the plant. Optionally this is under the control of an auxin-inducible promoter from tomato as described above,
(ii) preferably left and right P-DNA borders as described herein,
(iii) preferably a counter selectable marker situated outside of the P-DNA borders;

The vector above further comprising one, two, or three of the following between the P-DNA borders:
(i) a gene encoding AtMYB12 or a variant thereof to increase the levels of flavonols and/or chlorogenic acid in the plant. Optionally this is under the control of the B33 promoter,
(ii) a gene encoding resistance to at least one potato blight (*Phytophthora infestans*), optionally under the control of its native promoter,
(iii) optionally, nucleic acid capable of inhibiting chlorogenic acid production in the plant e.g. by encoding a sequence capable of silencing or downregulating a gene which encodes an enzyme present in the chlorogenic acid production pathway e.g. the HQT gene.

Methods, materials and processes for using the same—e.g. for transformation and a simple visual screen for transformed single cells, by virtue of the pigment that they produce. Preferably the transformation is performed in media which ensures transcription of the promoter controlling the anthoxcyanin marker e.g. in high levels of auxin.

Isogenic plants obtained by said processes, particularly those isogenic for the traits described herein.

Figure 12:
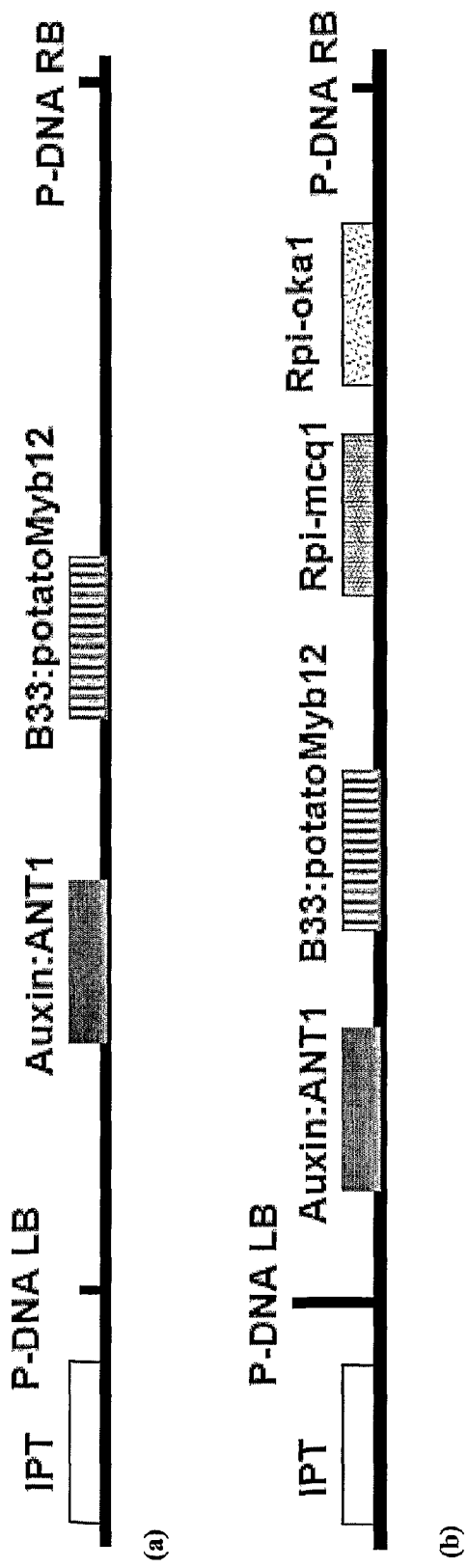

Those skilled in the art will appreciate that the construct may also include e.g. terminators, and other sequences as appropriate Non-limiting illustrations of vectors of the invention include those shown in FIGS. 12(*a*) and (*b*).

Any sub-titles herein are included for convenience only, and are not to be construed as limiting the disclosure in any way.

Having generally described this invention, with respect to various aspects and preferred embodiments thereof, the following examples are provided to extend the written description and to ensure that those skilled in the art are enabled to practice all aspects of this invention, including its best mode. However, those skilled in the art should not take the specifics of the examples which follow as limiting on the scope of this invention, for which reference rather should be made to the appended claims and equivalents thereof.

The disclosure of all references cited herein, inasmuch as it may be used by those skilled in the art to carry out the invention, is hereby specifically incorporated herein by cross-reference.

EXAMPLES

Example 1

High Flavonol and Hydroxycinnamic Acid Tomatoes and Tobacco Plants

Many food products from plants are rich in protective compounds with health benefits. Among these, metabolites derived from the phenylpropanoid pathway—polyphenols—have gained considerable attention recently.

One subclass of plant polyphenols, flavonoids, exhibits a broad spectrum of biological effects including antioxidant, antitumor (Braganhol et al., 2006), antiinflammatory, antiviral, antibacterial (Rigano et al., 2007), and antifungal activities. There is robust evidence to suggest that dietary flavonoids inhibit low density lipid (LDL) oxidation once absorbed, so reducing the primary risk factor for artherosclerosis and related diseases. Longer term administration of dietary flavonoids offers cardioprotection in both ex vivo and in vivo ischaemia-reperfusion assays in rats (Toufektsian et al., 2008) and improves the levels of risk factors in mouse models of cardiovascular disease (Rein et al., 2006), although it is likely that they protect indirectly by inducing reactive oxygen species (ROS)-scavenging mechanisms. In cell-based assays not all flavonoids are equally efficacious at inhibiting LDL peroxidation; the flavonols quercetin and kaempferol are particularly effective against chemically-induced lipid peroxidation. Quercetin is more active than kaempferol, possibly because it has an ortho-dihydroxyl functionality which confers higher antioxidant activity (Zhou et al., 2004; FIG. 1). Dietary flavonoids may confer protection against other diseases. For example, continuous administration of quercetin can reduce blood glucose levels and oxidative stress in STZ-induced diabetic rats, suggesting a protective role against diabetes (Asian et al., 2007). Flavonols also protect by mechanisms beyond their activities as antioxidants or as inducers of ROS-scavenging mechanisms. For example, flavonols are effective inhibitors of platelet aggregation and hence factors contributing to stroke and thrombosis (Nijveldt et al., 2001).

Supporting the results of cell-based assays and feeding trials with animals, several epidemiological studies have established a strong inverse correlation between the occurrence of cardiovascular disease, certain cancers and age-related degenerative diseases, and consumption of flavonol-rich diets (Hertog et al., 1993, Renaud and de Lorgeril, 1992, Joseph et al., 1999, Seeram et al., 2004, Hou et al., 2004). Based on such studies, it has been suggested that a systemic increase in the daily intake of certain flavonoids could lead to between 7 and 31% reduction in the incidence of all cancers and between 30 and 40% reduction in death from coronary heart diseases (Hertog et al, 1993, Soobrattee et al., 2005).

Another important group of plant-based bioactive polyphenols are the caffeoyl quinic acids (CQAs) of which chlorogenic acid (CGA) is the major soluble phenolic in solanaceous species such as potato, tomato and eggplant, and in coffee. Consequently, CGA forms one of the most abundant polyphenols in the human diet, and is the major antioxidant in the average US diet. CQAs have strong antioxidant activity and can limit low-density lipid (LDL) oxidation. CGA protects against environmentally-induced carcinogenesis through its up-regulation of cellular ROS-scavenging enzymes and suppression of ROS-mediated NFκβ, AP-1, and MAPK activation (Feng et al., 2005). Other caffeoyl quinic acids with multiple caffeoyl groups, such as dicaffeoylquinic acid (diCQA) and tricaffeoylquinic acid (triCQA), offer even greater protection than monocaffeoyl quinic acid (CGA), when included in the diet (Islam, 2006). High antioxidant capacity may be the explanation for the efficacy of these compounds because they have additional ortho dihydroxyl functionalities (Zhou et al., 2004, Cheng et al., 2007). Dietary CQAs are also beneficial in specific ways. For example, oral administration of triCQA to diabetic model rats reduces significantly their blood glucose content. Caffeoylquinic acid derivatives are neuroprotective against retinal damage (Nakajima et al., 2007), 3,4,5-triCQA inhibits HIV/AIDS (18), and diCQA has antihepatotoxic activity (Choi et al., 2005), suggesting that CQAs protect humans (Matsui et al., 2004, Kim et al., 2005) by a range of different mechanisms (Islam, 2003).

In addition to their individual health-promoting effects, synergistic effects of plant phenolics have also been reported. For example, the antibacterial activities of flavonoids are enhanced when they are administered in combination. The antibacterial activities of quercetin can be enhanced by the presence of rutin (Arima et al., 2002). Synergistic antiproliferative effects of quercetin and kaempferol on cancer cell proliferation have been reported (Ackland et al., 2005), suggesting that combinations of flavonoids, which are naturally present in whole fruits and vegetables, are more effective in inhibiting growth of malignant cells than individual flavonoids.

Several different strategies have been used to increase the production of polyphenolic compounds such as CQAs and flavonol glycosides in food plants (FIG. 1). Over-expression of genes encoding individual biosynthetic enzymes such as hydroxycinnamoyl CoA quinate transferase (HQT), a key enzyme of CGA synthesis, leads to nearly a doubling of CGA levels in tomato leaves (Niggeweg et al., 2004) and over-expression of the gene encoding chalcone isomerase (CHI) results in a more than 70-fold increase of rutin levels in tomato fruit peel (Muir et al., 2001). The problem with this type of strategy is that the whole biosynthetic pathway is not activated, and the overall increase in end products is usually not high enough for practical application purposes. Even in the case of CHI overexpression, because peel accounts for less than 10% of the fruit mass, the overall content of flavonols was increased to no more than 200 ug/g fresh weight. An alternative engineering strategy involves the overexpression of regulatory genes that induce these pathways. For example, increases of up to 20-fold in flavonols were obtained by simultaneous expression of maize transcription factors Lc and C1 (which induce anthocyanin biosynthesis in maize) in tomato fruit (Bovy et al., 2002). When the endogenous photomorphogenesis regulatory gene DET1 was suppressed in a fruit-specific manner in tomato, modest increases in carotenoid and flavonoid contents of fruits were achieved (Davuluri et al., 2005). Although this type of strategy provides a more effective means of engineering metabolism to achieve significant enhancements in the levels of end products, care is needed when choosing the transcription factor(s) to use, to ensure they have the appropriate specificity in target crop species. For example, because Lc and C1 transcription factors did not induce both general phenylpropanoid and flavonol biosynthetic pathways in tomato, the overall levels of flavonol derivatives (20 times more than in the control) were not great enough for application purposes.

Here, we show that it is possible to engineer massive increases of multiple health-promoting polyphenolic compounds from the phenylpropanoid pathway by tissue-specific expression of a single gene encoding a transcription factor, AtMYB12, from *Arabidopsis thaliana*. We show that even though identified as a flavonol-specific transcriptional activator in *arabidopsis*, AtMYB12 can activate additional pathways when over-expressed in a tissue-specific manner in tomato, and can be used to produce fruit with extremely high levels of several health-promoting hydrophilic polyphenolic antioxidants. Tomatoes with improved antioxidant activities of this order of magnitude should offer significant protection against heart disease, cancers and age-related degenerative diseases, if included in the diet.

Materials and Methods
Plasmid Construction, Plant Transformation and Confirmation of Transgenic Lines For tobacco transformation: The binary vector pBin-35S-AtMYB12 was produced by cloning the cDNA of AtMYB12 between the double 35S promoter from CaMV and the CaMV Terminator in pBin19 (Bevan, 1984). The T-DNA region of pBin-35S-AtMYB12 was transformed using *A. tumefaciens* (LBA4404) into *N. tabaccum* var. *Samsun* using the leaf disc transformation method (Horsch et al., 1985). Insertion of the T-DNA was confirmed by PCR of genomic DNA extracted from the kanamycin-resistant plants. AtMYB12 transcript levels were measured by RNA gel blots using the tobacco ubiquitin gene as a control.

For tomato transformation: The binary vector pSLJ-E8-MYB12 was constructed by replacing the double 35S promoter in pJIT160 (Gerineau and Mullineaux, 1993) by the E8 promoter between the Kpnl site and BamHI site to make pJIT160-E8. The full length sequence of the AtMYB12cDNA was amplified and inserted between the BamHI and EcoRI cloning sites of pJIT160-E8 to make pJIT160-E8-MYB12. The fragment between SstI and XhoI in pJIT160-E8-MYB12 was inserted into the same sites in pSLJ7291 to make pSLJ-E8-MYB12. The binary plasmid pSLJ-E8-MYB12was then transferred to Agrobacterium strain GV3101 by the triparental mating (Ditta et al., 1980). Tomato varieties Micro-Tom and Money Maker were transformed by Agrobacterium-mediated transformation of cotyledons (Fillatti, 1987). Insertion of the AtMYB12-containing T-DNA was confirmed by PCR of genomic DNA extracted from the kanamycin-resistant plants. Transcript levels of AtMYB12 were measured by real-time RT-PCR by the following procedure; RNA was extracted from the fruit of kanamycin-resistant plants, cDNA was prepared, and real-time RT-PCR was carried out using the primers 5'-CTTCAGTCT-TGTCCATCGGTG-3' (SEQ ID NO: 23) and 5'-CTAACG-GTTCTCCAAAGTTCTCAC-3'(SEQ ID NO: 24). The tomato ASR1 gene was amplified as a control using primers CCTGTTCCACCACAAGGACAA-3' (SEQ ID NO: 25) and 5'-GTGCCAAGTTTACCGATTTGC-3' (SEQ ID NO: 26).

Analysis of Total Anthocyanin

Anthocyanin was extracted from the petals of the flowers by acidified MeOH (3% HCl) and was quantified as previously described (Martin et al., 1985).

Analysis and Identification of Phenylpropanoids by LC-MS/MS

Phenylpropanoids were extracted either from fresh samples with 100% methanol or from freeze-dried samples with 70% methanol. HPLC analysis of the phenylpropanoids and the identification of peaks have been described elsewhere (Luo et al., 2007). Quantification of phenylpropanoids was achieved by calculating the area of each individual peak and comparing this to the standard curves obtained from the pure compounds. Pure flavonoids, kaempferol rutinoside, naringenin, naringenin chalcone were purchased from Apin Chemicals Ltd (available on the world wide web at apin.co.uk/new) or Extrasynthese (available on the world wide web at extrasynthase.com). Quercetin rutinoside (rutin), chlorogenic acid (CGA), and lycopene were purchased from Sigma (available on the world wide web at sigmaaldrich.com)

Quantitative RT-PCR

Total RNA was obtained using an RNeasy Plant Mini Kit (Qiagen). First-strand cDNA was synthesized using the adaptor oligoDT17 primer (Frohman et al., 1988) (Sigma) and SuperScript III (Invitrogen) from 5 µg of total RNA. Quantitative real-time RT-PCR was carried out using gene specific primers as shown in supplementary Table S3. All quantifications were normalized to abscisic stress ripening gene1 (ASR1) amplified under the same conditions using primers 5'-CCTGTTCCACCACAAGGACAA-3' and 5'-GTGC-CAAGTTTACCGATTTGC-3' (SEQ ID NO: 28).

RNA Gel Blot Analysis

Total RNA was purified from tobacco leaves using TRI-REAGENT (Sigma Chemical Co.; available on the world wide web at sigmaaldrich.com/) according to procedures provided by the manufacturer. Total RNA (20 µg) was then separated on denaturing agarose and transferred onto nylon membranes (GE Healthcare, available on the world wide web at 4.gelifesciences.com) and hybridized to radioactive DNA probes.

Cloning of SIMYB12 and Assaying its Expression in Tomato Fruit

The tomato EST database was searched for sequences homologous to AtMYB12 and the EST with the highest sequence similarity to AtMYB12 (TC172990) was used to identify a full-length cDNA from tomato fruit using 3'RACE PCR (Frohmann et al., 1988). Total RNA was isolated and first-strand cDNA was synthesized as described previously (Luo et al., 2007). The 3' end of the cDNA was amplified using oligonucleotides: 5'-ATGGGAAGAACACCT-TGTTG-3' (SEQ ID NO: 29) and the 3' adaptor sequence, 5' GACTCGAGTCGACATCG-3' (SEQ ID NO: 30) (Frohmann et al., 1988). The amplified sequence was cloned into pGEM-T easy and sequenced. The full-length cDNA was then reamplified using the forward oligo 5'-ATGGGAA-GAACACCTTGTTG-3'(SEQ ID NO: 31)and the reverse oligo 5'-CTAAGACAAAAGCCAAGATACAA-3'(SEQ ID NO: 32) based on the 3' sequence amplified by 3'-RACE. The sequence for SIMYB12 has been submitted to the EMBL database with the accession number EU419748.

The expression of SIMYB12 in Micro Tom tomato fruit was assayed by quantitative RT-PCR (Luo et al., 2007) using oligonucleotides 5'-GAGCAATAATGTAGGGAATAG-3' (SEQ ID NO: 33)and 5'-TTGAAGTAAGTTAGTGTCAG-TAT-3' (SEQ ID NO: 34).

Phylogenetic Analysis

Amino acid sequences were aligned using the CLUST-ALW program (Thompson et al, 1994). Phylogenetic analysis was performed with PHYLIP programs (version 3.67) using the region of the alignment corresponding to the MYB DNA binding domain (indicated by '=' characters). A distance matrix method employing the Jones-Taylor-Thornton model was used to compare the sequences and a tree was derived using the Neighbour-joining clustering method (Saitou and Nei, 1987). 1000 bootstapped data sets were used to indicate the confidence of each tree clade.

Total Antioxidant Activity

Wild type and transgenic tomatoes were washed, deprived of seeds, homogenized in liquid nitrogen in a mortar, and then freeze-dried. For the total antioxidant activity assay, 50 mg of the freeze-dried sample was extracted with 4 mL of water by vortexing for 20 min at room temperature, centrifugation at 10,000×g for 10 min and the supernatant was collected. The extraction was repeated with 2 mL of water and the two supernatants were combined. The pulp residue was re-extracted by the addition of 4 mL of acetone and vortexing for 20 min at room temperature, centrifugation at 10,000×g for 10 min and then the supernatant was collected. The extraction was repeated with 2 mL of acetone and the two supernatants were combined. Tomato extracts were immediately analyzed for their antioxidant capacity. The trolox equivalent antioxidant capacity (TEAC), based on the ability of antioxidant molecules to quench the long-lived ABTS [2,2'-azinobis(3-ethylbenzthiazoline-6-sulfonate), Sigma-Aldrich, UK] radical cation, a blue-green chromophore with characteristic absorption at 734 nm, compared with that of trolox (6-hydroxy-2,5,7,8-tetramethylchroman-2-carboxylic acid, Fluka, Germany), a water-soluble vitamin E analog, was determined (Pellegrini, 1999). Results were expressed as TEAC in mmol of trolox per kg of dry weight.

Analysis of Total Carotenoids

Total carotenoids were extracted from freeze-dried tomato fruit samples and extracted twice in the dark with tetrafuroran for 20 min followed by centrifugation (10,000 g) at room temperature for 10 min. The supernatants were combined and absorbance was measured at 472 nm. Quantification of total carotenoid levels was done using a calibration curve obtained for the pure compound, lycopene.

Results

Figure 2:
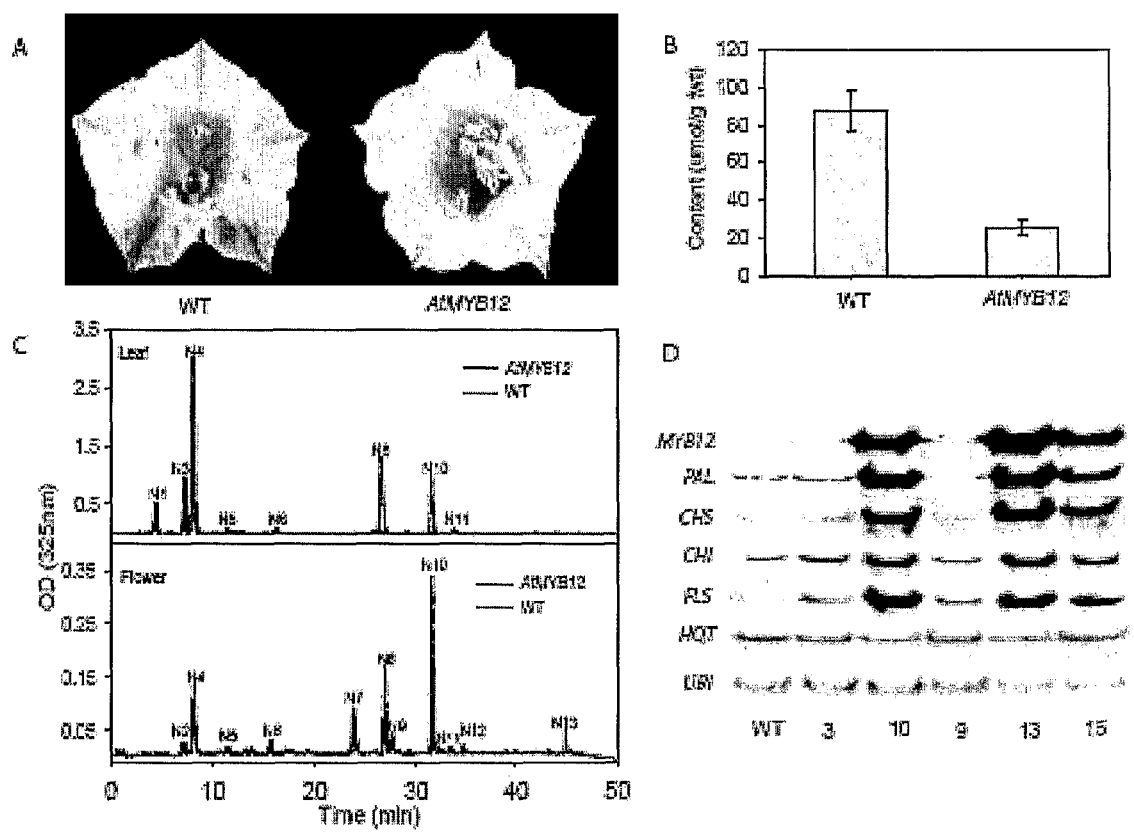
FIG. 2. Expression of AtMYB12 in tobacco. (A) Flowers of wild type (left) and an AtMYB12 expressing line (right). (B) Total anthocyanin contents in wild type and AtMYB12 flower petals. (C) HPLC analysis of methanol extracts from leaf and flowers of wild type and AtMYB12-expressing tobacco plants. N1,3-caffeoyl quinic acid; N2, caffeoyl-spermidnine; N3,4-caffeoyl quinic acid; N4,5-Caffeoyl quinic acid N5, quercetin glucosyl-glucoside rhamnoside; N6, kaempferol glucosyl-glucoside rhamnoside; N7, N-caffeoyl-N'-dihydrocaffeoyl spermidine; N8, quercetin rutinoside (rutin); N9, dicaffeoyl spermidine; N10, kaempferol rutinoside; N11, kaempferol malonylglucoside; N12, unknown; N13, tricoumaroyl spermidine. Identification of peaks is described in Table 1. (D) RNA gel blot of some structural genes involved in phenylpropanoid biosynthesis in tobacco. Genes that have been analyzed are described in FIG. 1, except the transgene AtMYB12, and the tobacco ubiquitin gene (UBI) which was used as a control. FW, fresh weight.

AtMYB12 has been identified as a transcription factor that specifically activates flavonol accumulation in *arabidopsis* (29). To determine whether AtMYB12 could work the same way in other species, we first introduced the AtMYB12 cDNA into tobacco (*Nicotiana tabaccum*) under the control of the strong, constitutive CaMV35S promoter. From more than 15 independent transformants, three lines (lines 10, 13, and 15) with different levels of transgene expression were investigated further. The transgenic lines grew normally compared to controls; the only visible difference was that the flowers of the transgenic plants were more palely coloured than their wild type counterparts (FIG. 2A). This phenotype was correlated with the expression level of the AtMYB12 transgene (FIG. 2B). The levels of phenolics in leaves and flowers of transgenic plants were compared to those in wild type plants (FIG. 2C, Table S1). CQAs (specifically the three isomers of chlorogenic acid; 3-caffeoyl quinic acid, 4-caffeoyl quinic acid and 5-caffeoyl quinic acid) were, by far, the most abundant phenolics in wild type leaves, although low levels of quercetin glycosides (mainly rutin) were identified, but kaempferol glycosides were barely detectable. Expression of AtMYB12 resulted in 46-fold and 83-fold increases of rutin (quercetin rutinoside) and kaempferol rutinoside in leaves, respectively. An acylated kaempferol derivative, kaempferol malonylglucoside was detected from AtMYB12 leaves but not in extracts from control leaves. In addition, a 2-fold increase in CGA levels was detected in leaves of the transgenic lines.

Flowers of tobacco expressing AtMYB12 also had increased rutin, kaempferol rutinoside, CGA and kaempferol malonylglucoside contents compared to wild type flowers, and lower levels of anthocyanins (FIG. 2B). The polyamine conjugates, remained unchanged in abundance in flowers of transgenic plants.

The expression of the genes encoding enzymes involved in flavonol and CGA biosynthesis were compared between control plants and lines expressing AtMYB12, by RNA gel blots (FIG. 2D). Among the genes that were tested, those encoding phenylalanine ammonia lyase (PAL), chalcone synthase (CHS), chalcone isomerase (CHI) and flavonol synthase (FLS) were induced by AtMYB12 expression in tobacco. HQT, which is involved in CGA biosynthesis (Niggeweg et al., 2004), was not induced, and dihydroflavonol 4-reductase (DFR), which is required specifically for anthocyanin biosynthesis, could not be detected in either the control or the AtMYB12-expressing plants.

These results showed that AtMYB12 can act as a positive regulator of the flavonoid biosynthetic pathway in tobacco. To exploit the potential of AtMYB12 for metabolic engineering, the gene was then introduced into tomato driven by the fruit-specific E8 promoter, which is most active in developing fruit after the breaker stage. Two varieties of tomato (*Solanum lycopersicum* cv. Micro-Tom and cv Money Maker) were transformed with SLJ-E8-MYB12 and more than 30 independent kanamycin resistant plants (T0) were obtained for each variety.

Figure 3:
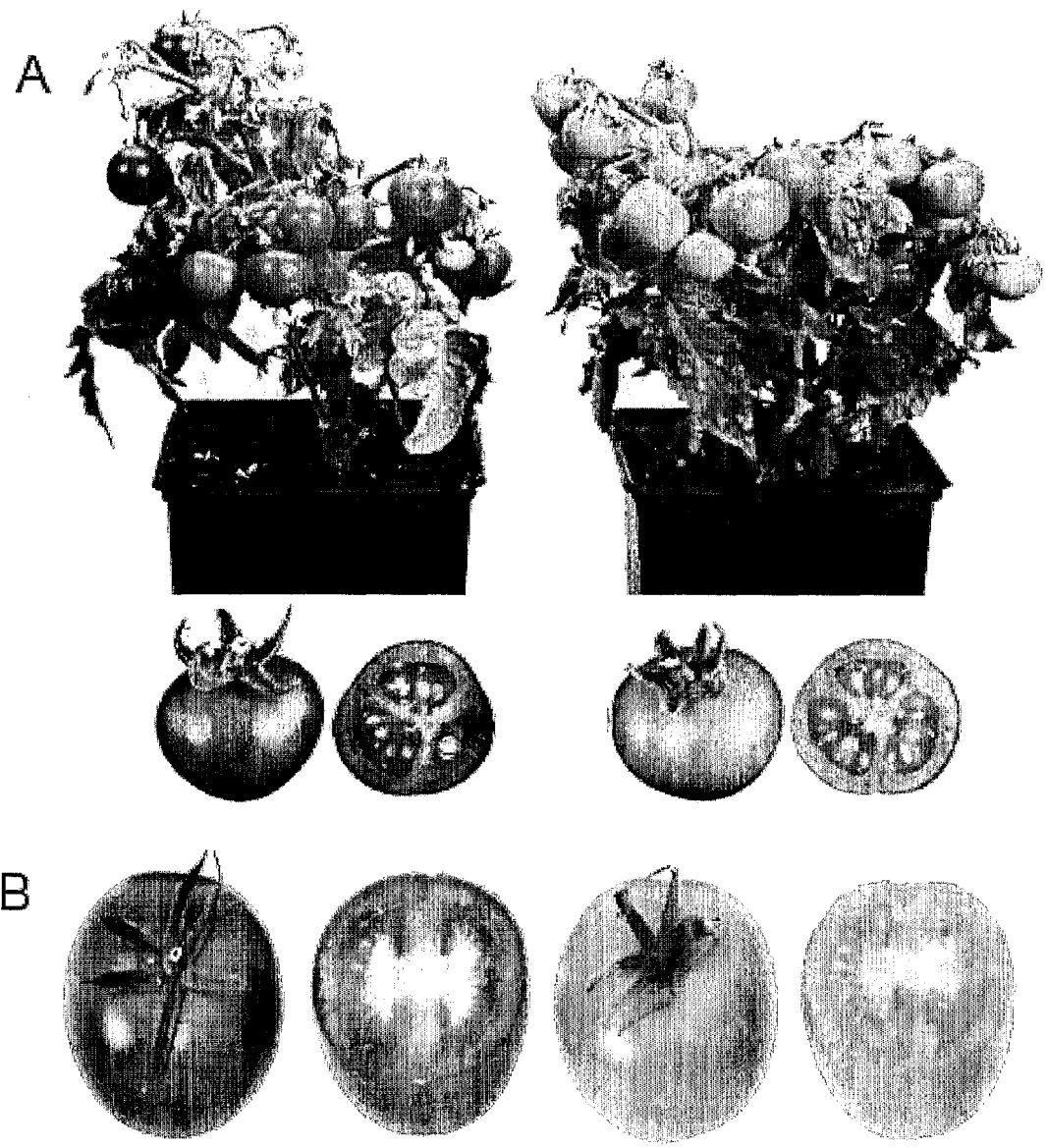
FIG. 3. Phenotypes of wild type and AtMYB12-expressing tomato fruit. (A) Phenotype of AtMYB12 expression in 'Micro Tom' tomato. Pictures show whole plants; wild type (upper left) and AtMYB12-expressing line (upper right), and fruit of wild type (lower left) and AtMYB12-expressing line (lower right) tomato. (B) Phenotype of AtMYB12 expression in 'Money Maker' tomato. Pictures show fruit of wild type (left) and an AtMYB12-expressing line (right).

AtMYB12 primary transformants developed normally during vegetative growth and were indistinguishable from controls. Transgenic fruit also developed normally and were indistinguishable from fruit from control plants until the turning stage. At maturity, instead of turning the pink-red colour of control fruit, the transgenic fruit were orange (FIG. 3A). This phenotype was correlated with the expression level of AtMYB12 and the content of flavonol derivatives in the transgenic fruit. The same orange fruit phenotype was observed in the fruit of the transformants in the Money Maker background (FIG. 3B)

Figure 4:
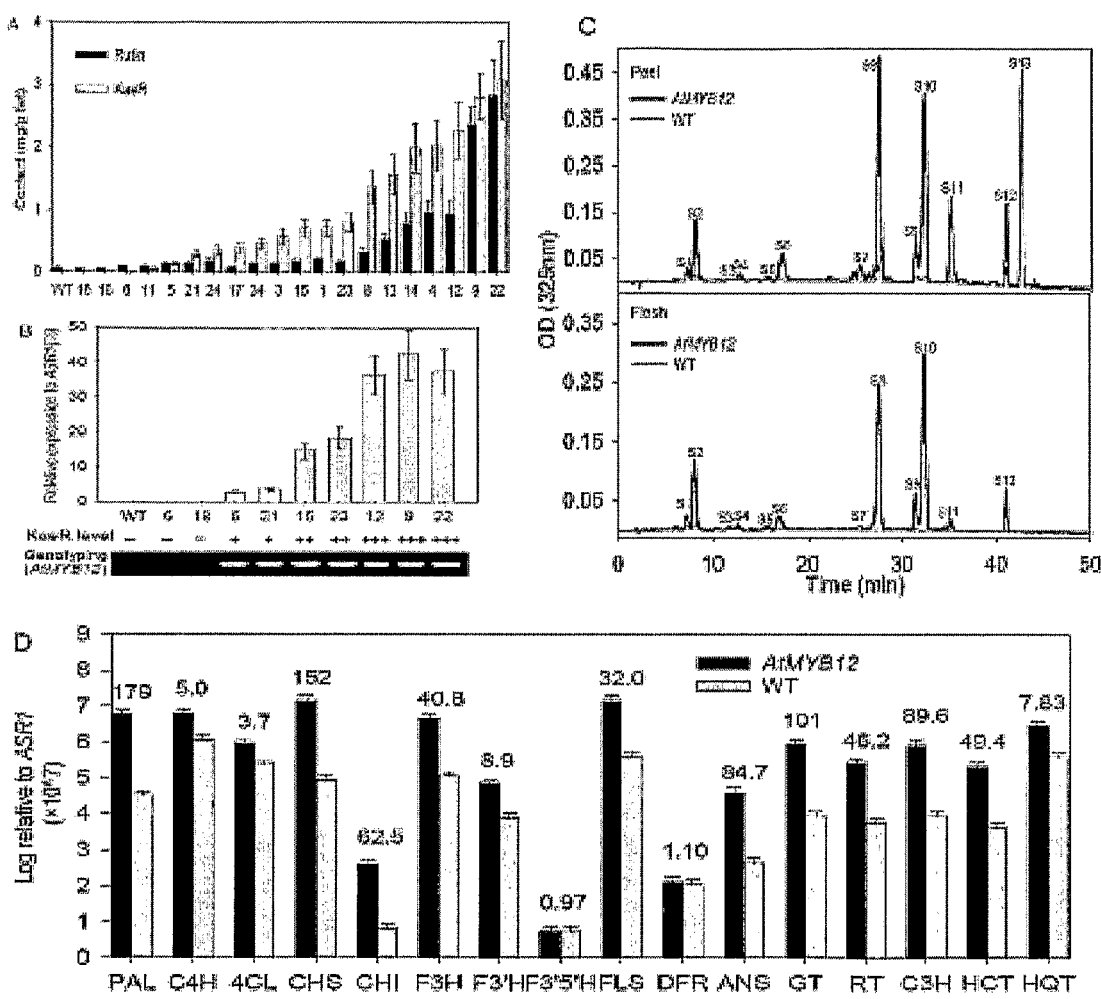
FIG. 4. Screening of T0 tomato transformants expressing AtMYB12, phenylpropanoid levels and structural gene expression in wild type and AtMYB12-expressing 'Micro Tom' tomato fruit. (A) Flavonoid levels in whole fruit of wild type and T0 transgenic 'Micro Tom' tomato fruit. (B) Transcription of AtMYB12 (upper), kaempferol rutinoside (KaeR) levels (middle) and AtMYB12 genotyping (lower) of wild type and selected T0 transgenic tomato fruit. FW, fresh weight. (C) HPLC analysis of methanol extracts from peel and flesh of wild type and AtMYB12-expressing tomato fruits. S1, coumaric acid glucoside; S2,5-caffeoyl quinic acid; S3, quercetin diglucoside; S4, quercetin glucosyl-glucoside rhamnoside; S5, kaempferol diglucoside; S6, kaempferol glucosyl-glucoside rhamnoside; S7, naringenin; S8, quercetin rutinoside (rutin); S9, dicaffeoyl quinic acid; S10, kaempferol rutinoside; S11, naringenin chalcone glucoside; S12, tricaffeoyl quinic acid; S13, naringenin chalcone. Identification of peaks is described in Supplementary Table S2. (D) Analysis of transcript levels of structural genes of phyenylpropanoid metabolism by real-time RT-PCR. Genes analyzed are described in FIG. 1. Transcript levels relative to abiotic stress responsive 1 (ASR) are presented using a Log 10 scale and the fold-increase in levels in AtMYB12-expressing fruit compared to wild type is given above the bars for each gene. The data represent the mean values (±SD) of triplicate experiments from two independent biological samples. CQA, caffeoyl quinic acid; diCQA, di caffeoyl quinic acid; triCQA, tricaffeoyl quinic acid; KaeR, kaempferol rutinoside; KGGR, kaempferol glucosyl-glucoside rhamnoside; NCG, Naringenin chalcone glucoside; NC, Naringenin chalcone.
Figure 8:
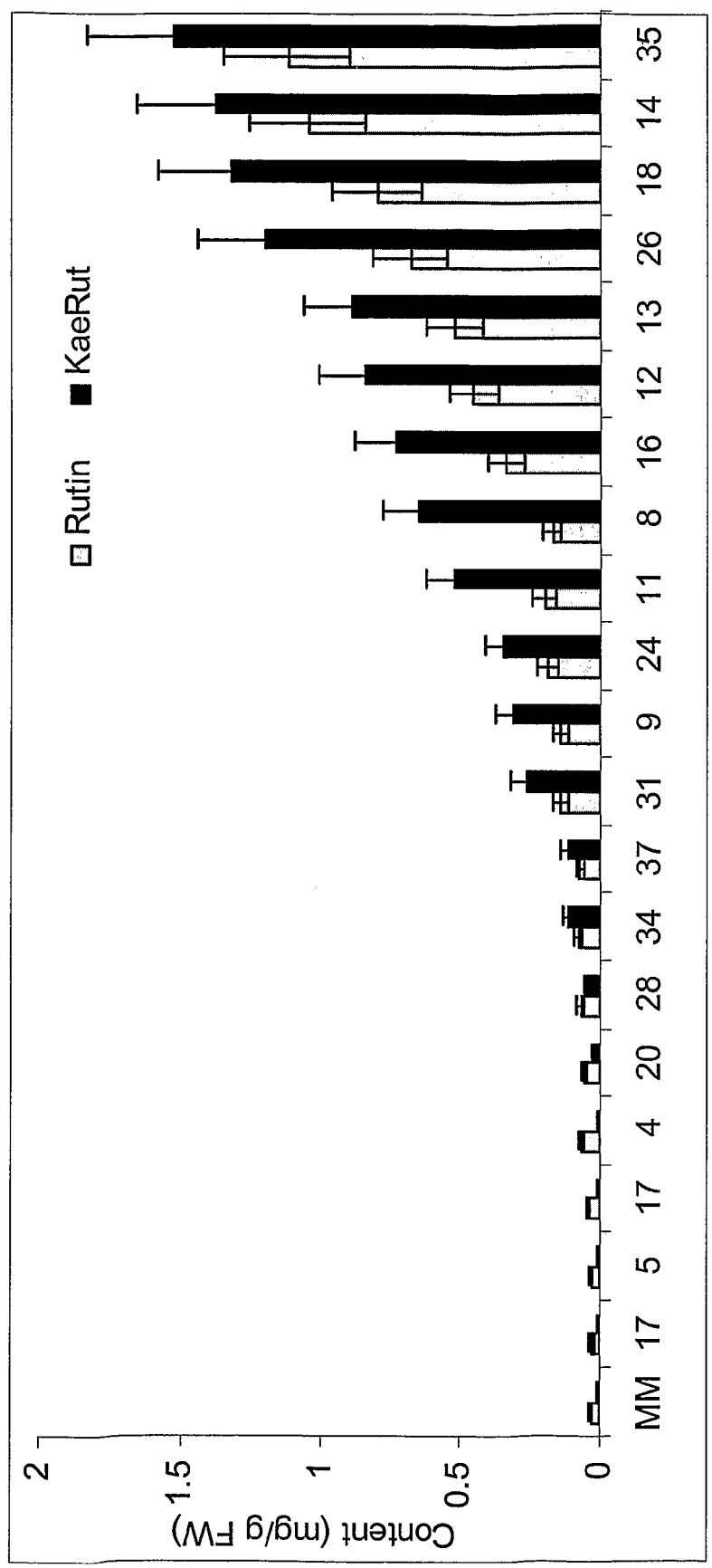
FIG. 8 Flavonoid levels in the whole fruit of wild type and T0 transgenic 'Money Maker' tomato fruit.

Mature T0 fruits of each variety were screened for their quercetin rutinoside (rutin) and kaempferol rutinoside contents (FIG. 4A and FIG. 8 for Micro Tom and Money Maker, respectively). Because of the shorter generation time and relative ease of cultivation of dwarf varieties, transgenic plants in the MicroTom background with different levels of flavonol derivatives were selected for further genotyping and the transcript levels of AtMYB12 in the fruit of these plants were analyzed by real-time qRT-PCR (FIG. 4B). Control fruit showed no AtMYB12 transcript, while all transgenic plants tested showed clear transcripts for the transgene in fruit. Furthermore, there was a good correlation between the transcript levels of the AtMYB12 gene and the kaempferol rutinoside contents of the fruit. Three of the transgenic plants (lines 9, 12, and 22) were then used for further analyses, on the basis of their high AtMYB12 transcript levels and their high levels of flavonol accumulation in fruit. For all three lines, the transgene was inherited in a 3:1 ratio by the $T_1$ progeny, as expected for single copy transgene insertions.

Ripe fruit from both transgenic and control lines were harvested and peel and flesh were analyzed separately for their polyphenol contents by LC/MS (FIG. 4C and Table S2). The main flavonoid in wild type peel extract was naringinin chalcone, accompanied by small amounts of rutin, kaempferol rutinoside, CGA, diCQA and triCQA, confirming results recently reported by Moco et al (2006). Wild type flesh produced only small amounts of CQAs, and other phenolics at detectable levels. In both the peel and the flesh of transgenic fruit, massive levels of flavonol derivatives (mainly rutin and kaempferol rutinoside) were detected. Kaempferol glucosyl-glucoside rhamnoside and chalcone glucose were among the flavonoids that also were elevated in the peel of transgenic fruit. Surprisingly, high levels of CQAs (CGA, diCQA, and triCQA) were also detected in the fruit of the lines expressing AtMYB12. The major phenolics in whole fruit were quantified using purified standards (FIG. 4D). On a whole-fruit basis, more than 15 mg/g DW of CQAs and 72 mg/g DW of flavonols (rutin and kaempferol rutinoside) were detected in the transgenic fruit in the MicroTom background, which is equivalent to 22, and 65-fold higher levels respectively compared to wild type fruit. In the Money Maker background AtMYB12 also increased the levels of both CQAs and flavonols (to more than 3 mg/g DW and 48 mg/g DW respectively). The total levels of these polyphenols were lower in the Money Maker than in the MicroTom background, but this was probably because the levels of these compounds are generally lower in this variety than in MicroTom; a feature shared by larger fruited varieties compared to cherry tomatoes (Raffo et al., 2002). However, the fold increases in polyphenols induced by AtMYB12 were higher in the Money Maker background than in the MicroTom back ground; more than 30-fold for CQAs and more than 125-fold for flavonols (FIG. 4D).

The high-polyphenol phenotype was maintained in mature fruit of hemizygous T1 and homozygous T2 individuals of three single-copy AtMYB12 lines (Supplemental Table S3), showing that the high-flavonol/high CQA phenotype is inherited stably in subsequent generations and is, in fact, somewhat enhanced as the AtMYB12 transgene is brought to homozygosity.

The effect of AtMYB12 on the expression of genes involved in flavonoid biosynthesis was examined by real-time qRT-PCR in fruit from the T1 generation of plants. RNA was extracted from fruit of AtMYB12 and control plants at the turning stage. Expression levels of phenylpropanoid pathway genes encoding PAL, cinnamate 4-hydroxylase (C4H), 4-hydroxycinnamoyl-CoA ligase (4CL), CHS, CHI, flavanone-3-hydroxylase (F3H), flavonoid-3'-hydroxylase (F3'H), flavonoid-3'5'-hydroxylase (F3'5'H), FLS, DFR, anthocyanidin synthase (ANS), flavonol-3-glucosyltransferase (GT), flavonol 3-glucoside-rhamnosyltransferase (RT), p-coumaroyl ester 3-hydroxylase (C3H), hydroxycinnamoyl-CoA shikimate/quinate transferase (HCT), and HQT were compared in control and transgenic fruit expressing AtMYB12. Expression of the abscisic stress ripening 1 (ASR1) gene (Iusem et al., 1993) was used as an internal control due to its high and stable mRNA expression levels in different ripening stages and different tissues of tomato fruit (Bovy et al., 2002).

As shown in FIG. 4E, transcripts of PAL, F3H, F3'H, FLS, GT, and RT genes were readily detectable in wild-type fruit. In AtMYB12 fruit, however, we observed more than 100-fold induction of the genes encoding PAL, CHS, and GT, between 50- and 100-fold induction of the genes encoding CHI, ANS, C3H, between 10- and 50-fold induction of genes encoding F3H, RT, and HCT, and between 3- and 10-fold induction of genes encoding F3'H, C4H, 4CL and HQT relative to the wild-type fruit. Neither F3'5'H nor DFR were up-regulated in AtMYB12 fruit. In conclusion, these results showed that fruit-specific expression of AtMYB12 in tomato leads to the induction of all of the biosynthetic genes required for the production of flavonols and their derivatives and, in addition, those required for the synthesis of CGA and its derivatives, while at least some of the genes involved in anthocyanin production remain uninduced. The exception was ANS which is involved in anthocyanin biosynthesis and was highly induced by AtMYB12 expression.

Figure 5:
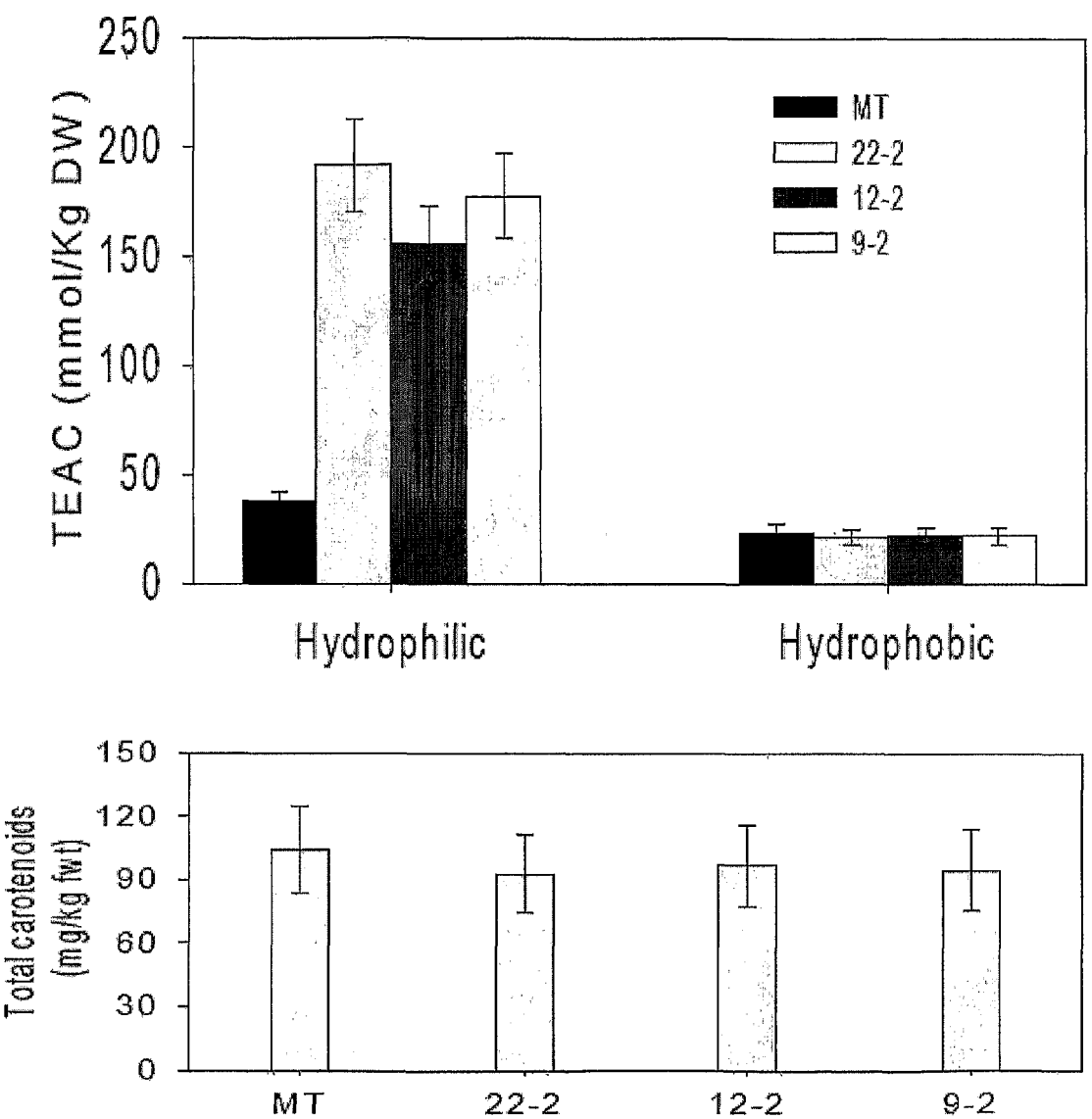
FIG. 5. Total antioxidant capacity and total carotenoids in wild type and T2 generation AtMYB12-expressing tomato fruit. (A) Hydrophilic and lipophilic antioxidant activities in mature tomato fruit from wild type and AtMYB12-expressing lines. (B) Total carotenoid levels in mature tomato fruit from wild type and AtMYB12-expressing lines.

Differences in the total antioxidant capacity between transgenic and control tomato fruit were measured using the Trolox Equivalent Antioxidant Capacity (TEAC) assay. In AtMYB12 fruit the TEAC activity of the water-soluble fraction (containing phenolics) was increased up to 5-fold compared to the control (FIG. 5A) whereas no significant difference could be detected for the TEAC activities of the lipophilic fraction between control and transgenic fruit. This suggested that the increase of the phenylpropanoids was not achieved at the expense of carotenoid accumulation in tomato fruit. No significant difference in total carotenoid content was detected between transgenic and wild type tomato fruit (FIG. 5B).

Figure 6:
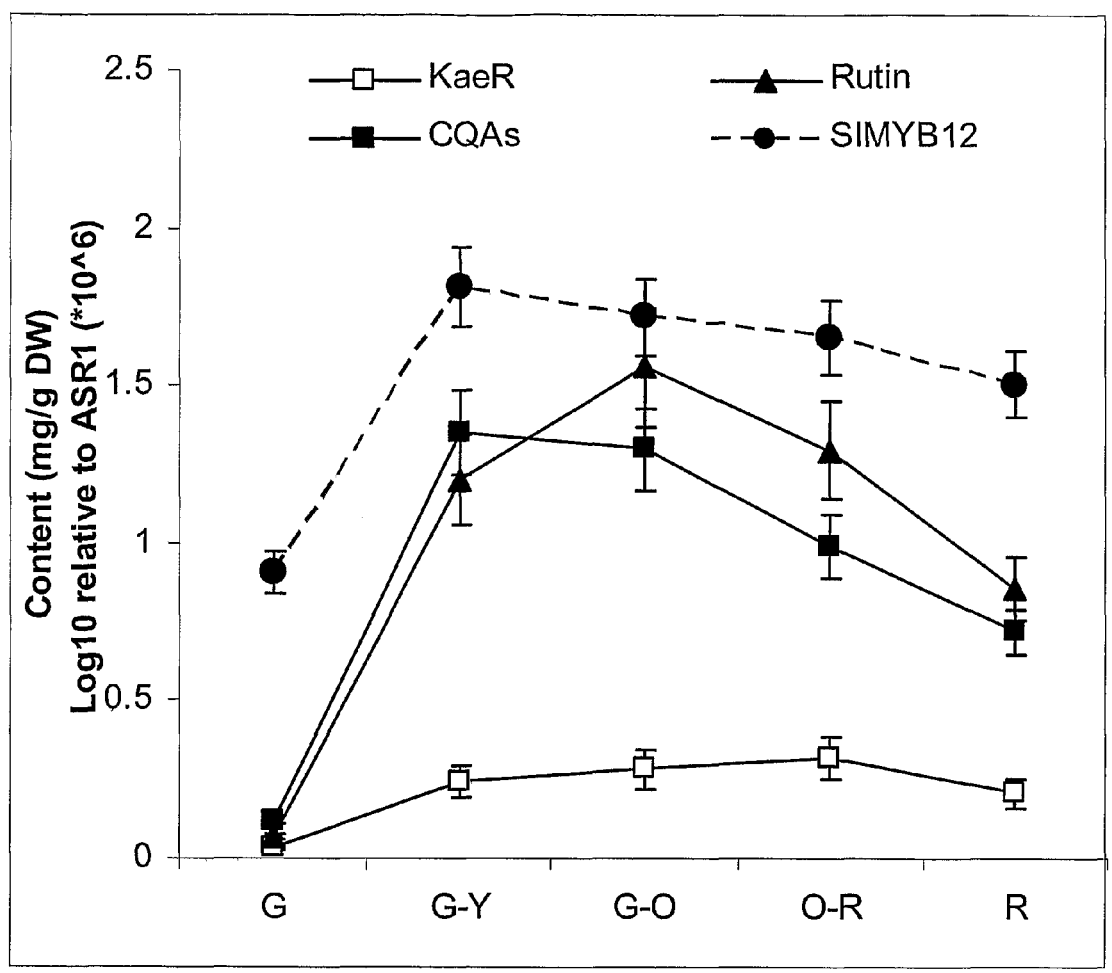
FIG. 6. Polyphenolic contents and SlMYB12 transcript levels in developing 'Micro Tom' tomato fruit. Levels of SlMYB12 transcript levels in tomato fruit at different ripening stages. Transcript levels determined by real time RT-PCR are expressed relative to ASR1 using a Log 10 scale. CQAs and flavonol rutinoside levels in 'Micro Tom' tomato fruit at different ripening stages. Results are averages ±SD from three measurements of two independent biological replicates.

To investigate the role of AtMYB12-like transcription factors in tomato, the tomato EST data-base was searched and three ESTs encoding different MYB12-like proteins were identified. The sequence of one EST, which showed the greatest similarity to AtMYB12, was identified as being expressed early during fruit development. This EST sequence was used to identify a full-length cDNA clone which encodes a protein very similar to AtMYB12, and which we named SlMYB12 (*Solanum lycopersicum* MYB12; FIG. 9A,B). The expression of SlMYB12 was analysed by real-time qRT-PCR during tomato fruit development and compared to the levels of flavonols and CQAs at the same stages (FIG. 6A,B). SlMYB12 transcript levels increased markedly between the green and green-yellow stages of fruit development, a time at which the levels of both flavonols and CQAs also rose sharply. At later stages of ripening SlMYB12 transcript levels did not increase further (and in fact declined slightly). The levels of CQAs and flavonols also increased no further, but rather declined in red tomatoes. SlMYB12 was expressed most highly in the peel of developing fruit but was also expressed at a lower level in the flesh where lower amounts of CQAs and flavonols accumulate (FIG. 6C,D). Taken together, these data support the idea that regulation of CQA biosynthesis is a function of SlMYB12 in tomato fruit as well as regulation of flavonol biosynthesis. Our data show that MYB12-like transcription factors are powerful tools for engineering levels of both types of polyphenols, at least in some species that operate both metabolic pathways.

Discussion

Our study demonstrates that expression of the transcription factor, AtMYB12, results in unprecedentedly high levels of flavonol accumulation in both tobacco and tomato (up to about 10% of the dry weight in whole tomato fruit). In tomato fruit significantly higher levels of CQAs also accumulate as a result of expression of AtMYB12. In ripe fruit there were up to 70-fold higher levels of total flavonols and 20-fold higher levels of CQAs, compared to controls. Enhanced levels of both types of polyphenol were observed in MicroTom and Money Maker varieties, indicating that these increases were not variety-specific. The increases in soluble phenolics resulted in very significant increases in the hydrophilic antioxidant capacity of fruit; up to five-fold higher capacities in MicroTom. This is higher than previous attempts to elevate antioxidant capacity in tomato (Schijlen et al., 2006, Giovinazzo et al., 2005). Such elevated antioxidant capacities could contribute significantly to the dietary antioxidant capacity if such tomatoes were consumed as part of a regular diet.

When AtMYB12 was expressed at high levels in tobacco, significant increases in two flavonols only, rutin and kaempferol glycoside, were observed. This ability of AtMYB12 to stimulate flavonol accumulation was predicted from analysis of AtMYB12 function in *arabidopsis* (Mehrtens et al., 2005). The effect of AtMYB12 on CQA levels in tobacco leaves was relatively modest, especially in comparison to the effects of the transcription factor in tomato fruit. It is very likely that the 2-fold increase in CQA levels observed in tobacco expressing AtMYB12 resulted from the transcription factor stimulating the expression of the genes encoding PAL, rather than any direct effect on CQA biosynthesis— since we observed no stimulation of the transcript levels for the genes encoding HQT nor C3H (FIG. 2D and unpublished results) in tobacco. In fact increases of between 2 and 3-fold have been reported for overexpression of PAL in tobacco (Howles et al., 1996), which is the same order of magnitude of increase in CQA levels as observed in our experiments with AtMYB12 in tobacco.

However, AtMYB12 expression induced not only the production of flavonols (quercetin and kaempferol rutinosides), but also CQA levels: 20-fold increases in hydroxycinnamic acid derivatives (CQA, diCQA, and triCQA) were achieved in tomato fruit on whole fruit basis.

The very significant increases in levels of polyphenols from different branches of the phenylpropanoid pathway in tomato fruit was due to the increases in transcript levels of the genes encoding the enzymes of both flavonoid and CQA biosynthesis. Expression of the gene encoding PAL was induced more than 100-fold by AtMYB12. PAL has been suggested to be a major control point determining the flux into phenylpropanoid metabolism, and its induction is likely to be crucial to achieving high levels of accumulation of any polyphenolics. Induction of expression of the gene encoding PAL by AtMYB12 represents a significant difference between the effects of AtMYB12 and the effects of Lc and C1 transcription factors from maize which did not induce PAL expression in tomato (Bovy et al., 2002). Lc and C1 increased flavonol levels to about 0.13 mg per g fresh weight of tomato whereas AtMYB12 increased flavonol levels to over 90 mg per g dry weight (equivalent to 7.1 mg per g fresh weight) and enhanced the already high levels of CQAs by up to 20-fold (total 20 mg per g dry weight, equivalent to 1.6 mg per g fresh weight). In addition, AtMYB12 induced the production of both quercetin and kaempferol-type flavonols. This is in contrast to the activity of Lc and C1 in tomato which induced primarily the production of kaempferol derivatives (Bovy et al., 2002). This difference is attributable to the activation of the gene encoding F3'H, which is necessary for the production of quercetin (FIG. 1), by AtMYB12, which Lc and C1 did not induce. Our data emphasise the importance of the specificity of transcription factors for their target genes in heterologous hosts, for determining the efficacy of engineering strategies to improve metabolite accumulation and antioxidant capacity of crops.

Identified originally as a flavonol-specific transcription factor in arabidopsis, AtMYB12 has been shown to target flavonol-specific genes, and the general phenylpropanoid pathway gene encoding 4CL (38). Our results show that the overexpression of AtMYB12 in tomato results in the induction of not only the above mentioned genes but also all other genes that are involved in the biosynthesis of flavonol derivatives, including those encoding PAL, C4H and 4CL. In addition, AtMYB12 also induces the transcript levels of genes involved in CQA biosynthesis including HCT, C3H, and HQT in tomato. The increased accumulation of both diCQA and triCQA, which are the products of further steps in the CQA biosynthetic pathway, suggests that the additional gene(s) required for the biosynthesis of these compounds are probably also induced by the expression of AtMYB12, although these genes remain to be identified at the molecular level.

We do not have a ready explanation for why AtMYB12 might induce CQA and flavonol biosynthesis in tomato but only flavonol biosynthesis in tobacco. AtMYB12 does not induce CQA biosynthesis in arabidopsis, but arabidopsis lacks HQT, one of the genes required for CQA production (Arima et al., 2002; Niggeweg et al., 2004). Interestingly, however, the P gene of maize and a close homologue (IF35), which encode transcription factors closely related structurally to AtMYB12 (FIG. 9A), and which share some of its target genes, do appear to regulate the production of CGA in maize (Zhang et al., 2003). P lies at a major QTL determining CGA levels in silks of this crop (Szalma et al., 2005) and IF35 maps closely to a minor QTL for the same trait. These observations coupled to ours for the effects of AtMYB12 on CQA levels in tomato fruit suggest that regulation of the pathways for CQA biosynthesis may be an additional and perhaps an ancient function of AtMYB12-like transcription factors. In tobacco it would appear that MYB12-like proteins no longer have the capacity to activate transcription of the genes encoding C3H and HQT, and that alternative regulatory mechanisms have evolved to regulate CQA accumulation. However, the fact that, in tomato, AtMYB12 and likely the endogenous MYB12-like gene SlMYB12, regulate both flavonol and CQA production makes MYBs of the R2R3-MYB subgroup 7 powerful tools for metabolic engineering and improving the health promoting properties of foods, particularly in species that maintain both flavonol and CQA biosynthetic pathways.

Unlike natural foods which usually accumulate a mixture of bioactive compounds including a range of polyphenolics, functional foods produced by metabolic engineering usually have enhanced levels of a single bioactive. Considering the synergistic effects of combinations of different bioactives in the diet (quercetin, kaempferol, CGA and the particularly beneficial diCQA and triCQA; Arima et al., 2002, Ackland et al., 2005), functional foods with increases in several distinct bioacitves (as demonstrated here for tomato fruit-specific expression of AtMYB12) offer significant advantages for health promotion through improving the phytonutrient and hydrophilic antioxidant content of foods.

TABLE 1

Quantification of major phenolics in wild type (MicroTom [MT], Money Maker [MM]) and AtMYB12-expressing tomatoes[a].

| Compound | MT (mg/g DW) | MT-MYB12 (mg/g DW) | Fold increase | MM (mg/g DW) | MM-MYB12 (mg/g DW) | Fold increase |
|---|---|---|---|---|---|---|
| CGA | 0.25 ± 0.04 | 4.96 ± 0.72 | 19.8 | 0.04 ± 0.01 | 1.17 ± 0.25 | 27.2 |
| diCQA | 0.19 ± 0.04 | 4.21 ± 0.69 | 22.2 | 0.03 ± 0.01 | 0.85 ± 0.14 | 26.6 |
| triCQA | 0.28 ± 0.05 | 6.59 ± 1.09 | 23.5 | 0.04 ± 0.01 | 1.36 ± 0.28 | 42.5 |
| QueRut | 0.92 ± 0.20 | 30.90 ± 5.21 | 33.6 | 0.30 ± 0.05 | 20.20 ± 3.40 | 67.3 |
| KaeRut | 0.20 ± 0.04 | 41.70 ± 6.74 | 209.0 | 0.05 ± 0.01 | 28.50 ± 5.62 | 593.5 |
| KaeGRG | ND | 4.47 ± 0.64 | — | ND | 1.12 ± 0.21 | — |
| NCG | ND | 1.55 ± 0.27 | — | ND | 0.43 ± 0.08 | — |
| NC | 0.89 ± 0.24 | 0.85 ± 0.22 | 1.0 | 0.03 ± 0.01 | 0.03 ± 0.01 | 0.9 |

[a]MT, Micro Tom; MM, Monkey Maker; CGA, chlorogenic acid; diCQA, dicaffeoyl quinic acid; triCQA, tricaffeoyl quinic acid; QueRut, quercetin rutinoside; KaeRut, kaempferol rutinoside; KGRG, kaempferol glucosyl- rhamnosyl-glucoside; NCG, naringenin chalcone glucoside; NC, naringenin chalcone.

TABLE 2

Stability of the AtMYB12 -expression phenotype in T1 and T2 generations of transgenic lines in Micro Tom[a].

| Line | Caffeoyl quinic acids (mg/g DW) | Quercetin rutinoside (mg/g DW) | Kaempferol derivatives[b] (mg/g DW) |
|---|---|---|---|
| T1 generation | | | |
| MT | 0.8 ± 0.1 | 1.0 ± 0.1 | 0.2 ± 0.1 |
| 22-1 | 20.3 ± 2.9 | 34.9 ± 4.4 | 46.0 ± 6.9 |
| 12-1 | 18.8 ± 2.6 | 21.9 ± 3.6 | 31.0 ± 4.1 |
| 9-1 | 16.1 ± 2.1 | 18.8 ± 2.7 | 35.1 ± 4.3 |
| T2 | | | |

TABLE 2-continued

Stability of the AtMYB12-expression phenotype in T1 and T2 generations of transgenic lines in Micro Tom[a].

| Line | Caffeoyl quinic acids (mg/g DW) | Quercetin rutinoside (mg/g DW) | Kaempferol derivatives[b] (mg/g DW) |
|---|---|---|---|
| generation | | | |
| MT | 0.7 ± 0.1 | 1.0 ± 0.1 | 0.3 ± 0.1 |
| 22-2 | 16.8 ± 2.0 | 40.5 ± 5.0 | 50.4 ± 6.3 |
| 12-2 | 15.5 ± 1.7 | 35.4 ± 4.1 | 42.7 ± 5.1 |
| 9-2 | 20.8 ± 2.2 | 32.6 ± 4.0 | 46.9 ± 5.4 |

[a]Mature fruits were harvested from hemizygous T1 (A) and homozygous T2 (B) populations of three independent transgenic lines (line 22, 12 and 9). Eight plants from each transgenic line were analyzed. From each plant 2-3 fruits were pooled, methanol extracts were prepared, and phenylpropanoid levels were determined. DW, dry weight.
[b]Total amount of kaempferol rutinoside and kaempferol glucosyl-rhamnosylglucoside

TABLE S1

Identification of major phenylpropanoids in leaf and flower of wild type and AtMYB12-expressing tobacco plants.

| Peak | Putative Identification | UV/Vis λmax(nm) | [M − H]+ (m/z) | MS/MS Fragments |
|---|---|---|---|---|
| N1 | 3-Caffeoyl quinic acid | (298), 326 | 355 | 355 (163) |
| N2 | Caffeoyl-spermidnine | (295), 320 | 308 | 308 (163) |
| N3 | 4-Caffeoyl quinic acid | (298), 326 | 355 | 355 (163) |
| N4 | 5-Caffeoyl quinic acid | (298), 326 | 355 | 355 (163) |
| N5 | Quercetin glucosyl-glucoside rhamnoside | 258, 353 | 773 | 773 (627, 611, 465, 449, 303) |
| N6 | Kaempferol glucosyl-glucoside rhamnoside | 266, 347 | 757 | 757 (611, 595, 449, 433, 287) |
| N7 | N-Caffeoyl-N'-dihydrocaffeoyl spermidine | (290), 320 | 472 | 472 (310, 163) |
| N8 | Quercetin rutinoside (rutin) | 256, 353 | 611 | 611 (465, 303) |
| N9 | Dicaffeoyl spermidine | (294), 320 | 470 | 470 (308, 163) |
| N10 | Kaempferol rutinoside | 265, 348 | 595 | 595 (449, 433, 287) |
| N11 | Kaempferol malonylglucoside | 266, 345 | 535 | 535 (287) |
| N12 | unknown | 287, 328 | 273 | 273, 195 |
| N13 | tricoumaroyl spermidine | 297, 305 | 584 | 584 (438, 292, 147) |

TABLE S2

Identification of major phenylpropanoids in peel and flesh of wild type and AtMYB12-expressing tomato fruit.

| Peak | Putative Identification | UV/Vis λmax(nm) | [M − H]+ (m/z) | MS/MS Fragments |
|---|---|---|---|---|
| S1 | coumaric acid glucoside I | (295), 313 | 327 | 327 (163) |
| S2 | 5-Caffeoyl quinic acid | (298), 326 | 355 | 355 (163) |
| S3 | Quercetin diglucoside | 258, 353 | 627 | 627 (465, 303) |
| S4 | Quercetin glucosyl-glucoside rhamnoside | 256, 353 | 773 | 773 (627, 611, 465, 449, 303) |
| S5 | Kaempferol diglucoside | 265, 346 | 611 | 611 (449, 287) |
| S6 | Kaempferol glucosyl-glucoside rhamnoside | 266, 347 | 757 | 757 (611, 595, 449, 433, 287) |
| S7 | Naringenin | 284, (329) | 273 | 273 (153, 147) |
| S8 | Quercetin rutinoside (rutin) | 256, 353 | 611 | 611 (465, 303) |
| S9 | Dicaffeoyl quinic acid | (300), 330 | 539 | 539 (377, 163) |
| S10 | Kaempferol rutinoside | 265, 345 | 595 | 595 (449, 287) |
| S11 | Naringenin chalcone glucoside | (315), 367 | 435 | 435 (273) |
| S12 | Tricaffeoyl quinic acid | (303), 329 | 701 | 701 (539, 377) |
| S13 | Naringenin chalcone | 369 | 273 | 273 (153, 147) |

TABLE S3

Primers used for real-time RT-PCR of structural genes in phenylpropanoid biosynthetic pathway in tomato.

| Primer | Gene | Sequence (5' to 3') |
|---|---|---|
| PAL_TOM_F | PAL | AACCTATCTCGTGGCTCTTT (SEQ ID NO: 35) |
| PAL_TOM_R | PAL | TCTTTTTCGCTGAATCTTGC (SEQ ID NO: 36) |
| C4H_TO M_F | C4H | CAACAGAAAGGAGAGATCAACGAG (SEQ ID NO: 37) |
| C4H_TOM_R | C4H | CACAGCCTGAAGGTATGGAAGC (SEQ ID NO: 38) |
| 4CL_TOM_F | 4CL | ACACACAAAGGCTTAGTCACGA (SEQ ID NO: 39) |
| 4CL_TOM_R | 4CL | AACAGAGGCAACACACACATCA (SEQ ID NO: 40) |
| CHSTOM_F | CHS | TGGTCACCGTGGAGGAGTATC (SEQ ID NO: 41) |
| CHS_TOM_R | CHS | GATCGTAGCTGGACCCTCTGC (SEQ ID NO: 42) |
| CHI_TOM_F | CHI | GTTTTTCACAAACCAACAGTTCTGAT (SEQ ID NO: 43) |
| CHI_TOM_R | CHI | GAAGCAGTGCTCGATTCCATAAT (SEQ ID NO: 44) |
| F3H_TOM_F | F3H | CACACCGATCCAGGAACCAT (SEQ ID NO: 45) |
| F3H_TOM_R | F3H | GCCCACCAACTTGGTCTTGTA (SEQ ID NO: 46) |
| F3'H_TOM_F | F3'H | GCACCACGAATGCACTTGC (SEQ ID NO: 47) |
| F3'H_TOM_R | F3'H | CGTTAGTACCGTCGGCGAAT (SEQ ID NO: 48) |
| F3'5'H_TOM_F | F3'5'H | GGCAATTGGACGAGATCCTG (SEQ ID NO: 49) |
| F3'5'H_TOM_R | F3'5'H | AAGGAACCTCTCGGGAGTGAA (SEQ ID NO: 50) |
| FLS_TOM_F | FLS | GAGCATGAAGTTGGGCCAAT (SEQ ID NO: 51) |
| FLS_TOM_R | FLS | TGGTGGGTTGGCCTCATTAA (SEQ ID NO: 52) |
| DFR_TOM_F | DFR | TCCGAAGACGACAACGGTTT (SEQ ID NO: 53) |
| DFR_TOM_R | DFR | TGACAAGCCAAGAGCCGATAA (SEQ ID NO: 54) |
| ANS_TOM_F | ANS | GAACTAGCACTTGGCGTCGAA (SEQ ID NO: 55) |
| ANS_TOM_R | ANS | TTGCAAGCCAGGCACCATA (SEQ ID NO: 56) |
| GT_TOM_F | GT | CGAACGACGAAACACTGTTGA (SEQ ID NO: 57) |
| GT_TOM_R | GT | TGCAGCATAGATGGCATTGG (SEQ ID NO: 58) |
| RT_TOM_F | RT | CTGGCAATGCAAACAGAGTGA (SEQ ID NO: 59) |

TABLE S3-continued

Primers used for real-time RT-PCR of structural genes in phenylpropanoid biosynthetic pathway in tomato.

| Primer | Gene | Sequence (5' to 3') |
|---|---|---|
| RT_TOM_R | RT | TCGACTTGCGGAAGAGTGAGA (SEQ ID NO: 60) |
| C3H_TOM_F | C3H | CATAAACTCTACCACCGTCTCC (SEQ ID NO: 61) |
| C3H_TOM_R | C3H | AATCCATCCCATTTCTACTCAA (SEQ ID NO: 62) |
| HCT_TOM_F | HCT | AGGTGAAAAACTCAACGATGGT (SEQ ID NO: 63) |
| HCT_TOM_R | HCT | ACACTAGGCGTGTGGAAATTAG (SEQ ID NO: 64) |
| HQT_TOM_F | HQT | GTGTTTTGTTTGTTGAGGCTGA (SEQ ID NO: 65) |
| HQT_TOM_R | HQT | TGATGAAGTGGATGGATGAGAG (SEQ ID NO: 66) |
| ASR1_TOM_F | ASR1 | CCTGTTCCACCACAAGGACAA (SEQ ID NO: 67) |
| ASR1_TOM_R | ASR1 | GTGCCAAGTTTACCGATTTGC (SEQ ID NO: 68) |

REFERENCES CITED IN THIS EXAMPLE

Ackland, M. L., van de Waarsenburg, S., & Jones, R. (2005) *In Vivo* 19, 69-76.

Arima, H., Ashida, H., & Danno, G. (2002) *Biosci Biotechnol Biochem* 66, 1009-1014.

Asian, M., Orhan, D. D., Orhan, N., Sezik, E., & Yesilada, E. (2007) *J Med Food* 10, 396-400.

Bevan, M. (1984) *Nucl Acids Res* 12, 8711-8721.

Bovy, A., de Vos, R., Kemper, M., Schijlen, E., Almenar Pertejo, M., Muir, S., Collins, G., Robinson, S., Verhoeyen, M., Hughes, S., et al. (2002) *Plant Cell* 14, 2509-2526.

Braganhol, E., Zamin, L. L., Canedo, A. D., Horn, F., Tamajusuku, A. S., Wink, M. R., Salbego, C., & Battastini, A. M. (2006) *Anticancer Drugs* 17, 663-671.

Cheng, J. C., Dai, F., Zhou, B., Yang, L., & Liu, Z. L. (2007) *Food Chem* 104, 132-139.

Choi, J., Park, J. K., Lee, K. T., Park, K. K., Kim, W. B., Lee, J. H., Jung, H. J., & Park, H. J. (2005) *J Med Food* 8, 348-352.

Davuluri, G. R., van Tuinen, A., Fraser, P. D., Manfredonia, A., Newman, R., Burgess, D., Brummell, D. A., King, S. R., Palys, J., Uhlig, J., et al. (2005) *Nat Biotechnol* 23, 890-895.

Ditta, G., Stanfield, S., Corbin, D., & Helinski, D. R. (1980) *Proc Natl Acad Sci USA* 77, 7347-7351

Feng, R., Lu, Y., Bowman, L. L., Qian, Y., Castranova, V., & Ding, M. (2005) *J Biol Chem* 280, 27888-27895.

Fillatti, J. J. (1987) *Bio Technol* 5, 726-730.

Frohman, M. A., Dush, M. K., & Martin, G. R. (1988) *Proc Natl Acad Sci USA* 85, 8998-9002.

Giovinazzo, G., D'Amico, L., Paradiso, A., Bollini, R., Sparvoli, F., & DeGara, L. (2005) *Plant Biotechnol J* 3, 57-69.

Guerineau, F. & Mullineaux, P. (1993) in *Plant Molecular Biology Labfax*, ed. Croy, R. R. D. (BIOS Scientific Publishers Ltd, Oxford), pp. 121-147.

Hertog, M. G., Feskens, E. J., Hollman, P. C., Katan, M. B., & Kromhout, D. (1993) *Lancet* 342, 1007-1011.

Horsch et al., (1985) *Science* 227, 1229-1231.

Hou, D. X., Fujii, M., Terahara, N., & Yoshimoto, M. (2004) *J Biomed Biotechnol* 2004, 321-325.

Howles, P. A., Sewalt, V., Paiva, N. L., Elkind, Y., Bate, N. J., Lamb, C., & Dixon, R. A. (1996) *Plant Physiol* 112, 1617-1624.

Islam, M. S. (2003) *J Am Soc Hortic Sci* 128, 182-187.

Islam, S. (2006) *J Food Sci* 71, R13-R21.

Iusem, N. D., Bartholomew, D. M., Hitz, W. D., & Scolnik, P. A. (1993) *Plant Physiol* 102, 1353-1354.

Jones, D. T., W. R. Taylor and J. M. Thornton. (1992). *Computer Applications in the Biosciences (CABIOS)* 8: 275-282.

Joseph, J. A., Shukitt-Hale, B., Denisova, N. A., Bielinski, D., Martin, A., McEwen, J. J., & Bickford, P. C. (1999) *J Neurosci* 19, 8114-8121.

Kim, S. S., Park, R. Y., Jeon, H. J., Kwon, Y. S., & Chun, W. (2005) *Phytother Res* 19, 243-245.

Knekt, P., Kumpulainen, J., Jarvinen, R., Rissanen, H., Heliovaara, M., Reunanen, A., Hakulinen, T., & Aromaa, A. (2002) *Am J Clin Nutr* 76, 560-568.

Luo, J., Nishiyama, Y., Fuell, C., Taguchi, G., Elliott, K., Hill, L., Tanaka, Y., Kitayama, M., Yamazaki, M., Bailey, P., et al. (2007) *Plant J* 50, 678-695.

Martin, C., Carpenter, R., Sommer, H., Saedler, H., & Coen, E. S. (1985) *Embo J* 4, 1625-1630.

Matsui, T., Ebuchi, S., Fujise, T., Abesundara, K. J., Doi, S., Yamada, H., & Matsumoto, K. (2004) *Biol Pharm Bull* 27, 1797-1803.

Mehrtens, F., Kranz, H., Bednarek, P., & Weisshaar, B. (2005) *Plant Physiol* 138, 1083-1096.

Moco, S., Bino, R. J., Vorst, O., Verhoeven, H. A., de Groot, J., van Beek, T. A., Vervoort, J., & de Vos, C. H. (2006) *Plant Physiol* 141, 1205-1218.

Muir, S. R., Collins, G. J., Robinson, S., Hughes, S., Bovy, A., Ric De Vos, C. H., van Tunen, A. J., & Verhoeyen, M. E. (2001) *Nat Biotechnol* 19, 470-474.

Nakajima, Y., Shimazawa, M., Mishima, S., & Hara, H. (2007) *Life Sci* 80, 370-377.

Niggeweg, R., Michael, A. J., & Martin, C. (2004) *Nat Biotechnol* 22, 746-754.

Nijveldt, R. J., van Nood, E., van Hoorn, D. E., Boelens, P. G., van Norren, K., & van Leeuwen, P. A. (2001) *Am J Clin Nutr* 74, 418-425.

Pellegrini, N. (1999) *Methods Enzymol* 299, 379-389.

Raffo, A., Leonardi, C., Fogliano, V., Ambrosino, P., Salucci, M., Gennaro, L., Bugianesi, R., Giuffrida, F., & Quaglia, G. (2002) *J Agric Food Chem* 50, 6550-6556.

Rein, D., Schijlen, E., Kooistra, T., Herbers, K., Verschuren, L., Hall, R., Sonnewald, U., Bovy, A., & Kleemann, R. (2006) *J Nutr* 136, 2331-2337.

Renaud, S. & de Lorgeril, M. (1992) *Lancet* 339, 1523-1526.

Rigano, D., Formisano, C., Basile, A., Lavitola, A., Senatore, F., Rosselli, S., & Bruno, M. (2007) *Phytother Res* 21, 395-397.

Saitou, N., and M. Nei. (1987). *Molecular Biology and Evolution* 4: 406-425.

Schijlen, E., Ric de Vos, C. H., Jonker, H., van den Broeck, H., Molthoff, J., van Tunen, A., Martens, S., & Bovy, A. (2006) *Plant Biotechnol J* 4, 433-444

Seeram, N. P., Adams, L. S., Hardy, M. L., & Heber, D. (2004) *J Agric Food Chem* 52, 2512-2517.

Soobrattee, M. A., Bahorun, T., & Aruoma, O. I. (2006) *Biofactors* 27, 19-35.

Stracke, R., Ishihara, H., Huep, G., Barsch, A., Mehrtens, F., Niehaus, K., & Weisshaar, B. (2007) *Plant J* 50, 660-677.

Szalma, S. J., Buckler, E. S. t., Snook, M. E., & McMullen, M. D. (2005) *Theor Appl Genet.* 110, 1324-1333.

Tamura, H., Akioka, T., Ueno, K., Chujyo, T., Okazaki, K., King, P. J., & Robinson, W. E., Jr. (2006) *Mol Nutr Food Res* 50, 396-400.

Thompson, J. D., Higgins, D. G. and Gibson, T. J. (1994) *Nucleic Acids Research,* 22:4673-4680.

Zhang, P. F., Wang, Y. B., Zhang, J. B., Maddock, S., Snook, M., & Peterson, T. (2003) *Plant Mol Biol* 52, 1-15.

Zhou, B., Yang, L., & Liu, Z. L. (2004) *Chem Phys Lipids* 131, 15-25.

Example 2

Ectopic Production of Anthocyanins Results in Purple Tomatoes with Increased Antioxidant Capacity and Extended Shelf Life As part of the human diet, flavonoids offer protection against a broad range of human diseases. Consumption of foods containing high levels of flavonoids is associated with a lower risk of cancer, cardiovascular and neurological diseases.

Anthocyanins represent a subset of flavonoids with particularly high antioxidant capacity, and concomitantly strong health-promoting effects. With the objective of producing fruit with high levels of anthocyanins, we expressed two transcription factors from snapdragon in tomato fruit. Expression of the two genes together caused an increase in the expression of all the genes committed to anthocyanin biosynthesis and resulted in fruit which displayed an intense purple coloration in both peel and flesh. Anthocyanins accumulated at levels significantly higher than anything previously reported and enhanced the antioxidant capacity three-fold. High flavonoid fruit were associated with delayed ripening, resistance to opportunistic infection and, consequently, a considerably longer shelf life.

In any attempt to improve crops through metabolic engineering, the amounts of target metabolites induced are of primary importance. For applications, changes in flux need to be large, meaning that much of the metabolic engineering that has been reported for crop plants has not yet been applied successfully. Anthocyanins are pigments produced by most higher plants. As part of the human diet they offer protection against cardiovascular disease, certain cancers and age-related degenerative diseases (1-4). There is evidence that anthocyanins also have anti-inflammatory activity (5), promote visual acuity (6), and hinder obesity and diabetes(7). The health-promoting role of anthocyanins has been linked to their high antioxidant activities (8) although recent reports suggest that some of the biological effects of anthocyanins and flavonoids are actually related to their ability to modulate mammalian cell signalling pathways (9, 10). However all these effects are dependent on relatively high levels of dietary flavonoids.

Figures from the National Cancer Institute of America (11) argue strongly for the development of strategies to increase the levels of health-promoting bioactive compounds such as anthocyanins in the fruits and vegetables that people actually consume in significant amounts.

Tomato is an excellent candidate for enhancement of its flavonoid content. It is an important food crop worldwide and its levels of flavonoids are considered sub-optimal, with only small amounts of naringenin chalcone and rutin accumulating in tomato peel (12). Flavonoids represent an important source of hydrophilic dietary antioxidants, whereas the most abundant antioxidant in tomato fruit is lycopene, a lipophilic antioxidant. Generally, foods rich in both soluble and membrane-associated antioxidants are considered to offer the best protection against disease.

Although most tomato cultivars do not produce anthocyanins in fruit, low and light-dependent accumulation of anthocyanins in sectors of the skin has been achieved by introgression of a trait from a wild relative of tomato (13). Genetic engineering strategies have also provided modest success. Silencing of the tomato DET1 gene which represses photomorphogenesis, resulted in increases in flavonoid levels of up to 3.5-fold (14). Constitutive, high-level activity of chalcone isomerase (CHI) in tomato resulted in up to 78-fold increases in the levels of flavonols in fruit peel (12). However, because peel accounts for only about 5% of fruit mass, the total levels were no more than 300 µg per g fresh weight.

Generally, transcription factors that regulate the expression of the genes involved in entire metabolic pathways provide the most effective tools for engineering metabolic flux (15, 16). Consequently, overexpression of a gene encoding a transcription factor that regulates anthocyanin production in tomato resulted in limited purple spotting on the skin and pericarp (17). However, overexpression of Lc and C1, two regulatory genes that encode transcription factors that control anthocyanin biosynthesis in maize, resulted in tomato fruit containing increased levels of flavonols (130 µg per g fresh weight) but no anthocyanins (18).

While regulatory proteins offer the greatest potential to enhance anthocyanin biosynthesis, their specificity may differ in different plant species. Differences in their efficacy in inducing anthocyanin production and in their target gene specificity have been reported (19-22), and may explain the lack of anthocyanin production following expression of Lc and C1 in tomato fruit (18).

With the objective of producing tomato fruit with significantly elevated levels of anthocyanins by harnessing the broad target specificity of selected transcription factors, we have expressed the Delila (Del) and Rosea1 (Ros1) genes from *A. majus* in the fruit of transgenic tomatoes. Del encodes a basic helix-loop-helix transcription factor and Ros1 encodes a MYB-related transcription factor (20, 23). See materials and methods section at the end of this example.

A binary vector was constructed containing the Del and Ros1 cDNAs each under the control of the fruit-specific E8 promoter (FIG. 10.1A). Tomato leaf discs (*Solanum lycopersicum* cv. Micro-Tom) were transformed with the construct and four primary transformants were investigated in detail; designated Del/Ros1 lines C, N, Y and Z. The presence of the transgenes was confirmed by both DNA gel blots and PCR analysis of genomic DNA. The transgenes were inherited stably in later generations and could be transferred to other genetic backgrounds with no loss of phenotype (Money Maker, Ailsa Craig and VF36) by cross-pollination (FIG. 10.5).

Del/Ros1 primary transformants developed normally during vegetative growth and were indistinguishable from controls. Stems and leaves showed no abnormal anthocyanin accumulation. Transgenic fruit developed normally and started to show visible signs of purple pigmentation at the end of the mature green stage (FIG. 10.1B). Pigmentation matched the expression pattern of the E8 gene (24) and intensified rapidly in the few days after its onset, initially associated with the vascular tissue but quickly extending to peel, pericarp and inner flesh (FIGS. 10.1, C and D). At maturity, the different transgenic tomato lines showed a range of phenotypes, with medium (Del/Ros1Z), strong (Del/Ros1C and Del/Ros1Y) or very strong accumulation of anthocyanin (Del/Ros1N). Fruit from plants of the $T_1$ and $T_2$ generations showed more intense pigmentation than those from the $T_0$ generation. For line Del/Ros1N, the highest pigment accumulator, fruit from plants of the $T_1$, $T_2$ and $T_3$ generations were almost black.

The total anthocyanin content was determined in the fruit of the $T_0$ Del/Ros1 lines and compared to those in wild type Micro-Tom fruit (FIG. 10.6A). The highest concentrations were found in the fruit of line N, which averaged 2.83±0.46 mg of anthocyanin per g fresh weight. Anthocyanins were virtually undetectable in wild type fruit. Ripe tomatoes from both transgenic Del/Ros1N and wild type lines were harvested and peel and flesh were analyzed separately by HPLC for their phenylpropanoid contents (FIG. 10.2). High levels of anthocyanins were detected in both peel and flesh of purple fruit (FIGS. 10.2, A and B). The major anthocyanins were 3,5-diglucosides acylated with cinnamic acids (FIGS. 10.2C and 10.7). In peel of purple fruit several methanol-soluble phenolic compounds were detected that were barely detectable in peel of wild type tomatoes (FIG. 10.2D) including the main natural flavonol, rutin, and other flavonol derivatives (FIG. 10.2, D and F). There were no increases in flavonols in the flesh of transgenic tomatoes (FIG. 10.2E). Comparative HPLC data showed that the same anthocyanins and flavonols accumulated in all four independent lines (FIGS. 10.6, B and C).

The alterations in gene expression induced by Del and Ros1 in fruit from line N were determined by comparison to control fruit by suppression subtractive hybridization (SSH). Differentially expressed genes in tomato fruit are listed in table 2.S1. Expression of Del and Ros1 increased the transcript levels of almost all of the genes encoding anthocyanin biosynthetic enzymes and genes encoding enzymes required for side-chain modification; a putative anthocyanin acyltransferase and two genes likely involved in the transport of anthocyanins into the vacuole including a putative anthocyanin transporter.

The differential expression of the genes identified by SSH was validated by RNA gel blot hybridization (FIG. 10.3A), which was also used to verify the expression of Del and Ros1 and to demonstrate the induction of expression of the gene encoding flavanone 3-hydroxylase (F3H) by Del and Ros1, since this gene was not isolated by SSH. With the exception of PAL, there was no detectable expression of any of these genes in wild type tomato fruit. The induction of expression of these anthocyanin biosynthetic genes was confirmed by micro-array analysis for all the independent transformed lines (table 2.S2). The induction of PAL expression by Del and Ros1 significantly enhanced PAL enzyme activity, increasing it 200-fold in Del/Ros1 line N (FIG. 10.3C). The transcription factors also increased chalcone isomerase (CHI) activity three-fold, but only transiently during fruit development (FIG. 10.8)

Changes in total antioxidant activity between transgenic and wild type tomato fruit was measured using the trolox equivalent antioxidant capacity (TEAC). In Del/Ros1N fruit the activity of the water-soluble fraction (containing anthocyanins) was increased 3-fold compared to the control (FIG. 10.3D) and was not obtained at the expense of the lipo-soluble antioxidants (extracted with acetone). The increase in antioxidant activity in line C was less pronounced, but still significantly higher than controls (FIG. 10.3D).

Fruit from Del/Ros1 line N had normal size, shape and number of seeds. However, fruit from this line exhibited delayed softening when compared to control fruit. This was apparent from the appearance of the fruit both on the vine and during post-harvest storage (FIG. 10.4A) and the reduced level of opportunistic fungal infection of fruit under either condition (FIG. 10.4B). To confirm these striking visual observations, purple and red fruit in two genetic backgrounds—Micro-Tom and fruit obtained by crossing Del/Ros1N with tomato cv. Money Maker—were compared in a series of mechanical property tests. Tensile tests revealed significant differences in strength and stiffness between purple and red tomatoes for skin (Table 2.S3). Tomato lines expressing Del and Ros1 had significantly stiffer and stronger fruit skin than control fruit ($p<0.01$). Cutting and compression tests on cut halves of the same tomatoes, for which the flesh is the major component, were less conclusive, although purple Micro-Tom tomatoes were significantly firmer than red Micro-Tom tomatoes, at $p<0.01$ and $<0.04$ respectively.

To test whether the extended shelf life was specific to tomatoes accumulating anthocyanins, Del/Ros1N was crossed to aw mutants in two different genetic backgrounds (Ailsa Craig and VF36). aw mutants lack DFR activity and can not make anthocyanins(25). In the $F_2$ generation of both crosses plants, harbouring the transgene and lacking DFR activity were selected. These plants produced orange fruit which accumulated high levels of kaempferol, quercetin and myricetin glycosides (FIG. 10.9). Measurement of antioxidant capacities showed that the orange fruit had antioxidant capacities that were two-fold higher than for the parental aw lines although TEAC values were never as high as for purple fruit segregating in the same population (FIG. 10.4E). The lower antioxidant capacities of the orange fruit compared to the purple fruit probably reflect the lower intrinsic antioxidant capacities of dihydroflavonols compared to anthocyanins. Most strikingly, orange, high flavonol tomatoes also had markedly extended shelf lives compared to parental lines (FIG. 10.4D).

Longer shelf life, associated with slower fruit softening, integrity of stored fruit, ease of transportation and resistance to post-harvest pathogens, is probably the most important trait for commercially-grown tomatoes. Since neither cell wall phenolics nor lignin composition were significantly increased in purple fruit (FIG. 10.10), it is possible that slower fruit softening is the result of delayed ripening from the breaker stage in transgenic fruit. To test this possibility, expression of two genes that are markers for different stages of fruit development (26) was compared in purple and red fruit aged by date of reaching the breaker stage. For the genes encoding phytoene synthase (PSY) and S-adenosyl-L methionine synthase 1 (SAM1), ripening related expression changes were slowed relative to controls (FIG. 10.11A).

Production of ethylene, required for full ripening in climacteric fruit such as tomato, was transiently increased 2-fold in purple transgenic fruit compared to controls (FIG. 10.11), suggesting that the effects of elevated flavonoids on fruit ripening were not due to reduced ethylene production. Confirming this, application of exogenous ethylene to detached fruits was unable to restore the normal rate of softening to Del/Ros1 fruit.

As an alternative explanation, we suggest an ethylene-independent mechanism where ripening is slower in high flavonoid fruit because of their increased antioxidant capacity. The levels of reactive oxygen species (ROS) do increase markedly in the later stages of tomato ripening and are needed to facilitate many of the metabolic changes associated with maturation of tomato fruit (27). Accordingly, cultivars with short shelf life show reduced scavenging ability and associated increases in oxidative stress (28). We suggest that the significant elevation in the antioxidant capacities achieved by increasing flavonoid biosynthesis (with the accumulation of either dihydroflavonols or anthocyanins) reduces the tissue-damaging activity of ROS and delays the final stages of ripening, resulting in the marked extension in shelf life of the transgenic tomatoes. Increases in polyamines have also been reported to extend shelf life of tomatoes (29), and may achieve their effects through their activities as antioxidants. The increased production of antimicrobial phenolic intermediates in Del/Ros1 tomatoes, may explain the reduced levels of opportunistic infection of these fruit (30).

Our study demonstrates that expression of the specific anthocyanin-regulating transcription factors, Del and Ros1, induces the accumulation of unprecedentedly high levels of anthocyanins. The reasons underlying the success of this regulatory combination are multifold. Firstly, expression of both the MYB and the bHLH transcription factors gives rise to much higher levels of gene induction throughout all the tissues of the fruit, in contrast to expression of either the MYB or the bHLH protein on its own (17, 31). Secondly, Del and Ros1 activate a broader spectrum of genes in the phenylpropanoid/flavonoid pathway than Lc and C1 in tomato. PAL transcript levels and enzyme activity were increased very significantly by Del and Ros1 in contrast to the effects of Lc and C1 (18). There are several reports that PAL activity determines flux through phenylpropanoid metabolism in Solanaceous species (32,33) and the effects of Del and Ros1 on PAL activity may explain the very high levels of anthocyanins that accumulated in Del/Ros1 tomato fruit. Thirdly, Del and Ros1 induced CHI activity which Lc and C1 did not (18). Since CHI activity may limit the flux through flavonoid metabolism in tomato skin (12), the ability of Del and Ros1 to induce the activity of this enzyme may also have contributed to the high levels of anthocyanin or dihydroflavonol accumulation achieved. Fourthly, Del/Ros1 activated F3'5'H whereas Lc/C1 failed to activate the expression of this gene meaning that dihydrokaempferol rather than dihydromyricetin would have been formed as an intermediate in flavonoid biosynthesis. In Solanaceous species, DFR is specific for dihydromyricetin and will not accept dihydrokaempferol as a substrate, which may explain why Lc and C1 failed to induce anthocyanin accumulation in tomato fruit (18).

The high anthocyanin tomatoes already developed represent a registered food source for extraction of high levels of purple anthocyanins. Crude extraction can be achieved very easily by squeezing the tomatoes. The crude extracts of the purple tomatoes have a good color (stronger and more blue than that of purple sweet potato) but they are less stable than the sweet potato anthocyanins.

In terms of improving the color of the anthocyanins and giving stronger blues, a high flavonol, high anthocyanin tomato has been developed (AtMYB12/Del/Ros1) which is more intensely colored with a pigment that is far bluer than with anthocyanins on their own (indigo as compared to purple; FIG. 10.12). This is due to the copigmentation effect of the flavonols in combination with the anthocyanins. These tomatoes represent an excellent source of this new color which would be easy to extract for preparation of food colorants. Alternatively the anthocyanins and flavonols could be prepared separately from the lines producing high levels of each, and then mixed, post extraction, to develop the color required.

Our results show that selective use of transcription factors with broad target specificity can achieve very significant increases in flux along secondary metabolic pathways in plants. They also shed new light on the processes involved in the later stages of fruit ripening in tomato and, unexpectedly, positively impact an important quality trait as well as providing health-promoting fruit in this important crop.

TABLE 2.S1

Genes upregulated in Del/Ros1N tomato fruit.

| Clone | Clone ID (first hit blast X) | accession | E-value | total clones | expression level |
|---|---|---|---|---|---|
| PAL | Phenylalanine ammonia-lyase *Lycopersicon esculentum* | P26600 | 8e−134 | 39 | +++ |
| C3H | Putative p-coumaroyl 3'-hydroxylase CYP98A-C1 *Coffea canephora* | ABB83676.1 | 7e−51 | 1 | ++ |
| CHI (like) | Putative chalcone isomerase 4 *Glycine max* | AAT94362.1 | 4e−48 | 2 | + |
| F3'5'H | Flavonoid 3',5'-hydroxylase *Solanum tuberosum* | AAV85472.1 | 5e−113 | 3 | ++ |
| DFR | Dihydroflavonol reductase *Solanum tuberosum* | AAZ57436.1 | 7e−39 | 2 | + |
| ANS | Leucoanthocyanidin dioxygenase (LDOX) *Petunia × hybrida* | P51092 | 8e−82 | 9 | +++ |
| 3-GT | Flavonoid 3-glucosyl transferase *Solanum tuberosum* | AAX63403.1 | 5e−62 | 6 | ++ |
| 5-GT | Anthocyanin 5-O-glucosyltransferase *Petunia × hybrida* | BAA89009.1 | 5e−39 | 5 | ++ |
| RT | UDP rhamnose: anthocyanidin-3-glucoside rhamnosyltransferase *Petunia × hybrida* | CAA81057.1 | 1e−18 | 1 | ++ |
| AAC | Transferase *Arabidopsis thaliana* | NP_173852.1 | 8e−12 | 2 | ++ |
| GST | Glutathione S-transferase *Petunia × hybrida* | CAA68993.1 | 5e−36 | 10 | ++ |
| PAT | Putative anthocyanin permease *Lycopersicon esculentum* | AAQ55183.1 | 3e−59 | 3 | ++ |
| Defensin | Gamma-thionin *Lycopersicon esculentum* | CAB42006.1 | 3e−37 | 5 | +++ |
| Del | Delila *Antirrhinum majus* | AAA32663.1 | 0.14 | 1 | + | cDNA fragments identified by SSH were cloned and sequenced. The putative identity of the corresponding genes was assigned based on a BLASTX search against the nonredundant protein database in GenBank. Accession numbers and e-values of the best hits are shown. Number of total clones isolated corresponding to individual genes and level of expression in Del/Ros1N tomato fruit, determined by dot blot analysis, are also reported.

TABLE 2.S2

Expression of anthocyanin biosynthetic genes in independent Del/Ros1 lines compared to untransformed controls.

| EST ID | Control 1 | Control 2 | Del/Ros1 Z | Del/Ros1 C | Del/Ros1 Y | Del/Ros1 N | gene |
|---|---|---|---|---|---|---|---|
| (TC84666) phenylalanine ammonia-lyase | −3.92 | −9.32 | −2.19 | 1.48 | 1.57 | 1.75 | PAL |
| (TC93956) cinnamic acid 4-hydroxylase | −1.73 | −2.55 | −1.54 | −1.22 | −1.04 | 1.57 | C4H |
| (TC89693) 4-coumarate--CoA ligase 1 | −1.59 | −1.22 | −1.06 | 1.09 | 1.23 | −1.09 | 4CL |
| (TC86565) chalcone synthase 1 | −2.73 | −4.79 | −1.27 | 2.17 | 1.16 | −1.04 | CHS1 |
| (TC90271) chalcone synthase 2 | −1.60 | −3.07 | 1.16 | 1.01 | 1.06 | 1.01 | CHS2 |
| (TC86916) flavanone 3-hydroxylase | −2.20 | −2.36 | 2.01 | 1.33 | −1.37 | −1.01 | F3H |
| c32-TOM__f3p5ph__ flavonoid 3'5' hydroxylase (tomato) | −1.51 | −1.78 | 2.50 | 1.66 | −1.71 | 4.92 | F3'5'H |
| (c32-TOM__ANS__cont) anthocyanidin synthase (tomato) | −1.53 | −1.14 | −1.22 | 2.06 | −1.24 | 2.08 | ANS |
| (TC90395) flavonol 3-O-glucosyltransferase | −3.20 | −2.89 | −2.36 | 1.61 | 1.39 | −1.84 | F-3-GT |
| (TC91185) anthocyanidin 3-O-glucosyltransferase | −2.23 | −2.10 | 1.27 | 2.85 | −1.46 | 3.34 | A-3-GT |
| (TC89444) anthocyanin 5-O-glucosyltransferase (Petunia) | −3.71 | −4.11 | −1.13 | 1.10 | −1.04 | 1.04 | A-5-GT |

Fold-changes in flavonoid gene expression of non-transgenic and Del/Ros1 overexpressing tomato lines from DNA microarray data are given in relation to a common reference which comprised equal amounts of RNA from all sample types. A negative value indicates a down regulation relative to the common reference and a positive value an up regulation. Controls are untransformed wild type Micro Tom.

TABLE 2.S3

Expression of Del and Ros1 delays softening of tomato fruit.

| a | E (MPa) | p | n = | σ (MPa) | p | n = |
|---|---|---|---|---|---|---|
| Average purple big (MM × MT) | 70.9 | 0.009 | 15 | 5.3 | 0.000 | 15 |
| Average red big (MM × MT) | 50.3 | | 15 | 2.9 | | 15 |
| Average purple cherry (MT) | 60.5 | 0.003 | 12 | 4.2 | 0.008 | 12 |
| Average red cherry (MT) | 29.7 | | 12 | 2.6 | | 12 |

Young's modulus, E, and tensile strength, σ, for red and purple tomatoes, averaged over n fruit. Significance levels, p, between red and purple tomatoes are shown in each case. For the larger tomatoes in the Money Maker background, the average value of E was 70.9 Pa for purple fruit compared to 50.3 Pa for red fruit. Likewise, σ for purple tomatoes (5.3 Pa) was significantly greater than for red ones (2.9 Pa). Similar significant differences were observed for red and purple tomatoes in the Micro-Tom background.

REFERENCES AND NOTES CITED IN THIS EXAMPLE

1. S. Renaud, M. de Lorgeril, *Lancet* 339, 1523 (1992).
2. J. A. Joseph et al., *J. Neurosci.* 19, 8114 (1999).
3. N. P. Seeram, L. S. Adams, M. L. Hardy, D. Heber, *J. Agric. Food Chem.* 52, 2512 (2004).
4. D. X. Hou, M. Fujii, N. Terahara, M. Yoshimoto, *J. Biomed. Biotechnol.* 5, 321
5. W. H. Shin, S. J. Park, E. J. Kim, *Life Sci.* 79, 130 (2006).
6. H. Matsumoto, Y. Nakamura, S. Tachibanaki, S. Kawamura, M. Hirayama, *J. Agric. Food Chem.* 51, 3560 (2003).
7. T. Tsuda, F. Horio, K. Uchida, H. Aoki, T. Osawa, *J. Nutr.* 133, 2125 (2003).
8. O. K. Chun, D. O. Kim, C. Y. Lee, *J. Agric. Food Chem.* 51, 8067 (2003).
9. S. Meiers et al., *J. Agric. Food Chem.* 49, 958 (2001).
10. R. J. Williams, J. P. Spencer J P, C. Rice-Evans, *Free Radical Biol. Med.* 36, 838 (2004).
11. Data available at on the world wide web at 5aday.gov.
12. S. R. Muir et al., *Nat. Biotechnol.* 19, 470 (2001).
13. C. M. Jones, P. Mes, J. R. Myers, *J. Hered.* 94, 449 (2003).
14. G. R. Davuluri et al., *Nat. Biotechnol.* 23, 890 (2005).
15. P. Broun, C. Somerville, *Proc. Natl. Acad. Sci. USA*, 98, 8925-8927 (2001)
16 C. Martin, *Curr. Opin. Biotech.* 7, 130-138 (1996).
17. H. Mathews et al., *Plant Cell* 15, 1689 (2003).
18. A. Bovy et al., *Plant Cell* 14, 2509 (2002).
19. C. Martin, A. Prescott, S. Mackay, J. Bartlett, E. Vrijlandt, *Plant J.* 1, 37 (1991).
20. K. Schwinn et al., *Plant Cell* 18, 831-851 (2006).
21. H. K. Dooner, *Mol. Gen. Genet.* 67, 345 (1983).
22. F. Quattrocchio, J. F. Wing, H. Leppen, J. Mol, R. E. Koes, *Plant Cell* 5, 1497 (1993).
23. J. Goodrich, R. Carpenter, E. S. Coen, *Cell* 68, 955 (1992).
24. M. L. Kneissl, J. Deikman, *Plant Physiol.* 112, 537 (1996).
25. A. Goldsborough, F. Belzile, J. I. Yoder, *Plant Physiol.* 105, 491-496 (1994)

26. R. Alba R. et al., *Plant Cell* 17, 2954 (2005).
27. A. Jimenez et al., *Planta* 214, 751 (2002).
28. K. Mondal, N. S. Sharma, S. P. Malhotra, K. Dhawan, R. Singh, *Biol Plantarum* 48, 49 (2004).
29. R. A. Mehta et al., *Nat. Biotechnol.* 20, 613 (2002).
30. E. J. Smid, L. Hendriks, H. A. M. Boerrigter, L. G. M. Garris, *Postharvest Biol. Tech.* 9, 343-350 (1996).
31. M. Mooney et al., *Plant J.* 7, 333 (1995).
32. N. J. Bate et al., *Proc. Natl. Acad. Sci. USA* 91, 7608-7612 (1994).
33. P. A. Howles et al., *Plant Physiol.* 112, 1617-1624 (1996).

Materials and Methods Used for Example 2

Plasmid Construction and Plant Transformation

A binary vector was constructed containing both the Del and Ros1 cDNAs under the control of the fruit-specific E8 promoter from tomato. The E8 promoter was amplified from tomato genomic DNA by PCR with the following primers: E8FK, 5'-GGGGTACCCATCCCTAATGATATTGT-TCACGTAA-3' (SEQ ID NO: 69) and E8RB 5'-CGGG-GATCCGCACTGTGAATGATTAGAATAATTTCT-3' (SEQ ID NO: 70). A DNA fragment was obtained which included 2175 bp upstream of the transcriptional start of the E8 gene and 27 nucleotides of 5' untranslated region. The promoter was cloned using KpnI and BamHI restriction enzyme sites in pJIT60 (S1) to replace the CaMV 35S promoter and in pJAM1500, (pJIT60 containing a Gateway cassette, Invitrogen, Carlsbad, Calif., USA) between the CaMV35S promoter and the CaMVpolyA polyadenylation signal again by replacing the 35S promoter. This resulted in plasmids pE8.60 and pE8.1500 respectively. The region containing E8-Gateway-CaMVpolyA from pE8.1500 was cloned in pSLJ7291, a binary vector containing the nopaline synthase promoter, the neomycin phosphotransferase gene and the octopine synthase polyadenylation sequence (S2). This resulted in plasmid pSLJ.E8.1500. The full-length Del cDNA was amplified by PCR using primers: DELF, 5'-GGG-GACAAGTTTGTACAAAAAAGCAGGCTAC-CATGGCTACTGGTATCCAAAACCAAAAG-3' (SEQ ID NO: 71) and DELR, 5'-GGGGACCACTTTGTACAA-GAAAGCTGGGATCCAACTGCAAGACT-TCATAGTAACTTTCTG-3' (SEQ ID NO: 72) inserted in this plasmid using Gateway recombination technology, resulting in the binary construct pSLJ.E8.DEL. The full-length Ros1 cDNA was amplified with the following primers: ROSF, 5'-CGGGGATCCATGGAAAAGAATTGTCGTG-GAGT-3' (SEQ ID NO: 73) and ROSR, 5'-TCCCCCGGGT-TAATTTCCAATTTGTTGGGCCT-3' (SEQ ID NO: 74) and inserted in the plasmid pE8.60 as a BamHI-SmaI fragment, resulting in plasmid pE8.ROS. After the introduction of a double strand oligonucleotide containing a SalI restriction site in this plasmid, the region containing E8-Ros1 cDNA-CaMVpolyA was cloned as a SalI-XhoI fragment in XhoI-digested and dephosphorylated pSLJ.E8.DEL resulting in the binary construct pDEL.ROS. The binary plasmid pDEL.ROS was transferred to *Agrobacterium* strain LBA4404 by the triparental mating method (S3) Tomato variety Micro-Tom was transformed by *Agrobacterium*-mediated transformation of cotyledons (S4). Four independent transformed lines that showed accumulation of anthocyanin in fruit were generated, and called Del/Ros1 lines C, N, Y and Z. Southern blots and segregation analysis of the T1 generation of each line suggested that line N had 4 copies of the T-DNA inserted at 2 unlinked loci, line C had 3 copies of the T-DNA inserted at 2 unlinked loci, line Y had 2 copies of the T-DNA inserted at 1 locus and line Z had 1 copy of the T-DNA inserted at 1 locus.

Analysis and Identification of Anthocyanins and Phenylpropanoids

To estimate the total concentration of anthocyanins in tomato fruit, anthocyanins were extracted from chopped fruit with 5 ml of acidified (0.3% HCl, v/v) methanol in darkness for 24 h at 4° C. The extraction was repeated three times with 5 ml of acidified methanol shaking the samples for 20 min at room temperature. At the end of the extraction, samples were vortexed and centrifuged for 20 min at 5000×g. The samples were diluted in acidified methanol and the concentration was determined spectrophotometrically at 535 nm. The total amount of anthocyanins was expressed as mg of petunidin-3-(p-coumaroyl rutinoside)-5-glucoside (the main compound identified in Del/Ros1 tomatoes) per g fresh weight, based on an extinction coefficient of 17,000 and a molecular mass of 934 (S5).

For the extraction and HPLC analysis of phenylpropanoid compounds in wild type and Del/Ros1 N tomato fruit, all chemicals were obtained from Fluka (Neu-Ulm, Germany), Roth (Karlsruhe, Germany), Sigma-Aldrich (Munich, Germany), Serva (Heidelberg, Germany) and Merck (Darmstadt, Germany) and were of the highest quality available.

Powdered plant material (100 mg) was extracted with 400 µl of 50% MeOH and 400 µl of 100% MeOH. Phenylpropanoids in the cleared extracts were analysed by HPLC (Alliance, Waters, Eschborn, Germany) combined with a photodiode array detector (996, Waters). Separation was performed by reverse-phase chromatography on an Aqua C18, 5 µm, 4.6×250 mm column (Phenomenex, Aschaffenburg, Germany), maintained at 25° C. The mobile phase was composed of 87% water, 3% ACN and 10% acetic acid (solvent A) as well as 40% water, 50% ACN and 10% acetic acid (solvent B) at a flow rate of 1 ml/min. The gradient was as follows: initial 6% B; 20 min, 20% B; 35 min, 40% B; 40 min, 60% B; 45 min, 90% B; 60 min, 6% B. Absorbance spectra were recorded every 1 s, between 210 and 600 nm, with a bandwidth of 1.2 nm, and chromatograms were acquired at 280 and 535 nm. Data were analyzed using Waters Empower software.

For the identification of the major anthocyanins in Del/Ros1 N tomato fruit, extracts were prepared from 5 g powdered tomato fruit with 50 ml of 50% MeOH and 25 ml of 100% MeOH. The respective extracts were cleared by filtration through paper, combined and finally cleared by filtration through a membrane filter (0.22 µm, Millipore, Schwalbach, Germany). The cleared extract was then concentrated in a rotary evaporator to a final volume of 20 ml. A W600 pump system (Waters) with a preparative HPLC column (X-Bridge MS C18, 5 µm, 10×150 mm, Waters), maintained at 24° C. was used for separation. The mobile phase was composed as described above at a flow rate of 2 ml/min. For elution the following gradient was used: initial 5% B; 80 min, 40% B; 85-90 min, 100% B; 98 min, 5% B. Detection of eluted compounds was as mentioned above. Separated anthocyanins were collected and the fractions were subjected to analytical HPLC analysis as described above for confirmation. For identification the purified substances were subjected to ESI-MS/MS. Samples were injected by a syringe pump in 50% MeOH with 1% formic acid. The nanoscale effluent from the syringe pump was directed to the NanoLockSpray source of a Q/T of Premier hybrid orthogonal accelerated Time-of-Flight (oa-ToF) mass spectrometer (Waters Corporation, MS Technologies Centre, Manchester, UK). The mass spectrometer operated in a positive ion mode with a source temperature of 80° C. and a cone gas flow of 30 l/h. A voltage of approximately 2 kV was applied to the nano flow sample tip. The mass spectra were acquired with the TOF mass analyzer in V-mode of operation and spectra were integrated over 1 s intervals. MS and MS/MS data were acquired in a continuum mode using MassLynx 4.0 software (Waters Corporation, Technologies Centre). The instrument was calibrated with a multi-point calibration using selected fragment ions of the CID of Glu-Fibrinopeptide B (Sigma-Aldrich).

For comparison of individual flavonoids, tomatoes were extracted in 75% aqueous methanol with 10 minutes of sonication. HPLC analysis was performed on a C18 reverse phase HPLC column (Phenomenex Luna, 3 µm, 150×40 mm, 40° C.) with photodiode array detection (type 996, Waters, The Netherlands). A gradient of 5 to 50% acetonitrile in 0.1% tri-fluoro acetic acid was used as the mobile phase. Absorbance spectra (240-600 nm) and retention times of eluting peaks were used for identification by comparison with authentic flavonoid standards (Apin chemicals, Abingdon, UK).

For the identification of acyl moieties, 20 µl of pure anthocyanin fractions were subjected to alkaline hydrolysis with 250 µl 10% KOH for 30 min at room temperature, respectively. The lysate was acidified to pH 1.0 with 250 µl 2 N HCl and the decomposition products were extracted with three volume ethyl acetate. The organic phase was evaporated to dryness and the phenylpropanoids were resuspended in 100 µl of solvent A for HPLC-analysis as described above.

For identification of sugar moieties, 20 µl of pure anthocyanin fractions were subjected to acid hydrolysis with 120 µl 2 M HCL for 30 min at 95° C. in a sealed vial. After cooling of the lysate in an ice bath the aglycones were extracted with 1 ml 1-pentanol. The organic and the water phase were evaporated to dryness. The phenylpropanoids were resuspended in 100 µl of solvent A for HPLC analysis as described above. The sugar moieties were resuspended in 100 µl of water for HPLC-analysis as recommended by DIONEX (S6).

Gene Expression Analysis

Total RNA was extracted from tomato fruit by an established procedure (S7). Samples to be used in SSH were obtained from fruit harvested at the turning, pink and red stages. To minimize the effect of ripening-related genes, minor RNA amounts (11%) extracted from fruit at the breaker and over-ripe stages were also included in the wild type, control RNA pool. PolyA+mRNA was purified from total RNA using mRNA purification kit (Amersham Biosciences, UK) according to the manufacturer's instructions. Approximately 2 µg each of Del/Ros1 N and wild type polyA+mRNA were transcribed into cDNA and further processed according to the protocol supplied with the Clontech PCR-Select cDNA Subtraction Kit. PCR products were cloned using T/A cloning vector (Invitrogen) and used to transform $E.$ Coli cells (DH5α). Two hundred colonies were randomly selected for colony PCR amplification and the reaction products were spotted on four nylon membranes according to the protocol supplied with the Clontech PCR-Select Differential Screening Kit and probed in duplicate with radiolabeled cDNA obtained from either wild type or Del/Ros1 N transgenic Micro-Tom fruit. Clones showing changes in expression between the wild type and transgenic samples were selected for DNA sequencing and validated by Northern blot hybridization. Four identical 1.2% agarose formaldehyde gels where prepared, each containing 15 µg of total RNA extracted from wild type and Del/Ros1 N tomato fruit. The RNA was transferred to nylon membranes and equal RNA loading and transfer were confirmed by methylene blue staining. The membranes were hybridized (S8) with labeled cDNA fragments corresponding to regulated transcripts isolated by SSH and obtained from EcoRI-digested plasmids. The radioactivity on the membranes was detected with a PhosphorImager (Fuji BAS1000) or with Kodak Biomax film (Kodak, New Haven, Conn.). The membranes were stripped after each round of hybridization and exposed to a PhosphorImager to verify complete removal of the probe.

To investigate the expression of ripening-related genes, tomato fruit were tagged at the breaker stage. For Del/Ros1 N tomatoes, only fruit showing a visible break in color from green to tannish-yellow (despite the developing purple pigmentation) were selected. Total RNA was extracted from fruit harvested at 5, 12 and 19 days after tagging using the RNeasy Plant Mini Kit (Qiagen, Stanford, Calif.). For each sample, 4 µg of total RNA were used for Northern blot analysis as described above. Probes corresponding to phytoene synthase (PSY) and S-adenosyl-L-methionine synthase1 (SAM1) were obtained by PCR amplification of wild type double strand cDNA using the following primers: PSYF, 5'-ATGAGTTAGAAGTGAAGCGG-3' (SEQ ID NO: 75) and PSYR, 5'-ATCCCCAGAGCCAAAGCAGCA-3' for PSY, and SAMF, 5'-GTGTCCACGG-GCCATCTGACCA-3' (SEQ ID NO: 77) and SAMR, 5'-GCTCAGGCACAC-CGATGGCA-3' (SEQ ID NO: 78) for SAM1.

DNA Micro-Arrays: Preparation

The PROFOOD oligonucleotide microarray was constructed using 1034 70-mer oligonucleotides (Qiagen Operon), each representing a tomato EST selected by bioinformatic analysis. The 1034 selected ESTs represented genes involved in metabolic and regulatory pathways related to fruit quality and nutritional value. Control oligo's were included for background subtraction and normalisation. Each oligonucleotide was printed four times on amino-silane coated glass slides (Corning BV) by a capillary spotting device (Cartesian Technologies). After printing the slides were air-dried for several days, rehydrated and the DNA was cross-linked using an UV-cross linker at 150 m Joules. The slides were soaked twice in 0.2% SDS for 2 minutes, twice in MQ water for 2 minutes and once in boiling MQ water for 2 minutes. After drying, the slides were rinsed three times in 0.2% SDS for 1 min and once in MQ water for 1 min. Finally the slides were submerged in boiling MQ water for 2 sec.

DNA Micro-Arrays: cDNA Labelling and Hybridisation

Cy3- and CY5-labelled cDNA probes were prepared using 5 µg total RNA with a kit from Genisphere Inc. Hybridsations were performed with CY3-labelled cDNA from duplicate biological samples of each individual Del/Ros1 line, and two control lines compared to a common CY5-labelled reference (i.e. pooled cDNA composed of equal amounts from each individual line).

All micro-arrays were pre-hybridised for 3 hours at 45° C. prior to overnight hybridisation in a 120 µl hybridisation volume. All hybridisation and washing steps were carried out using an automatic hybridisation station (HybArray 12, Perkin Elmer). The slides were dried by centrifugation prior to scanning. Detection of the CY3 and CY5 signals was performed (ScanArray Express HT, Perkin Elmer). Spot identification and signal quantification was performed using Analytical Imaging Station AIS 4.0 software (IMAGING Research inc.)

DNA Micro-Arrays: Data Analysis:

The background levels of signal in the micro-array experiments were calculated from the raw data signals from oligo spots of non-plant origin. The mean values of these were subtracted from all others. Normalisation was carried out against the median for each experiment. For statistical analysis of micro-array data from the different tomato lines, mean values for genes from the biological replicates were used for pair-wise comparison between all values.

Determination of PAL Activity

Samples (300 mg) of frozen tomato fruit were finely ground and homogenized 1:1 (mg/µl) in 100 mM sodium borate buffer, pH 8.8 containing protease inhibitors (Protease Inhibitor Mix HP, Serva, Heidelberg, Germany) and 5 mM 2-mercaptoethanol. Insoluble PVP was added (10% w/w) to minimize oxidative protein loss. After 30 min incubation on ice, the extracts were sonicated (2×30 s) and then centrifuged at 13000×g for 5 min. Protein was quantified using the Bradford protein assay (Sigma-Aldrich, UK) following desalting the extracts by gel filtration on Nap5 columns (GE Healthcare/Amersham Biosciences, Freiburg, Germany). PAL assays were performed (S9) using 100 µl of desalted enzyme extract from the transgenic lines. For the PAL determination from wild type line Micro-Tom, desalted protein extracts were concentrated ten-fold by Ultrafiltration on Microcon Centrifugal Filter Units with cut-off of 10 kDa (Millipore, Schwalbach, Germany). PAL activity was calculated from intervals of linear product formation. The enzymatic product was quantified using authentic t-cinnamic acid as a standard.

Determination of CHI Activity

Naringenin chalcone was chemically prepared from naringenin (Sigma-Aldrich) as described (S10). Samples (1 g) of fresh tomato fruit were finely ground at 4° C. in 3 ml 0.1 M potassium phosphate buffer, pH 7.4 containing 50 mM 2-mercaptoethanol 0.5 g quartz sand and 0.5 g insoluble PVPP. Each extract was centrifuged at 13000×g for 5 min and the supernatant was used in the assay. Protein was quantified using the Bradford protein assay (Sigma-Aldrich, UK). CHI activity was measured spectrophotometrically at 375 nm, a decrease in absorbance indicating a conversion of naringenin chalcone to naringenin. Assays were carried out at 25° C. The reaction mixture contained 1 ml 0.1 M potassium phosphate buffer, pH 7.4, 1 µg/ml BSA and a final concentration of naringenin chalcone of 16 µM. The reaction was started by adding 20-50 µl of the appropriate enzyme preparation. The background rate of spontaneous conversion was subtracted from the enzyme-mediated rate of conversion in all experiments.

Total Antioxidant Activity

Wild type and transgenic tomatoes were washed, deprived of seeds and homogenized in liquid nitrogen in a mortar. One g of the homogenized sample was extracted with 4 ml of water under agitation for 20 min at room temperature, centrifuged at 1000×g for 10 min and the supernatant collected. The extraction was repeated with 2 ml of water and the two supernatants were combined. The pulp residue was reextracted by the addition of 4 ml of acetone under agitation for 20 min at room temperature, centrifuged at 1000×g for 10 min and the supernatant collected. The extraction was repeated with 2 ml of acetone and the two supernatants were combined. Tomato extracts were immediately analyzed for their antioxidant capacity. The trolox equivalent antioxidant capacity (TEAC), based on the ability of antioxidant molecules to quench the long-lived ABTS [2,2'-azinobis(3-ethylbenzthiazoline-6-sulfonate), Sigma-Aldrich, UK] radical cation, a blue-green chromophore with characteristic absorption at 734 nm, compared with that of trolox (6-hydroxy-2,5,7,8-tetramethylchroman-2-carboxylic acid, Fluka, Germany), a water-soluble vitamin E analog, was determined (S11). Results were expressed as TEAC in mmol of trolox per kg of fresh weight.

Mechanical Properties

For the analysis of tomato skin, a rectangular piece of skin (width, 3 mm) was removed horizontally from the equatorial area of the tomato. Each extremity of the piece was glued (Cyanoacrylate) on a stainless steel tab to give a sample length of 35 mm and the two tabs were positioned in the tensile grips of a universal test machine (Stable Microsystems, Godalming, Surrey, TAXT2) using a transfer jig. Care was taken so as not to tear and to damage the skin whilst excising and preparing the sample. The test-speed was 0.3 mm/sec. The Youngs modulus, E, and strength, σ, were approximated from the formulae for uniaxial specimens:

$$E = \frac{dF}{dx} * \frac{\text{length}}{\text{thickness} * \text{width}}$$

$$\sigma = \frac{F\text{max}}{\text{thickness} * \text{width}}$$

where dF/dx is the slope of the initial linear force (F)–displacement (x) curve and $F_{max}$ is the sample breaking force.

For the analysis of whole tomato fruit, a razor blade was attached to a vice on the crosshead of the test machine. Cutting was carried out with a test speed of 0.1 mm/sec on halved tomatoes with the cut surface in contact with the base plate. The other half of tomato from the cutting test was compressed, again with cut surface in contact with the base plate, at a crosshead speed of 0.1 mm/sec between parallel plates (diameter, 100 mm).

Ethylene Measurements and Treatment

Ethylene was measured from fruit harvested at or just before the breaker stage. Fruit were sealed in airtight tubes for 20 h after which a 1 mL sample of the headspace was taken and injected into a gas chromatograph (Shimadzu model GC-14B, Kyoto, Japan) equipped with a flame ionization detector. Samples were compared to a standard of known concentration and normalized for fruit mass. For ethylene treatment, wild type and Del/Ros1 N ripe tomato fruit were placed together in a sealed chamber and gassed with 25 µL/L ethylene or air. After two and four weeks, fruit were manually inspected for firmness.

Determination of Lignin

The content of lignin was determined as the thioglycolate derivative according to the protocol described (S12). Recovery rates for each individual experiment were determined by analyzing parallel samples with appropriate amounts of authentic lignin (Sigma).

References Cited in Materials and Methods Section of this Example

1 F. Guerineau, P. Mullineaux, Plant transformation and expression vectors. In Croy, R. R. D. (ed.), Plant Molecular Biology Labfax. BIOS Scientific Publishers Ltd, Oxford, UK, pp. 121-147 (1993).
2 K. E. Hammond-Kosack, S. Tang, K. Harrison, J. D. Jones, *Plant Cell* 10, 1251 (1998).
3 G. Ditta, S. Stanfield, D. Corbin, D. R. Helinski, *Proc. Natl. Acad. Sci. USA.* 77, 7347 (1980).
4 J. J. Fillatti, J. Kiser, R. Rose, L. Comai, *Bio. Technol.* 5, 726 (1987).
5 C. L. Price, R. E. Wrolstad, *J. Food Sci.* 60, 369 (1995).
6 Application Note 82: Analysis of fruit juice adulterated with medium invert sugar from beets, Method B, DIONEX.
7 S. Chang, J. Puryear, J. Cairney, *Plant Mol. Biol. Rep.* 11, 113 (1993).
8 Current Protocols in Molecular Biology, John Wiley & Sons, Inc. 4.9.1-4.9.8 (1997).
9 A. Matros et al., Plant, *Cell Environ.* 29, 126 (2006).
10 E. Moustafa, E. Wong, *Phytochemistry* 6, 625 (1967).

11 N. Pellegrini, R. Re, M. Yang, C. A. Rice-Evans, *Methods. Enzymol.* 299, 379 (1999).

12 M. M. Campbell, B. E. Ellis, *Planta* 196, 409 (1992).

Example 3

Tobacco Transformation with ROSEA1

This example provides a variation of the work disclosed above in which tomato fruit with significantly elevated levels of anthocyanins was produced by harnessing the broad target specificity of selected transcription factors, via expression of the Della (Del) and Rosea1 (Ros1) genes from *A. majus* in the fruit of transgenic tomatoes. In this example, Ros1 was cloned and transformed alone into tobacco. The Ros 1 cDNA (Schwinn et al, 2006, *The Plant Cell,* 18, 831-851) was inserted between the double 35S promoter from CaMV and the CaMV Terminator in pJIT 60 (Gerineau and Mullineaux, 1993, in *Plant Molecular Biology Labfax*, ed. Croy, R. R. D. (BIOS Scientific Publishers Ltd, Oxford), pp. 121-147.). This gene construct was inserted as a KpnI/XhoI fragment into the KpnI and SalI sites of pBin19 (Bevan, 1984, *Nucl Acids Res* 12, 8711-8721.). The T-DNA of this binary vector was transformed into tobacco using *Agrobacterium tumifaciens*, LBA4404.

In FIG. 11.1, we show that utilizing this strategy, it was possible to generate and identify transformed tobacco material due to induction of anthocyanin production only in the transformed tissue.

Example 4

Provision of Tomato Homologue of AtMYB12

The tomato EST database was searched for sequences homologous to AtMYB12 and the EST (TC172990) with the highest sequence similarity to AtMYB12 was used to identify a full-length cDNA from tomato fruit using 3'RACE PCR[5]. Total RNA was isolated and first-strand cDNA was synthesized. The 3' end of the cDNA was amplified using oligonucleotides: 5'-ATGGGAAGAACACCTTGTTG-3' (SEQ ID NO: 29) and the 3' adaptor sequence, 5' GACTCGAGTC-GACATCG-3'(SEQ ID NO: 30). The amplified sequence was cloned into pGEM-T easy and sequenced. The full-length cDNA was then reamplified using the forward oligo 5'-ATGGGAAGAACACCTTGTTG-3' (SEQ ID NO: 31) and the reverse oligo 5'-CTAAGACAAAAGCCAAGATA-CAA-3' (SEQ ID NO: 32) based on the 3' sequence amplified by 3'-RACE. The sequence for SlMYB12 has been submitted to the EMBL database with the accession number EU419748 (embargoed).

The sequence of the cDNA and expressed polypeptide are shown in SEQUENCE ANNEX I (SEQ ID NO: 11 and 12, respectively).

Figure 7:
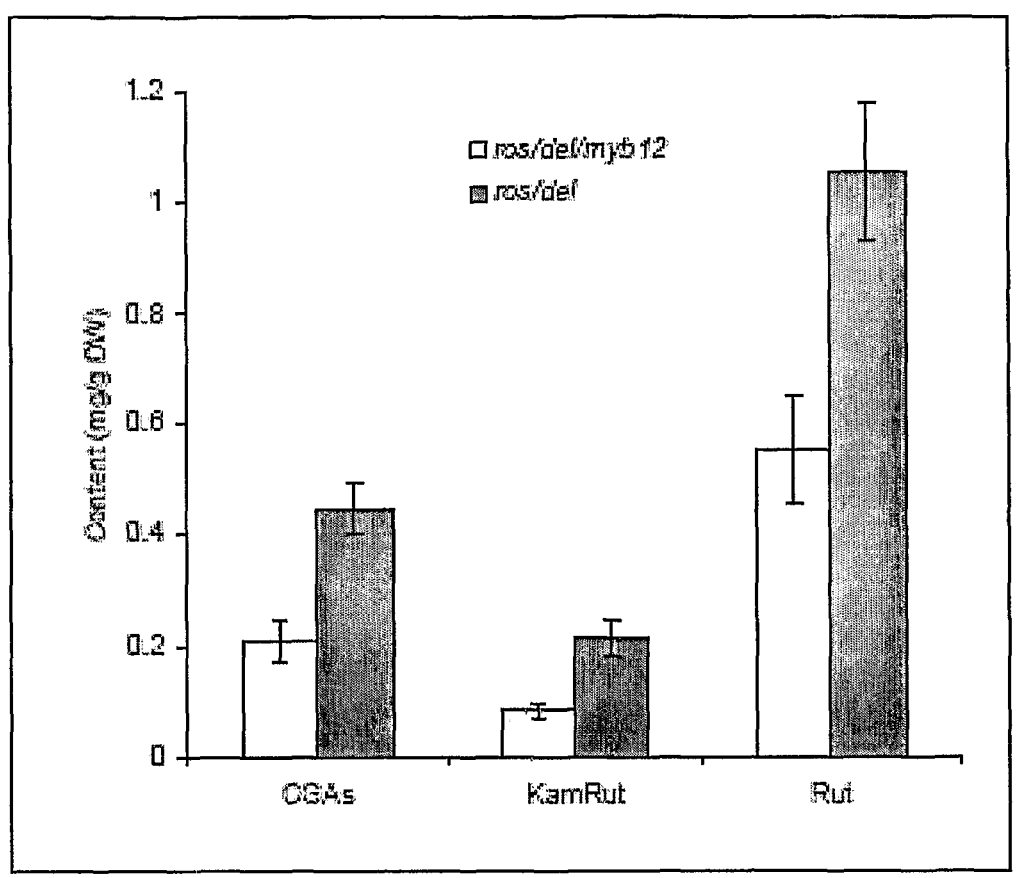
FIG. 7 Effect of SlMYB12 silencing by Agro-injection of tomato fruit on the production of CQAs (caffeoyl Quinic Acids) and flavonols. CGA is chlorogenic acid; KanRut is kaempferol rutinoside; Rut is rutin(quercetin rutinoside); DW is dry weight;. The data represent the mean values (+/− SD) of two, independent biological samples. Ros/del indicates tissues from fruit silenced for the marker genes only, ros/del/myb12 indicates tissues from fruit silenced for the markers and SlMYB12, together.

A virus-induced gene silencing protocol (VIGS) for use in tomato fruit was performed as follows:

We inserted a fragment of the tomato MYB12 gene (SlMYB12; see FIG. 9; SEQUENCE ANNEX I) into the sequences of the PVX virus along with sequences of other genes that mark the silenced tissues in agro-injected tomato fruit. The silenced tissue was dissected from the fruit and compared by metabolic profiling to tissue silenced for the markers genes but without the SlMYB12 sequences. The results showed that silencing of SlMYB12 reduces the levels of flavonols and of chlorogenic acid (FIG. 7) confirming its functional equivalence to AtMYB12 (Luo et al., 2008).

Example 5

Provision of Potato Homologue of AtMYB12

A blast search using SlMyb12 (see Example 4) against solanaceae database revealed one EST annotated as SGN U282939. An oligonucleotide was designed (LB60F 5'-ATGGGAAGAACACCTTGTTGTG-3'; SEQ ID NO: 79) and used with the oligo dT to amplify the whole fragment.

RNA was extracted from *solanum tuberosum* flowers using RNeasy plant RNA mini kit (Qiagen®) and 3µ was used to reverse transcribe the messenger into cDNA (Superscript® II, Invitrogen). The full length transcript (1089 nt) was obtained by PCR (Turbo Pfu® polymerase, Stratagene) using LB 60F and oligo dT. The resulting fragment was sub-cloned into pGEM-T® vector (Promega) and then sequenced.

The sequence of the cDNA and expressed polypeptide are shown in SEQUENCE ANNEX II.

The StMYB12 cDNA sequence (see SEQUENCE ANNEX II) was tested for its functionality in regulating expression of the genes involved in flavonol biosynthesis using a transient assay system in *Nicotiana benthamiana*. In this system we expressed the StMYB12 cDNA under the control of a strong promoter (2×35S) in a binary vector. We also prepared reporter gene constructs from the F3H and DFR genes linked to GUS in separate binary vectors. promF3H should be activated by functional homologues of AtMYB12, whereas promDFR should not. We used AtMYB12 as a positive control. All binary vectors were transferred to *Agrobacterium tumefaciens* and combinations of the vectors expressing the transcription factors and the different reporter genes were agro-infiltrated into *N. benthamiana* leaves. Assays of GUS activity by histochemical staining showed the potato MYB12 gene (StMYB12) could activate the promF3H but not the promDFR in the same way as the positive control (AtMYB12).

Example 6

Cis-genic Production of Potato Utilising Genetic Constructs Comprising a Cis-genic Marker Linked to an Auxin Inducible Promoter The 'T-DNA mimic' sequences for potato, termed 'P-DNA' are available from Simplot (Boise, Id., USA) for example, supplied in a vector such as pSIM108 (see SEQUENCE ANNEX V) together with sequence information detailing restriction sites that are used for cloning. The 35S promoter: nptII: nos terminator sequences that lie between the P-DNA border sequences are removed and replaced by a series of gene constructs in which 1) colour-based selection/screening system are enabled, 2) the tuber-expressed MYB12 gene (StMYB12) from potato is included, 3) late blight resistance genes, or other desirable disease resistance genes, are included. Incorporated by reference herein for this purpose are the details of late blight resistance genes which have been cloned, sequenced and, as disclosed and claimed in UK priority patent application number 0714241.7. Other genes of value in this regard include, but are not limited to, for example, a gene encoding plant resistance protein to the tomato mosaic tobamovirus or related viruses, as disclosed in EP1247867 and references cited therein. See also Smilde et al, Theor. Appl. Genet (2005) 110: 252-258, which describes chromosomal location of a novel late blight resistance gene, Rpi-moc1.

The pan1 gene was isolated as follows and is included for implementing colour selection. Pan1 cDNA has been amplified from *Solanum tuberosum* cultivar salad blue with the following oligonucleotides LB3F 5'-ATGAGTACTCCTAT- GATGTGTA-3' (SEQ ID NO: 80) and LB4R 5'-CTAAT-TAAGTAGATTCCATATATC-3'(SEQ ID NO: 81).

The sequence of the cDNA and expressed polypeptide are shown in SEQUENCE ANNEX VII (SEQ ID NO: 19 and 20, respectively).

The isolated potato MYB12 gene (StMYB12; see SEQUENCE ANNEX II; SEQ ID NO: 13) is also included This was obtained by using the SlMYB12 sequence to search a potato EST collection, and identifying a single EST from a mixed tissue RNA preparation.

A first colour-selection construct, pNPS1, comprises the pan1 gene (coding sequences plus optionally a stabilising 3'UTR) driven by the IAA4 promoter (see SEQUENCE ANNEX IV; SEQ ID NO: 15) inserted between the P-DNA borders in pSIM108 (see SEQUENCE ANNEX V; SEQ ID NO: 16).

A preferred 3'UTR for stabilisation and localisation of the mRNA in the cell is the 3'UTR region from Slpan2. The 3'UTR has the following sequence (SEQ ID NO: 82):

```
Atagtaatttctttttttgattttt cgtgatgtccggtactt atattagaatctgactgaattcagattcacgcgactccttat ctaggggg actcgaacccaacacctctgattaagaatgaatg agtacttattactccgacatatggttggtattaaagaaatat gtaatggtaattaatattattgtaaacttgtaatagggatcc aatcgtcctttatactttgtatcctaattacaagttgttagg aatgtaatttt aagaattattgtaagtgcatgcactctattt ttatatttgatgtgaatttaaggattgagcataaatatgaaa aatcaaaat
```

An IAA4:Stpan1 gene fusion is constructed in pBluescript, for transfer as a KpnI/PstI fragment into KpnI/PstI digested pSIM108, thus replacing the 35S: nptII gene construct between the P-DNA borders. The IAA4:Stpan1 gene fusion is also directly inserted into pSIM108 without intermediate passage through pBluescript. pNPS1 is transferred to *Agrobacterium tumifaciens* (strain GV3101) by electroporation. The construct is used to transform tobacco to test the functionality of the IAA4:pan1 construct by transient assays, as well as by stable transformation of tobacco callus, which we anticipate will be just as quick a means of verifying functionality, and which also confirms the effectiveness of the construct for screening for transformed cells, mirroring the potato transformation protocol.

The frequency of recovering colour +plants is compared with the frequency of obtaining explants using a system utilizing the 35S:codA counter selection for transient expression of kanamycin resistance on a separate plasmid in *Agrobacterium* (see U.S. Pat. No. 7,250,554 which describes example vectors for this purpose). The colour selection system is anticipated to provide a higher transformation frequency, permitting the discontinuance of the transient kanamycin resistance system, which has negative regulatory implications for production of crops for human or animal consumption.

pNPS1 is used to transform potato (for example, cv Desireé, although, of course, other varieties may be used analogously) tuber discs, and, due to the action of the IAA4:Stpan1 construct, colour is used to select transformed potato cells. Foci of coloured cells are transferred onto shooting medium for regeneration of shoots.

Shoots from red calli are transferred to hormone-free medium for the induction of roots, and plants that have grown to a suitable size are subsequently transferred to soil. The phenotypes of these primary transformants are recorded compared to controls, especially with respect to colouring of vegetative tissues by anthocyanins. The fidelity of P-DNA transfer and the copy number of inserted P-DNAs is confirmed by Southern blots and PCR analysis.

A second construct, pNPS2, is produced as a refinement of the first construct by inclusion of the StMYB12 gene with its 3' UTR fused to the B33 promoter of the patatin 1 gene from potato. This gene construct is combined with the IAA4:Stpan1 sequences in pBluescript and then reassembled as a KpnI/PstI fragment in pSIM108. pNPS2 is trialled using stable transformation of tobacco in which high levels of flavonol production is induced by growing plantlets on 7% sucrose to induce the B33 promoter. This construct is also transferred to potato (as described above), and the tubers of mature T0 plants exhibiting high flavonoid and hydroxycinnamate content by LC/MS are selected for further use.

Thus we inserted the Pan1 cDNA driven by the auxin-inducible promoter from the tomato IAA4 gene and used the pan2 terminator 3'UTR sequence, derived from the *S. okadae* BAC library, in pSim108 in recombination deficient *E. coli* and then transferred this binary vector to *Agrobacterium tumefaciens* strains GV3101 and LBA4404 by electroporation. To test the functionality of this screenable marker for transformation, we transformed tobacco (var *Samsun*) which never makes anthocyanins in vegetative tissues. We used the leaf disc method of transformation but omitted any antibiotics to select for transformed cells or plantlets. Callus developed in abundance on the cut edges of the leaf discs. Amongst these calli were foci coloured red, due to the production of anthocyanin as a result of pan1 activity (FIG. 11.2). These foci were dissected away from the uncoloured callus and placed onto shoot regeneration medium, with high auxin levels. The explants remained coloured especially at their growing apices, and started to develop into shoots. This suggested that the promIAA:pan1:pan2 3'UTR construct in pSim108 was functional and worked efficiently as a screenable marker for transformed shoots of tobacco.

The construct was also used to transform potato ('Desiree' and 'Maris Piper') using stem explants. This system does not involve production of large amounts of callus as an intermediary in the procedure. Rather, shoots are produced from the callus at the cut ends of the explants. When the promIAA:pan1:Sopan2 3'UTR construct in pSim108 was used for the transformation, shoots were produced which were coloured red, particularly around the edges of the leaflets (results not shown).

This was not observed with other constructs used to transform potato, although potato explants of the cv. Desiree do produce some anthocyanin when stressed, which can occur during the transformation and selection procedures. The transformed shoots were identified by screening for the production of anthocyanin, in the absence of any selection requiring antibiotics.

Selected shoots (colored) of both tobacco and potato were rooted and then grown on in soil. Normally vegetative tissues lack anthocyanins completely. However adult tobacco plants carrying promIAA:pan1:Sopan2 3'UTR showed anthocyanin in the epidermal tissues overlying veins in the leaves and anthocyanin production in the stems and petioles. Anthocyanin production in flowers was enhanced, particularly in the regions of epidermis overlying the main veins in the petals (results not shown)

One, two or more disease resistance genes, including but not limited to, for example, late blight resistance genes Rpi-mcq, Rpi-oka1, or both, are incorporated into the pNPS2 vector in stages 3 and 4. These genes are driven by their own promoters. These genes are incorporated into the IAA4: Stpan1+833: SoMY812 sequences in pBluescript and are then transferred to pSIM108 to attach the P-DNA sequences, thereby providing pNPS3 and pNPS4. Transformation of potato is conducted following the protocols described above.

```
SEQUENCE ANNEX I (SEQ ID NO: 12, amino acid sequence; SEQ ID NO: 11,
nucleotide sequence);
LOCUS       bankit1056867 1248 bp mRNA linear
PLN
22-JAN-2008
DEFINITION  solanum lycopersicum (tomato) MYB12 mRNA, complete
            cds.
ACCESSION   1056867
VERSION
KEYWORDS    .
SOURCE      Solanum lycopersicum (Lycopersicon esculentum)
ORGANISM    Solanum lycopersicum
            Eukaryota; Viridiplantae; Streptophyta; Embryophyta;
            Tracheophyta; Spermatophyta; Magnoliophyta; eudicotyledons;
            core eudicotyledons; asterids; lamiids; Solanales; Solanaceae;
            Solanoideae; Solaneae; Solanum; Lycopersicon.
REFERENCE   1 (bases 1 to 1248)
AUTHORS     Luo, J. and Martin, C.
TITLE       Metabolic engineering to enhance levels of both flavonols
and
            hydroxycinnamic acids in tomato fruit
JOURNAL     Unpublished
REFERENCE   2 (bases 1 to 1248)
AUTHORS     Luo, J. and Martin, C.
TITLE       Direct Submission
JOURNAL     Submitted (22-JAN-2008) Metabolic Biology, John Innes Centre,
            Norwich Research Park, Colney, Norwich, Norfolk NR4
            7UH, UK
FEATURES    Location/Qualifiers
   source   1 . . . 1248
            /organism = "Solanum lycopersicum"
            /mol_type = "mRNA"
            /db_xref = "taxon: 4081"
gene        1 . . . 1248
            /gene = "MYB12"
CDS         1 . . . 1017
            /gene = "MYB12"
            /codon_start = 1
            /product = "MYB12"

/translation = "MGRTPCCEKVGIKRGRWTAEEDQILTNYIISNGEGSWRSLPKNAGLLRCGKSCRLRWI
NYLRSDLKRGNITSQEEDIIIKLHATLGNRWSLIAEHLSGRTDNEIKNYWNSHLSRKVDSLRIPSDEKLPKAVV
DLAKKGIPKPIKKSSISRPKNKKSNLLEKEALCCTNMPACDSAMELMQEDLAKIEVPNSWAGPIEAKGSLSSDS
DIEWPRLEEIMPDVVIDDEDKNTNFILNCFREEVTSNNVGNSYSCIEEGNKKISSDDEKIKLLMDWQDNDELVW
PTLPWELETDIVPSWPQWDDTDTNLLQNCTNDNNNYEEATTMEINNQNHSTIVSWLLS"

BASE COUNT 481 a 156 c 257 g 354 t
ORIGIN
    1 atgggaagaa caccttgttg tgaaaaagtg ggcatcaaga gaggcagatg gactgcagaa
   61 gaagatcaaa ttctcactaa ttatattatt tctaatggag aaggctcttg gaggtcgtta
  121 cctaaaaatg ccggattatt gagatgcgga aagagttgta gactacgatg gattaattat
  181 ttgaggtctg atctcaagag agggaacatt acttctcaag aggaagatat aattataaag
  241 ttacatgcaa ctttgggtaa cagatggtct cttatagcag aacatttatc aggtagaaca
  301 gacaatgaga taaaaaacta ttggaactct catctaagtc gaaaagttga tagcttaagg
  361 ataccaagcg atgagaagtt acctaaagcc gtagttgatt tggctaaaaa aggtataccg
  421 aagccaatta aaaaatcatc gattagtcga ccaaaaaata aaaagtcaaa cttattagaa
  481 aaagaagcat tgtgttgtac aaatatgcca gcttgtgata gtgccatgga attaatgcaa
  541 gaagatctag caaagataga ggtgccaaat tcttgggcag gacctataga ggccaaggga
  601 agccttagtt cagatagtga tatcgaatgg ccaagactcg aggagattat gccagacgtg
  661 gtgattgatg atgaagataa gaacacaaat ttcatattga attgtttcag agaagaagta
  721 acgagcaata atgtagggaa tagttattca tgtatcgagg aaggtaataa aaagatatca
  781 agcgacgatg aaaaaatcaa attattaatg gattggcaag ataatgatga gttagtatgg
  841 ccaacgttac catgggaatt agaaacggat atagttccca gttggccaca atgggacgat
  901 actgacacta acttacttca aaattgcacc aatgataata ataattatga agaagcaaca
  961 acaatggaaa ttaataacca aaatcatagt accattgtat cttggctttt gtcttagaaa
 1021 tataataata tgacattata tattgctttt gaatatatta ctcaactctt tttgtttcgt
 1081 tttatatttg gaatgtggga attagaatga ctagtttatg tacatatttt aagtttcgtt
 1141 agaaatatcg tcaagtcaga ttaaaatatg tatgagttga tgtagtaata aatgttattg
 1201 ttattacttt ttttgatgta aaaaaaaaaa aaaaaaaaaa aaaaaaaa
```

SEQUENCE ANNEX II (SEQ ID NO: 14, amino acid sequence; SEQ ID NO: 13, nucleotide sequence);
>StMyb12
MGRTPCCEKVGIKRGRWTAEEDQILTNYILSNGEGSWRSLPKNAGLLRCGKSCRLRWINYLRSDLKRGNITSQE
EDIIIKLHATLGNRWSLIAGHLSGRTDNEIKNYWNSHLSRKVDSLRIPSDEKLPKAVVDLAKKGTLKPIKHCRK
SLISRSKNKKSNLLEAKENSTSGALIGIVPMPSTPNIEKEALCCTNMPACDSAMALMQEDVAKVEVPNSWAGSI
EAKGSLSSDSGMEWPRLEEIMPDVVIDDEDMNPNFILNGLEEEVMSNNAGNNYSCIDEGNKNVSSDDEKSKLLM
DWQDDDELVWPTPPWELETDIIPSWPQWDDTDTDLLQNCTNNNYEEATTMEINNQNHSAIVSWLLS >StMyb12
atgggaagaacaccttgttgtgaaaaagtgggtatcaagagaggcagatggactgcagaagaagatcaaattct
cactaattatattctttctaatggagaaggctcttggaggtcattacccaaaaatgccggattactgagatgtg
gaaagagttgtagactaagatggattaattatttgaggtctgacctcaagagagggaacattacttctcaagag
gaagatataatcataaagttacatgcaactttgggtaacaggtggtctctaatagcgggacatttatcaggtag
aacagacaatgagattaaaaattattggaactctcatctaagtcgaaaagttgatagcttaaggataccaagcg
atgaaagttgcctaaagctgtagttgatttggctaaaaagggtacattgaagccaattaaacattgtagaaaa
tcattgattagtcgatcgaaaataaaaaatcaaacttattagaagctaaagaaaatagtactagtgggcttt
gattggaattgttcctatgccttcaacaccaaacatagaaaaagaagcattgtgttgtacaaatatgccagctt
gtgatagtgccatggcattaatgcaagaagatgtagcaaaggtagaggtgccaaattcttgggcagggtctata
gaggccaagggaagccttagttcagatagtggtatggaatggccaaggctcgaggagattatgccagacgtggt
gattgatgatgaagatatgaacccaaatttcattttgaatggtttagaagaagaagtaatgagcaataatgcag
ggaataattattcatgtatcgacgaaggaaataaaaacgtatcaagcgattgataaaaaagcaaattattaatg
gattggcaagatgatgatgaattagtatggccaacgccaccatgggaattagaaacagacataattcctagttg
gccacaatgggacgatactgacactgatttacttcaaaattgcaccaataataattatgaagaagcaacaacaa
tggaaattaataaccaaatcatagtgccattgtatcttggcttttgtcttag SEQUENCE ANNEX III
SEQ ID NO: 1 = NUCLEIC ACID SEQUENCE OF Rpi-oka1
     1 atggctgaaa ttcttctcac agcagtcatc aataaatcaa tagaaatagc tggaaatgta
    61 ctcttttcaag aaggtacgcg tttatattgg ttgaaagagg acatcgattg gctccagaga
   121 gaaatgagac acattcgatc atatgtagac aatgcaaagg caaaggaagt tggaggcgat
   181 tcaagggtga aaaacttatt aaaagatatt caacaactgg caggtgatgt ggaggatcta
   241 ttagatgagt tccttccaaa aattcaacaa tccaataagt tcatttgttg ccttaagacg
   301 gtttctttttg ccgatgagtt tgctatggag attgagaaga taaaagaag agttgctgat
   361 attgaccgtg taaggacaac ttacagcatc acagataca gtaacaataa tgatgattgc
   421 attccattgg accggagaag attgttcctt catgctgatg aaacagaggt catcggtctg
   481 gaagatgact caatacact acaagccaaa ttacttgatc atgatttgcc ttatggagtt
   541 gtttcaatag ttggcatgcc cggtttggga aaaacaactc ttgccaagaa actttatagg
   601 catgtctgtc atcaatttga gtgttcggga ctggtctatg tttcacaaca gccaagggcg
   661 ggagaaatct acatgdacat agccaaacaa gttggactga cggaagagga aaggaaagaa
   721 aacttggaga caacctacg atcactcttg aaaataaaaa ggtatgttat tctcttagat
   781 gacatttggg atgttgaaat ttgggatgat ctaaaacttg tccttcctga atgtgattca
   841 aaaattggca gtaggataat tataacctct cgaaatagta atgtaggcag atacataga
   901 ggggatttct caatcccacgt gttgcaaccc ctagattcag agaaaagctt tgaactcttt
   961 accaagaaaa tcttttaattt tgttaatgat aattgggcca atgcttcacc agacttggta
  1021 aatattggta gatgtatagt tgagagatgt ggaggtatac cgctagcaat tgtggtgact
  1081 gcaggcatgt taagggcaag aggaagaaca gaacatgcat ggaacagagt acttgagagt
  1141 atggctcata aaattcaaga tggatggtg aaggtattgg ctctgagtta caatgatttg
  1201 cccattgcat taaggccatg tttcttgtac tttggtcttt acccgaggaa ccatgaatt
  1261 cgtgctttg atttgacaaa tatgtggatt gctgagaagc tgatagttgt aaatactggc
  1321 aatgggcgag aggctgaaag ttttggcggat gatgtcctaa atgattttgt ttcaagaaac
  1381 ttgattcaag ttgccaaaag gacatatgat ggaagaattt caagttgtcg catacatgac
  1441 ttgttacata gtttgtgtgt ggacttggct aaggaaagta acttcttcaa cacggagcac
  1501 aatgcatttg gtgatcctag caatgttgct agggtgcgaa ggattacatt ctactctgat
  1561 gataatgcca tgaatgagtt cttccattta aatcctaagc ctatgaagct tcgttcactt
  1621 ttctgtttca caaagaccg ttgcatattt tctcaaatgg ctcatctaa cttcaaatta
  1681 ttgcaagtgt tggttgtagt catgtctcaa aaggtttatc agcatgttac ttttcccaaa
  1741 aaaattggga acatgagttg cctacgttat gtgcgattgg aggggcaat tagagtaaaa
  1801 ttgccaaata gtattgtcaa gctcaaatgt ctagagaccc tggatatatt tcatagctct
  1861 agtaaactcc ctttggtgt ttgggagtct aaaatattga gacatctttg ttacacagaa
  1921 gaatgttact gtgtctcttt tgcaagtcca ttttgccgaa tcatgcctcc taataaatcta
  1981 caaactttga tgtgggtgga tgataatt tgtgaaccaa gattgttgca ccgattgata
  2041 aatttaagaa cattgtgtat aatggatgta tccggttcta ccattaagat attatcagca
  2101 ttgagccctg tgcctagagc gttggaggtt ctgaagctca gattttcaa gaacacgagt
  2161 gagcaaataa acttgtcgtc ccatccaaat attgtcgagt tgggtttggt tggtttctca
  2221 gcaatgctct tgaacattga agcattccct ccaaatcttg tcaagctaa tcttgtcggc
  2281 ttgatggtag acggtcatct attggcagtg cttaagaaat tgcccaaatt aaggatactt
  2341 atattgcttt ggtgcagaca tgatgcagaa aaatggatc tctctggtga tagctttccg
  2401 caacttgaag ttttgtatat tgaggatgca caaggggttgt ctgaagtaac gtgcatgggat
  2461 gatatgagta tgcctaaatt gaaaaagcta tttcttgtac aaggcccaaa catttcccca
  2521 attagtctca gggtctcgga acggcttgca aagttgagaa tatcacaggt actataa SEQ ID NO: 7 = NUCLEIC ACID SEQUENCE OF Rpi-oka2
     1 atggctgaaa ttcttctcac agcagtcatc aataaatcaa tagaaatagc tggaaatgta
    61 ctcttttcaag aaggtacgcg tttatattgg ttgaaagagg acatcgattg gctccagaga
   121 gaaatgagac acattcgatc atatgtagac aatgcaaagg caaaggaagt tggaggcgat
   181 tcaagggtga aaaacttatt aaaagatatt caacaactgg caggtgatgt ggaggatcta
   241 ttagatgagt tccttccaaa aattcaacaa tccaataagt tcatttgttg ccttaagacg
   301 gtttctttttg ccgatgagtt tgctatggag attgagaaga taaaagaag agttgctgat
   361 attgaccgtg taaggacaac ttacagcatc acagatacaa gtaacaataa tgatgattgc
   421 attccattgg accggagaag attgttcctt catgctgatg aaacagaggt catcggtctg

```
 481 gaagatgact tcaatacact acaagccaaa ttacttgatc atgatttgcc ttatggagtt
 541 gtttcaatag ttggcatgcc cggtttggga aaaacaactc ttgccaagaa actttatagg
 601 catgtctgtc atcaatttga gtgttcggga ctggtctatg tttcacaaca gccaagggcg
 661 ggagaaatct tacatgacat agccaaacaa gttggactga cggaagagga aggaaagaa
 721 aacttggaga caacctacg atcactcttg aaaataaaaa ggtatgttat tctcttagat
 781 gacatttggg atgttgaaat ttgggatgat ctaaaacttg tccttcctga atgtgattca
 841 aaaattggca gtaggataat tataacctct cgaaatagta atgtaggcag atacatagga
 901 ggggatttct caatccacgt gttgcaccc ctagattcag agaaaagctt tgaactcttt
 961 accaagaaaa tctttaattt tgttaatgat aattgggcca atgcttcacc agacttggta
1021 aatattggta gatgtatagt tgagagatgt ggaggtatac cgctagcaat tgtggtgact
1081 gcaggcatgt taagggcaag aggaagaaca gaacatgcat ggaacagagt acttgagagt
1141 atggctcata aaattcaaga tggatgtggt aaggtattgg ctctgagtta caatgatttg
1201 cccattgcat taaggccatg tttcttgtac tttggtcttt accccgagga ccatgaaatt
1261 cgtgcttttg atttgacaaa tatgtggatt gctgagaagc tgatagttgt aaatactggc
1321 aatgggcgag aggctgaaag tttggcggat gatgtcctaa atgatttggt ttcaagaaac
1381 ttgattcaag ttgccaaaag gacatatgat ggaagaattt caagttgtcg catacatgac
1441 ttgttacata gtttgtgtgt ggacttggct aaggaaagta acttcttca cacggagcac
1501 tatgcatttg gtgatcctaa caatgttgct agggtgcgaa ggattacatt ctactctgat
1561 gataatgcca tgaatgagtt cttccattta aatcctaagc ctatgaagct tcgttcactt
1621 ttctgtttca caaaagaccg ttgcatattt tctcaaatgg ctcatcttaa cttcaaatta
1681 ttgcaagtgt tggttgtagt catgtctcaa aagggttatc agcatgttac tttccccaaa
1741 aaaattggga acatgagttg cctacgctat gtgcgattga gggggcaat tagagtaaaa
1801 ttgccaaata gtattgtcaa gctcaaatgt ctagagaccc tggatatatt tcatagctct
1861 agtaaacttc cttttggtgt ttgggagtct aaaatattga gacatctttg ttacacagaa
1921 gaatgttact gtgtctcttt tgcaagtcca ttttgccgaa tcatgcctcc taataatcta
1981 caaactttga tgtgggtgga tgataaattt tgtgaaccaa gattgttgca ccgattgata
2041 aatttaagaa cattgtgtat aatggatgta tccggttcta ccattaagat attatcagca
2101 ttgagccctg tgcctaaagc gttggaggtt ctgaagctca gattttcaa gaacacgagt
2161 gagcaaataa acttgtcgtc ccatccaaat attgtcgagt tgggtttggt tggtttctca
2221 gcaatgctct tgaacattga agcattccct ccaaatcttg tcaagcttaa tcttgtcggc
2281 ttgatggtag acggtcatct attggcagtg cttaagaaat tgcccaaatt aaggatactt
2341 atattgcttt ggtgcagaca tgatgcagaa aaaatggatc tctctggtga tagctttccg
2401 caacttgaag ttttgtatat tgaggatgca caagggttgt ctgaagtaac gtgcatggat
2461 gatatgagta tgcctaaatt gaaaaagcta tttcttgtac aaggcccaaa catttcccca
2521 attagtctca gggtctcgga acggcttgca aagttgagaa tatcacaggt actataa
```

SEQ ID NO: 2 = NUCLEIC ACID SEQUENCE OF Rpi-mcq1
If candidate 1 then:
```
   1 atggctgaaa ttcttcttac agcagtcatc aataaatctg tagaaatagc tggaaatgta
  61 ctcttcaag aaggtacgcg tttatattgg ttgaaggagg atatagattg gctccaaaga
 121 gaaatgagac acattcgatc atatgtagac aatgcaaagg ccaaggaagt tggaggtgat
 181 tcaagggtga aaaacttatt aaaagatatt caacaactcg caggtgatgt ggaggatctc
 241 ctagatgagt ttcttccaaa aattcaacaa tccagtaagt tcaaaggcgc aatttgttgc
 301 cttaagaccg tttcttttgc ggatgagttt gctatgagga ttgagaagat aaaaagaagg
 361 gttgtggaca ttgatcgtgt aaggacaact tacaacatca tggatacaaa taacaacaat
 421 gattgcattc cattggacca gagaagattg ttccttcatg ttgatgaaac agaggtcatc
 481 ggtttggatg atgacttcaa tacactacaa gccaaattac ttgaccaaga tttgccttat
 541 ggagttgttt caatagttgg catgcccggt ctaggaaaaa caactcttg caagaaactt
 601 tataggcatg tccgtcataa atttgagtgt tcgggactgg tctatgtttc acaacagcca
 661 agggcgggag aaatcttaat cgacatagcc aaacaagttg gactgacgga agacgaaagg
 721 aaagaaaact tggagaacaa cctacggtca ctcttgaaaa gaaaaaggta tgttattctc
 781 ttagatgaca tttgggatgt tgaaatttgg gatgatctaa aacttgtcct tcctgaatgt
 841 gattcaaaaa ttggcagtag gataattata acctctcgaa atagtaatgt aggcagatac
 901 ataggagggg atttctcaat tcacgtgttg caacctctaa attcggagaa cagttttgaa
 961 ctcttttacca agaaaatctt tattttgat aacaataaa attgaccaaa tgcttcacca
1021 aacttggtag atattggtag aagtatagtt ggtagatgtg gtggtatacc actagccatt
1081 gtggtgactg caggcatgtt aagggcaaga gaaagaacag aacgtgcatg gaacaggtta
1141 cttgagagta tgagccataa agttcaagat ggatgtgcta aggtattggc tctgagttac
1201 aatgatttgc caattgcatt aaggccatgt ttcttgtatt ttggcctta ccccgaggat
1261 catgaaattc gtgctttga tttgacaaat atgtggatt ctgagaagtt gatagttgta
1321 aatagtggca atgggcgaga ggctgaaagt ttggcggatg atgtcctaaa tgatttggtt
1381 tcaagaaaca tgattcaagt tgccaaaagg acatatgatg gaagaatttc aagttgtcgc
1441 atacatgact tgttacatag tttgtgtgtt gacttggcta aggaaagcaa cttcttcac
1501 accgagcaca atgcattggg tgatcccgga aatgttgcta ggctgcgaag gattacattc
1561 tactctgata ataatgccat gaatgagttc ttccgttcaa atcctaagct tgagaagctt
1621 cgtgcacttt tctgtttac agaagaccct tgcatatttt ctcaactggc tcatcttgat
1681 ttcaaattat tgcaagtgtt ggttgtagtc atctttgttg atgatatttg ggtgtcagt
1741 atcccaaaca catttgggaa catgaggtgc ttacgttatc tgcgattcca ggggcatttt
1801 tatgggaaac tgccaaattg tatggtgaag ctcaaacgtc tagagaccct cgatattggt
1861 tatagcttaa ttaaatttcc tactggtgt tggaagtcta cacaattgaa acatcttcgt
1921 tatggaggtt ttaatcaagc atctaacagt tgcttttcta taagcccatt tttcccaaac
1981 ttgtactcat tgcctcataa taatgtacaa acttgatgt ggctggatga taaattttt
2041 gaggcgggat tgttgcaccg attgatcaat ttaagaaaac tgggtatagc aggagtatct
2101 gattctacag ttaagatatt atcagcattg agcctgtgc aacggcgct ggaggttctg
2161 aagctcaaaa tttacaggga catgagtgca caaataatt ttcgtccta tccaaatatt
2221 gttaagttgc ctttgaatgt tgcgaaga atgcgcttga actgtgaagc atttcctcca
2281 aatcttgtca agcttactct tgtcggcgat gaggtagacg tcatgtagt ggcagagctt
2341 aagaaattgc ccaaattaag gatacttaaa atgtttgggt gcagtcataa tgaagaaaag
2401 atggatctct ctggtgatgg tgatagcttt ccgcaacttg aagttctgca tattgatgaa
2461 ccagatgggt tgtctgaagt aacgtgtagg gatgatgtca gtatgcctaa attgaaaaag
```

2521 ttgttacttg tacaacgccg cccttctcca attagtctct cagaacgtct tgcaaagctc
2581 agaatatga SEQ ID NO: 8 = NUCLEIC ACID SEQUENCE OF Rpi-mcq1
If candidate 2 then:
   1 atggctgaaa ttcttcttac aacagtcatc aataaatctg taggaatagc tgcaaatgta
  61 ctctttcaag aaggaacgcg tttatattgg ttgaaagagg acatagattg gctccacaga
 121 gaaatgagac acattcgatc atatgtagac gatgcaaagg ccaaggaagt tggaggcgat
 181 tcaagggtca gaaacttatt aaaagatatt caacaactgg caggtgatgt ggaggatcta
 241 ttagatgagt ttcttccaaa aattcaacaa tccaataagt tcatttgttg ccttaagaca
 301 gtttcttttg ccgatgagtt tgccatggag attgagaaga taaaaagaag agttgctgat
 361 attacccgtg taaggacaac ttacaacatc acagatacaa gtaacaataa tgatgattgc
 421 attccattgg accggagaag attgttcctt catgctgatg aaacagaggt catcggtctg
 481 gaagatgact tcaatacact aaaagccaaa ttacttgatc aagatttgcc ttatggagtt
 541 gtttcaatag ttggcatgcc cggtctagga aaaacaactc ttgccaagaa actttatagg
 601 catgtccgtg atcaatttga gagctcggga ctggtctacg tgtcccaaca gccaagagcg
 661 ggagaaatct acgtgacatc agccaaacaa gttggactgc caaagagga aggaaagaa
 721 aacttggagg gcaacctacg atcactcttg aaaacaaaaa ggtatgttat cctcctagat
 781 gacatttggg atgttgaaat ttgggatgat ctaaaactcg tccttcctga atgtgattca
 841 gaaattggca gtaggataat tataacctct cgaaatagta atgtaggcag atacatagga
 901 ggggatttct caattcacat gttgcaacct ctagattcgg agaacagttt tgaactcttt
 961 accaagaaaa tctttacttt tgataacaat aataattggg ccaatgcttc accagactta
1021 gtagatattg gtagaagtat agttggtaga tgcggaggta tacctctagc cattgtggtc
1081 actgcaggca tgttaagggc aagagaaaga acagaacatg catggaacag agtacttgag
1141 agtatgggcc ataaagttca agatggatgt gctaaggtat ggctttgag ttacaatgat
1201 ttgcccattg cattaaggcc atgtttcttg taccttggcc ttttcccga ggaccatgaa
1261 attcgtgcct ttgatttgac aaatatgtgg attgctgaga agctgatagt tgtaaatagt
1321 ggcaatgggc gagaggctga agtttggcg gaggatgttc taaatgattt tgtttctaga
1381 aacttgattc aagtttccca agaaaatgt aatggaagaa tttcaagtta tcgcatacat
1441 gacttgttac atagtttgtg cgtcgaattg ggcaaggaaa gtaacttttt tcacactgaa
1501 cacaatgcat ttggtgatcc agacaatgtt gctagggtgc gaaggattac attctactct
1561 gataataatg ccatgagtaa gttcttccgt tcaaatccta agcctaagaa acttcgtgca
1621 cttttctgtt tcacaaattt agactcttgc atatttctc atttggctca tcatgacttc
1681 aaattattac aagtgttggt tgtagttatc tcttataatt ggttgagtgt cagtatctca
1741 aacaaatttg ggaagatgag ttgcttgcgc tatttgagat tggaggggcc aattgtggga
1801 gaactgtcaa atagtattgt gaagctcaaa cgtgtagaga ccatagatat tgcaggggat
1861 aacattaaaa ttccttgtgg tgtttgggag tctaaacaat tgagacatcc ccgtaataga
1921 gaagaacgtc gctatttctt ttctgtaagc ccattttgcc taaacatgta cccattgcct
1981 cctaataatc tacaaacttt ggtgtggatg gatgataaat tttttgaacc gagattgttg
2041 caccgattga tcaatttaag aaaattgggt atatgggggca catctgattc tacaattaag
2101 atattatcag cattgagccc tgtgccaaca gcgttggagg ttctgaagct ctacttttg
2161 agggacctga gtgagcaaat aaacttgtca acctatccaa atattgttaa gttgaattg
2221 caaggattcg taagagtgcg cttgaactct gaagcattcc ctccaaatct tgtcaagctt
2281 attcttgaca aaattgaggt agagggtcat gtagtggcaa ttcttaagaa attgcccaca
2341 ttaaggatac ttaaaatgta tgggtgcaaa cataatgaag aaaagatgga tctctctggt
2401 gatggtgatg tgatagctt tccgcaactt gaagttttgc atattgagag accattcttc
2461 ttgtttgaaa taacgtgcac agatgatgac agtatgccta aattgaaaaa gctattactt
2521 accacttcga acgttaggct ctcggaaaga cttgcaaaac tgagagtatg a SEQ ID NO: 3 = NUCLEIC ACID SEQUENCE OF Rpi-nrs1
   1 atggctgaaa ttcttctcac agcagtcatc aataaatcac tagaaatagc tggaaatgta
  61 ctctttcaag aaggtacgcg tttatattgg ttgaaagagg acatcgattg gctccagaga
 121 gaaatgagac acattcgatc atatgtagac aatgcaaagg caaaggaagt tggaggcgat
 181 tcaagggtga aaaacttatt aaaagatatt caacaactgg caggtgatgt ggaggatcta
 241 ttagatgagt ttcttccaaa aattcaacaa tccaataagt tcatttgttg ccttaagacg
 301 gtttcttttg ccgatgagtt tgccatggag attgagaaga taaaaagaag agttgctgat
 361 attgaccgtg taaggacaac ttacagcatc acagatacaa gtaacaataa tgatgattgc
 421 attccattgg accggagaag attgttcctt catgctgatg aaacagaggt catcggtctg
 481 gaagatgact tcaatacact acaagccaaa ttacttgatc atgatttgcc ttatggagtt
 541 gtttcaatag ttggcatgcc cggtttggga aaaacaactc ttgccaagaa actttatagg
 601 catgtctgtc atcaatttga gtgttcggga ctggtctatg tttcacaaca gccaagggcg
 661 ggagaaatct acatgacatc agccaaacaa gttggactga cggaagagga aggaaagaa
 721 aacttggaga caacctacg atcactcttg aaaataaaaa ggtatgttat tctcttagat
 781 gacatttggg atgttgaaat ttgggatgat ctaaaactcg tccttcctga atgtgattca
 841 aaaattggca gtaggataat tataacctct cgaaatagta atgtaggcag atacatagga
 901 ggggatttct caattccacgt gttgcaaccc ctagattcag agaaaagctt tgaactcttt
 961 accaagaaaa tctttaattt tgttaatgat aattgggcca atgcttcacc agacttggta
1021 atatgtggta gatgtatagt tgagagatgt ggaggtatac cgctagcact tgtggtgact
1081 gcaggcatgt taagggcaag aggaagaaca gaacatgcat ggaacagagt acttgagagt
1141 atggctcata aaattcaaga tggatgtgt aagtattgg ctctgagtta caatgatttg
1201 cccattgcat taaggccatg ttcttgtac tttggtcttt accccgagga ccatgaaatt
1261 cgtgcttttg atttgacaaa tatgtggatt gctgagaagc ttagtagttgt aaatactggc
1321 aatgggcgag aggctgaaag tttggcggag gatgtcctaa atgatttggt ttcaagaaac
1381 ttgattcaag ttgccaaaag gacatatgat ggaagaattt caagttgtcg catacatgac
1441 ttgttacata gtttgtgtgt ggacttggct aaggaaagta acttctttca cacggagcac
1501 tatgcatttg gtgatcctag caatgttgct agggtgcgaa ggattacatt ctactctgat
1561 gataatgcca tgaatgagtt cttccattta aatcctaagc ctatgaagct tcgttcactt
1621 ttctgtttca caaaagaccg ttgcatattt tctcaaatgg ctcatcttaa cttcaaatta
1681 ttgcaagtgt tggttgtagt catgtctcaa aagggttatc agcatgttac ttttcccaaa
1741 aaaattggga acatgagttg cctacgctat gtgcgattgg aggggcaat tagagtaaaa
1801 ttgccaaaata gtattgtcaa gctcaaatgt ctagagaccc tggatatatt tcatagctct -continued
```
1861 agtaaacttc cttttggtgt ttgggagtct aaaatattga gacatctttg ttacacagaa
1921 gaatgttact gtgtctcttt tgcaagtcca ttttgccgaa tcatgcctcc taataatcta
1981 caaactttga tgtgggtgga tgataaattt tgtgaaccaa gattgttgca ccgattgata
2041 aatttaagaa cattgtgtat aatggatgta tccggttcta ccattaagat attatcagca
2101 ttgagccctg tgcctaaagc gttggaggtt ctgaagctca gatttttcaa gaacacgagt
2161 gagcaaataa acttgtcgtc ccatccaaat attgtcgagt tgggtttggt tggtttctca
2221 gcaatgctct tgaacattga agcattccct ccaaatcctg tcaagctcta tcttgtcggc
2281 ttgatggtag acggtcatct attggcagtg cttaagaaat tgcccaaatt aaggatactt
2341 atattgcttt ggtgcagaca tgatgcagaa aaaatggatc tctctggtga tagctttccg
2401 caacttgaag ttttgtatat tgaggatgca caagggttgt ctgaagtaac gtgcatggat
2461 gatatgagta tgcctaaatt gaaaaagcta tttcttgtac aaggcccaaa catttcccca
2521 attagtctca gggtctcgga acggcttgca aagttgagaa tatcacaggt actataa
```

SEQ ID NO: 4 = AMINO ACID SEQUENCE OF Rpi-oka1
```
   1 MAEILLTAVI NKSIEIAGNV LFQEGTRLYW LKEDIDWLQR EMRHIRSYVD NAKAKEVGGD
  61 SRVKNLLKDI QQLAGDVEDL LDEFLPKIQQ SNKFICCLKT VSFADEFAME IEKIKRRVAD
 121 IDRVRTTYSI TDTSNNNDDC IPLDRRRLFL HADETEVIGL EDDFNTLQAK LLDHDLPYGV
 181 VSIVGMPGLG KTTLAKKLYR HVCHQFECSG LVYVSQQPRA GEILHDIAKQ VGLTEEERKE
 241 NLENNLRSLL KIKRYVILLD DIWDVEIWDD LKLVLPECDS KIGSRIIITS RNSNVGRYIG
 301 GDFSIHVLQP LDSEKSFELF TKKIFNFVND NWANASPDLV NIGRCIVERC GGIPLAIVVT
 361 AGMLRARGRT EHAWNRVLES MAHKIQDGCG KVLALSYNDL PIALRPCFLY FGLYPEDHEI
 421 RAFDLTNMWI AEKLIVVNTG NGREAESLAD DVLNDLVSRN LIQVAKRTYD GRISSCRIHD
 481 LLHSLCVDLA KESNFFHTEH NAFGDPSNVA RVRRITFYSD DNAMNEFFHL NPKPMKLRSL
 541 FCFTKDRCIF SQMAHLNFKL LQVLVVVMSQ KGYQHVTFPK KIGNMSCLRY VRLEGAIRVK
 601 LPNSIVKLKC LETLDIFHSS SKLPFGVWES KILRHLCYTE ECYCVSFASP FCRIMPPNNL
 661 QTLMWVDDKF CEPRLLHRLI NLRTLCIMDV SGSTIKILSA LSPVPRALEV LKLRFFKNTS
 721 EQINLSSHPN IVELGLVGFS AMLLNIEAFP PNLVKLNLVG LMVDGHLLAV LKKLPKLRIL
 781 ILLWCRHDAE KMDLSGDSFP QLEVLYIEDA QGLSEVTCMD DMSMPKLKKL FLVQGPNISP
 841 ISLRVSERLA KLRISQVL*
```

SEQ ID NO: 9 = AMINO ACID SEQUENCE OF Rpi-oka2
```
   1 MAEILLTAVI NKSIEIAGNV LFQEGTRLYW LKEDIDWLQR EMRHIRSYVD NAKAKEVGGD
  61 SRVKNLLKDI QQLAGDVEDL LDEFLPKIQQ SNKFICCLKT VSFADEFAME IEKIKRRVAD
 121 IDRVRTTYSI TDTSNNNDDC IPLDRRRLFL HADETEVIGL EDDFNTLQAK LLDHDLPYGV
 181 VSIVGMPGLG KTTLAKKLYR HVCHQFECSG LVYVSQQPRA GEILHDIAKQ VGLTEEERKE
 241 NLENNLRSLL KIKRYVILLD DIWDVEIWDD LKLVLPECDS KIGSRIIITS RNSNVGRYIG
 301 GDFSIHVLQP LDSEKSFELF TKKIFNFVND NWANASPDLV NIGRCIVERC GGIPLAIVVT
 361 AGMLRARGRT EHAWNRVLES MAHKIQDGCG KVLALSYNDL PIALRPCFLY FGLYPEDHEI
 421 RAFDLTNMWI AEKLIVVNTG NGREAESLAD DVLNDLVSRN LIQVAKRTYD GRISSCRIHD
 481 LLHSLCVDLA KESNFFHTEH YAFGDPSNVA RVRRITFYSD DNAMNEFFHL NPKPMKLRSL
 541 FCFTKDRCIF SQMAHLNFKL LQVLVVVMSQ KGYQHVTFPK KIGNMSCLRY VRLEGAIRVK
 601 LPNSIVKLKC LETLDIFHSS SKLPFGVWES KILRHLCYTE ECYCVSFASP FCRIMPPNNL
 661 QTLMWVDDKF CEPRLLHRLI NLRTLCIMDV SGSTIKILSA LSPVPKALEV LKLRFFKNTS
 721 EQINLSSHPN IVELGLVGFS AMLLNIEAFP PNLVKLNLVG LMVDGHLLAV LKKLPKLRIL
 781 ILLWCRHDAE KMDLSGDSFP QLEVLYIEDA QGLSEVTCMD DMSMPKLKKL FLVQGPNISP
 841 ISLRVSERLA KLRISQVL*
```

SEQ ID NO: 5 = AMINO ACID SEQUENCE OF Rpi-mcq1
If candidate 1 then:
```
   1 MAEILLTAVI NKSVEIAGNV LFQEGTRLYW LKEDIDWLQR EMRHIRSYVD NAKAKEVGGD
  61 SRVKNLLKDI QQLAGDVEDL LDEFLPKIQQ SSKFKGAICC LKTVSFADEF AMEIEKIKRR
 121 VVDIDRVRTT YNIMDTNNNN DCIPLDQRRL FLHVDETEVI GLDDDFNTLQ AKLLDQDLPY
 181 GVVSIVGMPG LGKTTLAKKL YRHVRHKFEC SGLVYVSQQP RAGEILIDIA KQVGLTEDER
 241 KENLENNLRS LLKRKRYVIL LDDIWDVEIW DDLKLVLPEC DSKIGSRIII TSRNSNVGRY
 301 IGGDFSIHVL QPLNSENSFE LFTKKIFIFD NNNNWTNASP NLVDIGRSIV GRCGGIPLAI
 361 VVTAGMLRAR ERTERAWNRL LESMSHKVQD GCAKVLALSY NDLPIALRPC FLYFGLYPED
 421 HEIRAFDLTN MWIAEKLIVV NSGNGREAES LADDVLNDLV SRNMIQVAKR TYDGRISSCR
 481 IHDLLHSLCV DLAKESNFFH TEHNALGDPG NVARLRRITF YSDNNAMNEF FRSNPKLEKL
 541 RALFCFTEDP CIFSQLAHLD FKLLQVLVVV IFVDDICGVS IPNTFGNMRC LRYLRFQGHF
 601 YGKLPNCMVK LKRLETLDIG YSLIKFPTGV WKSTQLKHLR YGGFNQASNS CFSISPFFPN
 661 LYSLPHNNVQ TLMWLDDKFF EAGLLHRLIN LRKLGIAGVS DSTVKILSAL SPVPTALEVL
 721 KLKIYRDMSE QINLSSYPNI VKLRLNVCGR MRLNCEAFPP NLVKLTLVGD EVDGHVVAEL
 781 KKLPKLRILK MFGCSHNEEK MDLSGDGDSF PQLEVLHIDE PDGLSEVTCR DDVSMPKLKK
 841 LLLVQRRPSP ISLSERLAKL RI*
```

SEQ ID NO: 10 = AMINO ACID SEQUENCE OF Rpi-mcq1
If candidate 2 then:
```
   1 MAEILLTTVI NKSVGIAANV LFQEGTRLYW LKEDIDWLHR EMRHIRSYVD DAKAKEVGGD
  61 SRVRNLLKDI QQLAGDVEDL LDEFLPKIQQ SNKFICCLKT VSFADEFAME IEKIKRRVAD
 121 ITRVRTTYNI TDTSNNNDDC IPLDRRRLFL HADETEVIGL EDDFNTLQAK LLDQDLPYGV
 181 VSIVGMPGLG KTTLAKKLYR HVRDQFESSG LVYVSQQPRA GEILRDIAKQ VGLPKEERKE
 241 NLEGNLRSLL KTKRYVILLD DIWDVEIWDD LKLVLPECDS EIGSRIIITS RNSNVGRYIG
 301 GDFSIHMLQP LDSENSFELF TKKIFTFDNN NNWANASPDL VDIGRSIVGR CGGIPLAIVV
 361 TAGMLRARER TEHAWNRVLE SMGHKVQDGC AKVLALSYND LPIALRPCFL YLGLFPEDHE
 421 IRAFDLTNMW IAEKLIVVNS GNGREAESLA EDVLNDFVSR NLIQVSQRKC NGRISSYRIH
 481 DLLHSLCVEL GKESNFFHTE HNAFGDPDNV ARVRRITFYS DNNAMSKFFR SNPKPKKLRA
 541 LFCFTNLDSC IFSHLAHHDF KLLQVLVVVI SYNWLSVSIS NKFGKMSCLR YLRLEGPIVG
 601 ELSNSIVKLK RVETIDIAGD NIKIPCGVWE SKQLRHLRNR EERRYFFSVS PFCLNMYPLP
 661 PNNLQTLVWM DDKFFEPRLL HRLINIRKLG IWGTSDSTIK ILSALSPVPT ALEVLKLYFL
 721 RDLSEQINLS TYPNIVKLNL QGFVRVRLNS EAFPPNLVKL ILDKIEVEGH VVAVLKKLPT
```

-continued

```
781 LRILKMYGCK HNEEKMDLSG DGDGDSFPQL EVLHIERPFF LFEITCTDDD SMPKLKKLLL
841 TTSNVRLSER LAKLRV*
```

SEQ ID NO: 6 = AMINO ACID SEQUENCE OF Rpi-nrs1

```
  1 MAEILLTAVI NKSIEIAGNV LFQEGTRLYW LKEDIDWLQR EMRHIRSYVD NAKAKEVGGD
 61 SRVKNLLKDI QQLAGDVEDL LDEFLPKIQQ SNKFICCLKT VSFADEFAME IEKIKRRVAD
121 IDRVRTTYSI TDTSNNNDDC IPLDRRRLFL HADETEVIGL EDDFNTLQAK LLDHDLPYGV
181 VSIVGMPGLG KTTLAKKLYR HVCHQFECSG LVYVSQQPRA GEILHDIAKQ VGLTEEERKE
241 NLENNLRSLL KTKRYVILLD DIWDVEIWDD LKLVLPECDS KIGSRIIITS RNSNVGRYIG
301 GDFSIHVLQP LDSEKSFELF TKKIFNFVND NWANASPDLV NIGRCIVERC GGIPLAIVVT
361 AGMLRARGRT EHAWNRVLES MAHKIQDGCG KVLALSYNDL PIALRPCFLY FGLYPEDHEI
421 RAFDLTNMWI AEKLIVVNTG NGREAESLAD DVLNDLVSRN LIQVAKRTYD GRISSCRIHD
481 LLHSLCVDLA KESNFFHTEH YAFGDPSNVA RVRRITFYSD DNAMNEFFHL NPKPMKLRSL
541 FCFTKDRCIF SQMAHLNFKL LQVLVVVMSQ KGYQHVTFPK KIGNMSCLRY VRLEGAIRVK
601 LPNSIVKLKC LETLDIFHSS SKLPFGVWES KILRHLCYTE ECYCVSFASP FCRIMPPNNL
661 QTLMWVDDKF CEPRLLHRLI NLRTLCIMDV SGSTIKILSA LSPVPKALEV LKLRFFKNTS
721 EQINLSSHPN IVELGLVGFS AMLLNIEAFP PNLVKLNLVG LMVDGHLLAV LKKLPKLRIL
781 ILLWCRHDAE KMDLSGDSFP QLEVLYIEDA QGLSEVTCMD DMSMPKLKKL FLVQGPNISP
841 ISLRVSERLA KLRISQVL*
```

SEQUENCE ANNEX IV (SEQ ID NO: 15):
>S1 IAAp

```
taaagcttcgtttttattaaaaaacgttaataagaaattatttgatataaatttaaattgaattgtatttcaaa
atacatatcgaattgaatgaaaaatccaaaagaaaaaattatatcagattagacttttttttgtgtttgtttta
aatttatacactaaaaattgtaataaatatttttttccattttaatttatttatcttattttaacttgacatata
atttaaaaatgaagattttgtaaaataatttaaatgaataagaaaaatattcttttttaaaactattacaaaaaa
gtagaacagctatatcaaaacaaaattagcagtaaatttaaacttatatctcaaataatagcaaagacttaaa
attaagaatcgatctaaaaagacatatttcttatttaatactatacttaatgactttatttatttattattcat
gttaatctcacttagttatttgacaatgttcacaataatataatctctgtatttgaaatttcatttatattaaa
aataatttttaaacattaaacgtcttctgttatgaacaaaatttacgcatgtaatcacggccgtgttaaatgttt
ttatgtttacatacatctgtatcttatttacaaaaaaaaaaaatatatatccttataatcgcgtcagttccnac
ttccatgtaacgtaacgttaattcttccctccatttcgtcaaactaactcatcattatcagtgtcggagtcnaa
aaatttattaaaaagtcaaaaatacgaagaatagaaatacgagaaatgcaagaggtcttatatataatatcgga
aaatctttctggccagaagaatttagataaaatttataaatgatattttacgttaccttttttgaacattttcat
tttaacttttagtatattttgattaaaaaataagaaaaagagctgtttatttttaatttctttttgaatttctgaaca
ctttttttttgaccatttagcactacccttaaaccatatatatatatatatatatgttcgacccttttgctagctccac
cctcgatcaagggtggagCtagcttatggtcagcggttcatctactatttattaatagttaaatttactttata
tatatactctatttttgttcttacttgtctattttgacaaataaaaaattcttacctattatactcttaattgat
tactgtgaaaaatatagaattttttgctaaatcttaaattttttaatttatccacgtcataattaatatgagtaaa
atgataaactcgctaaatcaaataattattttttcttaatagatgtgttaattcaagagtagacaaataactaggg
atagagaaagtatactgtagatgttgaactctcttgattaattagtctgtatattttattcttcacctaataaa
aatctgtcgattttcggtagcaaaggcattgaatactagcgtgtggagtgtccctcttgtgttccctcattgcc
ggttatgtgagggaacaccattccctgttgcatcaaatttgtgttccaaaactaacgtaacttccgtgcaaaaat
cgcacccaacgtgcgtctgtttacctggctgcaagcaagcgcgtattgacaacgaatcgtaggcgagttgtttt
ctccgtgttattatttatgagattcatgcacacacaaagaataactcgcctacatattgtcttttttcctatata
acaatcctcacaattcacagcaattcaaatcaatcattctttctaaatc
```

SEQUENCE ANNEX V (SEQ ID NO: 16):
>pSIM108

```
agctttggcaggatatataccggtgtgtaaacgaagtgtgtgtggttgatccaaaatctatcgtacctttagaaag
tgtagctatgaaggatagtctcacttatgaagaactacctattgagattcttgatcgtcaggtccgaaggttga
gaaaaatagaagtcgcttcagttacggctttgtggaggagtaagggtacccggggatcaattcccgatctagta
acatagatgacaccgcgcgcgataatttatcctagtttgcgcgctatatttttgttttctatcgcgtattaaatg
tataattgcgggactctaatcataaaaacccatctcataaataacgtcatgcattacatgttaattattacatg
cttaacgtaattcaacagaaatttatatgataatcatcgcaagacccggcaacaggattcaatcttaagaaacttt
attgccaaatgtttgaacgatcggggaaattcgagctctcagaagaactcgtcaagaaggcgatagaaggcgat
gcgctgcgaatcgggagcggcgataccgtaaagcacgaggaagcggtcagcccattcgccgccaagctcttcag
caatatcacgggtagccaacgctatgtcctgatagcggtccgccacacccagccggccacagtcgatgaatcca
gaaaagcggccattttccaccatgatattcggcaagcaggcatcgccatgggtcacgacgagatcatcgccgtc
gggcatgcgcgccttgagcctggcgaacatcggctggcgcgaacatcggctgcttcgtcctgcagttcattcagg
gcaccggacaggtcggtcttgacaaaaagaaccgggcgcccctgcgctgacagccggaacacgcggcatcaga
gcagccgattgtctgttgtgcccagtcatagccgaatagcctctccacccaagcggccgagaacctgcgtgca
atccatcttgttcaatcatacccgggatcctctagagtccccgtgttctctccaaatgaaatgaacttcctt
atataggaagggtcttgcgaaggatagtgggattgtgcgtcatccctttacgtcagtggagatatcacatcaa
tccacttgctttgaagacgtggttggaacgtcttctttttccacgatgctcctcgtgggtggggggtccatcttt
gggaccactgtcggcagaggcatcttcaacgatggccttttccttttatcgcaatgatggcatttgtaggagccac
cttccttttccactatcttcacaataaagtgacagatagctgggcaatggaatccgaggaggtttccggatatt
acccttttgttgaaaagtctcaattgcccttttggtcttctgagactgtatctttttggagtagacaag
tgtgtcgtgctccaccatgttgacgaagattttcttcttgtcattgagtcgtaagagactctgtatgaactgtt
cgccagtctttacggcgagttctgttaggtcctctatttgaatctttgactccatggccttttgattcagtggga
actacctttttagagactccaatctctattacttgccttggtttgtgaagcaagccttgaatcgtccatactgg
aatagtacttctgatcttgagaaatatatctttctctgtgttcttgatgcagttagtcctgaatctttttgactg
catctttaaccttcttgggaaggtatttgattctcctggagattattgctcgggtagatcgtcttgatgagacct
gctgcgtaagcctctctaaccatctgtgggttagcattcttttctgaaattggaaaaggctaatctgggacctg
cagttatgctataaatttcatatatttagttgggagtaggctttataccgagttggactacggtcagtcactt
caagtcctagaactacgtgcccctgtaggttataagtctcctctgtgggcatcaatttagtgatcatgccagtc
atgcctctataccctctgacaggatatatgtgctactgtaaacactagttgtgaataagtcgctgtgtatgtttgtt
```

-continued

```
tgagatctctaagagaaaagagcgtttattagaataacggatatttaaaagggcgtgaaaaggtttatccgttc
gtccatttgtatgtggtcacctatctcgagcatgccaaccacagggttccctcgggatcaaagtactttgatc
caaccctccgctgctatagtgcagtcggcttctgacgttcagtgcagccgtcttctgaaaacgacatgtcgca
caagtcctaagttacgcgacaggctgccgccctgccctttcctggcgttttcttgtcgcgtgttttagtcgca
taaagtagaatacttgcgactagaaccggagacattacgccatgaacaagagcgccgccgctggcctgctggc
tatgccgcgtcagcaccgacgaccaggacttgaccaaccaacgggccgaactgcacggggccggctgcaccaa
gctgttttccgagaagatcaccggcaccaggcgcgaccgcccggagctggccaggatgcttgaccacctacgcc
ctggcgacgttgtgacagtgaccaggctagaccgcctggcccgcagcacccgcgacctactggacattgccgag
cgcatccaggaggccggcgcgggcctgcgtagcctggcagagccgtgggccgacaccaccacgccggccggccg
catggtgttgaccgtgttcgccggcattgccgagttcgagcgttccctaatcatcgaccgcaccggagcgggc
gcgaggccgccaaggcccgaggcgtgaagtttggccccgccctaccctcacccggcacagatcgcgcacgcc
cgcgagctgatcgaccaggaaggccgcaccgtgaaagaggcggctgcactgcttggcgtgcatcgctcgaccct
gtaccgcgcacttgagcgcagcgaggaagtgacgccaccgaggccaggcggcgcggtgccttccgtgaggacg
cattgaccgaggccgacgccctggcggccgccgagaatgaacgccaagaggaacaagcatgaaaccgcaccagg
acggccaggacgaaccgttttcattaccgaagagatcgaggcggagatgatcgcggcgggtacgtgttcgag
ccgcccgcgcacgtctcaaccgtgcgctgcatgaaatcctggccggtttgtctgatgccaagctggcggcctg
gccggccagcttggccgctgaagaaaccgagcgccgccgtctaaaaaggtgatgtgtatttgagtaaaacagct
tgcgtcatgcggtcgctgcgtatatgatgcgatgagtaaataaacaaatacgcaagggaacgcatgaaggtta
tcgctgtacttaaccagaaaggcgggtcaggcaagacgaccatcgcaacccatctagcccgcgccctgcaactc
gccggggccgatgttctgttagtcgattccgatccccagggcagtgcccgcgattgggcggccgtgcgggaaga
tcaaccgctaaccgttgtcggcatcgaccgcccgacgattgaccgcgacgtgaaggccatcggccggcgcgact
tcgtagtgatcgacggagcgccccaggcggacgacttggctgtgtccgcgatcaaggcagccgacttcgtgctg
attccggtgcagccaagcccttacgacatatgggccaccgccgacctggtggagctggttaagcagcgcattga
ggtcacggatggaaggctacaagcggcctttgtcgtgtcgcgggcgatcaaaggcacgcgcatcggcggtgagg
ttgccgaggcgctggccgggtacgagctgcccattcttgagtcccgtatcacgcagcgcgtgagctacccaggc
actgccgccgccggcacaaccgttcttgaatcagaacccgagggcgacgctgcccgcgaggtccaggcgctggc
cgctgaaattaaatcaaaactcatttgagttaatgaggtaaagagaaaatgcaaaagcacaaacacgctaag
tgccggccgtccgagcgcacgcagcagcaaggctgcaacgttggccagcctggcagacacgccagccatgaagc
gggtcaacttcagttgccggcggaggatcacaccaagctgaagatgtacgcggtacgccaaggcaagaccatt
accgagctgctatctgaatacatcgcgcagctaccagagtaaatgagcaaatgaatagtgatgagtagatttt
tagccggctaaaggaggcggcatggaaaatcaagaacaaccaggcaccgacgccgtgaatgcccccatgtgtgga
ggaacgggcggttggccaggcgtaagcggctgggttgtctgccggccctgcaatggcactggaaccccccaagcc
cgaggaatcggcgtgacggtcgcaaaccatccggcccggtacaaatcggcgcggcgctgggtgatgacctggtg
gagaagttgaaggccgcgcaggccgcccagcggcaacgcatcgaggcagaagcacgcccggtgaatcgtggca
agcggccgctgatcgaatccgcaaagaatcccggcaacgccggcgacgtggtgccgtcgattaggaagccgc
ccaagggcgacgagcaaccagatttttcgttccgatgctctatgacgtgggcacccgcgatagtcgcagcatc
atggacgtggccgttttccgtctgtcgaagcgtgaccgacgagctggcgaggtgatccgctacgagcttccaga
cgggcacgtagaggtttccgcagggccggccggcatggccagtgtgtgggattacgacctggtactgatggcgg
tttccatctaaccgaatccatgaaccgataccgggaagggaagagacaaacccggccgcgtgttccgtcca
cacgttgcggacgtactcaagttctgccggcgagccgatggcgaaagcagaaagacgacctggtagaaacctg
cattcggttaaacaccacgcacgttgccatgcagcgtacgaagaaggccaagaacggccgcctggtgacggtat
ccgagggtgaagccttgattagccgctacaagatcgtaaagagcgaaaccgggcggccggagtacatcgagatc
gagctagctgattggatgtaccgcgagatcacagaaggcaagaaccgcgtgacggttcaccccgatta
ctttttgatcgatcccggcatcggccgttttctctaccgcctggcacgccgcgccgcaggcaaggcagaagcca
gatggttgttcaagacgatctacgaacgcagtggcagcgccggagagttcaagaagttctgtttcaccgtgcgc
aagctgatcgggtcaaatgacctgccggagtacgatttgaaggaggaggcggggcaggctggcccgatcctagt
catgcgctaccgcaacctgatcgagggcgaagcatccgccggttcctaatgtacggagcagatgctagggcaaa
ttgccctagcagggaaaaggtcgaaaaggtctcttctgtggatagcacgtacattgggaacccaaagccg
tacattgggaaccggaacccgtacattgggaacccaaagccgtacattgggaaccggtcacacatgtaagtgac
tgatataaaagagaaaaaggcgattttccgcctaaaactctttaaaacttattaaaactcttaaaacccgcc
tggcctgtgcataactgtctggccagcgcacagccgaagagctgcaaaaaggcctaccctccggtcgctgcgc
tccctacgccccgccgcttcgcgtcggcctatcgcggccgctggccgctcaaaaatggctggcctacggccagg
caatctaccagggcgcggacaagccgcgccgtcgccactcgaccgccggcgcccacatcaaggcaccctgcctc
gcgcgtttcggtgatgacggtgaaaacctctgacacatgcagctcccggagacggtcacagcttgtctgtaagc
ggatgccgggagcagacaagcccgtcagggcgcgtcagcgggtgttggcgggtgtcggggcgcagccatgaccc
agtcacgtagcgatagcggagtgtatactggcttaactatgcggcatcagagcagattgtactgagagtgcacc
atatgcggtgtgaaataccgcacagatgcgtaaggagaaaataccgcatcaggcgctcttccgcttcctcgctc
actgactcgctgcgctcggtcgttcggctgcggcgagcggtatcagctcactcaaaggcggtaatacggttatc
cacagaatcaggggataacgcaggaaagaacatgtgagcaaaaggccagcaaaaggccaggaaccgtaaaaagg
ccgcgttgctggcgtttttccataggctccgcccccctgacgagcatcacaaaaatcgacgctcaagtcagagg
tggcgaaacccgacaggactataaagataccaggcgtttccccctggaagctccctcgtgcgctctcctgttcc
gaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgac
cgctgcgccttatccggtaactatcgtcttgagtccaacccggtaagacacgacttatcgccactggcagcagc
cactggtaacaggattagcagagcgaggtatgtaggcggtgctacagagttcttgaagtggtggcctaactacg
gctacactagaaggacagtatttggtatctgcgctctgctgaagccagttaccttcggaaaaagagttggtagc
tcttgatccggcaaacaaaccaccgctggtagcggtggtttttttgtttgcaagcagcagattacgcgcagaaa
aaaaggatctcaagaagatccttttgatcttttctacggggtctgacgctcagtggaacgaaaactcacgttaag
ggattttggtcatgcattctaggtactaaaacaattcatccagtaaaatataatattttattttctcccaatca
ggcttgatccccagtaagtcaaaaaatagctcgacatactgttcttccccgatatcctccctgatcgaccggac
gcagaaggcaatgtcataccacttgtccgccctgccgcttctcccaagatcaataaagccacttactttgccat
ctttcacaaagatgttgctgtctcccaggtcgCcgtgggaaaagcaaagttcctcttcgggctttttccttt
aaaaaatcatcacagctcgcgcggatctttaaatggagtgtcttcttcccagttttcgcaatccacatcggccag
atcgttattcagtaagtaatccaattcggctaagcggctgtctaagctattcgtatagggacaatccgatatgt
cgatggagtgaaagagcctgatgcactccgcatacagctcgataatcttttcagggctttgttcatcttcatac
tcttccgagcaaaggacgccatcggcctcactcatgagcagattgctccagccatcatgccgttcaaagtgcag
gacctttggaacaggcagctttccttccagccatagcatcatgtcctttccccgttccacatcataggtggtcc
ctttataccggctgtccgtcatttttaaatataggttttcatttctcccaccagcttatataccttagcagga
gacattccttccgtatcttttacgcagcggtatttttcgatcagttttttcaattccggtgatattctcatttt
agccatttattatttccttcctcttttctacagtatttaaagataccccaagaagctaattataacaagacgaa
ctccaattcactgttccttgcattctaaaaccttaaataccgagaaaacagctttttcaaagttgtttttcaaagt
```

-continued

```
tggcgtataacatagtatcgacggagccgattttgaaaccgcggatcctgcagccaaagcacatacttatcgat
ttaaatttcatcgaagagattaatatcgaataatcatatacatacttaaatacataacaaattttaaatacat
atatctggtatataattaattttttaaagtcatgaagtatgtatcaaatacacatatggaaaaaattaactatt
cataatttaaaaaatagaaaagatacatctagtgaaattaggtgcatgtatcaaatacattaggaaaagggcat
atatcttgatctagataataattaacgattttgatttatgtataatttccaaatgaaggtttatatctacttcagaa
ataacaatatacttttatcagaacattcaacaaagtaacaaccaactagagtgaaaaatacacattgttctcta
aacatacaaaattgagaaaagaatctcaaaatttagagaaacaaatctgaatttctagaagaaaaaaataatta
tgcactttgctattgctcgaaaaataaatgaaagaaattagacttttttaaaagatgttagactagatatactc
aaaagctatcaaaggagtaatattcttcttacattaagtattttagttacagtcctgtaattaaagacacattt
tagattgtatctaaacttaaatgtatctagaatacatatatttgaatgcatcatatacatgtatccgacacacc
aattctcataaaaagcgtaatatcctaaactaatttatccttcaagtcaacttaagcccaatatacattttcat
ctctaaaggcccaagtggcacaaaatgtcaggcccaattacgaagaaaagggcttgtaaaacctaataaagtg
gcactggcagagcttacactctcattccatcaacaaagaaacccctaaaagccgcagcgccactgatttctctcc
tccaggcgaagatgcagatcttcgtgaagacccctaacggggaagacgatcacctagaggttgagtcttccgac
accatcgacaatgtcaaagccaagatccaggacaaggaagggattccccccagaccagcagcgtttgattttcgc
cggaaagcagcttgaggatggtcgtactcttgccgactacaacatccagaaggagtcaactctccatctcgtgc
tccgtctccgtggtggtggatccatggacctgcatctaatttcggtccaacttgcacaggaaagacgacgacc
gcgatagctcttgcccagcagacagggcttccagtcctttcgcttgatcgggtccaatgctgtcctcaactatc
aaccggaagcggacgaccaacagtggaagaactgaaaggaacgacgcgtctctaccttgatgatcggcctctgg
tggagggtatcatcgcagccaagcaagctcatcataggctgatcgaggaggtgtataatcatgaggccaacggc
gggcttattcttgagggaggatccacctcgttgctcaactgcatggcgcgaaacagctattggagtgcagattt
tcgttggcatattattcgccacaagttacccgaccaaggagaccttcatgaaagcggcCaaggccagagttaagc
agatgttgcaccccgctgcaggccattctattattcaagagttggtttatctttggaatgaacctccggctgagg
cccattctgaaagagatcgatggatatcgatatgccatgttgtttgctagccagaaccagatcacggcagatat
gctattgcagcttgacgcaaatatggaagtaagttgattaatgggatcgctcaggagtatttcatccatgcgc
gccaacaggaacagaaattcccccaagttaacgcagccgctttcgaagattcgaaggtcatccgttcggaatg
tattaggttacgccagccctcgctcgcacctgtcttcatctggataagatgttcgtaattgttttttggctttgt
cctgttgtggcagggcggcaaatacttccgacaatccatcgtgtcttcaaactttatgctggtgaacaagtctt
agtttccacgaaagtattatgttaaattttaaaatttcgatgtataatgtggctataattgtaaaaataaacta
tcgtaagtgtgcgtgttatgtataatttgtctaaatgtttaatatatatcatagaacgcaataaatattaaata
tagcgcttttatgaaatataaatacatcattacaagttgtttatatttcgggtggactagtttttaatgtttag
caaatgtcctatcagttttctcttttttgtcgaacggtaatttagagttttttttgctatatggattttcgttttt
tgatgtatgtgacaaccctcgggattgttgatttatttcaaaactaagagttttttgcttattgttctcgtctat
tttggatatcaatcttagttttatatcttttctagttctctacgtgttaaatgttcaacacactagcaatttgg
ctgcagcgtatggattatgaaactatcaagtctgtgggatcgaattgaaatttctcaggaattgagattttta
cagtcttatgctcattgggttgagtataatatagtaaaaaaataggaattctatccgcggtgatcacaggcag
caacgctctgtcatcgttacaatcaacatgctaccctcgcgagatcatccgtgtttcaaacccggcagcttag
ttgccgttcttccgaatagcatcggtaacatgagcaaagtctgccgcttacaacggctctcccgctgacgccg
tcccggactgatgggctgcctgtatcgagtggtgattttgtgccgagctgccggtcggggagctgttggctggc
tgga
```

SEQUENCE ANNEX VI (SEQ ID NO: 17, nucleotide sequence; SEQ ID NO: 18, amino acid sequence):
>Ant1 nucleotide sequence

```
Atgagtactcctatgatgtgtacattttggggagtaataaggaaaggttcatggactgaagaagaagatattct
tttgagggaaatgtattgataagtatggagaaggaaagtggcatcttgttccaactagagctggattaaacagat
gcagaaaaagttgtagactgaggtggctaaattatctaaggccacatatcaagagaggtgactttgaaccagat
gaagtggatctcatcttgagacttcataagctcttaggcaaccgatggtcacttattgctggtagacttccagg
aaggacagctaacgatgtgaaaaactattggaacactaaccttctaaggaagctaaatactagtactaaatttg
ctcctcaaccacaagaaggaattaatactagtactattgctcctcaaccacaagaaggaattaagtatgggcaa
gccaatgccataataagacctcaacctcagaaattcacaagctccatgaagattaatgtctcttggtgcaacaa
caatagtatggtaaataatgaagaagcatcgaaagacaacaacgatatgcaatggtgggcaaatatactggaaa
actgcaatgacattggagaaggagaagctgaaagaacactaccttcatgtaaggaaattaattgcaatgaaatt
gataaagcaccaagtttgttacatgagggaggcaactccatgcaacaaggacaaggtgatggtggtgggatga
atttgctctagatgatatatggaatctacttaattag
```

>Ant1 protein sequence

```
mstpmmctflgvirkgswteeedillrkcidkygegkwhlvptraglnrcrkscrlrwlnylrphikrgdfepd
evdlilrlhkllgnrwsliagrlpgrtandvknywntnllrklntstkfapqpqegintstiapqpqegikygq
anaiirpqpqkftssmkinvswcnnnmvnneeaskdnndmqwwanilencndigegeaertlpsckeincneid
kapsllheggnsmqgqgdggwdefalddiwnlln
```

SEQUENCE ANNEX VII (SEQ ID NO: 19, nucleotide sequence; SEQ ID NO: 20, amino acid sequence):
>pan1

```
atgagtactcctatgatgtgtacattttggggagtaataaggaaaggttcatggactgaagaagaagatattct
tttgagggaaatgtattgataagtatggagaaggaaagtggcatcttgttccaactagagctggattaaacagat
gcagaaaaagttgtagactgaggtggctaaattatctaaggccacatatcaagagaggtgactttgaaccagat
gaagtggatctcatcttgagacttcataagctcttaggcaaccgatggtcacttattgctggtagacttccagg
aaggacagctaacgatgtgaaaaactattggaacactaaccttctaaggaagctaaatactagtactaaatttg
ctcctcaaccacaagaaggaattaatactagtactattgctcctcaaccacaagaaggaattaagtatgggcaa
gccaatgccataataagacctcaacctcagaaattcacaagctccatgaagattaatgtctcttggtgcaacaa
caatagtatggtaaataatgaagaagcatcgaaagacaacaacgatatgcaatggtgggcaaatatactggaaa
actgcaatgacattggagaaggagaagctgaaagaacactaccttcatgtaaggaaattaattgcaatgaaatt
gataaagcaccaagtttgttacatgagggaggcaactccatgcaacaaggacaaggtgatggtggtgggatga
atttgctctagatgatatatggaatctacttaattag
```

>PAN1

```
MSTPMMCTFLGVIRKGSWTEEEDILLRKCIDKYGEGKWHLVPTRAGLNRCRKSCRLRWLNYLRPHIKRGDFEPD
EVDLILRLHKLLGNRWSLIAGRLPGRTANDVKNYWNTNLLRKLNTSTKFAPQPQEGINTSTIAPQPQEGIKYGQ
```

-continued
ANAIIRPQPQKFTSSMKINVSWCNNNSMVNNEEASICDNNDMQWWANILENCNDIGEGEAERTLPSCKEINCNE
IDKAPSLLHEGGNSMQQGQGDGGWDEFALDDIWNLLN SEQUENCE ANNEX VIII (StMyb12, SEQ ID NO: 20; SlMyb12, SEQ ID NO: 21;
AtMyb12, SEQ ID NO: 22
CLUSTAL W (1.83) multiple sequence alignment
StMyb12/1-362  MGRTPCCEKVGIKRGRWTAEEDQILTNYILSNGEGSWRSLPKNAGLLRCGKSCRLRWINY
SlMyb12/1-339  MGRTPCCEKVGIKRGRWTAEEDQILTNYIISNGEGSWRSLPKNAGLLRCGKSCRLRWINY
AtMyb12/1-371  MGRAPCCEKVGIKRGRWTAEEDQILSNYIQSNGEGSWRSLPKNAGLKRCGKSCRLRWINY StMyb12/1-362  LRSDLKRGNITSQEEDIIIKLHATLGNRWSLIAGHLSGRTDNEIKNYWNSHLSRKVD-SL
SlMyb12/1-339  LRSDLKRGNITSQEEDIIIKLHATLGNRWSLIAEHLSGRTDNEIKNYWNSHLSRKVD-SL
AtMyb12/1-371  LRSDLKRGNITPEEEELVVKLHSTLGNRWSLIAGHLPGRTDNEIKNYWNSHLSRKLHNFI StMyb12/1-362  RIPSDEKLPKAVVDLAKKGTLKPIKHCRKSLISRSKNKKSNLLEAKENSTSGALIGIVPM
SlMyb12/1-339  RIPSDEKLPKAVVDLAKKGIPKPIK---KSSISRPKNKKSNLLEK---------------
AtMyb12/1-371  RKPSISQDVSAVIMTNASSAPPPPQAKRRLGRTSRSAMKPKIHRTKTRKTKKTSAPPEPN StMyb12/1-362  PSTPNIEKEALCCTNMPACDSAMALMQEDVAKVEVPNSWAGSIEAKG-SLSSDSGMEWPR
SlMyb12/1-339  --------EALCCTNMPACDSAMELMQEDLAKIEVPNSWGRTYRGQGKPLVQIVISNGPR
AtMyb12/1-371  ADVAGADKEALMVE---SSGAEAELGRPCDYYGDDCNKNLMSINGDNGVLTFDDDIIDLL StMyb12/1-362  LEEIMPDVVIDDEDMNPNFILNGLEEEVMSNNAGNNYS-----CIDEGNKNVSSDDEKSK
SlMyb12/1-339  LEEIMPDVVIDDEDKNTNFILNCFREEVTSNNVGNSYS-----CIEEGNKKISSDDEKIK
AtMyb12/1-371  LDESDPGHLYTNTTCGGDGELHNIRDSEGARGFSDTWNQGNLDCLLQSCPSVESFLNYDH StMyb12/1-362  LLMDWQDDDELVWPTPPWELETDIIPSWPQWDDTDTDLLQN---CTN--NNYEEATTMEI
SlMyb12/1-339  LLMDWQDNDELVWPTLPWELETDIVPSWPQWDDTDTNLLQN---CTNDNNNYEEATTMEI
AtMyb12/1-371  QVNDASTDEFIDWDCVWQEGSDNNLWHEKENPDSMVSWLLDGDDEATIGNSNCENFGEPL StMyb12/1-362  NNQNHSAIVSWLLS
SlMyb12/1-339  NNQNHSTIVSWLLS
AtMyb12/1-371  DHDDESALVAWLLS

The invention claimed is:

1. A method for increasing the level of one or more anthocyanins in a plant of the family Solanaceae or in at least one part of the plant, said method comprising causing or allowing within the plant or in at least one part, the expression of:
   (a) a first heterologous nucleic acid comprising a first nucleotide sequence which encodes Rosea1, Pan1, or a functional variant of Rosea1 comprising at least 90% amino acid sequence identity to SEQ ID NO: 84; and
   (b) a second heterologous nucleic acid comprising a second nucleotide sequence which encodes Delila or a functional variant comprising at least 90% amino acid sequence identity to SEQ ID NO: 86;
wherein the level of one or more anthocyanins is increased in the plant or in at least one part when compared to the level of one or more anthocyanins in a wild-type plant or part thereof.

2. The method of claim 1, wherein the functional variant of (a) is a *Solanum* homolog of Rosea1.

3. The method as claimed in claim 1, wherein the first nucleotide sequence encodes-a Pan1 polypeptide comprising the amino acid sequence set forth in SEQ ID NO: 20.

4. The method of claim 3, wherein the first nucleotide sequence comprises SEQ ID NO: 19.

5. The method of claim 1, wherein the first nucleotide sequence encodes a Rosea1 polypeptide comprising the amino acid sequence set forth in SEQ ID NO: 84.

6. The method of claim 1, wherein the first nucleotide sequence comprises SEQ ID NO: 83.

7. The method of claim 1, wherein the second nucleotide sequence encodes a Delila polypeptide comprising the amino acid sequence set forth in SEQ ID NO: 86.

8. The method of claim 1, wherein the second nucleotide sequence comprises SEQ ID NO: 85.

9. The method of claim 1, wherein the plant is a tomato plant or a potato plant.

10. The method of claim 1, wherein the level of one of more anthocyanins is increased in a fruit or a tuber.

11. The method of claim 1, wherein the plant is a tomato plant and the level of one of more anthocyanins is increased in a tomato fruit.

12. The method of claim 1, wherein the first heterologous nucleic acid further comprises a first promoter, said first promoter operably linked to the first nucleotide sequence and wherein the second heterologous nucleic acid further comprises a second promoter, said second promoter operably linked to the second nucleotide sequence.

13. The method of claim 1, wherein the first promoter is an E8 promoter and the second promoter is an E8 promoter.

14. The method of claim 12, wherein the first heterologous nucleic acid and the second heterologous nucleic acid are incorporated into the genome of the plant.

15. A plant or part thereof comprising in its genome:
   (a) a first heterologous nucleic acid comprising a first promoter and an operably linked first nucleotide sequence which encodes Rosea1, Pan1, or a functional variant of Rosea1 comprising at least 90% amino acid sequence identity to SEQ ID NO: 84; and
   (b) a second heterologous nucleic acid comprising a second promoter and an operably linked second nucleotide sequence which encodes Delila or a functional variant comprising at least 90% amino acid sequence identity to SEQ ID NO: 86;
wherein the level of one of more anthocyanins is increased in the plant or part thereof when compared to the level of the one of more anthocyanins in a wild-type plant or part thereof.

16. The plant or part thereof of claim 15, wherein the first heterologous nucleic acid and the second heterologous nucleic acid are stably incorporated into the genome of the plant or part thereof.

17. The plant or part thereof of claim 15, wherein the functional variant of (a) is a *Solanum* homolog of Rosea1.

18. The plant or part thereof of claim 15, wherein the first nucleotide sequence encodes a Pan1 polypeptide comprising the amino acid sequence set forth in SEQ ID NO: 20.

19. The plant or part thereof of claim 15, wherein the first nucleotide sequence comprises SEQ ID NO: 19.

20. The plant or part thereof of claim 15, wherein the first nucleotide sequence encodes a Rosea1 polypeptide comprising the amino acid sequence set forth in SEQ ID NO: 84.

21. The plant or part thereof of claim 15, wherein the first nucleotide sequence comprises SEQ ID NO: 83.

22. The plant or part thereof of claim 15, wherein the second nucleotide sequence encodes a Delila polypeptide comprising the amino acid sequence set forth in SEQ ID NO: 86.

23. The plant or part thereof of claim 15, wherein the second nucleotide sequence comprises SEQ ID NO: 85.

24. The plant or part thereof of claim 15, wherein the plant is a plant of the family Solanaceae.

25. The plant or part thereof of claim 15, wherein the plant is a tomato plant or potato plant.

26. The plant or part thereof of claim 25, wherein the part is a tomato fruit or a potato tuber.

27. The plant or part thereof of claim 15, wherein the plant is a tomato plant and the part thereof is a tomato fruit.

28. The plant or part thereof of claim 15, wherein the plant is a seed.

29. A food product produced from the plant or part thereof of claim 15, wherein the food product comprises the first heterologous nucleic acid and the second heterologous nucleic acid.

* * * * *

SEQUENCE LISTING

<160> NUMBER OF SEQ ID NOS: 86

<210> SEQ ID NO 1
<211> LENGTH: 2577
<212> TYPE: DNA
<213> ORGANISM: Solanum okadae

<400> SEQUENCE: 1
atggctgaaa ttcttctcac agcagtcatc aataaatcaa tagaaatagc tggaaatgta      60 ctcttttcaag aaggtacgcg tttatattgg ttgaaagagg acatcgattg gctccagaga     120
gaaatgagac acattcgatc atatgtagac aatgcaaagg caaggaagt tggaggcgat       180 tcaagggtga aaaacttatt aaaagatatt caacaactgg caggtgatgt ggaggatcta     240
ttagatgagt tccttccaaa aattcaacaa tccaataagt tcatttgttg ccttaagacg     300
gtttcttttg ccgatgagtt tgctatggag attgagaaga taaaaagaag agttgctgat     360
attgaccgtg taaggacaac ttacagcatc acagatacaa gtaacaataa tgatgattgc     420
attccattgg accggagaag attgttcctt catgctgatg aaacagaggt catcggtctg     480
gaagatgact tcaatacact acaagccaaa ttacttgatc atgatttgcc ttatggagtt     540
gtttcaatag ttggcatgcc cggtttggga aaaacaactc ttgccaagaa actttatagg     600
catgtctgtc atcaatttga gtgttcggga ctggtctatg tttcacaaca gccaagggcg     660
ggagaaatct acatgacat agccaaacaa gttggactga cggaagagga aaggaaagaa       720
aacttgagaa caacctacg atcactcttg aaaataaaaa ggtatgttat tctcttagat       780
gacatttggg atgttgaaat tgggatgat ctaaaacttg tccttcctga atgtgattca        840
aaaattggca gtaggataat tataacctct cgaatagta atgtaggcag atacatagga        900
ggggatttct caatccacgt gttgcaaccc ctagattcag agaaaagctt tgaactcttt      960

```
accaagaaaa tctttaattt tgttaatgat aattgggcca atgcttcacc agacttggta    1020
aatattggta gatgtatagt tgagagatgt ggaggtatac cgctagcaat tgtggtgact    1080
gcaggcatgt taagggcaag aggaagaaca gaacatgcat ggaacagagt acttgagagt    1140
atggctcata aaattcaaga tggatgtggt aaggtattgg ctctgagtta caatgatttg    1200
cccattgcat taaggccatg tttcttgtac tttggtcttt accccgagga ccatgaaatt    1260
cgtgcttttg atttgacaaa tatgtggatt gctgagaagc tgatagttgt aaatactggc    1320
aatgggcgag aggctgaaag tttggcggat gatgtcctaa atgatttggt ttcaagaaac    1380
ttgattcaag ttgccaaaag gacatatgat ggaagaattt caagttgtcg catacatgac    1440
ttgttacata gtttgtgtgt ggacttggct aaggaaagta acttcttcca cacggagcac    1500
aatgcatttg gtgatcctag caatgttgct agggtgcgaa ggattacatt ctactctgat    1560
gataatgcca tgaatgagtt cttccattta aatcctaagc ctatgaagct tcgttcactt    1620
ttctgtttca caaagaccg ttgcatattt tctcaaatgg ctcatcttaa cttcaaatta    1680
ttgcaagtgt tggttgtagt catgtctcaa aagggttatc agcatgttac ttccccaaa     1740
aaaattggga acatgagttg cctacgttat gtgcgattgg aggggcaat tagagtaaaa      1800
ttgccaaata gtattgtcaa gctcaaatgt ctagagaccc tggatatatt tcatagctct    1860
agtaaacttc cttttggtgt tgggagtct aaaatattga gacatctttg ttacacagaa      1920
gaatgttact gtgtctcttt tgcaagtcca ttttgccgaa tcatgcctcc taataatcta    1980
caaactttga tgtgggtgga tgataaattt tgtgaaccaa gattgttgca ccgattgata    2040
aatttaagaa cattgtgtat aatggatgta tccggttcta ccattaagat attatcagca    2100
ttgagccctg tgcctagagc gttggaggtt ctgaagctca gattttcaa gaacacgagt      2160
gagcaaataa acttgtcgtc ccatccaaat attgtcgagt tgggtttggt tggtttctca    2220
gcaatgctct tgaacattga agcattccct ccaaatcttg tcaagcttaa tcttgtcggc    2280
ttgatggtag acggtcatct attggcagtg cttaagaaat tgcccaaatt aaggatactt    2340
atattgcttt ggtgcagaca tgatgcagaa aaaatggatc tctctggtga tagctttccg    2400
caacttgaag ttttgtatat tgaggatgca caagggttgt ctgaagtaac gtgcatggat    2460
gatatgagta tgcctaaatt gaaaaagcta tttcttgtac aaggcccaaa catttcccca    2520
attagtctca gggtctcgga acggcttgca aagttgagaa tatcacaggt actataa       2577
```

<210> SEQ ID NO 2
<211> LENGTH: 2589
<212> TYPE: DNA
<213> ORGANISM: Solanum mochiquense

<400> SEQUENCE: 2

```
atggctgaaa ttcttcttac agcagtcatc aataaatctg tagaaatagc tggaaatgta     60
ctctttcaag aaggtacgcg tttatattgg ttgaaggagg atatagattg gctccaaaga    120
gaaatgagac acattcgatc atatgtagac aatgcaaagg ccaaggaagt tggaggtgat    180
tcaagggtga aaaacttatt aaaagatatt caacaactcg caggtgatgt ggaggatctc    240
ctagatgagt ttcttccaaa aattcaacaa tccagtaagt tcaaaggcgc aatttgttgc    300
cttaagaccg tttcttttgc ggatgagttt gctatggaga ttgagaagat aaaaagaagg    360
gttgtggaca ttgatcgtgt aaggacaact tacaacatca tggatacaaa taacaacaat    420
gattgcattc cattggacca gagaagattg ttccttcatg ttgatgaaac agaggtcatc    480
ggtttggatg atgacttcaa tacactacaa gccaaattac ttgaccaaga tttgccttat    540
```

```
ggagttgttt caatagttgg catgcccggt ctaggaaaaa caactcttgc caagaaactt      600
tataggcatg tccgtcataa atttgagtgt tcgggactgg tctatgtttc acaacagcca      660
agggcgggag aaatcttaat cgacatagcc aaacaagttg gactgacgga agacgaaagg      720
aaagaaaact tggagaacaa cctacggtca ctcttgaaaa gaaaaggta tgttattctc       780 ttagatgaca tttgggatgt tgaaatttgg gatgatctaa aacttgtcct tcctgaatgt      840
gattcaaaaa ttggcagtag gataattata acctctcgaa atagtaatgt aggcagatac      900
ataggagggg atttctcaat tcacgtgttg caacctctaa attcggagaa cagttttgaa      960
ctctttacca agaaaatctt tattttgat aacaataata atttggaccaa tgcttcacca     1020 aacttggtag atattggtag aagtatagtt ggtagatgtg gtggtatacc actagccatt     1080
gtggtgactg caggcatgtt aagggcaaga gaaagaacag aacgtgcatg gaacaggtta     1140
cttgagagta tgagccataa agttcaagat ggatgtgcta aggtattggc tctgagttac     1200
aatgatttgc caattgcatt aaggccatgt ttcttgtatt ttggcccttta ccccgaggat    1260 catgaaattc gtgcttttga tttgacaaat atgtggattg ctgagaagtt gatagttgta    1320
aatagtggca atgggcgaga ggctgaaagt ttggcggatg atgtcctaaa tgatttggtt    1380
tcaagaaaca tgattcaagt tgccaaaagg acatatgatg gaagaatttc aagttgtcgc   1440
atacatgact tgttacatag tttgtgtgtt gacttggcta aggaaagcaa cttctttcac   1500
accgagcaca atgcattggg tgatcccgga aatgttgcta ggctgcgaag gattacattc   1560
tactctgata ataatgccat gaatgagttc ttccgttcaa atcctaagct tgagaagctt   1620
cgtgcacttt tctgttttac agaagaccct tgcatatttt ctcaactggc tcatcttgat   1680
ttcaaattat tgcaagtgtt ggttgtagtc atctttgttg atgatatttg tggtgtcagt   1740
atcccaaaca catttgggaa catgaggtgc ttacgttatc tgcgattcca ggggcatttt   1800
tatgggaaac tgccaaattg tatggtgaag ctcaaacgtc tagagaccct cgatattggt   1860
tatagcttaa ttaaatttcc tactggtgtt tggaagtcta cacaattgaa acatcttcgt   1920
tatggaggtt ttaatcaagc atctaacagt tgcttttcta taagcccatt ttttcccaaac  1980 ttgtactcat tgcctcataa taatgtacaa actttgatgt ggctggatga taaatttttt   2040
gaggcgggat tgttgcaccg attgatcaat ttaagaaaac tgggtatagc aggagtatct   2100
gattctacag ttaagatatt atcagcattg agccctgtgc caacggcgct ggaggttctg   2160
aagctcaaaa tttacaggga catgagtgag caaataaact tgtcgtccta tccaaatatt   2220
gttaagttgc gtttgaatgt ttgcggaaga atgcgcttga actgtgaagc atttcctcca   2280
aatcttgtca agcttactct tgtcggcgat gaggtagacg tcatgtagt ggcagagctt     2340 aagaaattgc ccaaattaag gatacttaaa atgtttgggt gcagtcataa tgaagaaaag    2400
atggatctct ctggtgatgg tgatagcttt ccgcaacttg aagttctgca tattgatgaa   2460
ccagatgggt tgtctgaagt aacgtgtagg gatgatgtca gtatgcctaa attgaaaaag   2520
ttgttacttg tacaacgccg cccttctcca attagtctct cagaacgtct tgcaaagctc   2580
agaatatga                                                            2589
```

<210> SEQ ID NO 3
<211> LENGTH: 2577
<212> TYPE: DNA
<213> ORGANISM: Solanum neorossii

<400> SEQUENCE: 3

-continued

```
atggctgaaa ttcttctcac agcagtcatc aataaatcaa tagaaatagc tggaaatgta      60
ctctttcaag aaggtacgcg tttatattgg ttgaaagagg acatcgattg gctccagaga     120
gaaatgagac acattcgatc atatgtagac aatgcaaagg caaaggaagt tggaggcgat     180
tcaagggtga aaaacttatt aaaagatatt caacaactgg caggtgatgt ggaggatcta     240
ttagatgagt ttcttccaaa aattcaacaa tccataagt  tcatttgttg ccttaagacg     300
gtttcttttg ccgatgagtt tgctatgag  attgagaaga taaaaagaag agttgctgat     360
attgaccgtg taaggacaac ttacagcatc acagatacaa gtaacaataa tgatgattgc     420
attccattgg accggagaag attgttcctt catgctgatg aaacagaggt catcggtctg     480
gaagatgact tcaatacact acaagccaaa ttacttgatc atgatttgcc ttatggagtt     540
gtttcaatag ttggcatgcc cggtttggga aaaacaactc ttgccaagaa actttatagg     600
catgtctgtc atcaatttga gtgttcggga ctggtctatg tttcacaaca gccaagggcg     660
ggagaaatct tacatgacat agccaaacaa gttggactga cggaagagga aggaaagaa      720
aacttggaga acaacctacg atcactcttg aaaataaaaa ggtatgttat tctcttagat     780
gacatttggg atgttgaaat ttgggatgat ctaaaacttg tccttcctga atgtgattca     840
aaaattggca gtaggataat tataacctct cgaaatagta atgtaggcag atacatagga     900
ggggatttct caatccacgt gttgcaaccc ctagattcag agaaaagctt tgaactcttt     960
accaagaaaa tctttaattt tgttaatgat aattgggcca atgcttcacc agacttggta    1020
aatattggta gatgtatagt tgagagatgt ggaggtatac cgctagcaat tgtggtgact    1080
gcaggcatgt taagggcaag aggaagaaca gaacatgcat ggaacagagt acttgagagt    1140
atggctcata aaattcaaga tggatgtggt aaggtattgg ctctgagtta caatgatttg    1200
cccattgcat taaggccatg tttcttgtac tttggtcttt accccgagga ccatgaaatt    1260
cgtgcttttg atttgacaaa tatgtggatt gctgagaagc tgatagttgt aaatactggc    1320
aatgggcgag aggctgaaag tttggcggat gatgtcctaa atgatttggt ttcaagaaac    1380
ttgattcaag ttgccaaaag gacatatgat ggaagaattt caagttgtcg catacatgac    1440
ttgttacata gtttgtgtgt ggacttggct aaggaaagta acttctttca cacggagcac    1500
tatgcatttg gtgatcctag caatgttgct agggtgcgaa ggattacatt ctactctgat    1560
gataatgcca tgaatgagtt cttccattta aatcctaagc ctatgaagct tcgttcactt    1620
ttctgtttca caaaagaccg ttgcatattt tctcaaatgg ctcatcttaa cttcaaatta    1680
ttgcaagtgt tggttgtagt catgtctcaa aagggttatc agcatgttac tttccccaaa    1740
aaaattggga acatgagttg cctacgctat gtgcgattgg aggggcaat  tagagtaaaa    1800
ttgccaaata gtattgtcaa gctcaaatgt ctagagaccc tggatatatt tcatagctct    1860
agtaaacttc cttttggtgt tgggagtct  aaaatattga cacatctttg ttacacagaa    1920
gaatgttact gtgtctcttt tgcaagtcca ttttgccgaa tcatgcctcc taataatcta    1980
caaactttga tgtgggtgga tgataaattt tgtgaaccaa gattgttgca ccgattgata    2040
aatttaagaa cattgtgtat aatggatgta tccggttcta ccattaagat attatcagca    2100
ttgagccctg tgcctaaagc gttggaggtt ctgaagctca gattttttcaa gaacacgagt    2160
gagcaaataa acttgtcgtc ccatccaaat attgtcgagt tgggtttggt tggtttctca    2220
gcaatgctct tgaacattga agcattccct ccaaatcttg tcaagcttaa tcttgtcggc    2280
ttgatggtag acggtcatct attggcagtg cttaagaaat tgcccaaatt aaggatactt    2340
atattgcttt ggtgcagaca tgatgcagaa aaaatggatc tctctggtga tagctttccg    2400
```

-continued

```
caacttgaag ttttgtatat tgaggatgca caagggttgt ctgaagtaac gtgcatggat    2460
gatatgagta tgcctaaatt gaaaaagcta tttcttgtac aaggcccaaa catttcccca    2520
attagtctca gggtctcgga acggcttgca aagttgagaa tatcacaggt actataa      2577
```

<210> SEQ ID NO 4
<211> LENGTH: 858
<212> TYPE: PRT
<213> ORGANISM: Solanum okadae

<400> SEQUENCE: 4

| | | | | | | | | | | | | | | |
|---|---|---|---|---|---|---|---|---|---|---|---|---|---|---|
| Met | Ala | Glu | Ile | Leu | Leu | Thr | Ala | Val | Ile | Asn | Lys | Ser | Ile | Glu | Ile |
| 1 | | | | 5 | | | | | 10 | | | | | 15 | |
| Ala | Gly | Asn | Val | Leu | Phe | Gln | Glu | Gly | Thr | Arg | Leu | Tyr | Trp | Leu | Lys |
| | | | 20 | | | | | 25 | | | | | 30 | | |
| Glu | Asp | Ile | Asp | Trp | Leu | Gln | Arg | Glu | Met | Arg | His | Ile | Arg | Ser | Tyr |
| | | 35 | | | | | 40 | | | | | 45 | | | |
| Val | Asp | Asn | Ala | Lys | Ala | Lys | Glu | Val | Gly | Gly | Asp | Ser | Arg | Val | Lys |
| | 50 | | | | | 55 | | | | | 60 | | | | |
| Asn | Leu | Leu | Lys | Asp | Ile | Gln | Gln | Leu | Ala | Gly | Asp | Val | Glu | Asp | Leu |
| 65 | | | | | 70 | | | | | 75 | | | | | 80 |
| Leu | Asp | Glu | Phe | Leu | Pro | Lys | Ile | Gln | Gln | Ser | Asn | Lys | Phe | Ile | Cys |
| | | | | 85 | | | | | 90 | | | | | 95 | |
| Cys | Leu | Lys | Thr | Val | Ser | Phe | Ala | Asp | Glu | Phe | Ala | Met | Glu | Ile | Glu |
| | | | 100 | | | | | 105 | | | | | 110 | | |
| Lys | Ile | Lys | Arg | Arg | Val | Ala | Asp | Ile | Asp | Arg | Val | Arg | Thr | Thr | Tyr |
| | | | 115 | | | | | 120 | | | | | 125 | | |
| Ser | Ile | Thr | Asp | Thr | Ser | Asn | Asn | Asn | Asp | Asp | Cys | Ile | Pro | Leu | Asp |
| | | 130 | | | | | 135 | | | | | 140 | | | |
| Arg | Arg | Arg | Leu | Phe | Leu | His | Ala | Asp | Glu | Thr | Glu | Val | Ile | Gly | Leu |
| 145 | | | | | 150 | | | | | 155 | | | | | 160 |
| Glu | Asp | Asp | Phe | Asn | Thr | Leu | Gln | Ala | Lys | Leu | Leu | Asp | His | Asp | Leu |
| | | | | 165 | | | | | 170 | | | | | 175 | |
| Pro | Tyr | Gly | Val | Val | Ser | Ile | Val | Gly | Met | Pro | Gly | Leu | Gly | Lys | Thr |
| | | | 180 | | | | | 185 | | | | | 190 | | |
| Thr | Leu | Ala | Lys | Lys | Leu | Tyr | Arg | His | Val | Cys | His | Gln | Phe | Glu | Cys |
| | | | 195 | | | | | 200 | | | | | 205 | | |
| Ser | Gly | Leu | Val | Tyr | Val | Ser | Gln | Gln | Pro | Arg | Ala | Gly | Glu | Ile | Leu |
| | | 210 | | | | | 215 | | | | | 220 | | | |
| His | Asp | Ile | Ala | Lys | Gln | Val | Gly | Leu | Thr | Glu | Glu | Arg | Lys | Glu |
| 225 | | | | | 230 | | | | | 235 | | | | | 240 |
| Asn | Leu | Glu | Asn | Asn | Leu | Arg | Ser | Leu | Leu | Lys | Ile | Lys | Arg | Tyr | Val |
| | | | | 245 | | | | | 250 | | | | | 255 | |
| Ile | Leu | Leu | Asp | Asp | Ile | Trp | Asp | Val | Glu | Ile | Trp | Asp | Asp | Leu | Lys |
| | | | | 260 | | | | | 265 | | | | | 270 | |
| Leu | Val | Leu | Pro | Glu | Cys | Asp | Ser | Lys | Ile | Gly | Ser | Arg | Ile | Ile | Ile |
| | | | 275 | | | | | 280 | | | | | 285 | | |
| Thr | Ser | Arg | Asn | Ser | Asn | Val | Gly | Arg | Tyr | Ile | Gly | Gly | Asp | Phe | Ser |
| | | 290 | | | | | 295 | | | | | 300 | | | |
| Ile | His | Val | Leu | Gln | Pro | Leu | Asp | Ser | Glu | Lys | Ser | Phe | Glu | Leu | Phe |
| 305 | | | | | 310 | | | | | 315 | | | | | 320 |
| Thr | Lys | Lys | Ile | Phe | Asn | Phe | Val | Asn | Asp | Asn | Trp | Ala | Asn | Ala | Ser |
| | | | | 325 | | | | | 330 | | | | | 335 | |
| Pro | Asp | Leu | Val | Asn | Ile | Gly | Arg | Cys | Ile | Val | Glu | Arg | Cys | Gly | Gly |

```
                    340                 345                 350
        Ile Pro Leu Ala Ile Val Val Thr Ala Gly Met Leu Arg Ala Arg Gly
                    355                 360                 365

Arg Thr Glu His Ala Trp Asn Arg Val Leu Glu Ser Met Ala His Lys
                    370                 375                 380

Ile Gln Asp Gly Cys Gly Lys Val Leu Ala Leu Ser Tyr Asn Asp Leu
        385                 390                 395                 400

Pro Ile Ala Leu Arg Pro Cys Phe Leu Tyr Phe Gly Leu Tyr Pro Glu
                            405                 410                 415

Asp His Glu Ile Arg Ala Phe Asp Leu Thr Asn Met Trp Ile Ala Glu
                        420                 425                 430

Lys Leu Ile Val Val Asn Thr Gly Asn Gly Arg Glu Ala Glu Ser Leu
                    435                 440                 445

Ala Asp Asp Val Leu Asn Asp Leu Val Ser Arg Asn Leu Ile Gln Val
                    450                 455                 460

Ala Lys Arg Thr Tyr Asp Gly Arg Ile Ser Ser Cys Arg Ile His Asp
        465                 470                 475                 480

Leu Leu His Ser Leu Cys Val Asp Leu Ala Lys Glu Ser Asn Phe Phe
                            485                 490                 495

His Thr Glu His Asn Ala Phe Gly Asp Pro Ser Asn Val Ala Arg Val
                        500                 505                 510

Arg Arg Ile Thr Phe Tyr Ser Asp Asp Asn Ala Met Asn Glu Phe Phe
                    515                 520                 525

His Leu Asn Pro Lys Pro Met Lys Leu Arg Ser Leu Phe Cys Phe Thr
                    530                 535                 540

Lys Asp Arg Cys Ile Phe Ser Gln Met Ala His Leu Asn Phe Lys Leu
        545                 550                 555                 560

Leu Gln Val Leu Val Val Met Ser Gln Lys Gly Tyr Gln His Val
                            565                 570                 575

Thr Phe Pro Lys Lys Ile Gly Asn Met Ser Cys Leu Arg Tyr Val Arg
                        580                 585                 590

Leu Glu Gly Ala Ile Arg Val Lys Leu Pro Asn Ser Ile Val Lys Leu
                    595                 600                 605

Lys Cys Leu Glu Thr Leu Asp Ile Phe His Ser Ser Ser Lys Leu Pro
                    610                 615                 620

Phe Gly Val Trp Glu Ser Lys Ile Leu Arg His Leu Cys Tyr Thr Glu
        625                 630                 635                 640

Glu Cys Tyr Cys Val Ser Phe Ala Ser Pro Phe Cys Arg Ile Met Pro
                            645                 650                 655

Pro Asn Asn Leu Gln Thr Leu Met Trp Val Asp Asp Lys Phe Cys Glu
                        660                 665                 670

Pro Arg Leu Leu His Arg Leu Ile Asn Leu Arg Thr Leu Cys Ile Met
                    675                 680                 685

Asp Val Ser Gly Ser Thr Ile Lys Ile Leu Ser Ala Leu Ser Pro Val
                    690                 695                 700

Pro Arg Ala Leu Glu Val Leu Lys Leu Arg Phe Phe Lys Asn Thr Ser
        705                 710                 715                 720

Glu Gln Ile Asn Leu Ser Ser His Pro Asn Ile Val Glu Leu Gly Leu
                            725                 730                 735

Val Gly Phe Ser Ala Met Leu Leu Asn Ile Glu Ala Phe Pro Pro Asn
                        740                 745                 750

Leu Val Lys Leu Asn Leu Val Gly Leu Met Val Asp Gly His Leu Leu
                    755                 760                 765
```

```
Ala Val Leu Lys Lys Leu Pro Lys Leu Arg Ile Leu Ile Leu Leu Trp
    770             775                 780

Cys Arg His Asp Ala Glu Lys Met Asp Leu Ser Gly Asp Ser Phe Pro
785             790                 795                 800

Gln Leu Glu Val Leu Tyr Ile Glu Asp Ala Gln Gly Leu Ser Glu Val
                805                 810                 815

Thr Cys Met Asp Asp Met Ser Met Pro Lys Leu Lys Lys Leu Phe Leu
            820                 825                 830

Val Gln Gly Pro Asn Ile Ser Pro Ile Ser Leu Arg Val Ser Glu Arg
        835                 840                 845

Leu Ala Lys Leu Arg Ile Ser Gln Val Leu
    850                 855

<210> SEQ ID NO 5
<211> LENGTH: 862
<212> TYPE: PRT
<213> ORGANISM: Solanum mochiquense

<400> SEQUENCE: 5

Met Ala Glu Ile Leu Leu Thr Ala Val Ile Asn Lys Ser Val Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Ser Lys Phe Lys Gly
                85                  90                  95

Ala Ile Cys Cys Leu Lys Thr Val Ser Phe Ala Asp Glu Phe Ala Met
            100                 105                 110

Glu Ile Glu Lys Ile Lys Arg Arg Val Val Asp Ile Asp Arg Val Arg
        115                 120                 125

Thr Thr Tyr Asn Ile Met Asp Thr Asn Asn Asn Asn Asp Cys Ile Pro
    130                 135                 140

Leu Asp Gln Arg Arg Leu Phe Leu His Val Asp Glu Thr Glu Val Ile
145                 150                 155                 160

Gly Leu Asp Asp Asp Phe Asn Thr Leu Gln Ala Lys Leu Leu Asp Gln
                165                 170                 175

Asp Leu Pro Tyr Gly Val Val Ser Ile Val Gly Met Pro Gly Leu Gly
            180                 185                 190

Lys Thr Thr Leu Ala Lys Lys Leu Tyr Arg His Val Arg His Lys Phe
        195                 200                 205

Glu Cys Ser Gly Leu Val Tyr Val Ser Gln Gln Pro Arg Ala Gly Glu
    210                 215                 220

Ile Leu Ile Asp Ile Ala Lys Gln Val Gly Leu Thr Glu Asp Glu Arg
225                 230                 235                 240

Lys Glu Asn Leu Glu Asn Asn Leu Arg Ser Leu Lys Arg Lys Arg
                245                 250                 255

Tyr Val Ile Leu Leu Asp Asp Ile Trp Asp Val Glu Ile Trp Asp Asp
            260                 265                 270

Leu Lys Leu Val Leu Pro Glu Cys Asp Ser Lys Ile Gly Ser Arg Ile
```

```
                275                 280                 285
Ile Ile Thr Ser Arg Asn Ser Asn Val Gly Arg Tyr Ile Gly Gly Asp
            290                 295                 300
Phe Ser Ile His Val Leu Gln Pro Leu Asn Ser Glu Asn Ser Phe Glu
305                 310                 315                 320
Leu Phe Thr Lys Lys Ile Phe Ile Phe Asp Asn Asn Asn Trp Thr
                325                 330                 335
Asn Ala Ser Pro Asn Leu Val Asp Ile Gly Arg Ser Ile Val Gly Arg
            340                 345                 350
Cys Gly Gly Ile Pro Leu Ala Ile Val Val Thr Ala Gly Met Leu Arg
            355                 360                 365
Ala Arg Glu Arg Thr Glu Arg Ala Trp Asn Arg Leu Leu Glu Ser Met
    370                 375                 380
Ser His Lys Val Gln Asp Gly Cys Ala Lys Val Leu Ala Leu Ser Tyr
385                 390                 395                 400
Asn Asp Leu Pro Ile Ala Leu Arg Pro Cys Phe Leu Tyr Phe Gly Leu
                405                 410                 415
Tyr Pro Glu Asp His Glu Ile Arg Ala Phe Asp Leu Thr Asn Met Trp
            420                 425                 430
Ile Ala Glu Lys Leu Ile Val Val Asn Ser Gly Asn Gly Arg Glu Ala
            435                 440                 445
Glu Ser Leu Ala Asp Asp Val Leu Asn Asp Leu Val Ser Arg Asn Met
    450                 455                 460
Ile Gln Val Ala Lys Arg Thr Tyr Asp Gly Arg Ile Ser Ser Cys Arg
465                 470                 475                 480
Ile His Asp Leu Leu His Ser Leu Cys Val Asp Leu Ala Lys Glu Ser
                485                 490                 495
Asn Phe Phe His Thr Glu His Asn Ala Leu Gly Asp Pro Gly Asn Val
            500                 505                 510
Ala Arg Leu Arg Arg Ile Thr Phe Tyr Ser Asp Asn Asn Ala Met Asn
            515                 520                 525
Glu Phe Phe Arg Ser Asn Pro Lys Leu Glu Lys Leu Arg Ala Leu Phe
    530                 535                 540
Cys Phe Thr Glu Asp Pro Cys Ile Phe Ser Gln Leu Ala His Leu Asp
545                 550                 555                 560
Phe Lys Leu Leu Gln Val Leu Val Val Ile Phe Val Asp Asp Ile
                565                 570                 575
Cys Gly Val Ser Ile Pro Asn Thr Phe Gly Asn Met Arg Cys Leu Arg
            580                 585                 590
Tyr Leu Arg Phe Gln Gly His Phe Tyr Gly Lys Leu Pro Asn Cys Met
            595                 600                 605
Val Lys Leu Lys Arg Leu Glu Thr Leu Asp Ile Gly Tyr Ser Leu Ile
    610                 615                 620
Lys Phe Pro Thr Gly Val Trp Lys Ser Thr Gln Leu Lys His Leu Arg
625                 630                 635                 640
Tyr Gly Gly Phe Asn Gln Ala Ser Asn Ser Cys Phe Ser Ile Ser Pro
                645                 650                 655
Phe Phe Pro Asn Leu Tyr Ser Leu Pro His Asn Asn Val Gln Thr Leu
            660                 665                 670
Met Trp Leu Asp Asp Lys Phe Phe Glu Ala Gly Leu Leu His Arg Leu
            675                 680                 685
Ile Asn Leu Arg Lys Leu Gly Ile Ala Gly Val Ser Asp Ser Thr Val
    690                 695                 700
```

```
Lys Ile Leu Ser Ala Leu Ser Pro Val Pro Thr Ala Leu Glu Val Leu
705                 710                 715                 720

Lys Leu Lys Ile Tyr Arg Asp Met Ser Glu Gln Ile Asn Leu Ser Ser
            725                 730                 735

Tyr Pro Asn Ile Val Lys Leu Arg Leu Asn Val Cys Gly Arg Met Arg
            740                 745                 750

Leu Asn Cys Glu Ala Phe Pro Pro Asn Leu Val Lys Leu Thr Leu Val
            755                 760                 765

Gly Asp Glu Val Asp Gly His Val Val Ala Glu Leu Lys Lys Leu Pro
770                 775                 780

Lys Leu Arg Ile Leu Lys Met Phe Gly Cys Ser His Asn Glu Glu Lys
785                 790                 795                 800

Met Asp Leu Ser Gly Asp Gly Asp Ser Phe Pro Gln Leu Glu Val Leu
            805                 810                 815

His Ile Asp Glu Pro Asp Gly Leu Ser Glu Val Thr Cys Arg Asp Asp
            820                 825                 830

Val Ser Met Pro Lys Leu Lys Lys Leu Leu Val Gln Arg Arg Pro
            835                 840                 845

Ser Pro Ile Ser Leu Ser Glu Arg Leu Ala Lys Leu Arg Ile
    850                 855                 860

<210> SEQ ID NO 6
<211> LENGTH: 858
<212> TYPE: PRT
<213> ORGANISM: Solanum neorossii

<400> SEQUENCE: 6

Met Ala Glu Ile Leu Leu Thr Ala Val Ile Asn Lys Ser Ile Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Asp Arg Val Arg Thr Thr Tyr
        115                 120                 125

Ser Ile Thr Asp Thr Ser Asn Asn Asn Asp Asp Cys Ile Pro Leu Asp
    130                 135                 140

Arg Arg Arg Leu Phe Leu His Ala Asp Glu Thr Glu Val Ile Gly Leu
145                 150                 155                 160

Glu Asp Asp Phe Asn Thr Leu Gln Ala Lys Leu Leu Asp His Asp Leu
                165                 170                 175

Pro Tyr Gly Val Val Ser Ile Val Gly Met Pro Gly Leu Gly Lys Thr
            180                 185                 190

Thr Leu Ala Lys Lys Leu Tyr Arg His Val Cys His Gln Phe Glu Cys
        195                 200                 205

Ser Gly Leu Val Tyr Val Ser Gln Gln Pro Arg Ala Gly Glu Ile Leu
```

-continued

```
                210                 215                 220
His Asp Ile Ala Lys Gln Val Gly Leu Thr Glu Glu Arg Lys Glu
225                 230                 235                 240

Asn Leu Glu Asn Asn Leu Arg Ser Leu Leu Lys Ile Lys Arg Tyr Val
                    245                 250                 255

Ile Leu Leu Asp Asp Ile Trp Asp Val Glu Ile Trp Asp Asp Leu Lys
                260                 265                 270

Leu Val Leu Pro Glu Cys Asp Ser Lys Ile Gly Ser Arg Ile Ile Ile
            275                 280                 285

Thr Ser Arg Asn Ser Asn Val Gly Arg Tyr Ile Gly Gly Asp Phe Ser
        290                 295                 300

Ile His Val Leu Gln Pro Leu Asp Ser Glu Lys Ser Phe Glu Leu Phe
305                 310                 315                 320

Thr Lys Lys Ile Phe Asn Phe Val Asn Asp Asn Trp Ala Asn Ala Ser
                    325                 330                 335

Pro Asp Leu Val Asn Ile Gly Arg Cys Ile Val Glu Arg Cys Gly Gly
                340                 345                 350

Ile Pro Leu Ala Ile Val Val Thr Ala Gly Met Leu Arg Ala Arg Gly
            355                 360                 365

Arg Thr Glu His Ala Trp Asn Arg Val Leu Glu Ser Met Ala His Lys
        370                 375                 380

Ile Gln Asp Gly Cys Gly Lys Val Leu Ala Leu Ser Tyr Asn Asp Leu
385                 390                 395                 400

Pro Ile Ala Leu Arg Pro Cys Phe Leu Tyr Phe Gly Leu Tyr Pro Glu
                    405                 410                 415

Asp His Glu Ile Arg Ala Phe Asp Leu Thr Asn Met Trp Ile Ala Glu
                420                 425                 430

Lys Leu Ile Val Val Asn Thr Gly Asn Gly Arg Glu Ala Glu Ser Leu
            435                 440                 445

Ala Asp Asp Val Leu Asn Asp Leu Val Ser Arg Asn Leu Ile Gln Val
        450                 455                 460

Ala Lys Arg Thr Tyr Asp Gly Arg Ile Ser Ser Cys Arg Ile His Asp
465                 470                 475                 480

Leu Leu His Ser Leu Cys Val Asp Leu Ala Lys Glu Ser Asn Phe Phe
                    485                 490                 495

His Thr Glu His Tyr Ala Phe Gly Asp Pro Ser Asn Val Ala Arg Val
                500                 505                 510

Arg Arg Ile Thr Phe Tyr Ser Asp Asp Asn Ala Met Asn Glu Phe Phe
            515                 520                 525

His Leu Asn Pro Lys Pro Met Lys Leu Arg Ser Leu Phe Cys Phe Thr
        530                 535                 540

Lys Asp Arg Cys Ile Phe Ser Gln Met Ala His Leu Asn Phe Lys Leu
545                 550                 555                 560

Leu Gln Val Leu Val Val Met Ser Gln Lys Gly Tyr Gln His Val
                    565                 570                 575

Thr Phe Pro Lys Lys Ile Gly Asn Met Ser Cys Leu Arg Tyr Val Arg
                580                 585                 590

Leu Glu Gly Ala Ile Arg Val Lys Leu Pro Asn Ser Ile Val Lys Leu
            595                 600                 605

Lys Cys Leu Glu Thr Leu Asp Ile Phe His Ser Ser Lys Leu Pro
        610                 615                 620

Phe Gly Val Trp Glu Ser Lys Ile Leu Arg His Leu Cys Tyr Thr Glu
625                 630                 635                 640
```

```
Glu Cys Tyr Cys Val Ser Phe Ala Ser Pro Phe Cys Arg Ile Met Pro
            645                 650                 655

Pro Asn Asn Leu Gln Thr Leu Met Trp Val Asp Asp Lys Phe Cys Glu
        660                 665                 670

Pro Arg Leu Leu His Arg Leu Ile Asn Leu Arg Thr Leu Cys Ile Met
    675                 680                 685

Asp Val Ser Gly Ser Thr Ile Lys Ile Leu Ser Ala Leu Ser Pro Val
690                 695                 700

Pro Lys Ala Leu Glu Val Leu Lys Leu Arg Phe Phe Lys Asn Thr Ser
705                 710                 715                 720

Glu Gln Ile Asn Leu Ser Ser His Pro Asn Ile Val Glu Leu Gly Leu
                725                 730                 735

Val Gly Phe Ser Ala Met Leu Leu Asn Ile Glu Ala Phe Pro Pro Asn
            740                 745                 750

Leu Val Lys Leu Asn Leu Val Gly Leu Met Val Asp Gly His Leu Leu
        755                 760                 765

Ala Val Leu Lys Lys Leu Pro Lys Leu Arg Ile Leu Ile Leu Leu Trp
    770                 775                 780

Cys Arg His Asp Ala Glu Lys Met Asp Leu Ser Gly Asp Ser Phe Pro
785                 790                 795                 800

Gln Leu Glu Val Leu Tyr Ile Glu Asp Ala Gln Gly Leu Ser Glu Val
                805                 810                 815

Thr Cys Met Asp Asp Met Ser Met Pro Lys Leu Lys Lys Leu Phe Leu
            820                 825                 830

Val Gln Gly Pro Asn Ile Ser Pro Ile Ser Leu Arg Val Ser Glu Arg
        835                 840                 845

Leu Ala Lys Leu Arg Ile Ser Gln Val Leu
    850                 855
```

<210> SEQ ID NO 7
<211> LENGTH: 2577
<212> TYPE: DNA
<213> ORGANISM: Solanum okadae

<400> SEQUENCE: 7

```
atggctgaaa ttcttctcac agcagtcatc aataaatcaa tagaaatagc tggaaatgta      60
ctctttcaag aaggtacgcg tttatattgg ttgaaagagg acatcgattg gctccagaga     120
gaaatgagac acattcgatc atatgtagac aatgcaaagg caaggaagt tggaggcgat      180
tcaagggtga aaaacttatt aaaagatatt caacaactgg caggtgatgt ggaggatcta     240
ttagatgagt tccttccaaa aattcaacaa tccataagt tcatttgttg ccttaagacg      300
gtttcttttg ccgatgagtt tgctatggag attgagaaga taaaagaag agttgctgat      360
attgaccgtg taaggacaac ttacagcatc acagatacaa gtaacaataa tgatgattgc     420
attccattgg accggagaag attgttcctt catgctgatg aaacagaggt catcggtctg     480
gaagatgact tcaatacact acaagccaaa ttacttgatc atgatttgcc ttatggagtt     540
gtttcaatag ttggcatgcc cggtttggga aaaacaactc ttgccaagaa actttatagg     600
catgtctgtc atcaatttga gtgttcggga ctggtctatg tttcacaaca gccaagggcg     660
ggagaaatct acatgacat agccaaacaa gttggactga cggaagagga aggaaagaa      720
aacttggaga caaccctacg atcactcttg aaaataaaaa ggtatgttat tctcttagat     780
gacatttggg atgttgaaat tgggatgat ctaaaacttg tccttcctga atgtgattca      840
```

```
aaaattggca gtaggataat tataacctct cgaaatagta atgtaggcag atacatagga      900
ggggatttct caatccacgt gttgcaaccc ctagattcag agaaaagctt tgaactcttt      960
accaagaaaa tctttaattt tgttaatgat aattgggcca atgcttcacc agacttggta     1020
aatattggta gatgtatagt tgagagatgt ggaggtatac cgctagcaat tgtggtgact     1080
gcaggcatgt aagggcaag aggaagaaca gaacatgcat ggaacagagt acttgagagt     1140
atggctcata aaattcaaga tggatgtggt aaggtattgg ctctgagtta caatgatttg     1200
cccattgcat taaggccatg tttcttgtac tttggtcttt accccgagga ccatgaaatt     1260
cgtgcttttg atttgacaaa tatgtggatt gctgagaagc tgatagttgt aaatactggc     1320
aatgggcgag aggctgaaag tttggcggat gatgtcctaa atgatttggt ttcaagaaac     1380
ttgattcaag ttgccaaaag gacatatgat ggaagaattt caagttgtcg catacatgac     1440
ttgttacata gtttgtgtgt ggacttggct aaggaaagta acttctttca cacggagcac     1500
tatgcatttg gtgatcctag caatgttgct agggtgcgaa ggattacatt ctactctgat     1560
gataatgcca tgaatgagtt cttccattta aatcctaagc ctatgaagct tcgttcactt     1620
ttctgtttca caaagaccg ttgcatattt tctcaaatgg ctcatcttaa cttcaaatta     1680
ttgcaagtgt tggttgtagt catgtctcaa aagggttatc agcatgttac tttccccaaa     1740
aaaattggga acatgagttg cctacgctat gtgcgattgg aggggcaat tagagtaaaa     1800 ttgccaaata gtattgtcaa gctcaaatgt ctagagaccc tggatatatt tcatagctct     1860
agtaaacttc cttttggtgt ttgggagtct aaaatattga gacatctttg ttacacagaa     1920
gaatgttact gtgtctcttt tgcaagtcca ttttgccgaa tcatgcctcc taataatcta     1980
caaactttga tgtgggtgga tgataaattt tgtgaaccaa gattgttgca ccgattgata     2040
aatttaagaa cattgtgtat aatggatgta tccggttcta ccattaagat attatcagca     2100
ttgagccctg tgcctaaagc gttggaggtt ctgaagctca gattttcaa gaacacgagt     2160 gagcaaataa acttgtcgtc ccatccaaat attgtcgagt tgggtttggt tggtttctca     2220
gcaatgctct tgaacattga agcattccct ccaaatcttg tcaagcttaa tcttgtcggc     2280
ttgatggtag acggtcatct attggcagtg cttaagaaat tgcccaaatt aaggatactt     2340
atattgcttt ggtgcagaca tgatgcagaa aaaatggatc tctctggtga tagctttccg     2400
caacttgaag ttttgtatat tgaggatgca caagggttgt ctgaagtaac gtgcatggat     2460
gatatgagta tgcctaaatt gaaaaagcta tttcttgtac aaggcccaaa catttcccca     2520
attagtctca gggtctcgga acggcttgca aagttgagaa tatcacaggt actataa      2577

<210> SEQ ID NO 8
<211> LENGTH: 2571
<212> TYPE: DNA
<213> ORGANISM: Solanum mochiquense

<400> SEQUENCE: 8
atggctgaaa ttcttcttac aacagtcatc aataaatctg taggaatagc tgcaaatgta       60
ctctttcaag aaggaacgcg tttatattgg ttgaaagagg acatagattg gctccacaga      120
gaaatgagac acattcgatc atatgtgac gatgcaaagg ccaaggaagt tggaggcgat      180
tcaagggtca gaaacttatt aaaagatatt caacaactgg caggtgatgt ggaggatcta      240
ttagatgagt tccttccaaa aattcaacaa tccaataagt tcatttgttg ccttaagaca      300
gtttcttttg ccgatgagtt tgccatggag attgagaaga taaaagaag agttgctgat      360 attcccgtg taaggacaac ttacaacatc acagatacaa gtaacaataa tgatgattgc      420
```

| | |
|---|---|
| attccattgg accggagaag attgttcctt catgctgatg aaacagaggt catcggtctg | 480 |
| gaagatgact tcaatacact aaaagccaaa ttacttgatc aagatttgcc ttatggagtt | 540 |
| gtttcaatag ttggcatgcc cggtctagga aaaacaactc ttgccaagaa actttatagg | 600 |
| catgtccgtg atcaatttga gagctcggga ctggtctacg tgtcccaaca gccaagagcg | 660 |
| ggagaaatct tacgtgacat agccaaacaa gttggactgc aaaagagga aggaaagaa | 720 |
| aacttggagg gcaacctacg atcactcttg aaaacaaaaa ggtatgttat cctcctagat | 780 |
| gacatttggg atgttgaaat ttgggatgat ctaaaactcg tccttcctga atgtgattca | 840 |
| gaaattggca gtaggataat tataacctct cgaaatagta atgtaggcag atacatagga | 900 |
| ggggatttct caattcacat gttgcaacct ctagattcgg agaacagttt tgaactcttt | 960 |
| accaagaaaa tctttacttt tgataacaat aataattggg ccaatgcttc accagacttg | 1020 |
| gtagatattg gtagaagtat agttggtaga tgcggaggta tacctctagc cattgtggtc | 1080 |
| actgcaggca tgtaagggc aagagaaaga acagaacatg catggaacag agtacttgag | 1140 |
| agtatgggcc ataaagttca agatggatgt gctaaggtat tggctttgag ttacaatgat | 1200 |
| ttgcccattg cattaaggcc atgtttcttg taccttggcc ttttccccga ggaccatgaa | 1260 |
| attcgtgcct ttgatttgac aaatatgtgg attgctgaga agctgatagt tgtaaatagt | 1320 |
| ggcaatgggc gagaggctga aagtttggcg gaggatgttc taaatgattt tgtttctaga | 1380 |
| aacttgattc aagtttccca agaaaatgt aatggaagaa tttcaagtta tcgcatacat | 1440 |
| gacttgttac atagtttgtg cgtcgaattg ggcaaggaaa gtaacttttt tcacactgaa | 1500 |
| cacaatgcat ttggtgatcc agacaatgtt gctagggtgc gaaggattac attctactct | 1560 |
| gataataatg ccatgagtaa gttcttccgt tcaaatccta agcctaagaa acttcgtgca | 1620 |
| cttttctgtt tcacaaattt agactcttgc atattttctc atttggctca tcatgacttc | 1680 |
| aaattattac aagtgttggt tgtagttatc tcttataatt ggttgagtgt cagtatctca | 1740 |
| aacaaatttg ggaagatgag ttgcttgcgc tatttgagat tggaggggcc aattgtggga | 1800 |
| gaactgtcaa atagtattgt gaagctcaaa cgtgtagaga ccatagatat tgcaggggat | 1860 |
| aacattaaaa ttccttgtgg tgtttgggag tctaaacaat tgagacatct ccgtaataga | 1920 |
| gaagaacgtc gctatttctt ttctgtaagc ccattttgcc taaacatgta cccattgcct | 1980 |
| cctaataatc tacaaacttt ggtgtggatg gatgataaat tttttgaacc gagattgttg | 2040 |
| caccgattga tcaattaag aaaattgggt atatggggca catctgattc tacaattaag | 2100 |
| atattatcag cattgagccc tgtgccaaca gcgttggagg ttctgaagct ctactttttg | 2160 |
| agggacctga gtgagcaaat aaacttgtca acctatccaa atattgttaa gttgaatttg | 2220 |
| caaggattcg taagagtgcg cttgaactct gaagcattcc ctccaaatct tgtcaagctt | 2280 |
| attcttgaca aaattgaggt agagggtcat gtagtggcag ttcttaagaa attgcccaca | 2340 |
| ttaaggatac ttaaaatgta tgggtgcaaa cataatgaag aaaagatgga tctctctggt | 2400 |
| gatggtgatg gtgatagctt tccgcaactt gaagttttgc atattgagag accattcttc | 2460 |
| ttgtttgaaa taacgtgcac agatgatgac agtatgccta aattgaaaaa gctattactt | 2520 |
| accacttcga acgttaggct ctcggaaaga cttgcaaaac tgagagtatg a | 2571 |

<210> SEQ ID NO 9
<211> LENGTH: 858
<212> TYPE: PRT
<213> ORGANISM: Solanum okadae

<400> SEQUENCE: 9

```
Met Ala Glu Ile Leu Leu Thr Ala Val Ile Asn Lys Ser Ile Glu Ile
1               5                   10                  15
Ala Gly Asn Val Leu Phe Gln Glu Gly Thr Arg Leu Tyr Trp Leu Lys
            20                  25                  30
Glu Asp Ile Asp Trp Leu Gln Arg Glu Met Arg His Ile Arg Ser Tyr
        35                  40                  45
Val Asp Asn Ala Lys Ala Lys Glu Val Gly Gly Asp Ser Arg Val Lys
    50                  55                  60
Asn Leu Leu Lys Asp Ile Gln Gln Leu Ala Gly Asp Val Glu Asp Leu
65                  70                  75                  80
Leu Asp Glu Phe Leu Pro Lys Ile Gln Gln Ser Asn Lys Phe Ile Cys
                85                  90                  95
Cys Leu Lys Thr Val Ser Phe Ala Asp Glu Phe Ala Met Glu Ile Glu
            100                 105                 110
Lys Ile Lys Arg Arg Val Ala Asp Ile Asp Arg Val Arg Thr Thr Tyr
        115                 120                 125
Ser Ile Thr Asp Thr Ser Asn Asn Asn Asp Asp Cys Ile Pro Leu Asp
    130                 135                 140
Arg Arg Arg Leu Phe Leu His Ala Asp Glu Thr Glu Val Ile Gly Leu
145                 150                 155                 160
Glu Asp Asp Phe Asn Thr Leu Gln Ala Lys Leu Leu Asp His Asp Leu
                165                 170                 175
Pro Tyr Gly Val Val Ser Ile Val Gly Met Pro Gly Leu Gly Lys Thr
            180                 185                 190
Thr Leu Ala Lys Lys Leu Tyr Arg His Val Cys His Gln Phe Glu Cys
        195                 200                 205
Ser Gly Leu Val Tyr Val Ser Gln Gln Pro Arg Ala Gly Glu Ile Leu
    210                 215                 220
His Asp Ile Ala Lys Gln Val Gly Leu Thr Glu Glu Arg Lys Glu
225                 230                 235                 240
Asn Leu Glu Asn Asn Leu Arg Ser Leu Leu Lys Ile Lys Arg Tyr Val
                245                 250                 255
Ile Leu Leu Asp Asp Ile Trp Asp Val Glu Ile Trp Asp Asp Leu Lys
            260                 265                 270
Leu Val Leu Pro Glu Cys Asp Ser Lys Ile Gly Ser Arg Ile Ile Ile
        275                 280                 285
Thr Ser Arg Asn Ser Asn Val Gly Arg Tyr Ile Gly Gly Asp Phe Ser
    290                 295                 300
Ile His Val Leu Gln Pro Leu Asp Ser Glu Lys Ser Phe Glu Leu Phe
305                 310                 315                 320
Thr Lys Lys Ile Phe Asn Phe Val Asn Asp Asn Trp Ala Asn Ala Ser
                325                 330                 335
Pro Asp Leu Val Asn Ile Gly Arg Cys Ile Val Glu Arg Cys Gly Gly
            340                 345                 350
Ile Pro Leu Ala Ile Val Val Thr Ala Gly Met Leu Arg Ala Arg Gly
        355                 360                 365
Arg Thr Glu His Ala Trp Asn Arg Val Leu Glu Ser Met Ala His Lys
    370                 375                 380
Ile Gln Asp Gly Cys Gly Lys Val Leu Ala Leu Ser Tyr Asn Asp Leu
385                 390                 395                 400
Pro Ile Ala Leu Arg Pro Cys Phe Leu Tyr Phe Gly Leu Tyr Pro Glu
                405                 410                 415
```

```
Asp His Glu Ile Arg Ala Phe Asp Leu Thr Asn Met Trp Ile Ala Glu
            420                 425                 430

Lys Leu Ile Val Val Asn Thr Gly Asn Gly Arg Glu Ala Glu Ser Leu
            435                 440                 445

Ala Asp Asp Val Leu Asn Asp Leu Val Ser Arg Asn Leu Ile Gln Val
        450                 455                 460

Ala Lys Arg Thr Tyr Asp Gly Arg Ile Ser Ser Cys Arg Ile His Asp
465                 470                 475                 480

Leu Leu His Ser Leu Cys Val Asp Leu Ala Lys Glu Ser Asn Phe Phe
                485                 490                 495

His Thr Glu His Tyr Ala Phe Gly Asp Pro Ser Asn Val Ala Arg Val
            500                 505                 510

Arg Arg Ile Thr Phe Tyr Ser Asp Asp Asn Ala Met Asn Glu Phe Phe
            515                 520                 525

His Leu Asn Pro Lys Pro Met Lys Leu Arg Ser Leu Phe Cys Phe Thr
            530                 535                 540

Lys Asp Arg Cys Ile Phe Ser Gln Met Ala His Leu Asn Phe Lys Leu
545                 550                 555                 560

Leu Gln Val Leu Val Val Met Ser Gln Lys Gly Tyr Gln His Val
                565                 570                 575

Thr Phe Pro Lys Lys Ile Gly Asn Met Ser Cys Leu Arg Tyr Val Arg
            580                 585                 590

Leu Glu Gly Ala Ile Arg Val Lys Leu Pro Asn Ser Ile Val Lys Leu
            595                 600                 605

Lys Cys Leu Glu Thr Leu Asp Ile Phe His Ser Ser Lys Leu Pro
610                 615                 620

Phe Gly Val Trp Glu Ser Lys Ile Leu Arg His Leu Cys Tyr Thr Glu
625                 630                 635                 640

Glu Cys Tyr Cys Val Ser Phe Ala Ser Pro Phe Cys Arg Ile Met Pro
                645                 650                 655

Pro Asn Asn Leu Gln Thr Leu Met Trp Val Asp Asp Lys Phe Cys Glu
            660                 665                 670

Pro Arg Leu Leu His Arg Leu Ile Asn Leu Arg Thr Leu Cys Ile Met
            675                 680                 685

Asp Val Ser Gly Ser Thr Ile Lys Ile Leu Ser Ala Leu Ser Pro Val
            690                 695                 700

Pro Lys Ala Leu Glu Val Leu Lys Leu Arg Phe Phe Lys Asn Thr Ser
705                 710                 715                 720

Glu Gln Ile Asn Leu Ser Ser His Pro Asn Ile Val Glu Leu Gly Leu
            725                 730                 735

Val Gly Phe Ser Ala Met Leu Leu Asn Ile Glu Ala Phe Pro Pro Asn
            740                 745                 750

Leu Val Lys Leu Asn Leu Val Gly Leu Met Val Asp Gly His Leu Leu
            755                 760                 765

Ala Val Leu Lys Lys Leu Pro Lys Leu Arg Ile Leu Ile Leu Leu Trp
            770                 775                 780

Cys Arg His Asp Ala Glu Lys Met Asp Leu Ser Gly Asp Ser Phe Pro
785                 790                 795                 800

Gln Leu Glu Val Leu Tyr Ile Glu Asp Ala Gln Gly Leu Ser Glu Val
            805                 810                 815

Thr Cys Met Asp Asp Met Ser Met Pro Lys Leu Lys Lys Leu Phe Leu
            820                 825                 830
```

Val Gln Gly Pro Asn Ile Ser Pro Ile Ser Leu Arg Val Ser Glu Arg
            835                 840                 845

Leu Ala Lys Leu Arg Ile Ser Gln Val Leu
    850                 855

<210> SEQ ID NO 10
<211> LENGTH: 856
<212> TYPE: PRT
<213> ORGANISM: Solanum mochiquense

<400> SEQUENCE: 10

Met Ala Glu Ile Leu Leu Thr Thr Val Ile Asn Lys Ser Val Gly Ile
1               5                   10                  15

Ala Ala Asn Val Leu Phe Gln Glu Gly Thr Arg Leu Tyr Trp Leu Lys
            20                  25                  30

Glu Asp Ile Asp Trp Leu His Arg Glu Met Arg His Ile Arg Ser Tyr
        35                  40                  45

Val Asp Asp Ala Lys Ala Lys Glu Val Gly Gly Asp Ser Arg Val Arg
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Thr Arg Val Arg Thr Thr Tyr
        115                 120                 125

Asn Ile Thr Asp Thr Ser Asn Asn Asn Asp Asp Cys Ile Pro Leu Asp
    130                 135                 140

Arg Arg Arg Leu Phe Leu His Ala Asp Glu Thr Glu Val Ile Gly Leu
145                 150                 155                 160

Glu Asp Asp Phe Asn Thr Leu Lys Ala Lys Leu Leu Asp Gln Asp Leu
                165                 170                 175

Pro Tyr Gly Val Val Ser Ile Val Gly Met Pro Gly Leu Gly Lys Thr
            180                 185                 190

Thr Leu Ala Lys Lys Leu Tyr Arg His Val Arg Asp Gln Phe Glu Ser
        195                 200                 205

Ser Gly Leu Val Tyr Val Ser Gln Gln Pro Arg Ala Gly Glu Ile Leu
    210                 215                 220

Arg Asp Ile Ala Lys Gln Val Gly Leu Pro Lys Glu Glu Arg Lys Glu
225                 230                 235                 240

Asn Leu Glu Gly Asn Leu Arg Ser Leu Leu Lys Thr Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Glu Ile Gly Ser Arg Ile Ile Ile
        275                 280                 285

Thr Ser Arg Asn Ser Asn Val Gly Arg Tyr Ile Gly Gly Asp Phe Ser
    290                 295                 300

Ile His Met Leu Gln Pro Leu Asp Ser Glu Asn Ser Phe Glu Leu Phe
305                 310                 315                 320

Thr Lys Lys Ile Phe Thr Phe Asp Asn Asn Asn Trp Ala Asn Ala
                325                 330                 335

Ser Pro Asp Leu Val Asp Ile Gly Arg Ser Ile Val Gly Arg Cys Gly
            340                 345                 350

```
Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
        370                 375                 380

Lys Val Gln Asp Gly Cys Ala Lys Val Leu Ala Leu Ser Tyr Asn Asp
385                 390                 395                 400

Leu Pro Ile Ala Leu Arg Pro Cys Phe Leu Tyr Leu Gly Leu Phe Pro
                405                 410                 415

Glu Asp His Glu Ile Arg Ala Phe Asp Leu Thr Asn Met Trp Ile Ala
            420                 425                 430

Glu Lys Leu Ile Val Val Asn Ser Gly Asn Gly Arg Glu Ala Glu Ser
        435                 440                 445

Leu Ala Glu Asp Val Leu Asn Asp Phe Val Ser Arg Asn Leu Ile Gln
    450                 455                 460

Val Ser Gln Arg Lys Cys Asn Gly Arg Ile Ser Ser Tyr Arg Ile His
465                 470                 475                 480

Asp Leu Leu His Ser Leu Cys Val Glu Leu Gly Lys Glu Ser Asn Phe
                485                 490                 495

Phe His Thr Glu His Asn Ala Phe Gly Asp Pro Asp Asn Val Ala Arg
            500                 505                 510

Val Arg Arg Ile Thr Phe Tyr Ser Asp Asn Asn Ala Met Ser Lys Phe
        515                 520                 525

Phe Arg Ser Asn Pro Lys Pro Lys Lys Leu Arg Ala Leu Phe Cys Phe
    530                 535                 540

Thr Asn Leu Asp Ser Cys Ile Phe Ser His Leu Ala His His Asp Phe
545                 550                 555                 560

Lys Leu Leu Gln Val Leu Val Val Ile Ser Tyr Asn Trp Leu Ser
                565                 570                 575

Val Ser Ile Ser Asn Lys Phe Gly Lys Met Ser Cys Leu Arg Tyr Leu
            580                 585                 590

Arg Leu Glu Gly Pro Ile Val Gly Glu Leu Ser Asn Ser Ile Val Lys
        595                 600                 605

Leu Lys Arg Val Glu Thr Ile Asp Ile Ala Gly Asp Asn Ile Lys Ile
    610                 615                 620

Pro Cys Gly Val Trp Glu Ser Lys Gln Leu Arg His Leu Arg Asn Arg
625                 630                 635                 640

Glu Glu Arg Arg Tyr Phe Phe Ser Val Ser Pro Phe Cys Leu Asn Met
                645                 650                 655

Tyr Pro Leu Pro Pro Asn Asn Leu Gln Thr Leu Val Trp Met Asp Asp
            660                 665                 670

Lys Phe Phe Glu Pro Arg Leu Leu His Arg Leu Ile Asn Leu Arg Lys
        675                 680                 685

Leu Gly Ile Trp Gly Thr Ser Asp Ser Thr Ile Lys Ile Leu Ser Ala
    690                 695                 700

Leu Ser Pro Val Pro Thr Ala Leu Glu Val Leu Lys Leu Tyr Phe Leu
705                 710                 715                 720

Arg Asp Leu Ser Glu Gln Ile Asn Leu Ser Thr Tyr Pro Asn Ile Val
                725                 730                 735

Lys Leu Asn Leu Gln Gly Phe Val Arg Val Arg Leu Asn Ser Glu Ala
            740                 745                 750

Phe Pro Pro Asn Leu Val Lys Leu Ile Leu Asp Lys Ile Glu Val Glu
        755                 760                 765
```

```
Gly His Val Val Ala Val Leu Lys Lys Leu Pro Thr Leu Arg Ile Leu
        770                 775                 780

Lys Met Tyr Gly Cys Lys His Asn Glu Glu Lys Met Asp Leu Ser Gly
785                 790                 795                 800

Asp Gly Asp Gly Asp Ser Phe Pro Gln Leu Glu Val Leu His Ile Glu
                805                 810                 815

Arg Pro Phe Phe Leu Phe Glu Ile Thr Cys Thr Asp Asp Ser Met
            820                 825                 830

Pro Lys Leu Lys Lys Leu Leu Leu Thr Thr Ser Asn Val Arg Leu Ser
        835                 840                 845

Glu Arg Leu Ala Lys Leu Arg Val
        850                 855

<210> SEQ ID NO 11
<211> LENGTH: 1248
<212> TYPE: DNA
<213> ORGANISM: Solanum lycopersicum

<400> SEQUENCE: 11
atgggaagaa caccttgttg tgaaaaagtg ggcatcaaga gaggcagatg gactgcagaa        60
gaagatcaaa ttctcactaa ttatattatt tctaatggag aaggctcttg gaggtcgtta       120
cctaaaaatg ccggattatt gagatgcgga agagttgta gactacgatg gattaattat        180
ttgaggtctg atctcaagag agggaacatt acttctcaag aggaagatat aattataaag       240
ttacatgcaa ctttgggtaa cagatggtct cttatagcag aacatttatc aggtagaaca       300
gacaatgaga taaaaaacta ttggaactct catctaagtc gaaaagttga tagcttaagg       360
ataccaagcg atgagaagtt acctaaagcc gtagttgatt tggctaaaaa aggtataccg       420
aagccaatta aaaatcatc gattagtcga ccaaaaaata aaaagtcaaa cttattagaa        480
aaagaagcat tgtgttgtac aaatatgcca gcttgtgata gtgccatgga attaatgcaa       540
gaagatctag caaagataga ggtgccaaat tcttgggcag acctataga ggccaaggga        600 agccttagtt cagatagtga tatcgaatgg ccaagactcg aggagattat gccagacgtg       660
gtgattgatg atgaagataa gaacacaaat ttcatattga attgtttcag agaagaagta       720
acgagcaata atgtagggaa tagttattca tgtatcgagg aaggtaataa aaagatatca       780
agcgacgatg aaaaaatcaa attattaatg gattggcaag ataatgatga gttagtatgg       840
ccaacgttac catgggaatt agaaacggat atagttccca gttggccaca atgggacgat       900
actgacacta acttacttca aaattgcacc aatgataata ataattatga agaagcaaca       960
acaatggaaa ttaataacca aaatcatagt accattgtat cttggctttt gtcttagaaa      1020
tataataata tgacattata tattgctttt gaatatatta ctcaactctt tttgtttcgt      1080
tttatatttg gaatgtggga attagaatga ctagtttatg tacatatttt aagtttcgtt      1140
agaaatatcg tcaagtcaga ttaaaatatg tatgagttga tgtagtaata aatgttattg      1200
ttattacttt ttttgatgta aaaaaaaaa aaaaaaaaa aaaaaaaa                    1248

<210> SEQ ID NO 12
<211> LENGTH: 338
<212> TYPE: PRT
<213> ORGANISM: Solanum lycopersicum

<400> SEQUENCE: 12

Met Gly Arg Thr Pro Cys Cys Glu Lys Val Gly Ile Lys Arg Gly Arg
1                 5                  10                  15
```

Trp Thr Ala Glu Glu Asp Gln Ile Leu Thr Asn Tyr Ile Ile Ser Asn
             20                  25                  30
Gly Glu Gly Ser Trp Arg Ser Leu Pro Lys Asn Ala Gly Leu Leu Arg
         35                  40                  45
Cys Gly Lys Ser Cys Arg Leu Arg Trp Ile Asn Tyr Leu Arg Ser Asp
     50                  55                  60
Leu Lys Arg Gly Asn Ile Thr Ser Gln Glu Glu Asp Ile Ile Lys
65                  70                  75                  80
Leu His Ala Thr Leu Gly Asn Arg Trp Ser Leu Ile Ala Glu His Leu
                 85                  90                  95
Ser Gly Arg Thr Asp Asn Glu Ile Lys Asn Tyr Trp Asn Ser His Leu
            100                 105                 110
Ser Arg Lys Val Asp Ser Leu Arg Ile Pro Ser Asp Glu Lys Leu Pro
        115                 120                 125
Lys Ala Val Val Asp Leu Ala Lys Lys Gly Ile Pro Lys Pro Ile Lys
    130                 135                 140
Lys Ser Ser Ile Ser Arg Pro Lys Asn Lys Ser Asn Leu Leu Glu
145                 150                 155                 160
Lys Glu Ala Leu Cys Cys Thr Asn Met Pro Ala Cys Asp Ser Ala Met
                165                 170                 175
Glu Leu Met Gln Glu Asp Leu Ala Lys Ile Glu Val Pro Asn Ser Trp
            180                 185                 190
Ala Gly Pro Ile Glu Ala Lys Gly Ser Leu Ser Ser Asp Ser Asp Ile
        195                 200                 205
Glu Trp Pro Arg Leu Glu Glu Ile Met Pro Asp Val Val Ile Asp Asp
    210                 215                 220
Glu Asp Lys Asn Thr Asn Phe Ile Leu Asn Cys Phe Arg Glu Glu Val
225                 230                 235                 240
Thr Ser Asn Asn Val Gly Asn Ser Tyr Ser Cys Ile Glu Glu Gly Asn
                245                 250                 255
Lys Lys Ile Ser Ser Asp Asp Glu Lys Ile Lys Leu Leu Met Asp Trp
            260                 265                 270
Gln Asp Asn Asp Glu Leu Val Trp Pro Thr Leu Pro Trp Glu Leu Glu
        275                 280                 285
Thr Asp Ile Val Pro Ser Trp Pro Gln Trp Asp Thr Asp Thr Asn
    290                 295                 300
Leu Leu Gln Asn Cys Thr Asn Asp Asn Asn Tyr Glu Glu Ala Thr
305                 310                 315                 320
Thr Met Glu Ile Asn Asn Gln Asn His Ser Thr Ile Val Ser Trp Leu
                325                 330                 335
Leu Ser

<210> SEQ ID NO 13
<211> LENGTH: 1089
<212> TYPE: DNA
<213> ORGANISM: Solanum tuberosum

<400> SEQUENCE: 13
atgggaagaa caccttgttg tgaaaaagtg ggtatcaaga gaggcagatg gactgcagaa      60
gaagatcaaa ttctcactaa ttatattctt tctaatggag aaggctcttg gaggtcatta     120
cccaaaaatg ccggattact gagatgtgga aagagttgta gactaagatg gattaattat     180
ttgaggtctg acctcaagag agggaacatt acttctcaag gaagatat aatcataaag        240 ttacatgcaa cttttgggtaa caggtggtct ctaatagcgg acatttatc aggtagaaca      300

-continued

```
gacaatgaga ttaaaaatta ttggaactct catctaagtc gaaaagttga tagcttaagg    360
ataccaagcg atgagaagtt gcctaaagct gtagttgatt tggctaaaaa gggtacattg    420
aagccaatta acattgtag aaaatcattg attagtcgat cgaaaataa aaaatcaaac      480 ttattagaag ctaagaaaa tagtactagt ggggctttga ttggaattgt tcctatgcct    540
tcaacaccaa acatagaaaa agaagcattg tgttgtacaa atatgccagc ttgtgatagt    600
gccatggcat taatgcaaga agatgtagca aaggtagagg tgccaaattc ttgggcaggg    660
tctatagagg ccaagggaag ccttagttca gatagtggta tggaatggcc aaggctcgag    720
gagattatgc cagacgtggt gattgatgat gaagatatga acccaaattt cattttgaat    780
ggtttagaag aagaagtaat gagcaataat gcagggaata attattcatg tatcgacgaa    840
ggaaataaaa acgtatcaag cgatgatgaa aaaagcaaat tattaatgga ttggcaagat    900
gatgatgaat tagtatggcc aacgccacca tgggaattag aaacagacat aattcctagt    960
tggccacaat gggacgatac tgacactgat ttacttcaaa attgcaccaa taataattat   1020
gaagaagcaa caacaatgga aattaataac caaaatcata gtgccattgt atcttggctt   1080
ttgtcttag                                                          1089
```

<210> SEQ ID NO 14
<211> LENGTH: 362
<212> TYPE: PRT
<213> ORGANISM: Solanum tuberosum

<400> SEQUENCE: 14

Met Gly Arg Thr Pro Cys Cys Glu Lys Val Gly Ile Lys Arg Gly Arg
1               5                   10                  15

Trp Thr Ala Glu Glu Asp Gln Ile Leu Thr Asn Tyr Ile Leu Ser Asn
            20                  25                  30

Gly Glu Gly Ser Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Ser Gln Glu Asp Ile Ile Ile Lys
65                  70                  75                  80

Leu His Ala Thr Leu Gly Asn Arg Trp Ser Leu Ile Ala Gly His Leu
                85                  90                  95

Ser Gly Arg Thr Asp Asn Glu Ile Lys Asn Tyr Trp Asn Ser His Leu
            100                 105                 110

Ser Arg Lys Val Asp Ser Leu Arg Ile Pro Ser Asp Glu Lys Leu Pro
        115                 120                 125

Lys Ala Val Asp Leu Ala Lys Lys Gly Thr Leu Lys Pro Ile Lys
    130                 135                 140

His Cys Arg Lys Ser Leu Ile Ser Arg Ser Lys Asn Lys Lys Ser Asn
145                 150                 155                 160

Leu Leu Glu Ala Lys Glu Asn Ser Thr Ser Gly Ala Leu Ile Gly Ile
                165                 170                 175

Val Pro Met Pro Ser Thr Pro Asn Ile Glu Lys Glu Ala Leu Cys Cys
            180                 185                 190

Thr Asn Met Pro Ala Cys Asp Ser Ala Met Ala Leu Met Gln Glu Asp
        195                 200                 205

Val Ala Lys Val Glu Val Pro Asn Ser Trp Ala Gly Ser Ile Glu Ala
    210                 215                 220

```
Lys Gly Ser Leu Ser Ser Asp Ser Gly Met Glu Trp Pro Arg Leu Glu
225                 230                 235                 240

Glu Ile Met Pro Asp Val Val Ile Asp Asp Glu Asp Met Asn Pro Asn
            245                 250                 255

Phe Ile Leu Asn Gly Leu Glu Glu Val Met Ser Asn Asn Ala Gly
        260                 265                 270

Asn Asn Tyr Ser Cys Ile Asp Glu Gly Asn Lys Asn Val Ser Ser Asp
        275                 280                 285

Asp Glu Lys Ser Lys Leu Leu Met Asp Trp Gln Asp Asp Glu Leu
        290                 295                 300

Val Trp Pro Thr Pro Pro Trp Glu Leu Glu Thr Asp Ile Ile Pro Ser
305                 310                 315                 320

Trp Pro Gln Trp Asp Asp Thr Asp Thr Asp Leu Leu Gln Asn Cys Thr
                325                 330                 335

Asn Asn Asn Tyr Glu Glu Ala Thr Thr Met Glu Ile Asn Asn Gln Asn
            340                 345                 350

His Ser Ala Ile Val Ser Trp Leu Leu Ser
        355                 360

<210> SEQ ID NO 15
<211> LENGTH: 1751
<212> TYPE: DNA
<213> ORGANISM: Solanum lycopersicum
<220> FEATURE:
<221> NAME/KEY: misc_feature
<222> LOCATION: 664, 738
<223> OTHER INFORMATION: n is a or g or c or t

<400> SEQUENCE: 15
taaagcttcg tttttattaa aaaacgttaa taagaaatta tttgatataa atttaaattg      60
aattgtattt caaatacat  atcgaattga atgaaaaatc caaagaaaaa aattatatca    120
gattagactt ttttttgtgt tgttttaaa  tttatacact aaaaattgta ataaatattt    180
tttccatttt aatttattta tcttatttta acttgacata taattttaaa aatgaagatt    240
ttgtaaaata atttaaatga ataagaaaat attctttta  aaactattac aaaaaagtag    300
aacagctata tcaaaacaaa attagcagta aatttaaact tatatctcta aataatagca    360
aagacttaaa attaagaatc gatctaaaaa gacatatttc ttatttaata ctatacttaa    420 tgacttatt  tatttattat tcatgttaat ctcacttagt tatttgacaa tgttcacaat    480
aatataatct ctgtatttga aatttcattt atattaaaaa taattttaaa cattaaacgt    540
cttctgttat gaacaaaatt tacgcatgta atcacggccg tgttaaatgt ttttatgttt    600
acatacatct gtatcttatt tacaaaaaaa aaaatatat  atccttataa tcgcgtcagt    660 tcnacttcc  atgtaacgta acgttaattc ttccctccat ttcgtcaaac taactcatca    720
ttatcagtgt cggagtcnaa aaatttatta aaaagtcaaa aatacgaaga atagaaatac    780
gagaaatgca agaggtctta tatataatat cggaaaatct ttctggccag aagaatttag    840
ataaaattta taaatgatat tttacgttac ctttttgaac attttcattt taactttagt    900
atattttgat taaaaatag  gaaaagagc  tgtttatttt aattcttttg aatttctgaa    960 cactttttt  gaccatttag cactacccct taaaccatat atatatatat atgtgttcga   1020
cctttgctag ctccaccctc gatcaagggt ggagctagct tatggtcagc ggttcatcta   1080
ctatttatta atagttaaat ttactttata tatactct  attttgttct tacttgtcta   1140
ttttgacaaa taaaaaattc ttacctatta tactcttaat tgattactgt gaaaatata    1200
```

-continued

```
gaattttttgc taaatcttaa attttttaatt tatccacgtc ataattaata tgagtaaaat    1260
gataaactcg ctaaatcaaa taattatttt cttaatagat gtgttaattc aagagtagac    1320
aaataactag ggatagagaa agtatactgt agatgttgaa ctctcttgat taattagtct    1380
gtatatttat tctttcacct aataaaaatc tgtcgatttt cggtagcaaa ggcattgaat    1440
actagcgtgt ggagtgtccc tcttgtgttc cctcattgcc ggttatgtga gggacaccat    1500
tccctgttgc atcaaatttg tgttccaaaa ctaacgtaac ttccgtgcaa aaatcgcacc    1560
caacgtgcgt ctgtttacct ggctgcaagc aagcgcgtat tgacaacgaa tcgtaggcga    1620
gttgttttct ccgtgttatt atttatgaga ttcatgcaca cacaaagaat aactcgccta    1680
catattgtct ttttcctata taacaatcct cacaattcac agcaattcaa atcaatcatt    1740
ctttctaaat c                                                        1751
```

<210> SEQ ID NO 16
<211> LENGTH: 11252
<212> TYPE: DNA
<213> ORGANISM: Artificial sequence
<220> FEATURE:
<223> OTHER INFORMATION: Synthetic sequence: Vector pSIM108

<400> SEQUENCE: 16

```
agctttggca ggatatatac cggtgtaaac gaagtgtgtg tggttgatcc aaaatctatc      60
gtacctttag aaagtgtagc tatgaaggat agtctcactt atgaagaact acctattgag     120
attcttgatc gtcaggtccg aaggttgaga aaaatagaag tcgcttcagt tacggctttg     180
tggaggagta agggtacccg gggatcaatt cccgatctag taacatagat gacaccgcgc     240
gcgataattt atcctagttt gcgcgctata ttttgttttc tatcgcgtat taaatgtata     300
attgcgggac tctaatcata aaacccatc tcataaataa cgtcatgcat tacatgttaa     360
ttattacatg cttaacgtaa ttcaacagaa attatatgat aatcatcgca agaccggcaa     420
caggattcaa tcttaagaaa ctttattgcc aaatgtttga acgatcgggg aaattcgagc     480
tctcagaaga actcgtcaag aaggcgatag aaggcgatgc gctgcgaatc gggagcggcg     540
ataccgtaaa gcacgaggaa gcggtcagcc cattcgccgc caagctcttc agcaatatca     600
cgggtagcca acgctatgtc ctgatagcgg tccgccacac ccagccggcc acagtcgatg     660
aatccagaaa agcggccatt ttccaccatg atattcggca agcaggcatc gccatgggtc     720
acgacgagat catcgccgtc gggcatgcgc gccttgagcc tggcgaacag ttcggctggc     780
gcgagcccct gatgctcttc gtccagatca tcctgatcga caagaccggc ttccatccga     840
gtacgtgctc gctcgatgcg atgtttcgct tggtggtcga atgggcaggt agccggatca     900
agcgtatgca gccgccgcat tgcatcagcc atgatggata cttctcggc aggagcaagg     960
tgagatgaca ggagatcctg ccccggcact tcgcccaata gcagccagtc ccttcccgct    1020
tcagtgacaa cgtcgagcac agctgcgcaa ggaacgcccg tcgtggccag ccacgatagc    1080
cgcgctgcct cgtcctgcag ttcattcagg gcaccggaca ggtcggtctt gacaaaaaga    1140
accgggcgcc cctgcgctga cagccggaac acggcggcat cagagcagcc gattgtctgt    1200
tgtgcccagt catagccgaa tagcctctcc acccaagcgg ccggagaacc tgcgtgcaat    1260
ccatcttgtt caatcatacc cggggatcct ctagagtccc ccgtgttctc tccaaatgaa    1320
atgaacttcc ttatatagag gaagggtctt gcgaaggata gtgggattgt gcgtcatccc    1380
ttacgtcagt ggagatatca catcaatcca cttgctttga agacgtggtt ggaacgtctt    1440
ctttttccac gatgctcctc gtgggtgggg gtccatcttt gggaccactg tcggcagagg    1500
```

-continued

```
catcttcaac gatggccttt cctttatcgc aatgatggca tttgtaggag ccaccttcct  1560
tttccactat cttcacaata aagtgacaga tagctgggca atggaatccg aggaggtttc  1620
cggatattac cctttgttga aaagtctcaa ttgcccttg gtcttctgag actgtatctt  1680 tgatatttt ggagtagaca agtgtgtcgt gctccaccat gttgacgaag attttcttct  1740
tgtcattgag tcgtaagaga ctctgtatga actgttcgcc agtctttacg gcgagttctg  1800
ttaggtcctc tatttgaatc tttgactcca tggcctttga ttcagtggga actacctttt  1860
tagagactcc aatctctatt acttgccttg gtttgtgaag caagccttga atcgtccata  1920
ctggaatagt acttctgatc ttgagaaata tatctttctc tgtgttcttg atgcagttag  1980
tcctgaatct tttgactgca tctttaacct tcttgggaag gtatttgatt tcctggagat  2040
tattgctcgg gtagatcgtc ttgatgagac ctgctgcgta agcctctcta accatctgtg  2100
ggttagcatt ctttctgaaa ttggaaaagg ctaatctggg gacctgcagt tatgctataa  2160
atttcatata tttagttggg agtaggcttt ataccgagtt ggactacggt cagtcacttt  2220
caagtcctag aactacgtgc ccctgtaggt tataagtctc ctctgtgggc atcaatttag  2280
tgatcatgcc agtcatgcct ctatacctct gacaggatat atggtactgt aaacactagt  2340
tgtgaataag tcgctgtgta tgtttgtttg agatctctaa gagaaaagag cgtttattag  2400
aataacggat atttaaaagg gcgtgaaaag gtttatccgt tcgtccattt gtatgtggtc  2460
acctatctcg agcatgccaa ccacagggtt cccctcggga tcaaagtact ttgatccaac  2520
ccctccgctg ctatagtgca gtcggcttct gacgttcagt gcagccgtct tctgaaaacg  2580
acatgtcgca caagtcctaa gttacgcgac aggctgccgc cctgcccttt tcctggcgtt  2640
ttcttgtcgc gtgttttagt cgcataaagt agaatacttg cgactagaac cggagacatt  2700
acgccatgaa caagagcgcc gccgctggcc tgctgggcta tgcccgcgtc agcaccgacg  2760
accaggactt gaccaaccaa cgggccgaac tgcacgcggc cggctgcacc aagctgtttt  2820
ccgagaagat caccggcacc aggcgcgacc gcccggagct ggccaggatg cttgaccacc  2880
tacgccctgg cgacgttgtg acagtgacca ggctagaccg cctggcccgc agcacccgcg  2940
acctactgga cattgccgag cgcatccagg aggccggcgc gggcctgcgt agcctggcag  3000
agccgtgggc cgacaccacc acgccggccg ccgcatggt gttgaccgtg ttcgccggca  3060
ttgccgagtt cgagcgttcc ctaatcatcg accgcacccg gagcgggcgc gaggccgcca  3120
aggcccgagg cgtgaagttt ggcccccgcc ctaccctcac cccggcacag atcgcgcacg  3180
cccgcgagct gatcgaccag gaaggccgca ccgtgaaaga gcggctgca ctgcttggcg  3240 tgcatcgctc gaccctgtac cgcgcacttg agcgcagcga ggaagtgacg cccaccgagg  3300
ccaggcggcg cggtgccttc cgtgaggacg cattgaccga ggccgacgcc ctggcggccg  3360
ccgagaatga acgccaagag gaacaagcat gaaaccgcac caggacggcc aggacgaacc  3420
gtttttcatt accgaagaga tcgaggcgga gatgatcgcg gccgggtacg tgttcgagcc  3480
gcccgcgcac gtctcaaccg tgcggctgca tgaaatcctg gccggtttgt ctgatgccaa  3540
gctggcggcc tggccggcca gcttggccgc tgaagaaacc gagcgccgcc gtctaaaaag  3600
gtgatgtgta tttgagtaaa acagcttgcg tcatgcggtc gctgcgtata tgatgcgatg  3660
agtaaataaa caaatacgca aggggaacgc atgaaggtta tcgctgtact taaccagaaa  3720
ggcgggtcag gcaagacgac catcgcaacc catctagccc gcgccctgca actcgccggg  3780
gccgatgttc tgttagtcga ttccgatccc cagggcagtg cccgcgattg gcggccgtg  3840
```

```
cgggaagatc aaccgctaac cgttgtcggc atcgaccgcc cgacgattga ccgcgacgtg   3900
aaggccatcg gccggcgcga cttcgtagtg atcgacggag cgccccaggc ggcggacttg   3960
gctgtgtccg cgatcaaggc agccgacttc gtgctgattc cggtgcagcc aagcccttac   4020
gacatatggg ccaccgccga cctggtggag ctggttaagc agcgcattga ggtcacggat   4080
ggaaggctac aagcggcctt tgtcgtgtcg cgggcgatca aaggcacgcg catcggcggt   4140
gaggttgccg aggcgctggc cgggtacgag ctgcccattc ttgagtcccg tatcacgcag   4200
cgcgtgagct acccaggcac tgccgccgcc ggcacaaccg ttcttgaatc agaacccgag   4260
ggcgacgctg cccgcgaggt ccaggcgctg gccgctgaaa ttaaatcaaa actcatttga   4320
gttaatgagg taaagagaaa atgagcaaaa gcacaaacac gctaagtgcc ggccgtccga   4380
gcgcacgcag cagcaaggct gcaacgttgg ccagcctggc agacacgcca gccatgaagc   4440
gggtcaactt tcagttgccg gcggaggatc acaccaagct gaagatgtac gcggtacgcc   4500
aaggcaagac cattaccgag ctgctatctg aatacatcgc gcagctacca gagtaaatga   4560
gcaaatgaat aaatgagtag atgaatttta gcggctaaag gaggcggcat ggaaaatcaa   4620
gaacaaccag gcaccgacgc cgtggaatgc cccatgtgtg gaggaacggg cggttggcca   4680
ggcgtaagcg gctgggttgt ctgccggccc tgcaatggca ctggaacccc caagcccgag   4740
gaatcggcgt gacggtcgca aaccatccgg cccggtacaa atcggcgcgg cgctgggtga   4800
tgacctggtg gagaagttga aggccgcgca ggccgcccag cggcaacgca tcgaggcaga   4860
agcacgcccc ggtgaatcgt ggcaagcggc cgctgatcga atccgcaaag aatcccggca   4920
accgccggca gccggtgcgc cgtcgattag gaagccgccc aagggcgacg agcaaccaga   4980 tttttttcgtt ccgatgctct atgacgtggg cacccgcgat agtcgcagca tcatggacgt   5040
ggccgttttc cgtctgtcga agcgtgaccg acgagctggc gaggtgatcc gctacgagct   5100
tccagacggg cacgtagagg tttccgcagg gccggccggc atggccagtg tgtgggatta   5160
cgacctggta ctgatggcgg tttcccatct aaccgaatcc atgaaccgat accgggaagg   5220
gaagggagac aagcccggcc gcgtgttccg tccacacgtt gcggacgtac tcaagttctg   5280
ccggcgagcc gatggcggaa agcagaaaga cgacctggta gaaacctgca ttcggttaaa   5340
caccacgcac gttgccatgc agcgtacgaa gaaggccaag aacggccgcc tggtgacggt   5400
atccgagggt gaagccttga ttagccgcta caagatcgta aagagcgaaa ccgggcggcc   5460
ggagtacatc gagatcgagc tagctgattg gatgtaccgc gagatcacag aaggcaagaa   5520 cccgacgtg ctgacggttc accccgatta ctttttgatc gatcccggca tcggccgttt   5580
tctctaccgc ctggcacgcc gcgccgcagg caaggcagaa gccagatggt tgttcaagac   5640
gatctacgaa cgcagtggca gcgccggaga gttcaagaag ttctgtttca ccgtgcgcaa   5700
gctgatcggg tcaaatgacc tgccggagta cgatttgaag gaggaggcgg ggcaggctgg   5760
cccgatccta gtcatgcgct accgcaacct gatcgagggc gaagcatccg ccggttccta   5820
atgtacggag cagatgctag gcaaattgcc ctagcaggg gaaaaaggtc gaaaaggtct   5880
ctttcctgtg gatagcacgt acattgggaa cccaaagccg tacattggga accggaaccc   5940
gtacattggg aacccaaagc cgtacattgg gaaccggtca cacatgtaag tgactgatat   6000
aaaagagaaa aaggcgattt ttccgcctaa aaactcttta aaacttatta aaactcttaa   6060
aacccgcctg gcctgtgcat aactgtctgg ccagcgcaca gccgaagagc tgcaaaaagc   6120
gcctaccctt cggtcgctgc gctccctacg ccccgccgct tcgcgtcggc ctatcgcggc   6180
cgctggccgc tcaaaaatgg ctggcctacg gccaggcaat ctaccagggc gcggacaagc   6240
```

-continued

| | |
|---|---|
| cgcgccgtcg ccactcgacc gccggcgccc acatcaaggc accctgcctc gcgcgtttcg | 6300 |
| gtgatgacgg tgaaaacctc tgacacatgc agctcccgga gacggtcaca gcttgtctgt | 6360 |
| aagcggatgc cgggagcaga caagcccgtc agggcgcgtc agcgggtgtt ggcgggtgtc | 6420 |
| ggggcgcagc catgacccag tcacgtagcg atagcggagt gtatactggc ttaactatgc | 6480 |
| ggcatcagag cagattgtac tgagagtgca ccatatgcgg tgtgaaatac cgcacagatg | 6540 |
| cgtaaggaga aataccgca tcaggcgctc ttccgcttcc tcgctcactg actcgctgcg | 6600 |
| ctcggtcgtt cggctgcggc gagcggtatc agctcactca aaggcggtaa tacggttatc | 6660 |
| cacagaatca ggggataacg caggaaagaa catgtgagca aaaggccagc aaaaggccag | 6720 |
| gaaccgtaaa aaggccgcgt tgctggcgtt tttccatagg ctccgccccc ctgacgagca | 6780 |
| tcacaaaaat cgacgctcaa gtcagaggtg gcgaaacccg acaggactat aaagatacca | 6840 |
| ggcgtttccc cctggaagct ccctcgtgcg ctctcctgtt ccgaccctgc cgcttaccgg | 6900 |
| atacctgtcc gcctttctcc cttcgggaag cgtggcgctt tctcatagct cacgctgtag | 6960 |
| gtatctcagt tcggtgtagg tcgttcgctc caagctgggc tgtgtgcacg aaccccccgt | 7020 |
| tcagcccgac cgctgcgcct tatccggtaa ctatcgtctt gagtccaacc cggtaagaca | 7080 |
| cgacttatcg ccactggcag cagccactgg taacaggatt agcagagcga ggtatgtagg | 7140 |
| cggtgctaca gagttcttga agtggtggcc taactacggc tacactagaa ggacagtatt | 7200 |
| tggtatctgc gctctgctga agccagttac cttcggaaaa agagttggta gctcttgatc | 7260 |
| cggcaaacaa accaccgctg gtagcggtgg tttttttgtt tgcaagcagc agattacgcg | 7320 |
| cagaaaaaaa ggatctcaag aagatccttt gatcttttct acggggtctg acgctcagtg | 7380 |
| gaacgaaaac tcacgttaag ggattttggt catgcattct aggtactaaa acaattcatc | 7440 |
| cagtaaaata taatatttta ttttctccca atcaggcttg atccccagta agtcaaaaaa | 7500 |
| tagctcgaca tactgttctt ccccgatatc ctccctgatc gaccggacgc agaaggcaat | 7560 |
| gtcataccac ttgtccgccc tgccgcttct cccaagatca ataaagccac ttactttgcc | 7620 |
| atctttcaca aagatgttgc tgtctcccag gtcgccgtgg gaaaagacaa gttcctcttc | 7680 |
| gggcttttcc gtctttaaaa aatcatacag ctcgcgcgga tctttaaatg gagtgtcttc | 7740 |
| ttcccagttt tcgcaatcca catcggccag atcgttattc agtaagtaat ccaattcggc | 7800 |
| taagcggctg tctaagctat tcgtataggg acaatccgat atgtcgatgg agtgaaagag | 7860 |
| cctgatgcac tccgcataca gctcgataat cttttcaggg cttgttcat cttcatactc | 7920 |
| ttccgagcaa aggacgccat cggcctcact catgagcaga ttgctccagc catcatgccg | 7980 |
| ttcaaagtgc aggacctttg aacaggcag cttttccttcc agccatagca tcatgtcctt | 8040 |
| ttcccgttcc acatcatagg tggtccctt ataccggctg tccgtcattt ttaaatatag | 8100 |
| gttttcattt tctcccacca gcttatatac cttagcagga acattccttt ccgtatcttt | 8160 |
| tacgcagcgg tattttcga tcagtttttt caattccggt gatattctca ttttagccat | 8220 |
| ttattatttc cttcctcttt tctacagtat ttaaagatac cccaagaagc taattataac | 8280 |
| aagacgaact ccaattcact gttccttgca ttctaaaacc ttaaatacca gaaacagct | 8340 |
| ttttcaaagt tgtttcaa gttggcgtat aacatagtat cgacggagcc gattttgaaa | 8400 |
| ccgcggatcc tgcagccaaa gcacatactt atcgatttaa atttcatcga agagattaat | 8460 |
| atcgaataat catatacata ctttaaatac ataacaaatt ttaaatacat atatctggta | 8520 |
| tataattaat tttttaaagt catgaagtat gtatcaaata cacatatgga aaaaattaac | 8580 |

```
tattcataat ttaaaaaata gaaaagatac atctagtgaa attaggtgca tgtatcaaat      8640
acattaggaa aagggcatat atcttgatct agataattaa cgattttgat ttatgtataa      8700
tttccaaatg aaggtttata tctacttcag aaataacaat atactttat cagaacattc       8760 aacaaagtaa caaccaacta gagtgaaaaa tacacattgt tctctaaaca tacaaaattg      8820
agaaaagaat ctcaaaattt agagaaacaa atctgaattt ctagaagaaa aaataatta       8880 tgcactttgc tattgctcga aaaataaatg aaagaaatta acttttta aaagatgtta        8940 gactagatat actcaaaagc tatcaaagga gtaatattct tcttacatta agtattttag     9000
ttacagtcct gtaattaaag acacatttta gattgtatct aaacttaaat gtatctagaa     9060
tacatatatt tgaatgcatc atatacatgt atccgacaca ccaattctca taaaaagcgt     9120
aatatcctaa actaatttat ccttcaagtc aacttaagcc caatatacat tttcatctct     9180
aaaggcccaa gtggcacaaa atgtcaggcc caattacgaa gaaaagggct tgtaaaaccc     9240
taataaagtg gcactggcag agcttacact ctcattccat caacaaagaa accctaaaag     9300
ccgcagcgcc actgatttct ctcctccagg cgaagatgca gatcttcgtg aagaccctaa     9360
cggggaagac gatcacccta gaggttgagt cttccgacac catcgacaat gtcaaagcca     9420
agatccagga caaggaaggg attcccccag accagcagcc tttgattttc gccggaaagc     9480
agcttgagga tggtcgtact cttgccgact acaacatcca gaaggagtca actctccatc     9540
tcgtgctccg tctccgtggt ggtggatcca tggacctgca tctaattttc ggtccaactt     9600
gcacaggaaa gacgacgacc gcgatagctc ttgcccagca gacagggctt ccagtccttt     9660
cgcttgatcg ggtccaatgc tgtcctcaac tatcaaccgg aagcggacga ccaacagtgg     9720
aagaactgaa aggaacgacg cgtctctacc ttgatgatcg gcctctggtg gagggtatca     9780
tcgcagccaa gcaagctcat cataggctga tcgaggaggt gtataatcat gaggccaacg     9840
gcgggcttat tcttgaggga ggatccacct cgttgctcaa ctgcatggcg cgaaacagct     9900
attggagtgc agattttcgt tggcatatta ttcgccacaa gttacccgac caagagacct     9960
tcatgaaagc ggccaaggcc agagttaagc agatgttgca ccccgctgca ggccattcta    10020
ttattcaaga gttggtttat cttttggaatg aacctcggct gaggcccatt ctgaaagaga   10080
tcgatggata tcgatatgcc atgttgtttg ctagccagaa ccagatcacg gcagatatgc    10140
tattgcagct tgacgcaaat atggaaggta agttgattaa tgggatcgct caggagtatt    10200
tcatccatgc gcgccaacag gaacagaaat tcccccaagt taacgcagcc gctttcgacg    10260
gattcgaagg tcatccgttc ggaatgtatt aggttacgcc agccctgcgt cgcacctgtc    10320
ttcatctgga taagatgttc gtaattgttt ttggctttgt cctgttgtgg cagggcggca    10380
aatacttccg acaatccatc gtgtcttcaa actttatgct ggtgaacaag tcttagtttc    10440
cacgaaagta ttatgttaaa ttttaaaatt tcgatgtata atgtggctat aattgtaaaa    10500
ataaactatc gtaagtgtgc gtgttatgta taatttgtct aaatgtttaa tatatatcat    10560
agaacgcaat aaatattaaa tatagcgctt ttatgaaata taaatacatc attacaagtt    10620
gtttatattt cgggtggact agttttaat gtttagcaaa tgtcctatca gttttctctt     10680
tttgtcgaac ggtaatttag agtttttttt gctatatgga ttttcgtttt tgatgtatgt    10740
gacaaccctc gggattgttg atttatttca aaactaagag ttttttgctta ttgttctcgt   10800 ctattttgga tatcaatctt agttttatat cttttctagt tctctacgtg ttaaatgttc    10860
aacacactag caatttggct gcagcgtatg gattatggaa ctatcaagtc tgtgggatcg    10920
ataaatatgc ttctcaggaa tttgagattt tacagtcttt atgctcattg ggttgagtat    10980
```

```
aatatagtaa aaaaatagga attctatccg cggtgatcac aggcagcaac gctctgtcat    11040
cgttacaatc aacatgctac cctccgcgag atcatccgtg tttcaaaccc ggcagcttag    11100
ttgccgttct tccgaatagc atcggtaaca tgagcaaagt ctgccgcctt acaacggctc    11160
tcccgctgac gccgtcccgg actgatgggc tgcctgtatc gagtggtgat tttgtgccga    11220
gctgccggtc ggggagctgt tggctggctg ga                                  11252
```

<210> SEQ ID NO 17
<211> LENGTH: 777
<212> TYPE: DNA
<213> ORGANISM: Solanum lycopersicum

<400> SEQUENCE: 17

```
atgagtactc ctatgatgtg tacatttttg ggagtaataa ggaaaggttc atggactgaa      60
gaagaagata ttcttttgag gaaatgtatt gataagtatg gagaaggaaa gtggcatctt     120
gttccaacta gagctggatt aaacagatgc agaaaaagtt gtagactgag gtggctaaat     180
tatctaaggc cacatatcaa gagaggtgac tttgaaccag atgaagtgga tctcatcttg     240
agacttcata gctcttagg caaccgatgg tcacttattg ctggtagact tccaggaagg     300
acagctaacg atgtgaaaaa ctattggaac actaaccttc taaggaagct aaatactagt     360
actaaatttg ctcctcaacc acaagaagga attaatacta gtactattgc tcctcaacca     420
caagaaggaa ttaagtatgg gcaagccaat gccataataa gacctcaacc tcagaaattc     480
acaagctcca tgaagattaa tgtctcttgg tgcaacaaca atagtatggt aaataatgaa     540
gaagcatcga agacaacaa cgatatgcaa tggtgggcaa atatactgga aaactgcaat     600
gacattggag aaggagaagc tgaaagaaca ctaccttcat gtaaggaaat taattgcaat     660
gaaattgata agcaccaag tttgttacat gagggaggca actccatgca acaaggacaa     720
ggtgatggtg gttgggatga atttgctcta gatgatatat ggaatctact taattag       777
```

<210> SEQ ID NO 18
<211> LENGTH: 258
<212> TYPE: PRT
<213> ORGANISM: Solanum lycopersicum

<400> SEQUENCE: 18

```
Met Ser Thr Pro Met Met Cys Thr Phe Leu Gly Val Ile Arg Lys Gly
 1               5                  10                  15

Ser Trp Thr Glu Glu Asp Ile Leu Leu Arg Lys Cys Ile Asp Lys
             20                  25                  30

Tyr Gly Glu Gly Lys Trp His Leu Val Pro Thr Arg Ala Gly Leu Asn
         35                  40                  45

Arg Cys Arg Lys Ser Cys Arg Leu Arg Trp Leu Asn Tyr Leu Arg Pro
     50                  55                  60

His Ile Lys Arg Gly Asp Phe Glu Pro Asp Glu Val Asp Leu Ile Leu
 65                  70                  75                  80

Arg Leu His Lys Leu Leu Gly Asn Arg Trp Ser Leu Ile Ala Gly Arg
                 85                  90                  95

Leu Pro Gly Arg Thr Ala Asn Asp Val Lys Asn Tyr Trp Asn Thr Asn
            100                 105                 110

Leu Leu Arg Lys Leu Asn Thr Ser Thr Lys Phe Ala Pro Gln Pro Gln
        115                 120                 125

Glu Gly Ile Asn Thr Ser Thr Ile Ala Pro Gln Pro Gln Glu Gly Ile
    130                 135                 140
```

```
Lys Tyr Gly Gln Ala Asn Ala Ile Ile Arg Pro Gln Pro Gln Lys Phe
145                 150                 155                 160

Thr Ser Ser Met Lys Ile Asn Val Ser Trp Cys Asn Asn Asn Ser Met
            165                 170                 175

Val Asn Asn Glu Glu Ala Ser Lys Asp Asn Asp Met Gln Trp Trp
            180                 185                 190

Ala Asn Ile Leu Glu Asn Cys Asn Asp Ile Gly Glu Gly Glu Ala Glu
        195                 200                 205

Arg Thr Leu Pro Ser Cys Lys Glu Ile Asn Cys Asn Glu Ile Asp Lys
    210                 215                 220

Ala Pro Ser Leu Leu His Glu Gly Gly Asn Ser Met Gln Gln Gly Gln
225                 230                 235                 240

Gly Asp Gly Gly Trp Asp Glu Phe Ala Leu Asp Asp Ile Trp Asn Leu
            245                 250                 255

Leu Asn

<210> SEQ ID NO 19
<211> LENGTH: 777
<212> TYPE: DNA
<213> ORGANISM: Solanum tuberosum

<400> SEQUENCE: 19
atgagtactc ctatgatgtg tacatttttg ggagtaataa ggaaaggttc atggactgaa      60
gaagaagata ttcttttgag gaaatgtatt gataagtatg gagaaggaaa gtggcatctt     120
gttccaacta gagctggatt aaacagatgc agaaaaagtt gtagactgag gtggctaaat     180
tatctaaggc cacatatcaa gagaggtgac tttgaaccag atgaagtgga tctcatcttg     240
agacttcata agctcttagg caaccgatgg tcacttattg ctggtagact tccaggaagg     300
acagctaacg atgtgaaaaa ctattggaac actaaccttc taaggaagct aaatactagt     360
actaaatttg ctcctcaacc acaagaagga attaatacta gtactattgc tcctcaacca     420
caagaaggaa ttaagtatgg gcaagccaat gccataataa gacctcaacc tcagaaattc     480
acaagctcca tgaagattaa tgtctcttgg tgcaacaaca atagtatggt aaataatgaa     540
gaagcatcga agacaacaa cgatatgcaa tggtgggcaa atatactgga aaactgcaat     600
gacattggag aaggagaagc tgaaagaaca ctaccttcat gtaaggaaat taattgcaat     660
gaaattgata agcaccaag tttgttacat gagggaggca actccatgca acaaggacaa     720
ggtgatggtg gttgggatga atttgctcta gatgatatat ggaatctact taattag       777

<210> SEQ ID NO 20
<211> LENGTH: 258
<212> TYPE: PRT
<213> ORGANISM: Solanum tuberosum

<400> SEQUENCE: 20

Met Ser Thr Pro Met Met Cys Thr Phe Leu Gly Val Ile Arg Lys Gly
1               5                   10                  15

Ser Trp Thr Glu Glu Glu Asp Ile Leu Leu Arg Lys Cys Ile Asp Lys
            20                  25                  30

Tyr Gly Glu Gly Lys Trp His Leu Val Pro Thr Arg Ala Gly Leu Asn
        35                  40                  45

Arg Cys Arg Lys Ser Cys Arg Leu Arg Trp Leu Asn Tyr Leu Arg Pro
    50                  55                  60

His Ile Lys Arg Gly Asp Phe Glu Pro Asp Glu Val Asp Leu Ile Leu
```

-continued

```
                65                  70                  75                  80
Arg Leu His Lys Leu Leu Gly Asn Arg Trp Ser Leu Ile Ala Gly Arg
                85                  90                  95
Leu Pro Gly Arg Thr Ala Asn Asp Val Lys Asn Tyr Trp Asn Thr Asn
                100                 105                 110
Leu Leu Arg Lys Leu Asn Thr Ser Thr Lys Phe Ala Pro Gln Pro Gln
                115                 120                 125
Glu Gly Ile Asn Thr Ser Thr Ile Ala Pro Gln Pro Gln Gly Ile
                130                 135                 140
Lys Tyr Gly Gln Ala Asn Ala Ile Ile Arg Pro Gln Pro Gln Lys Phe
145                 150                 155                 160
Thr Ser Ser Met Lys Ile Asn Val Ser Trp Cys Asn Asn Ser Met
                165                 170                 175
Val Asn Asn Glu Glu Ala Ser Lys Asp Asn Asn Asp Met Gln Trp Trp
                180                 185                 190
Ala Asn Ile Leu Glu Asn Cys Asn Asp Ile Gly Glu Gly Glu Ala Glu
                195                 200                 205
Arg Thr Leu Pro Ser Cys Lys Glu Ile Asn Cys Asn Glu Ile Asp Lys
                210                 215                 220
Ala Pro Ser Leu Leu His Glu Gly Gly Asn Ser Met Gln Gln Gly Gln
225                 230                 235                 240
Gly Asp Gly Gly Trp Asp Glu Phe Ala Leu Asp Asp Ile Trp Asn Leu
                245                 250                 255
Leu Asn

<210> SEQ ID NO 21
<211> LENGTH: 339
<212> TYPE: PRT
<213> ORGANISM: Solanum lycopersicum

<400> SEQUENCE: 21

Met Gly Arg Thr Pro Cys Cys Glu Lys Val Gly Ile Lys Arg Gly Arg
1               5                   10                  15
Trp Thr Ala Glu Glu Asp Gln Ile Leu Thr Asn Tyr Ile Ile Ser Asn
                20                  25                  30
Gly Glu Gly Ser Trp Arg Ser Leu Pro Lys Asn Ala Gly Leu Leu Arg
                35                  40                  45
Cys Gly Lys Ser Cys Arg Leu Arg Trp Ile Asn Tyr Leu Arg Ser Asp
                50                  55                  60
Leu Lys Arg Gly Asn Ile Thr Ser Gln Glu Glu Asp Ile Ile Ile Lys
65                  70                  75                  80
Leu His Ala Thr Leu Gly Asn Arg Trp Ser Leu Ile Ala Glu His Leu
                85                  90                  95
Ser Gly Arg Thr Asp Asn Glu Ile Lys Asn Tyr Trp Asn Ser His Leu
                100                 105                 110
Ser Arg Lys Val Asp Ser Leu Arg Ile Pro Ser Asp Glu Lys Leu Pro
                115                 120                 125
Lys Ala Val Val Asp Leu Ala Lys Lys Gly Ile Pro Lys Pro Ile Lys
                130                 135                 140
Lys Ser Ser Ile Ser Arg Pro Lys Asn Lys Ser Asn Leu Leu Glu
145                 150                 155                 160
Lys Glu Ala Leu Cys Cys Thr Asn Met Pro Ala Cys Asp Ser Ala Met
                165                 170                 175
Glu Leu Met Gln Glu Asp Leu Ala Lys Ile Glu Val Pro Asn Ser Trp
```

```
                180                185                190
Gly Arg Thr Tyr Arg Gly Gln Gly Lys Pro Leu Val Gln Ile Val Ile
            195                200                205
Ser Asn Gly Pro Arg Leu Glu Glu Ile Met Pro Asp Val Val Ile Asp
            210                215                220
Asp Glu Asp Lys Asn Thr Asn Phe Ile Leu Asn Cys Phe Arg Glu Glu
225                230                235                240
Val Thr Ser Asn Val Gly Asn Ser Tyr Ser Cys Ile Glu Glu Gly
                245                250                255
Asn Lys Lys Ile Ser Ser Asp Asp Glu Lys Ile Lys Leu Leu Met Asp
            260                265                270
Trp Gln Asp Asn Asp Glu Leu Val Trp Pro Thr Leu Pro Trp Glu Leu
            275                280                285
Glu Thr Asp Ile Val Pro Ser Trp Pro Gln Trp Asp Asp Thr Asp Thr
            290                295                300
Asn Leu Leu Gln Asn Cys Thr Asn Asp Asn Asn Tyr Glu Glu Ala
305                310                315                320
Thr Thr Met Glu Ile Asn Asn Gln Asn His Ser Thr Ile Val Ser Trp
                325                330                335
Leu Leu Ser
```

<210> SEQ ID NO 22
<211> LENGTH: 371
<212> TYPE: PRT
<213> ORGANISM: Arabidopsis thaliana

<400> SEQUENCE: 22

```
Met Gly Arg Ala Pro Cys Cys Glu Lys Val Gly Ile Lys Arg Gly Arg
1               5                  10                 15
Trp Thr Ala Glu Glu Asp Gln Ile Leu Ser Asn Tyr Ile Gln Ser Asn
            20                 25                 30
Gly Glu Gly Ser Trp Arg Ser Leu Pro Lys Asn Ala Gly Leu Lys Arg
        35                 40                 45
Cys Gly Lys Ser Cys Arg Leu Arg Trp Ile Asn Tyr Leu Arg Ser Asp
50                 55                 60
Leu Lys Arg Gly Asn Ile Thr Pro Glu Glu Glu Leu Val Val Lys
65                 70                 75                 80
Leu His Ser Thr Leu Gly Asn Arg Trp Ser Leu Ile Ala Gly His Leu
                85                 90                 95
Pro Gly Arg Thr Asp Asn Glu Ile Lys Asn Tyr Trp Asn Ser His Leu
            100                105                110
Ser Arg Lys Leu His Asn Phe Ile Arg Lys Pro Ser Ile Ser Gln Asp
        115                120                125
Val Ser Ala Val Ile Met Thr Asn Ala Ser Ser Ala Pro Pro Pro
130                135                140
Gln Ala Lys Arg Arg Leu Gly Arg Thr Ser Arg Ser Ala Met Lys Pro
145                150                155                160
Lys Ile His Arg Thr Lys Thr Arg Lys Thr Lys Thr Ser Ala Pro
                165                170                175
Pro Glu Pro Asn Ala Asp Val Ala Gly Ala Asp Lys Glu Ala Leu Met
            180                185                190
Val Glu Ser Ser Gly Ala Glu Ala Glu Leu Gly Arg Pro Cys Asp Tyr
        195                200                205
Tyr Gly Asp Asp Cys Asn Lys Asn Leu Met Ser Ile Asn Gly Asp Asn
```

```
                  210                 215                 220
Gly Val Leu Thr Phe Asp Asp Ile Ile Asp Leu Leu Asp Glu
225                 230                 235                 240

Ser Asp Pro Gly His Leu Tyr Thr Asn Thr Thr Cys Gly Asp Gly
                245                 250                 255

Glu Leu His Asn Ile Arg Asp Ser Glu Gly Ala Arg Gly Phe Ser Asp
            260                 265                 270

Thr Trp Asn Gln Gly Asn Leu Asp Cys Leu Leu Gln Ser Cys Pro Ser
        275                 280                 285

Val Glu Ser Phe Leu Asn Tyr Asp His Gln Val Asn Asp Ala Ser Thr
    290                 295                 300

Asp Glu Phe Ile Asp Trp Asp Cys Val Trp Gln Glu Gly Ser Asp Asn
305                 310                 315                 320

Asn Leu Trp His Glu Lys Glu Asn Pro Asp Ser Met Val Ser Trp Leu
                325                 330                 335

Leu Asp Gly Asp Asp Glu Ala Thr Ile Gly Asn Ser Asn Cys Glu Asn
                340                 345                 350

Phe Gly Glu Pro Leu Asp His Asp Asp Glu Ser Ala Leu Val Ala Trp
            355                 360                 365

Leu Leu Ser
    370
```

```
<210> SEQ ID NO 23
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 23
cttcagtctt gtccatcggt g                                        21

<210> SEQ ID NO 24
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 24
ctaacggttc tccaaagttc tcac                                     24

<210> SEQ ID NO 25
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 25
cctgttccac cacaaggaca a                                        21

<210> SEQ ID NO 26
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 26
gtgccaagtt taccgatttg c                                        21
```

<210> SEQ ID NO 27
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 27
cctgttccac cacaaggaca a                                              21

<210> SEQ ID NO 28
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 28
gtgccaagtt taccgatttg c                                              21

<210> SEQ ID NO 29
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 29
atgggaagaa caccttgttg                                                20

<210> SEQ ID NO 30
<211> LENGTH: 17
<212> TYPE: DNA
<213> ORGANISM: Artificial sequence
<220> FEATURE:
<223> OTHER INFORMATION: Synthetic sequence: Oligonucleotide

<400> SEQUENCE: 30
gactcgagtc gacatcg                                                   17

<210> SEQ ID NO 31
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 31
atgggaagaa caccttgttg                                                20

<210> SEQ ID NO 32
<211> LENGTH: 23
<212> TYPE: DNA
<213> ORGANISM: Artificial sequence
<220> FEATURE:
<223> OTHER INFORMATION: Synthetic sequence: Oligonucleotide

<400> SEQUENCE: 32
ctaagacaaa agccaagata caa                                            23

<210> SEQ ID NO 33
<211> LENGTH: 21
<212> TYPE: DNA
<213> ORGANISM: Artificial sequence
<220> FEATURE:

<223> OTHER INFORMATION: Synthetic sequence: Oligonucleotide

<400> SEQUENCE: 33
gagcaataat gtagggaata g                                              21

<210> SEQ ID NO 34
<211> LENGTH: 23
<212> TYPE: DNA
<213> ORGANISM: Artificial sequence
<220> FEATURE:
<223> OTHER INFORMATION: Synthetic sequence: Oligonucleotide

<400> SEQUENCE: 34
ttgaagtaag ttagtgtcag tat                                            23

<210> SEQ ID NO 35
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 35
aacctatctc gtggctcttt                                                20

<210> SEQ ID NO 36
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 36 tcttttcgc tgaatcttgc                                                 20

<210> SEQ ID NO 37
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 37
caacagaaag gagagatcaa cgag                                           24

<210> SEQ ID NO 38
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 38
cacagcctga aggtatggaa gc                                             22

<210> SEQ ID NO 39
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 39
acacacaaag gcttagtcac ga                                             22

```
<210> SEQ ID NO 40
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 40
aacagaggca acacacacat ca                                              22

<210> SEQ ID NO 41
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 41
tggtcaccgt ggaggagtat c                                               21

<210> SEQ ID NO 42
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 42
gatcgtagct ggaccctctg c                                               21

<210> SEQ ID NO 43
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 43
gtttttcaca aaccaacagt tctgat                                          26

<210> SEQ ID NO 44
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 44
gaagcagtgc tcgattccat aat                                             23

<210> SEQ ID NO 45
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 45
cacaccgatc caggaaccat                                                 20

<210> SEQ ID NO 46
<211> LENGTH: 21
<212> TYPE: DNA
<213> ORGANISM: Artificial sequence
<220> FEATURE:
<223> OTHER INFORMATION: Synthetic sequence: Primer
```

```
<400> SEQUENCE: 46
gcccaccaac ttggtcttgt a                                              21

<210> SEQ ID NO 47
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 47
gcaccacgaa tgcacttgc                                                 19

<210> SEQ ID NO 48
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 48
cgttagtacc gtcggcgaat                                                20

<210> SEQ ID NO 49
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 49
ggcaattgga cgagatcctg                                                20

<210> SEQ ID NO 50
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 50
aaggaacctc tcgggagtga a                                              21

<210> SEQ ID NO 51
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 51
gagcatgaag ttgggccaat                                                20

<210> SEQ ID NO 52
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 52
tggtgggttg gcctcattaa                                                20

<210> SEQ ID NO 53
<211> LENGTH: 20
```

<210> SEQ ID NO 53
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 53
tccgaagacg acaacggttt                      20

<210> SEQ ID NO 54
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 54
tgacaagcca agagccgata a                    21

<210> SEQ ID NO 55
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 55
gaactagcac ttggcgtcga a                    21

<210> SEQ ID NO 56
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 56
ttgcaagcca ggcaccata                       19

<210> SEQ ID NO 57
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 57
cgaacgacga aacactgttg a                    21

<210> SEQ ID NO 58
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 58
tgcagcatag atggcattgg                      20

<210> SEQ ID NO 59
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 59

```
ctggcaatgc aaacagagtg a                                          21
```

<210> SEQ ID NO 60
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 60

```
tcgacttgcg gaagagtgag a                                          21
```

<210> SEQ ID NO 61
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 61

```
cataaactct accaccgtct cc                                         22
```

<210> SEQ ID NO 62
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 62

```
aatccatccc atttctactc aa                                         22
```

<210> SEQ ID NO 63
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 63

```
aggtgaaaaa ctcaacgatg gt                                         22
```

<210> SEQ ID NO 64
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 64

```
acactaggcg tgtggaaatt ag                                         22
```

<210> SEQ ID NO 65
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 65

```
gtgttttgtt tgttgaggct ga                                         22
```

<210> SEQ ID NO 66
<211> LENGTH: 22
<212> TYPE: DNA
<213> ORGANISM: Artificial sequence

```
<220> FEATURE:
<223> OTHER INFORMATION: Synthetic sequence: Primer

<400> SEQUENCE: 66
tgatgaagtg gatggatgag ag                                            22

<210> SEQ ID NO 67
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 67
cctgttccac cacaaggaca a                                             21

<210> SEQ ID NO 68
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 68
gtgccaagtt taccgatttg c                                             21

<210> SEQ ID NO 69
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 69
ggggtaccca tccctaatga tattgttcac gtaa                               34

<210> SEQ ID NO 70
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 70
cggggatccg cactgtgaat gattagaata atttct                             36

<210> SEQ ID NO 71
<211> LENGTH: 59
<212> TYPE: DNA
<213> ORGANISM: Artificial sequence
<220> FEATURE:
<223> OTHER INFORMATION: Synthetic sequence: Primer

<400> SEQUENCE: 71
ggggacaagt ttgtacaaaa aagcaggcta ccatggctac tggtatccaa aaccaaaag    59

<210> SEQ ID NO 72
<211> LENGTH: 63
<212> TYPE: DNA
<213> ORGANISM: Artificial sequence
<220> FEATURE:
<223> OTHER INFORMATION: Synthetic sequence: Primer

<400> SEQUENCE: 72
ggggaccact ttgtacaaga aagctgggtg gatccaactt caagacttca tagtaacttt   60
``` ctg                                                                 63

<210> SEQ ID NO 73
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 73
cggggatcca tggaaaagaa ttgtcgtgga gt                                  32

<210> SEQ ID NO 74
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 74
tcccccgggt aatttccaa tttgttgggc ct                                   32

<210> SEQ ID NO 75
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 75
atgagttaga agtgaagcgg                                                20

<210> SEQ ID NO 76
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 76
atccccagag ccaaagcagc a                                              21

<210> SEQ ID NO 77
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 77
gtgtccacgg gccatctgac ca                                             22

<210> SEQ ID NO 78
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 78
gctcaggcac accgatggca                                                20

<210> SEQ ID NO 79
<211> LENGTH: 22
<212> TYPE: DNA
<213> ORGANISM: Artificial sequence -continued
<220> FEATURE:
<223> OTHER INFORMATION: Synthetic sequence: Oligonucleotide

<400> SEQUENCE: 79
atgggaagaa caccttgttg tg                                            22

<210> SEQ ID NO 80
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 80
atgagtactc ctatgatgtg ta                                            22

<210> SEQ ID NO 81
<211> LENGTH: 24
<212> TYPE: DNA
<213> ORGANISM: Artificial sequence
<220> FEATURE:
<223> OTHER INFORMATION: Synthetic sequence: Oligonucleotide

<400> SEQUENCE: 81
ctaattaagt agattccata tatc                                          24

<210> SEQ ID NO 82
<211> LENGTH: 345
<212> TYPE: DNA
<213> ORGANISM: Solanum sp.

<400> SEQUENCE: 82
atagtaattt cttttttga tttttcgtga tgtccggtac ttatattaga atctgactga    60
attcagattc acgcgactcc ttatctaggg ggactcgaac ccaacacctc tgattaagaa   120
tgaatgagta cttattactc cgacatatgg ttggtattaa agaaatatgt aatggtaatt   180
aatattattg taaacttgta atagggatcc aatcgtcctt tatactttgt atcctaatta   240
caagttgtta ggaatgtaat tttaagaatt attgtaagtg catgcactct atttttatat   300
ttgatgtgaa tttaaggatt gagcataaat atgaaaaatc aaaat                   345

<210> SEQ ID NO 83
<211> LENGTH: 663
<212> TYPE: DNA
<213> ORGANISM: Antirrhinum majus
<220> FEATURE:
<221> NAME/KEY: CDS
<222> LOCATION: (1)...(663)

<400> SEQUENCE: 83 atg gaa aag aat tgt cgt gga gtg aga aaa ggt act tgg acc aaa gaa    48
Met Glu Lys Asn Cys Arg Gly Val Arg Lys Gly Thr Trp Thr Lys Glu
1               5                   10                  15 gaa gac act ctc ttg agg caa tgt ata gaa gag tat ggt gaa ggg aaa    96
Glu Asp Thr Leu Leu Arg Gln Cys Ile Glu Glu Tyr Gly Glu Gly Lys
            20                  25                  30 tgg cat caa gtt cca cac aga gca ggg ttg aac cgg tgt agg aag agt   144
Trp His Gln Val Pro His Arg Ala Gly Leu Asn Arg Cys Arg Lys Ser
        35                  40                  45 tgc agg ctg agg tgg ttg aat tat ctg agg cca aat atc aaa aga ggt   192
Cys Arg Leu Arg Trp Leu Asn Tyr Leu Arg Pro Asn Ile Lys Arg Gly
    50                  55                  60 cgg ttt tcg aga gat gaa gtg gac cta att gtg agg ctt cat aag ctg   240

```
Arg Phe Ser Arg Asp Glu Val Asp Leu Ile Val Arg Leu His Lys Leu
 65                  70                  75                  80 ttg ggt aac aaa tgg tcg ctg att gct ggt aga att cct gga agg aca      288
Leu Gly Asn Lys Trp Ser Leu Ile Ala Gly Arg Ile Pro Gly Arg Thr
                 85                  90                  95 gct aat gac gtg aag aac ttt tgg aat act cat gtg ggg aag aat tta      336
Ala Asn Asp Val Lys Asn Phe Trp Asn Thr His Val Gly Lys Asn Leu
            100                 105                 110 ggc gag gat gga gaa cga tgc cgg aaa aat gtt atg aac aca aaa acc      384
Gly Glu Asp Gly Glu Arg Cys Arg Lys Asn Val Met Asn Thr Lys Thr
        115                 120                 125 att aag ctg act aat atc gta aga ccc cga gct cgg acc ttc acc gga      432
Ile Lys Leu Thr Asn Ile Val Arg Pro Arg Ala Arg Thr Phe Thr Gly
    130                 135                 140 ttg cac gtt act tgg ccg aga gaa gtc gga aaa acc gat gaa ttt tca      480
Leu His Val Thr Trp Pro Arg Glu Val Gly Lys Thr Asp Glu Phe Ser
145                 150                 155                 160 aat gtc cgg tta aca act gat gag att cca gat tgt gag aag caa acg      528
Asn Val Arg Leu Thr Thr Asp Glu Ile Pro Asp Cys Glu Lys Gln Thr
                165                 170                 175 caa ttt tac aat gat gtt gcg tcg cca caa gat gaa gtt gaa gac tgc      576
Gln Phe Tyr Asn Asp Val Ala Ser Pro Gln Asp Glu Val Glu Asp Cys
            180                 185                 190 att cag tgg tgg agt aag ttg cta gaa aca acg gag gat ggg gaa tta      624
Ile Gln Trp Trp Ser Lys Leu Leu Glu Thr Thr Glu Asp Gly Glu Leu
        195                 200                 205 gga aac cta ttc gag gag gcc caa caa att gga aat taa                  663
Gly Asn Leu Phe Glu Glu Ala Gln Gln Ile Gly Asn *
    210                 215                 220

<210> SEQ ID NO 84
<211> LENGTH: 220
<212> TYPE: PRT
<213> ORGANISM: Antirrhinum majus

<400> SEQUENCE: 84

Met Glu Lys Asn Cys Arg Gly Val Arg Lys Gly Thr Trp Thr Lys Glu
 1               5                  10                  15

Glu Asp Thr Leu Leu Arg Gln Cys Ile Glu Glu Tyr Gly Glu Gly Lys
             20                  25                  30

Trp His Gln Val Pro His Arg Ala Gly Leu Asn Arg Cys Arg Lys Ser
         35                  40                  45

Cys Arg Leu Arg Trp Leu Asn Tyr Leu Arg Pro Asn Ile Lys Arg Gly
     50                  55                  60

Arg Phe Ser Arg Asp Glu Val Asp Leu Ile Val Arg Leu His Lys Leu
 65                  70                  75                  80

Leu Gly Asn Lys Trp Ser Leu Ile Ala Gly Arg Ile Pro Gly Arg Thr
                 85                  90                  95

Ala Asn Asp Val Lys Asn Phe Trp Asn Thr His Val Gly Lys Asn Leu
            100                 105                 110

Gly Glu Asp Gly Glu Arg Cys Arg Lys Asn Val Met Asn Thr Lys Thr
        115                 120                 125

Ile Lys Leu Thr Asn Ile Val Arg Pro Arg Ala Arg Thr Phe Thr Gly
    130                 135                 140

Leu His Val Thr Trp Pro Arg Glu Val Gly Lys Thr Asp Glu Phe Ser
145                 150                 155                 160

Asn Val Arg Leu Thr Thr Asp Glu Ile Pro Asp Cys Glu Lys Gln Thr
                165                 170                 175
```

```
Gln Phe Tyr Asn Asp Val Ala Ser Pro Gln Asp Glu Val Glu Asp Cys
            180                 185                 190

Ile Gln Trp Trp Ser Lys Leu Leu Glu Thr Thr Glu Asp Gly Glu Leu
        195                 200                 205

Gly Asn Leu Phe Glu Glu Ala Gln Gln Ile Gly Asn
    210                 215                 220

<210> SEQ ID NO 85
<211> LENGTH: 2075
<212> TYPE: DNA
<213> ORGANISM: Antirrhinum majus
<220> FEATURE:
<221> NAME/KEY: CDS
<222> LOCATION: (25)...(1959)

<400> SEQUENCE: 85
gtagagagga gagaggattc aaga atg gct act ggt atc caa aac caa aag        51
                          Met Ala Thr Gly Ile Gln Asn Gln Lys
                            1               5 ata gtg cct gag aat ttg agg aag caa ctt gct att gct gtg aga agt       99
Ile Val Pro Glu Asn Leu Arg Lys Gln Leu Ala Ile Ala Val Arg Ser
 10              15                  20                  25 atc caa tgg agt tat gca att ttc tgg tcc aat tca gtt gca caa cca      147
Ile Gln Trp Ser Tyr Ala Ile Phe Trp Ser Asn Ser Val Ala Gln Pro
                30                  35                  40 ggg gtc ttg gag tgg ggt gat ggg ttc tac aat gga gat att aaa act      195
Gly Val Leu Glu Trp Gly Asp Gly Phe Tyr Asn Gly Asp Ile Lys Thr
            45                  50                  55 cga aaa act gta caa tct gtc gaa ttg aat caa gat cag ctg gga ttg      243
Arg Lys Thr Val Gln Ser Val Glu Leu Asn Gln Asp Gln Leu Gly Leu
        60                  65                  70 cag aga agt gat caa ttg aga gaa ctt tat gag tct ctt tca ctt ggt      291
Gln Arg Ser Asp Gln Leu Arg Glu Leu Tyr Glu Ser Leu Ser Leu Gly
    75                  80                  85 gaa acc aac aca caa gct aaa agg cct act gct gca tta tca cca gaa      339
Glu Thr Asn Thr Gln Ala Lys Arg Pro Thr Ala Ala Leu Ser Pro Glu
 90                  95                 100                 105 gac ctc act gat gct gag tgg ttt ttc ttg gtt tgc atg tct ttc ata      387
Asp Leu Thr Asp Ala Glu Trp Phe Phe Leu Val Cys Met Ser Phe Ile
                110                 115                 120 ttc aat att ggc caa ggg ttg cct gga aga aca tta gca cga aat caa      435
Phe Asn Ile Gly Gln Gly Leu Pro Gly Arg Thr Leu Ala Arg Asn Gln
            125                 130                 135 gca gta tgg cta tgc aac gct cat cgt gcg gac acc aaa gtt ttc tcg      483
Ala Val Trp Leu Cys Asn Ala His Arg Ala Asp Thr Lys Val Phe Ser
        140                 145                 150 cgt tct ttg ctt gca aag agt gcg tca att cag aca gtt gtg tgc ttt      531
Arg Ser Leu Leu Ala Lys Ser Ala Ser Ile Gln Thr Val Val Cys Phe
    155                 160                 165 cca tat tca gaa ggt gta gtt gag ctg gga gca aca gag cta gta ccg      579
Pro Tyr Ser Glu Gly Val Val Glu Leu Gly Ala Thr Glu Leu Val Pro
170                 175                 180                 185 gag gat ttg aat cta atc cag cat ata aaa act tca ttc ttg gac agt      627
Glu Asp Leu Asn Leu Ile Gln His Ile Lys Thr Ser Phe Leu Asp Ser
                190                 195                 200 cct gcc acc gtt ccc aag att ccc aac tat gtc tcc aac agt att aca      675
Pro Ala Thr Val Pro Lys Ile Pro Asn Tyr Val Ser Asn Ser Ile Thr
            205                 210                 215 aac aac aat gac ctc att tgt gaa gcg ctt gaa cat gct aat ata cca      723
Asn Asn Asn Asp Leu Ile Cys Glu Ala Leu Glu His Ala Asn Ile Pro
```

-continued

```
                   220                 225                 230
gaa aac gat ctt gat cag ctt ttg aat tgt cca gac acg aac ata tgt      771
Glu Asn Asp Leu Asp Gln Leu Leu Asn Cys Pro Asp Thr Asn Ile Cys
    235                 240                 245 tct cct gat aac agt ttg gat gac ttt gca gac aat tta ctc ata gac      819
Ser Pro Asp Asn Ser Leu Asp Asp Phe Ala Asp Asn Leu Leu Ile Asp
250                 255                 260                 265 gaa tcg aat ttg gca gaa ggc atc aat ggg gag gtt cct caa aca caa      867
Glu Ser Asn Leu Ala Glu Gly Ile Asn Gly Glu Val Pro Gln Thr Gln
            270                 275                 280 agc tgg cct ttc atg gat gat gca atc agc aat tgt ctc aat agt tct      915
Ser Trp Pro Phe Met Asp Asp Ala Ile Ser Asn Cys Leu Asn Ser Ser
                285                 290                 295 atg aat tct agt gac tgt ata tct caa act cat gaa aat cta gag tct      963
Met Asn Ser Ser Asp Cys Ile Ser Gln Thr His Glu Asn Leu Glu Ser
300                 305                 310 ttt gct cca ctt tct gat gga aaa ggg cca ccg gag acg aat aat tgt     1011
Phe Ala Pro Leu Ser Asp Gly Lys Gly Pro Pro Glu Thr Asn Asn Cys
            315                 320                 325 atg cac agc act caa aaa tgc aat cag cag ata gaa aac acg ggt gtc     1059
Met His Ser Thr Gln Lys Cys Asn Gln Gln Ile Glu Asn Thr Gly Val
330                 335                 340                 345 caa ggc gat gag gtc cat tat caa ggg gta ctt tcc aat ctt ttg aag     1107
Gln Gly Asp Glu Val His Tyr Gln Gly Val Leu Ser Asn Leu Leu Lys
                350                 355                 360 agt tcc cat cag ttg gtt ctt ggt ccc tac ttc aga aat ggg aat aga     1155
Ser Ser His Gln Leu Val Leu Gly Pro Tyr Phe Arg Asn Gly Asn Arg
                365                 370                 375 gaa tca agc ttc gtt agt tgg aac aag gat gga tcg tcg ggt act cat     1203
Glu Ser Ser Phe Val Ser Trp Asn Lys Asp Gly Ser Ser Gly Thr His
            380                 385                 390 gtt ccc cga agc gga acc tca caa aga ttt ctg aag aaa gta ctt ttt     1251
Val Pro Arg Ser Gly Thr Ser Gln Arg Phe Leu Lys Lys Val Leu Phe
395                 400                 405 gaa gta gct aga atg cat gaa aac tcc agg ctt gat gct ggt aaa caa     1299
Glu Val Ala Arg Met His Glu Asn Ser Arg Leu Asp Ala Gly Lys Gln
410                 415                 420                 425 aag ggc aac agt gac tgc ctt gca aag cca acg gct gat gaa att gat     1347
Lys Gly Asn Ser Asp Cys Leu Ala Lys Pro Thr Ala Asp Glu Ile Asp
                430                 435                 440 aga aac cac gtc ttg tca gag aga aaa cgc aga gag aaa ata aac gaa     1395
Arg Asn His Val Leu Ser Glu Arg Lys Arg Arg Glu Lys Ile Asn Glu
                445                 450                 455 cgg ttt atg att ctt gca tcc cta gtc cca tcc ggt ggc aag gtt gac     1443
Arg Phe Met Ile Leu Ala Ser Leu Val Pro Ser Gly Gly Lys Val Asp
            460                 465                 470 aaa gta tca ata cta gac cat aca ata gat tac ttg aga ggg ctt gag     1491
Lys Val Ser Ile Leu Asp His Thr Ile Asp Tyr Leu Arg Gly Leu Glu
475                 480                 485 agg aaa gtc gac gag ctg gaa tct aac aaa atg gta aag ggc cgg ggg     1539
Arg Lys Val Asp Glu Leu Glu Ser Asn Lys Met Val Lys Gly Arg Gly
490                 495                 500                 505 cgg gaa tca act aca aaa act aaa cta cac gat gcc att gag agg acc     1587
Arg Glu Ser Thr Thr Lys Thr Lys Leu His Asp Ala Ile Glu Arg Thr
                510                 515                 520 tct gat aat tat ggc gca aca agg aca agt aac gtc aag aaa ccg ttg     1635
Ser Asp Asn Tyr Gly Ala Thr Arg Thr Ser Asn Val Lys Lys Pro Leu
            525                 530                 535 aca aac aag aga aag gct tct gat acg gac aag att gga gcc gta aat     1683
```

```
                Thr Asn Lys Arg Lys Ala Ser Asp Thr Asp Lys Ile Gly Ala Val Asn
                            540                 545                 550 agc aga ggt cga ttg aaa gat tcc tta aca gat aat ata act gtg aac        1731
Ser Arg Gly Arg Leu Lys Asp Ser Leu Thr Asp Asn Ile Thr Val Asn
555                 560                 565 att aca aac aag gat gtg ttg att gtc gtg act tgt tct tcc aag gag        1779
Ile Thr Asn Lys Asp Val Leu Ile Val Val Thr Cys Ser Ser Lys Glu
570                 575                 580                 585 ttt gta ttg ctt gaa gtg atg gaa gcc gta aga cga cta agt ttg gat        1827
Phe Val Leu Leu Glu Val Met Glu Ala Val Arg Arg Leu Ser Leu Asp
                590                 595                 600 tcc gaa act gtt caa tct tcc aac aga gat gga atg ata tct att acc        1875
Ser Glu Thr Val Gln Ser Ser Asn Arg Asp Gly Met Ile Ser Ile Thr
            605                 610                 615 ata aaa gcc aag tgc aag gga ttg aag gtt gca tca gca agt gtg atc        1923
Ile Lys Ala Lys Cys Lys Gly Leu Lys Val Ala Ser Ala Ser Val Ile
        620                 625                 630 aaa caa gct ctt cag aaa gtt act atg aag tct tga agttgattta             1969
Lys Gln Ala Leu Gln Lys Val Thr Met Lys Ser  *
635                 640 tgctcactat ctatagctag cttttgtgta aaaaatttgt attcataact tttgctaagt      2029
aatttgcagg gcttttccaa gtagttcaga tcaataaaaa aaaaaa                     2075

<210> SEQ ID NO 86
<211> LENGTH: 644
<212> TYPE: PRT
<213> ORGANISM: Antirrhinum majus

<400> SEQUENCE: 86

Met Ala Thr Gly Ile Gln Asn Gln Lys Ile Val Pro Glu Asn Leu Arg
1               5                   10                  15

Lys Gln Leu Ala Ile Ala Val Arg Ser Ile Gln Trp Ser Tyr Ala Ile
            20                  25                  30

Phe Trp Ser Asn Ser Val Ala Gln Pro Gly Val Leu Glu Trp Gly Asp
        35                  40                  45

Gly Phe Tyr Asn Gly Asp Ile Lys Thr Arg Lys Thr Val Gln Ser Val
    50                  55                  60

Glu Leu Asn Gln Asp Gln Leu Gly Leu Gln Arg Ser Asp Gln Leu Arg
65                  70                  75                  80

Glu Leu Tyr Glu Ser Leu Ser Leu Gly Glu Thr Asn Thr Gln Ala Lys
                85                  90                  95

Arg Pro Thr Ala Ala Leu Ser Pro Glu Asp Leu Thr Asp Ala Glu Trp
            100                 105                 110

Phe Phe Leu Val Cys Met Ser Phe Ile Phe Asn Ile Gly Gln Gly Leu
        115                 120                 125

Pro Gly Arg Thr Leu Ala Arg Asn Gln Ala Val Trp Leu Cys Asn Ala
    130                 135                 140

His Arg Ala Asp Thr Lys Val Phe Ser Arg Ser Leu Leu Ala Lys Ser
145                 150                 155                 160

Ala Ser Ile Gln Thr Val Val Cys Phe Pro Tyr Ser Glu Gly Val Val
                165                 170                 175

Glu Leu Gly Ala Thr Glu Leu Val Pro Glu Asp Leu Asn Leu Ile Gln
            180                 185                 190

His Ile Lys Thr Ser Phe Leu Asp Ser Pro Ala Thr Val Pro Lys Ile
        195                 200                 205

Pro Asn Tyr Val Ser Asn Ser Ile Thr Asn Asn Asn Asp Leu Ile Cys
```

```
              210                 215                 220
Glu Ala Leu Glu His Ala Asn Ile Pro Glu Asn Asp Leu Asp Gln Leu
225                 230                 235                 240

Leu Asn Cys Pro Asp Thr Asn Ile Cys Ser Pro Asp Asn Ser Leu Asp
                245                 250                 255

Asp Phe Ala Asp Asn Leu Leu Ile Asp Glu Ser Asn Leu Ala Glu Gly
                260                 265                 270

Ile Asn Gly Glu Val Pro Gln Thr Gln Ser Trp Pro Phe Met Asp Asp
                275                 280                 285

Ala Ile Ser Asn Cys Leu Asn Ser Ser Met Asn Ser Ser Asp Cys Ile
                290                 295                 300

Ser Gln Thr His Glu Asn Leu Glu Ser Phe Ala Pro Leu Ser Asp Gly
305                 310                 315                 320

Lys Gly Pro Pro Glu Thr Asn Asn Cys Met His Ser Thr Gln Lys Cys
                325                 330                 335

Asn Gln Gln Ile Glu Asn Thr Gly Val Gln Gly Asp Glu Val His Tyr
                340                 345                 350

Gln Gly Val Leu Ser Asn Leu Leu Lys Ser Ser His Gln Leu Val Leu
                355                 360                 365

Gly Pro Tyr Phe Arg Asn Gly Asn Arg Glu Ser Ser Phe Val Ser Trp
                370                 375                 380

Asn Lys Asp Gly Ser Ser Gly Thr His Val Pro Arg Ser Gly Thr Ser
385                 390                 395                 400

Gln Arg Phe Leu Lys Lys Val Leu Phe Glu Val Ala Arg Met His Glu
                405                 410                 415

Asn Ser Arg Leu Asp Ala Gly Lys Gln Lys Gly Asn Ser Asp Cys Leu
                420                 425                 430

Ala Lys Pro Thr Ala Asp Glu Ile Asp Arg Asn His Val Leu Ser Glu
                435                 440                 445

Arg Lys Arg Arg Glu Lys Ile Asn Glu Arg Phe Met Ile Leu Ala Ser
                450                 455                 460

Leu Val Pro Ser Gly Gly Lys Val Asp Lys Val Ser Ile Leu Asp His
465                 470                 475                 480

Thr Ile Asp Tyr Leu Arg Gly Leu Glu Arg Lys Val Asp Glu Leu Glu
                485                 490                 495

Ser Asn Lys Met Val Lys Gly Arg Gly Arg Glu Ser Thr Thr Lys Thr
                500                 505                 510

Lys Leu His Asp Ala Ile Glu Arg Thr Ser Asp Asn Tyr Gly Ala Thr
                515                 520                 525

Arg Thr Ser Asn Val Lys Lys Pro Leu Thr Asn Lys Arg Lys Ala Ser
530                 535                 540

Asp Thr Asp Lys Ile Gly Ala Val Asn Ser Arg Gly Arg Leu Lys Asp
                545                 550                 555                 560

Ser Leu Thr Asp Asn Ile Thr Val Asn Ile Thr Asn Lys Asp Val Leu
                565                 570                 575

Ile Val Val Thr Cys Ser Ser Lys Glu Phe Val Leu Leu Glu Val Met
                580                 585                 590

Glu Ala Val Arg Arg Leu Ser Leu Asp Ser Glu Thr Val Gln Ser Ser
                595                 600                 605

Asn Arg Asp Gly Met Ile Ser Ile Thr Ile Lys Ala Lys Cys Lys Gly
                610                 615                 620
```

```
Leu Lys Val Ala Ser Ala Ser Val Ile Lys Gln Ala Leu Gln Lys Val
625                 630                 635                 640
Thr Met Lys Ser
```